US012637675B2

(12) United States Patent
Yoneyama et al.

(10) Patent No.: US 12,637,675 B2
(45) Date of Patent: May 26, 2026

(54) SUGAR CHAIN-RELATED GENE AND USE THEREOF

(71) Applicant: STELIC INSTITUTE & CO., Tokyo (JP)

(72) Inventors: Hiroyuki Yoneyama, Tokyo (JP); Jun Koyama, Tokyo (JP); Masato Fujii, Tokyo (JP)

(73) Assignee: STELIC INSTITUTE & CO., Tokyo (JP)

( * ) Notice: Subject to any disclaimer, the term of this patent is extended or adjusted under 35 U.S.C. 154(b) by 1016 days.

(21) Appl. No.: 17/805,290

(22) Filed: Jun. 3, 2022

(65) Prior Publication Data

US 2022/0340910 A1 Oct. 27, 2022

Related U.S. Application Data

(63) Continuation of application No. 16/237,875, filed on Jan. 2, 2019, now abandoned, which is a continuation of application No. 15/216,231, filed on Jul. 21, 2016, now abandoned, which is a continuation of application No. 14/704,333, filed on May 5, 2015, now abandoned, which is a continuation of application No. 14/075,919, filed on Nov. 8, 2013, now abandoned, which is a continuation of application No. 12/809,969, filed as application No. PCT/JP2008/004025 on Dec. 26, 2008, now abandoned.

(30) Foreign Application Priority Data

Dec. 27, 2007 (JP) ................................ 2007-336518

(51) Int. Cl.

| | |
|---|---|
| ***C12N 15/113*** | (2010.01) |
| ***A61K 31/7105*** | (2006.01) |
| ***C12N 9/10*** | (2006.01) |
| ***C12Q 1/48*** | (2006.01) |
| ***G01N 33/50*** | (2006.01) |

(52) U.S. Cl.

CPC ...... *C12N 15/1137* (2013.01); *A61K 31/7105* (2013.01); *C12N 9/13* (2013.01); *C12Q 1/48* (2013.01); *C12Q 1/485* (2013.01); *G01N 33/5023* (2013.01); *C12N 2310/14* (2013.01); *G01N 2333/91194* (2013.01); *Y10T 436/143333* (2015.01)

(58) Field of Classification Search

None

See application file for complete search history.

(56) References Cited

U.S. PATENT DOCUMENTS

| | | |
|---|---|---|
| 10,689,650 B2 | 6/2020 | Yoneyama et al. |
| 2006/0069070 A1 | 3/2006 | Fiorucci et al. |
| 2006/0128659 A1 | 6/2006 | Habuchi et al. |
| 2009/0060892 A1 | 3/2009 | Yoneyama |
| 2009/0202514 A1 | 8/2009 | Yoneyama et al. |
| 2009/0202515 A1 | 8/2009 | Yoneyama et al. |
| 2009/0202517 A1 | 8/2009 | Yoneyama et al. |
| 2010/0329993 A1 | 12/2010 | Yoneyama |

FOREIGN PATENT DOCUMENTS

| | | |
|---|---|---|
| EP | 0 821 066 | 1/1998 |
| EP | 1 839 671 | 3/2007 |
| EP | 1941906 | 9/2008 |
| JP | 2004-504262 | 2/2004 |
| WO | WO 98/46258 | 10/1998 |
| WO | WO 01/39795 | 6/2001 |
| WO | WO 03/098184 | 11/2003 |
| WO | WP 2007/049424 | 5/2007 |
| WO | WO 2008/020489 A1 | 2/2008 |
| WO | WO 2008/023446 A1 | 2/2008 |
| WO | WO 2008/029493 | 3/2008 |
| WO | WO 2008/029868 | 3/2008 |

OTHER PUBLICATIONS

U.S. Appl. No. 16/237,875, filed Jan. 2, 2019, US-2019-0330637 A1, Yoneyama et al.

Bhattacharyya et al., "Increased arylsulfatase B Activity in cystic fibrosis cells following correction of CFTR" Clin. Chim. Acta. (May 1, 2007) 380(1-2):122-7; Epub Feb. 1, 2007.

Bishop et al., "Heparan sulphate proteoglycans fine-tune mammalian physiology" Nature (Apr. 26, 2007) 446 (7139):1030-7.

Galonic et al., "Chemical glycosylation in the synthesis of glycoconjugate antitumour vaccines" Nature (Apr. 26, 2007) 446(7139):1000-7.

Grunwell et al., "Carbohydrate Sulfotransferases of the BalNAc/Gal/GlcNAc6ST Family" Biochemistry (Nov. 5, 2002) 41(44):13117-26.

Habuchi, Osami "Diversity and functions of glycosaminoglycan sulfotransferases" Biochim. Biophys. Acta (Apr. 6, 2000): 1474(2):115-27.

Hart et al., "Cycling of O-linked-beta-N-acetylglucosamine on nucleocytoplasmic proteins" Nature (Apr. 26, 2007) 446(7139):1017-22.

Hemmerich et al., "Strategies for drug discovery by targeting sulfation pathways" Drug Discov. Today (Nov. 15, 2004) 9(22):967-75.

(Continued)

*Primary Examiner* — Christopher M Babic

*Assistant Examiner* — Kimberly A Aron

(74) *Attorney, Agent, or Firm* — Oblon, McClelland, Maier & Neustadt, L.L.P.

(57) ABSTRACT

As a result of dedicated studies, the present inventors succeeded in discovering, for the first time, that fibrogenesis could be suppressed at the physiological tissue level by inhibiting sulfation at position 4 or 6 of GalNAc, which is a sugar that constitutes sugar chains. Furthermore, the present inventors conducted studies using various disease model animals, and as a result, successfully demonstrated that inhibitors of sulfation at position 4 or 6 of GalNAc had therapeutic effects on diseases caused by tissue fibrogenesis (tissue fibrogenic disorders).

13 Claims, 78 Drawing Sheets

Specification includes a Sequence Listing.

(56) References Cited

OTHER PUBLICATIONS

Honke et al. "Sulfotransferases and SUifated Oligosaccharides" Med. Res. Rev. (Nov. 2002) 22(6):637-54.
Kai et al., "Treatment with chondroitinase ABC alleviates bleomycin-induced pulmonary fibrosis" Med. Mol. Morphol. (Sep. 2007) 40(3):128-40; Epub Sep. 18, 2007.
Kusche-Gullberg et al. "Sulfotransferases in glycosaminoglycan biosynthesis" Curr. Opin. Struct. Biol. (Oct. 2003) 13(5):605-11.
Mikami et al., "Specificities of Three Distinct Human Chondroitin/Dermatan N-Acetylgalactosamine 4-O-Sulfotransferases Demonstrated Using Partially Desulfated Dermatan Sulfate as an Acceptor" J. Biol. Chem. (Sep. 19, 2003) 278(38):36115-27; Epub Jul. 7, 2003.
Scanlan et al., "Exploiting the defensive sugars of HIV-1 for drug and vaccine design" Nature {Apr. 26, 2007) 446 (7139):1038-45.
Seeberger et al., "Synthesis and medical applications of oligosaccharides" Nature (Apr. 26, 2007) 446 (7139):1046-51.
Thibodeaux et al., "Unusual sugar biosynthesis and natural product glycodiversification" Nature (Apr. 26, 2007) 446 (7139):1008-16.
Varki, Ajit, "Glycan-based interactions involving vertebrate sialic-acid-recognizing proteins" Nature (Apr. 26, 2007) 446(7139): 1023-9.
English Translation of the International Preliminary Report on Patnetability for PCT/JP2008/004025 mailed Jul. 29, 2010 (to which the present application claims priority).
U.S. Appl. No. 14/415,515, filed Jul. 17, 2012 {submitted in the USPTO Jan. 16, 2015) entitled "Mucosal Healing Promoter". Inventors: Yoneyama, Hiroyuki and Masato, Fujii. To Be Assigned to Stelic Institute & Co.
Hinz, Boris et al., Biological Perspectives, The Myofibroblast One Function, Multiple Origins, The American Journal of Pathology, Jun. 2007, vol. 170, No. 6, American Society for Investigative Pathology.
Gao et al., "The Base and Clinic of Fibrosis Disease" Shanghai Science and Technology Press, 2004, p. 1.
Ye et al., "The Contemporary Therapeutics of Hepatic and Gall Diseases" Sichuan Science and Technology Press, 2000, p. 320.
U.S. Appl. No. 15/236,969, filed Aug. 15, 2016 and entitled "Mucosal Healing Promoter".
Daniel C. Baumgart, et al., "Inflammatory Bowel Disease: Clinical Aspects and Established and Evolving Therapies" The Lancet, vol. 369, No. 9573, May 12, 2007, pp. 1641-1657.
Christopher G. De Vry, et al., "Inflammatory Bowel Disease: Non-Viral Delivery of Nuclear Factor-kB Decoy Ameliorates Murine Inflammatory Bowel Disease and Restores Tissue Homeostasis" Gut, vol. 56, No. 4, 2007, pp. 524-533.
Pucilowska et al. Fibrogenesis. IV. Fibrosis and Inflammatory Bowel Disease: Cellular Mediators and Animal Models. American Journal of Physiology, Gastrointestinal and Liver Physiology, 2000. 279:G653-G659.
Rogliani et al. HRCT and Histopathological Evaluation of Fibrosis and Tissue Destruction in IPF Associated with Pulmonary Emphysema. Respiratory Medicine, 2008. 102:1753-1761, available online Aug. 23, 2008.

Day 0 (NORMAL)  Day 7: CONTROL  Day7: siRNA

Day 7: CONTROL

Day7: siRNA

Day 7: CONTROL

Day7: siRNA

GalNAcST siRNA (×100)

UNTREATED (×100)

GalNAc 4S-6ST siRNA

UNTREATED

NORMAL

SUGAR CHAIN-RELATED GENE AND USE THEREOF

CROSS-REFERENCE TO RELATED APPLICATIONS

The present application is a continuation of U.S. application Ser. No. 16/237,875, filed Jan. 2, 2019, which is a continuation of U.S. application Ser. No. 15/216,231, filed Jul. 21, 2016, which is a continuation of U.S. application Ser. No. 14/704,333, filed May 5, 2015, which is a continuation of U.S. application Ser. No. 14/075,919, filed Nov. 8, 2013, which is a continuation of U.S. application Ser. No. 12/809,969, filed Sep. 1, 2010, which is a 35 U.S.C. § 371 national stage patent application of International Application No. PCT/JP2008/004025, filed Dec. 26, 2008. The entire contents of all of the above applications are incorporated herein by reference.

REFERENCE TO A SEQUENCE LISTING

In accordance with 37 CFR § 1.52(e)(5), the present specification makes reference to a Sequence Listing (submitted electronically as a .txt file named "543107USSQ.txt"). The .txt file was generated on May 11, 2022 and is 141,479 bytes in size. The entire contents of the Sequence Listing are herein incorporated by reference.

TECHNICAL FIELD

The present invention relates to inhibitors of fibrogenesis at the physiological tissue level by inhibiting sugar chain-related genes.

BACKGROUND ART

Intensive studies have been conducted on nucleic acids and proteins, revealing many findings. However, these studies also showed that there are only about 22,000 human genes and also that post-translational modification of proteins plays an important role in vivo. They also suggested limitations of conventional study approaches. In recent years, the importance of sugar chains has been rediscovered with the post-genome and post-proteomics trends (the journal "Nature" extensively featured sugar chains in Vol. 446 published in Apr. 26, 2007 (Non-patent Documents 1 to 7). Sugar chains have not been analyzed intensively because of the difficulty to perform structural analysis, etc. Although they are assumed to be involved in cancer, inflammation, immunity, viral infection, etc., at present, little is known about their roles and such, and therefore, elucidation is being awaited.

There are various known sugars (monosaccharides) that constitute sugar chains. Such known sugars include, for example, glucose (Glc), galactose (Gal), mannose (Man), glucuronic acid (GlcUA), iduronic acid (IdoA), fucose (Fuc), glucosamine (GlcN), N-acetylglucosamine (GlcNAc), N-acetylgalactosamine (GalNAc), xylose (Xyl), and sialic acid (SA).

Furthermore, it has been reported that sugars constituting sugar chains are subject to a variety of chemical modifications. Such chemical modifications include, for example, methylation, acetylation, formylation, myristoylation, amidation, ubiquitination, acylation, phosphorylation, epimerization, and sulfation. Examples of chemical modifications also include sialylation, asialylation, fucosylation, glycosylation, galactosylation, lactosylation, and mannosylation.

Sugars have a number of sites for such chemical modifications. For example, it is known that GlcNAc can be chemically-modified in any of carbons at positions 1 to 6. It is reported that other sugars are also chemically-modified at various sites.

[Non-patent Document 1] Danica P. Galonic and David Y. Gin, Nature 446: 1000-1007 (2007)

[Non-patent Document 2] Christopher J. Thibodeaux et al., Nature 446: 1008-1016 (2007)

[Non-patent Document 3] Gerald W. Hart et al., Nature 446: 1017-1022 (2007)

[Non-patent Document 4] Ajit Varki, Nature 446: 1023-1029 (2007)

[Non-patent Document 5] Joseph R. Bishop et al., Nature 446: 1030-1037 (2007)

[Non-patent Document 6] Christopher N. et al., Nature 446: 1038-1045 (2007)

[Non-patent Document 7] Peter H. Seeberger and Daniel B. Werz, Nature 446: 1046-1051 (2007)

DISCLOSURE OF THE INVENTION

Problems to be Solved by the Invention

The present invention is based on a new finding obtained through studies on sugar chain-related genes. An objective of the present invention is to provide novel uses of sugar chain-related genes. Specifically, the objective is to provide agents that suppress fibrogenesis at the physiological tissue level by inhibiting the function of sugar chain-related genes, and methods of screening for the agents.

Means for Solving the Problems

Sugar chains have been suggested to play a very important role in vivo. However, little is known about the in vivo functions of sugar chains.

As described above, several types of sugars constituting sugar chains are known. Sugars are variously chemically-modified at multiple sites, and such modifications are considered to assume important physiological effects in vivo.

As described above, there are various types of sugars that constitute sugar chains, many types of chemical modifications that target sugars, and many chemical modification sites in the sugars. This suggests that possible sugar chain variations are innumerable. Thus, it is very difficult to determine a sugar chain structure that plays a certain role, and it is also extremely difficult to reveal the relationship between a pathological condition caused by a disease and a specific action of a sugar chain.

The present inventors conducted dedicated studies, and as a result succeeded for the first time in discovering that tissue fibrogenesis can be suppressed at the physiological level by inhibiting sulfation at position 4 or 6 of GalNAc, a sugar that constitutes sugar chains. Furthermore, by studies using various animal disease models, the present inventors demonstrated that inhibitors of sulfation at position 4 or 6 of GalNAc produce therapeutic effects against diseases caused by tissue fibrogenesis (tissue fibrogenic disorders).

The present invention relates to agents that suppress fibrogenesis at the physiological tissue level by inhibiting the functions of sugar chain-related genes, and methods of screening for the agents. Specifically, the present invention provides:

[1] a tissue fibrogenesis suppressing-agent, which comprises as an ingredient an inhibitor of sulfation at position 4 or 6 of N-acetylgalactosamine;

[2] the agent of [1], which has an effect of suppressing fibrogenesis of a physiological tissue;

[3] the agent of [1] or [2], wherein the inhibitor has the activity of inhibiting the function of a sulfotransferase that transfers a sulfate to position 4 or 6 of N-acetylgalactosamine;

[4] the agent of [3], wherein the inhibitor is an siRNA that suppresses the expression of the sulfotransferase that transfers a sulfate to position 4 or 6 of N-acetylgalactosamine;

[5] the agent of [1] or [2], wherein the inhibitor is a desulfating enzyme that desulfates at position 4 or 6 of N-acetylgalactosamine;

[6] the agent of any one of [1] to [5] for treating or preventing a fibrogenic disorder;

[7] a method of screening for a tissue fibrogenesis suppressing-agent, which comprises the step of selecting a compound that inhibits sulfation at position 4 or 6 of N-acetylgalactosamine that constitutes a sugar chain;

[8] a method of screening for a tissue fibrogenesis suppressing-agent, which comprises the steps of (a) contacting a test compound with N-acetylgalactosamine or a sugar chain comprising N-acetylgalactosamine;

(b) determining the degree of sulfation at position 4 or 6 of N-acetylgalactosamine; and (c) selecting a compound that reduces the degree of sulfation as compared to when the test compound is not contacted;

[9] a method of screening for a tissue fibrogenesis suppressing-agent, which comprises the steps of:

(a) contacting a test compound with a sulfotransferase that transfers a sulfate to position 4 or 6 of N-acetylgalactosamine;

(b) determining the sulfotransferase activity of the enzyme; and (c) selecting a compound that reduces the activity as compared to when the test compound is not contacted;

[10] a method of screening for a tissue fibrogenesis suppressing-agent, which comprises the steps of (a) contacting a test compound with a cell expressing a gene encoding a sulfotransferase that transfers a sulfate to position 4 or 6 of N-acetylgalactosamine;

(b) determining the expression level of the gene in the cell; and (c) selecting a compound that reduces the expression level of the gene as compared to when the test compound is not contacted;

[11] a method of screening for a tissue fibrogenesis suppressing-agent, which comprises the steps of (a) contacting a test compound with a cell or cell extract containing a DNA wherein a reporter gene is operably linked to the transcriptional regulatory region of the gene encoding a sulfotransferase that transfers a sulfate to position 4 or 6 of N-acetylgalactosamine;

(b) determining the expression level of the reporter gene; and (c) selecting a compound that reduces the expression level of the reporter gene as compared to when the test compound is not contacted; and

[12] a method of producing a pharmaceutical composition for treating or preventing a fibrogenic disorder, which comprises the steps of:

(a) selecting a tissue fibrogenesis suppressing-agent from test compounds by the method of any one of claims 7 to 11; and (b) combining the agent with a pharmaceutically acceptable carrier.

The Present Invention Also Provides:

[13] a method of suppressing tissue fibrogenesis, which comprises the step of administering an inhibitor of sulfation at position 4 or 6 of N-acetylgalactosamine to an individual;

[14] use of an inhibitor of sulfation at position 4 or 6 of N-acetylgalactosamine in the manufacture of a tissue fibrogenesis suppressing-agent; and

[15] an inhibitor of sulfation at position 4 or 6 of N-acetylgalactosamine for use in suppressing tissue fibrogenesis.

GalNAc4S-6ST (G #1) siRNA significantly suppresses the increase of serum creatinine, i.e., suppresses decline of renal function.

Figure 37:
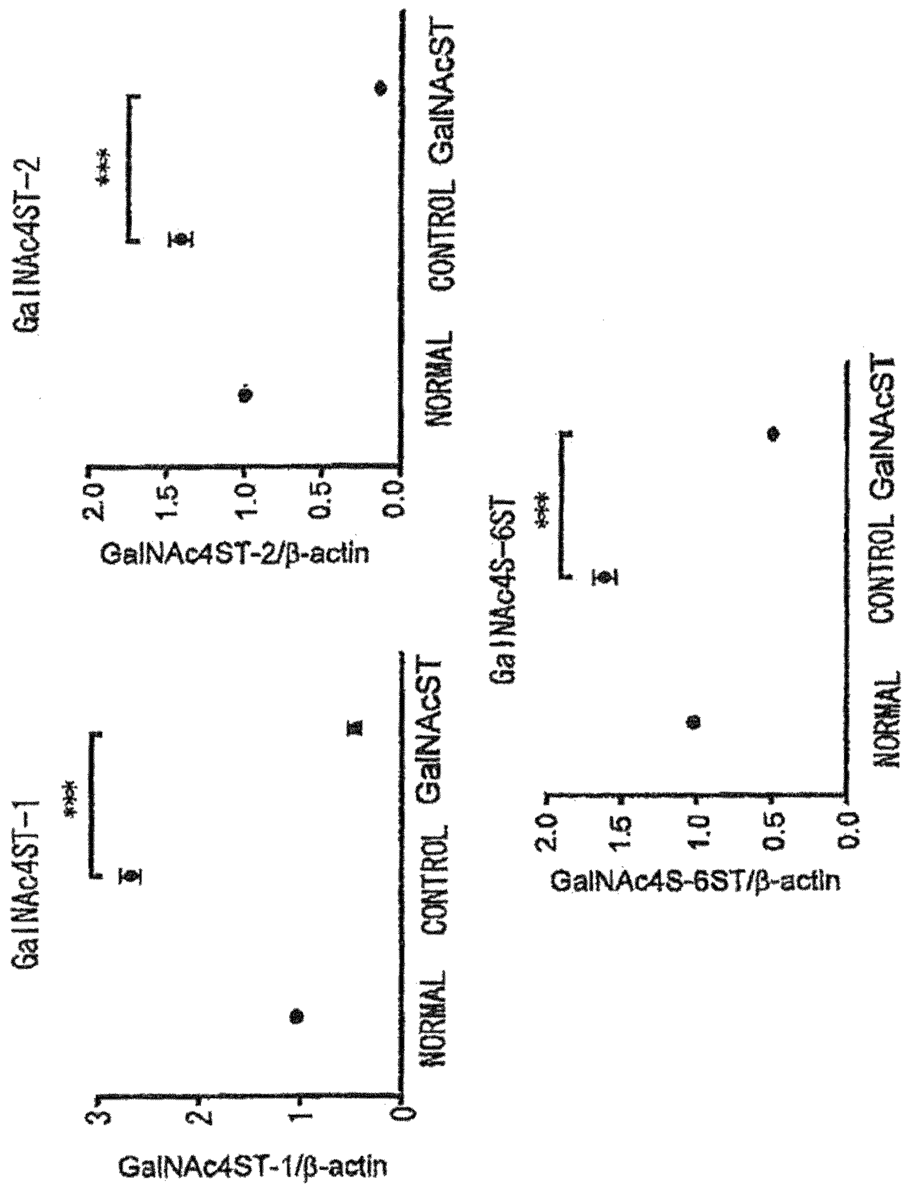

FIG. 37 depicts graphs showing gene expression in a mouse model for diabetic nephropathy. GalNAcST siRNA significantly suppresses the enhanced expression of GalNAc4ST-1, GalNAc4ST-2, and GalNAc4S-6ST in kidney tissues.

Figure 38:
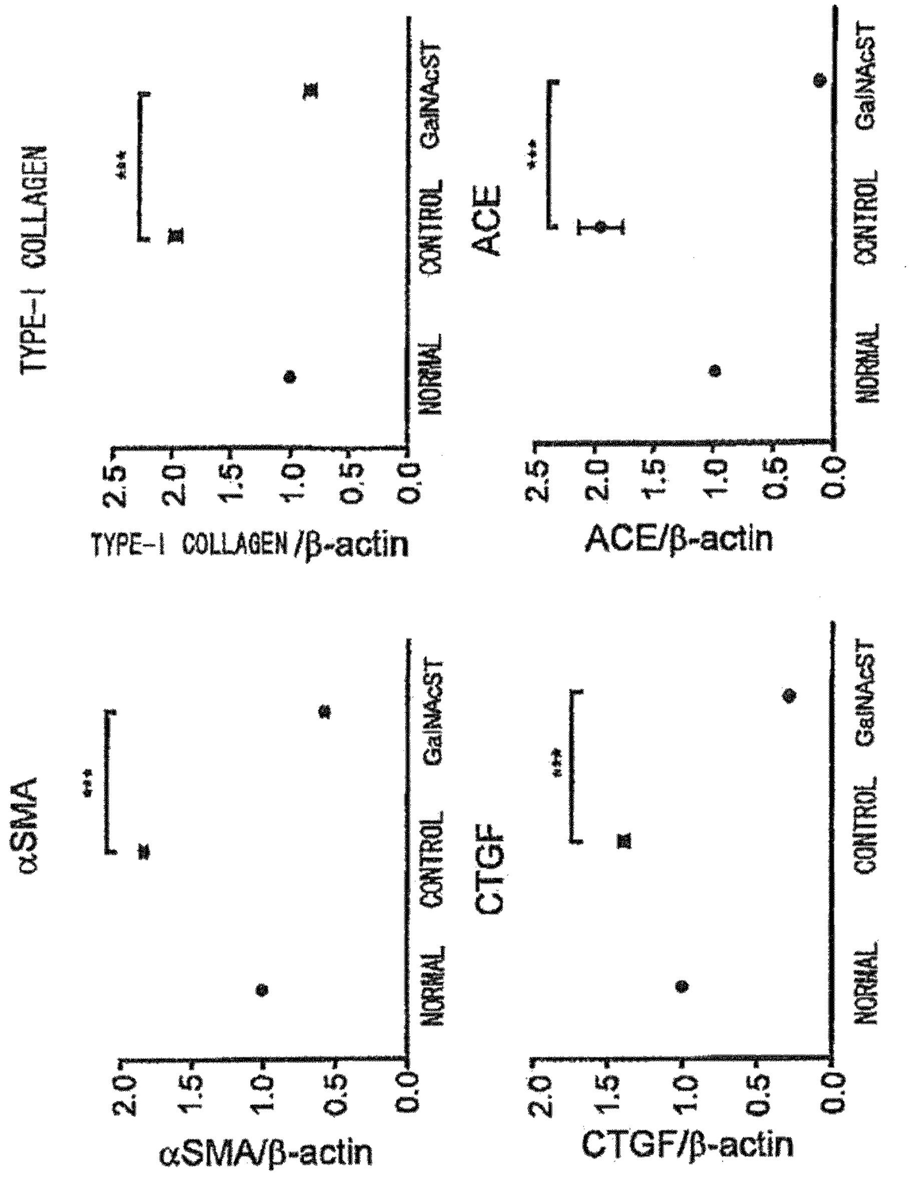

FIG. 38 depicts graphs showing an anti-fibrogenic effect in a mouse diabetic nephropathy model. GalNAcST siRNA significantly suppresses the enhanced expression of CTGF, αSMA, type I collagen, and ACE in kidney tissues.

Figure 39:
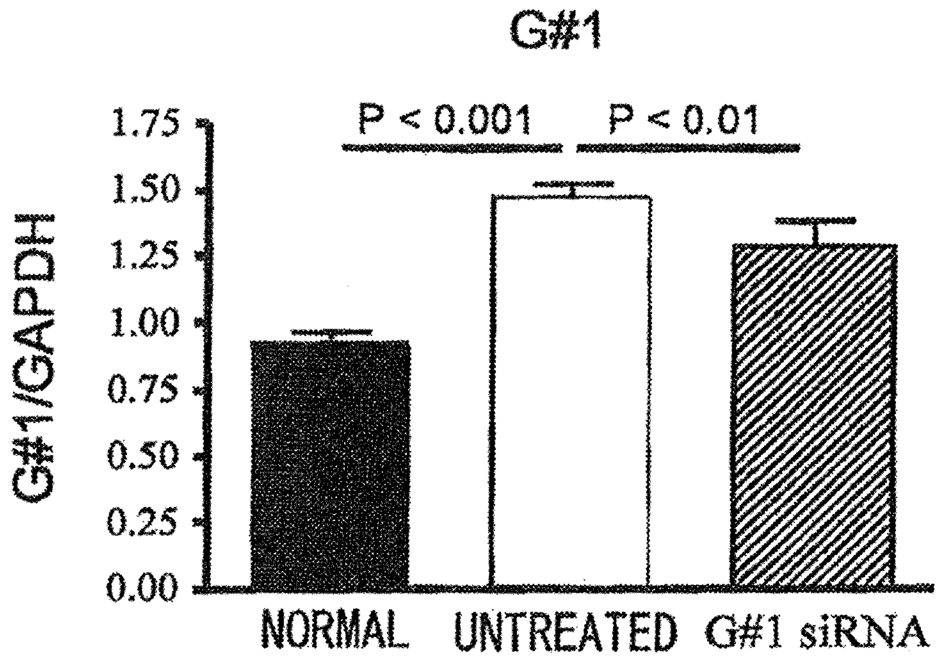

FIG. 39 depicts a graph showing gene expression in mice with drug-induced interstitial nephritis. GalNAc4S-6ST (G #1) siRNA significantly suppresses the enhanced expression of GalNAc4S-6ST (G #1) in kidney tissues.

Figure 40:
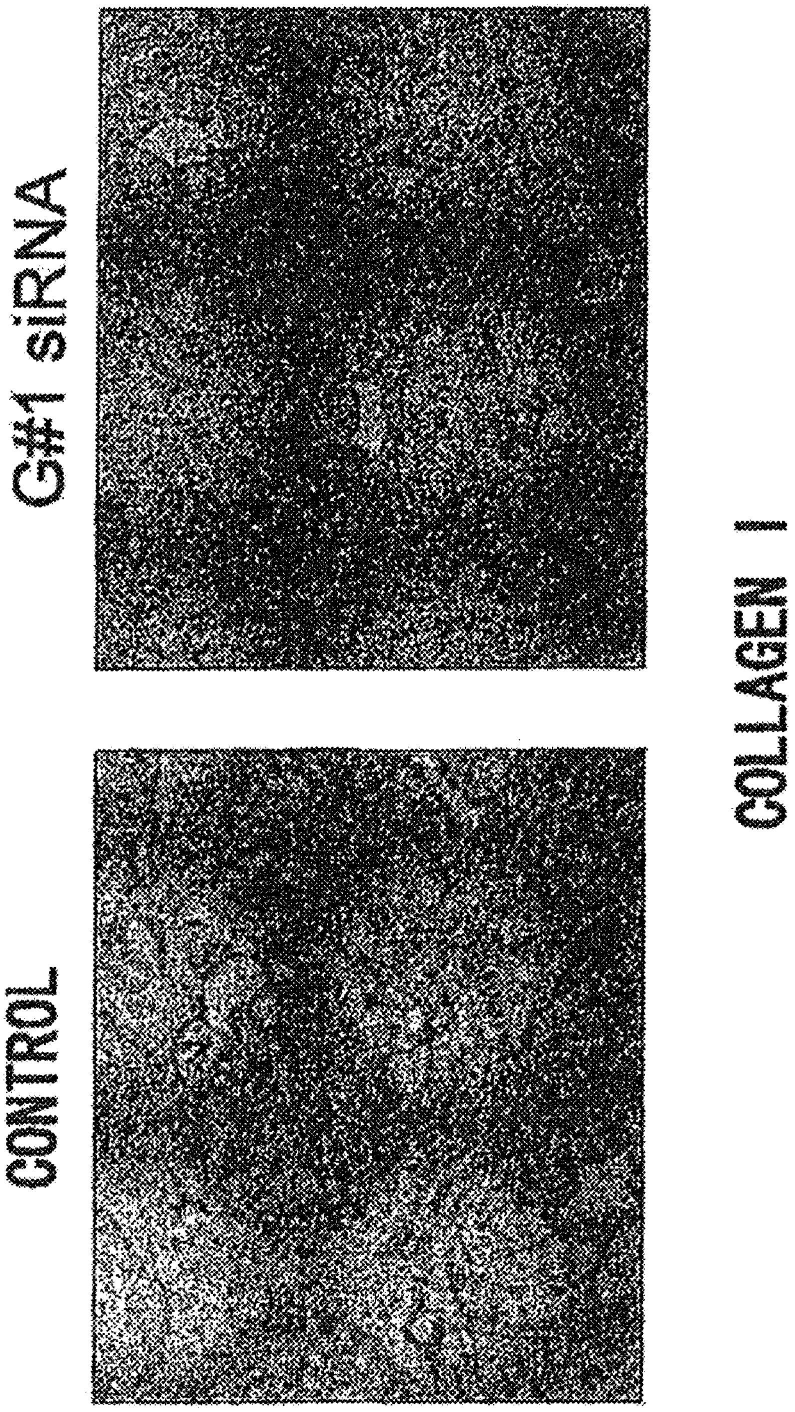

FIG. 40 depicts photographs showing collagen deposition in mice with drug-induced interstitial nephritis. GalNAc4S-6ST (G #1) siRNA significantly decreases the deposition of type I collagen in renal interstitium. Magnification: 200×.

Figure 41:
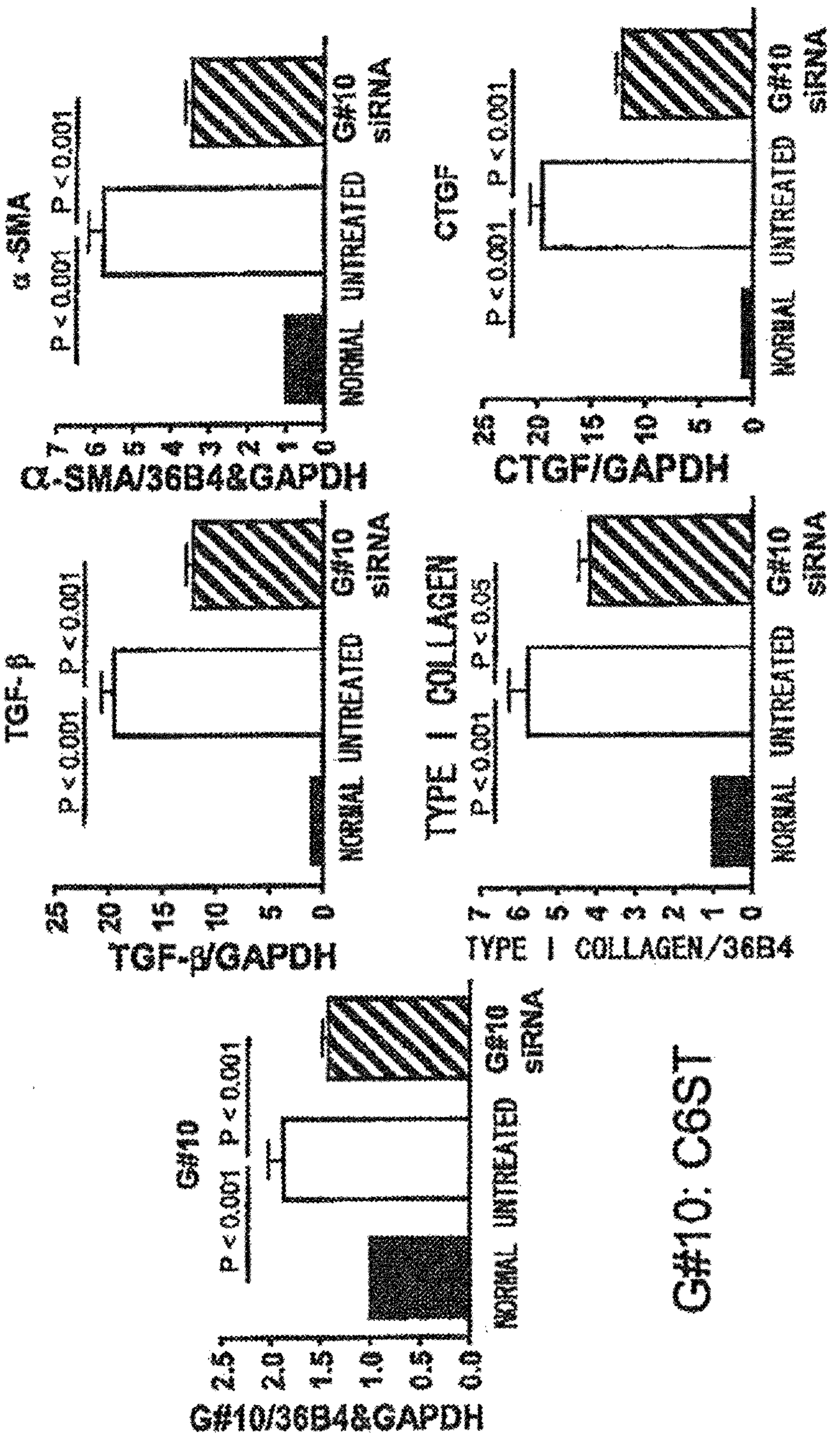

FIG. 41 depicts graphs showing an anti-fibrogenic effect in a mouse UUO fibrogenesis model. C6ST siRNA significantly suppresses the enhanced expression of C6ST-2 (G #10), TGFβ, αSMA, type I collagen, and CTGF in kidney tissues.

Figure 42:
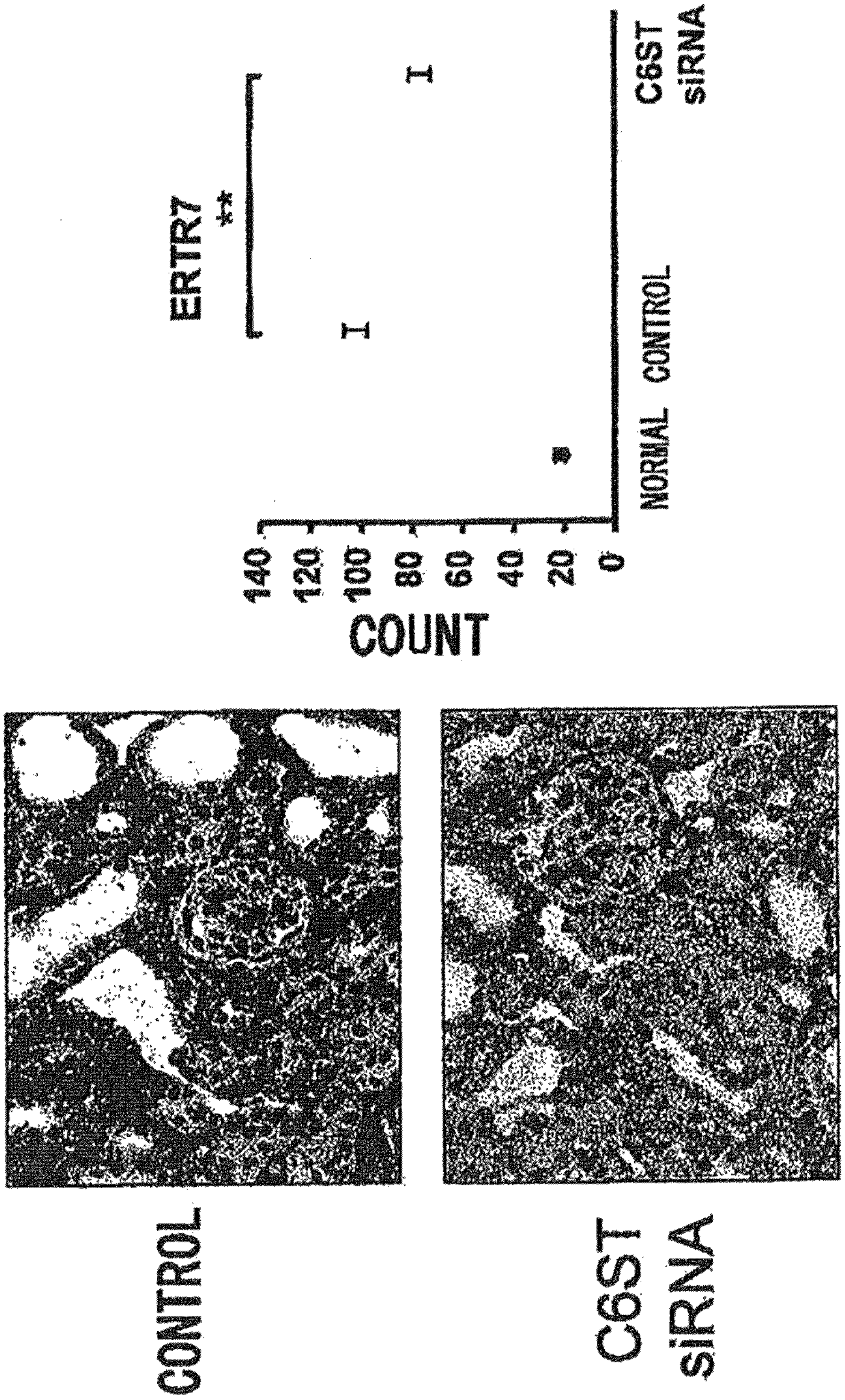

FIG. 42 depicts a graph and photographs showing fibroblast accumulation in the interstitium in a mouse UUO fibrogenesis model. C6ST siRNA significantly suppresses fibroblast accumulation in juxtaglomerular and interstitial area. Magnification: 200×.

Figure 43:
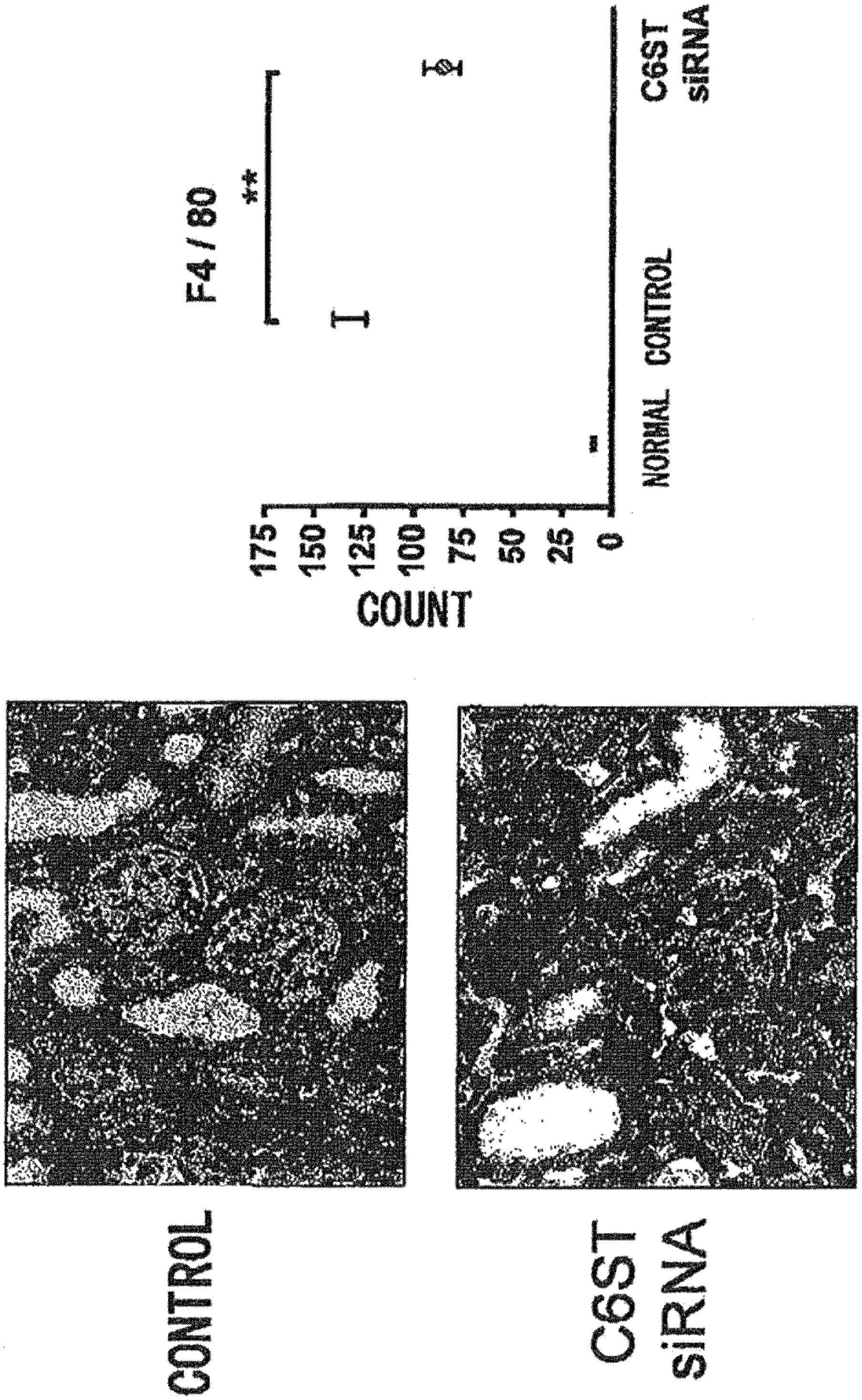

FIG. 43 depicts a graph and photographs showing macrophage accumulation in the interstitium in a mouse UUO fibrogenesis model. C6ST siRNA significantly suppresses the accumulation of macrophages in juxtaglomerular and interstitial area. Magnification: 200×.

Figure 44:
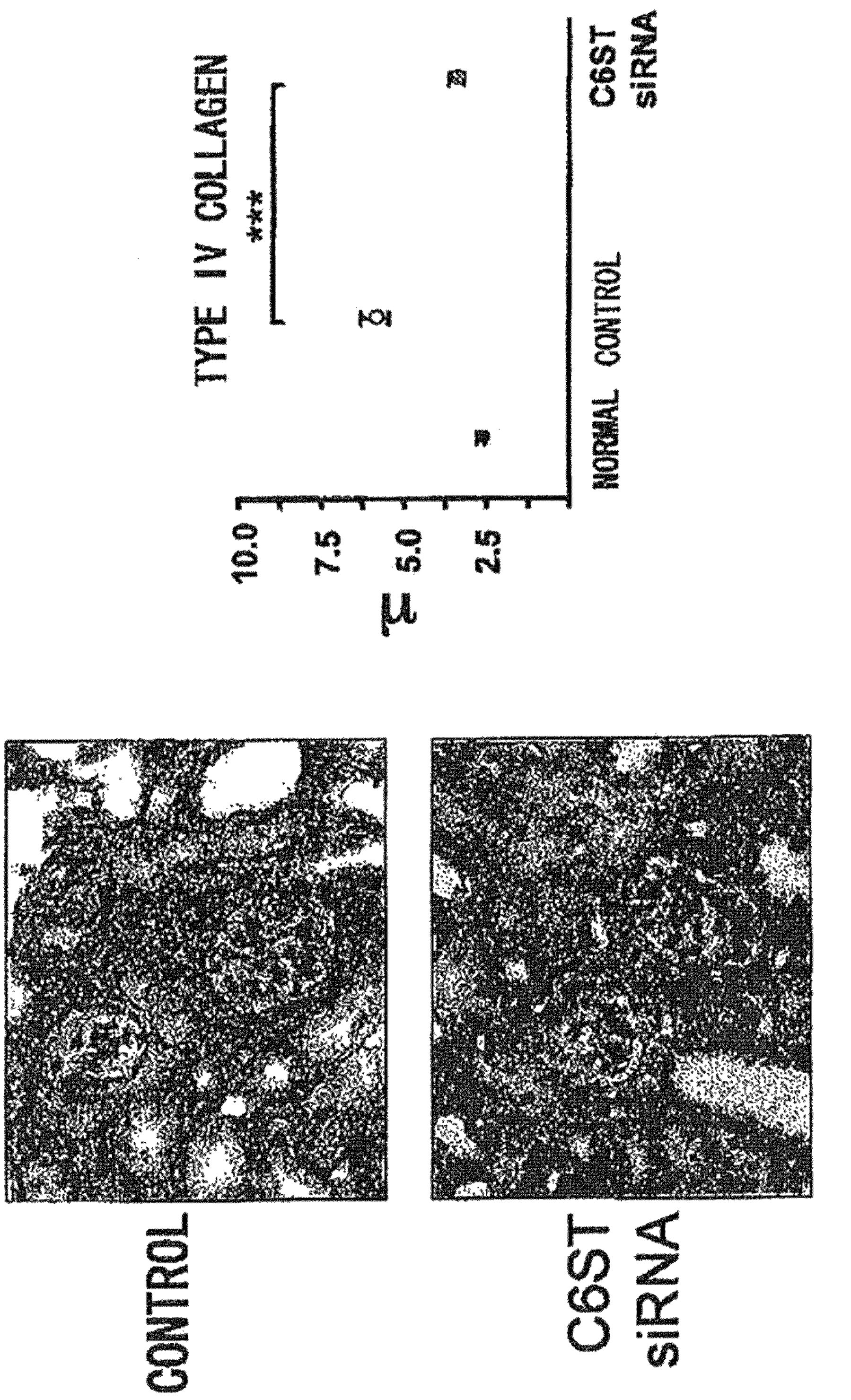

FIG. 44 depicts a graph and photographs showing collagen deposition in a mouse UUO fibrogenesis model. C6ST siRNA significantly suppresses the thickening of glomerular basement membrane, which can be confirmed by the positivity of type IV collagen. Magnification: 400×.

Figure 45:
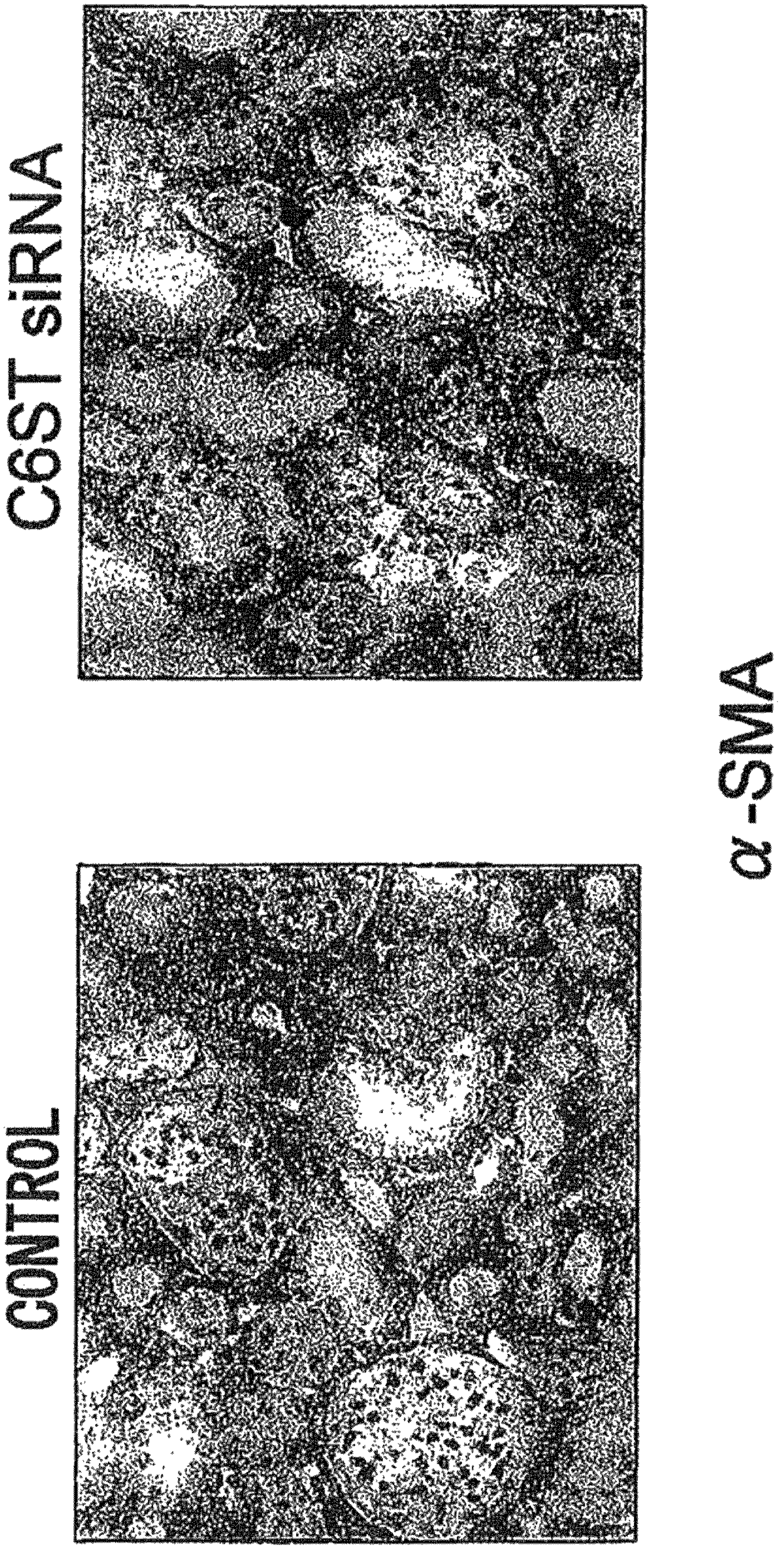

FIG. 45 depicts photographs showing the activation of fibroblasts accumulated in tissues in a mouse UUO fibrogenesis model. C6ST siRNA significantly suppresses the accumulation of αSMA-positive cells in juxtaglomerular and interstitial area. Magnification: 400×.

Figure 46:
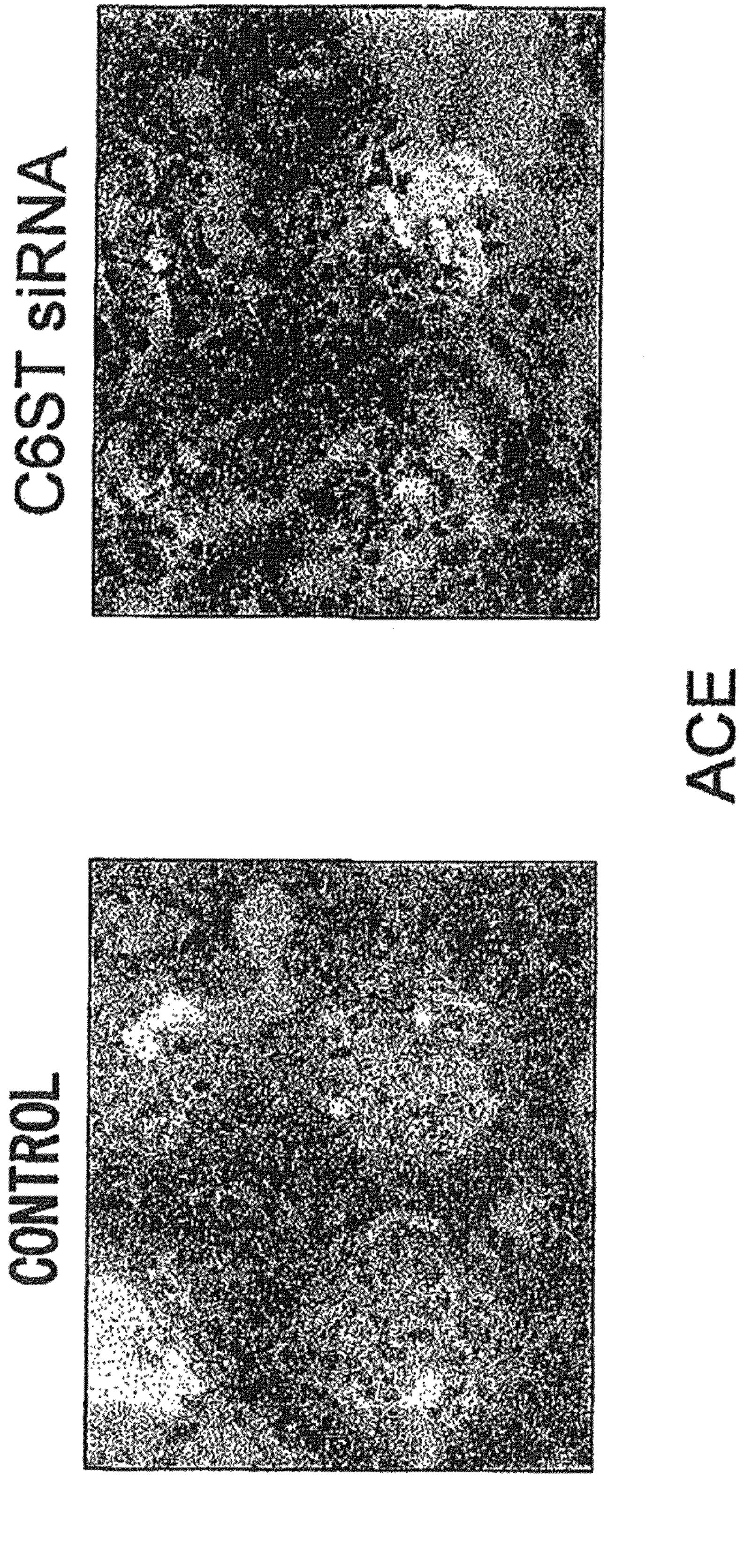

FIG. 46 depicts photographs showing the accumulation of ACE-producing cells in the interstitium in a mouse UUO fibrogenesis model. C6ST siRNA significantly suppresses the accumulation of ACE-producing cells in juxtaglomerular and interstitial area. Magnification: 400×.

Figure 47:
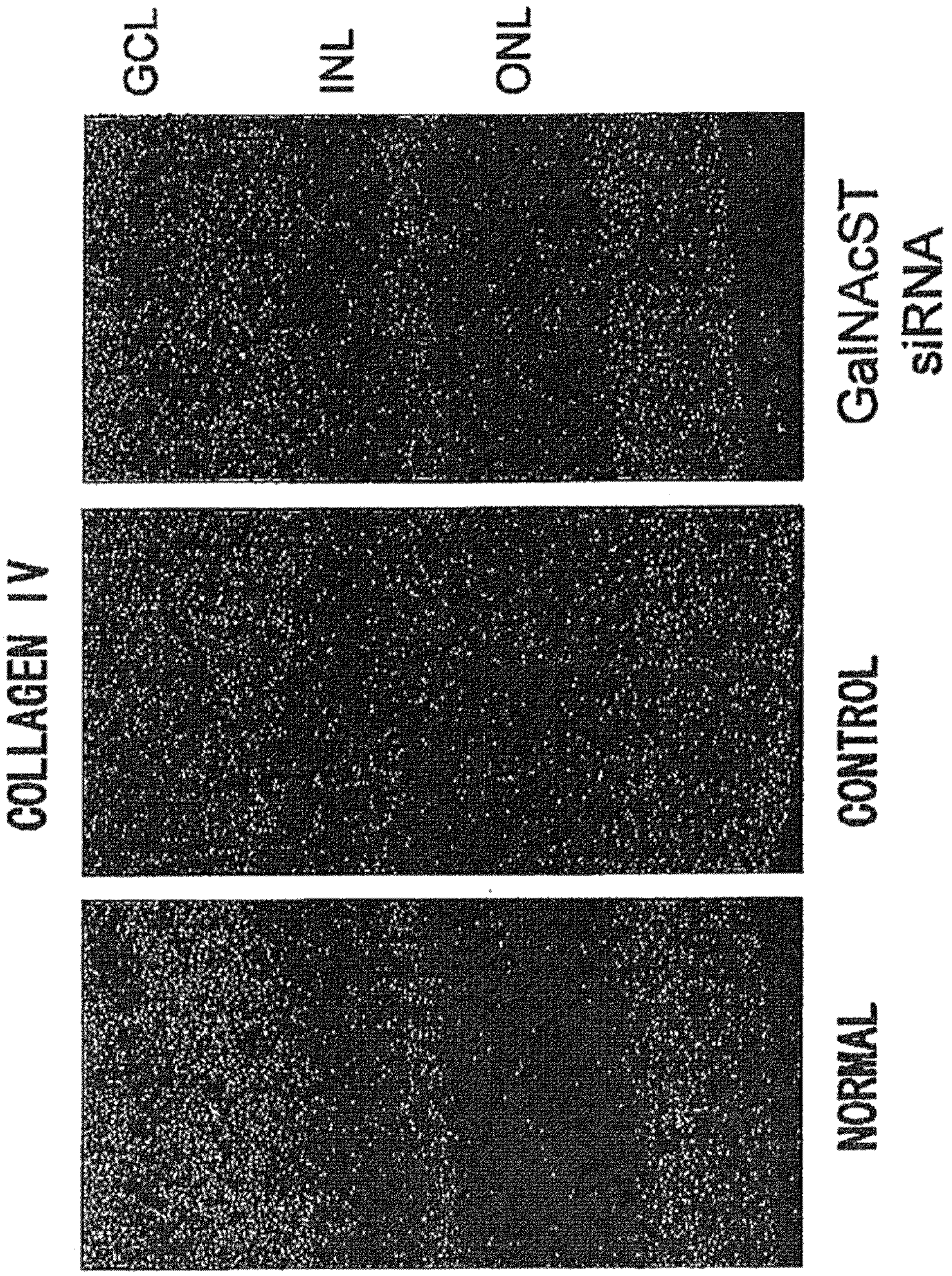

FIG. 47 depicts photographs showing the tissue accumulation of type IV collagen in a mouse diabetic retinopathy model. GalNac4S-6ST (G #1) siRNA significantly suppresses the accumulation of type IV collagen. Magnification: 200×. GCL, ganglion cell layer; INL, inner nuclear layer; ONL, external granular layer.

Figure 48:
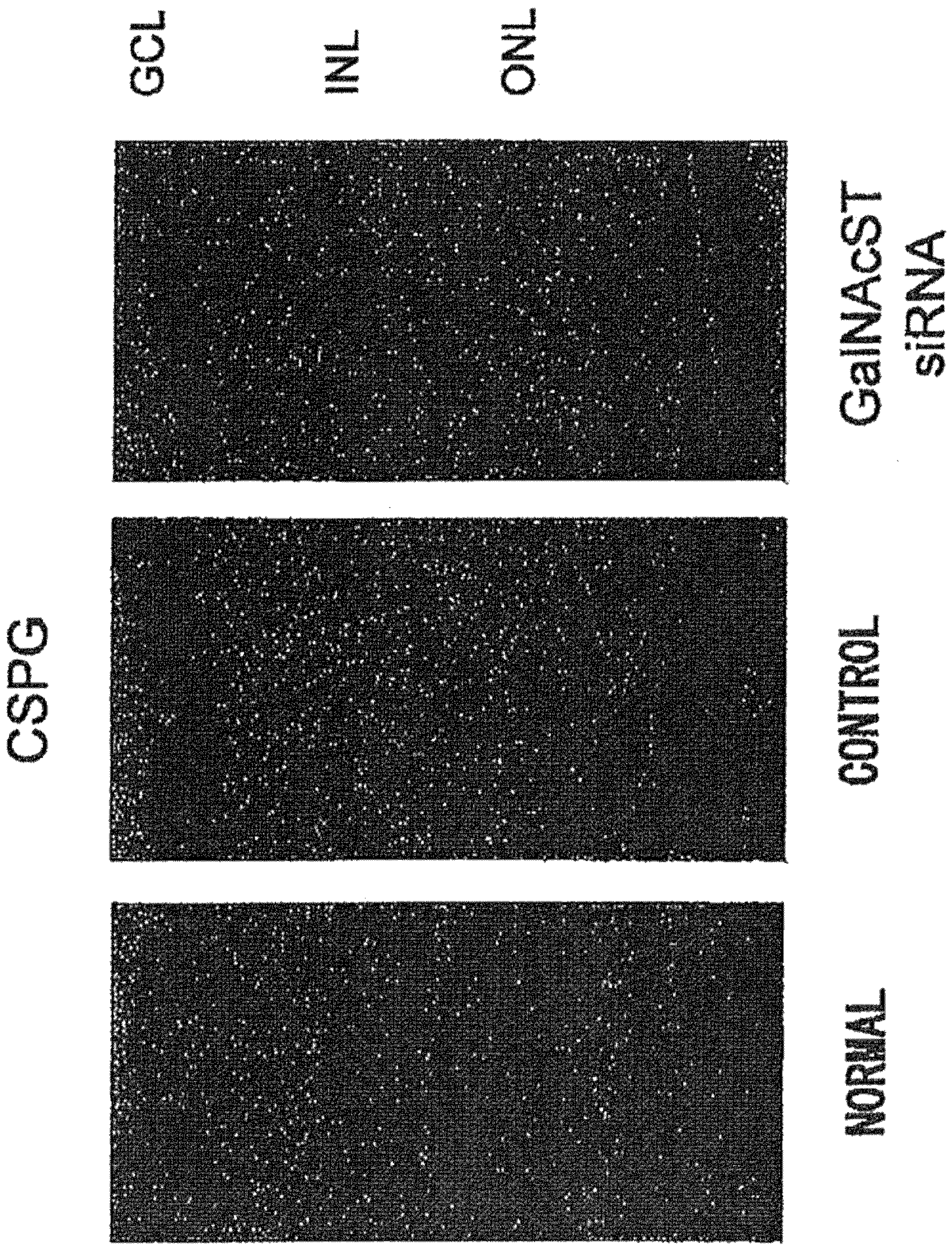

FIG. 48 depicts photographs showing the tissue accumulation of CSPG in a mouse diabetic retinopathy model. GalNac4S-6ST (G #1) siRNA significantly suppresses CSPG accumulation. In particular, the suppressing effect is prominent in GCL, ONL, and pigment epithelial cell layer. Magnification: 200×.

Figure 49:
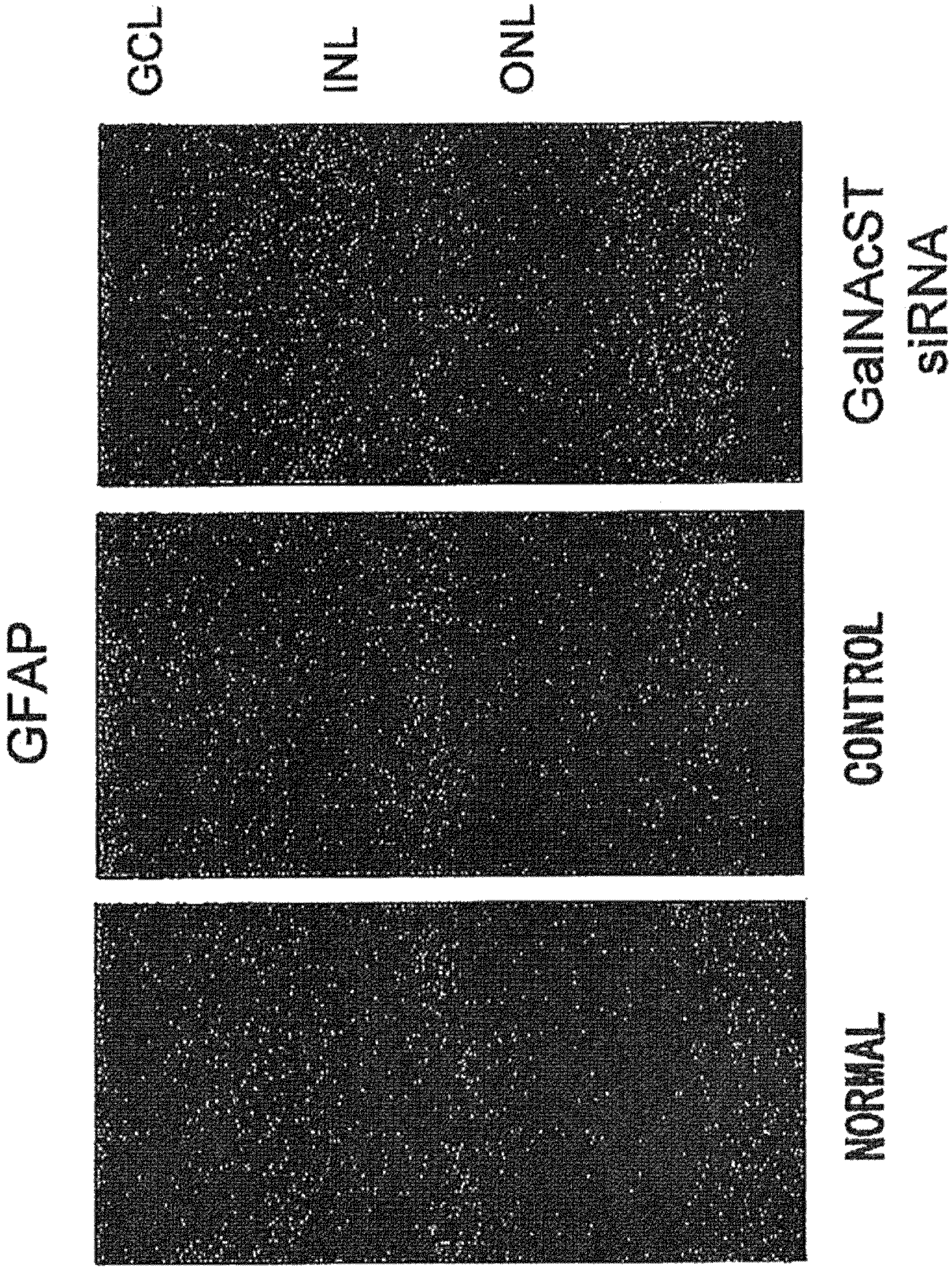

FIG. 49 depicts photographs showing GFAP-positive cells in a mouse diabetic retinopathy model. GalNac4S-6ST (G #1) siRNA significantly increases GFAP-positive cells in the region from INL to GCL. Magnification: 200×.

Figure 50:
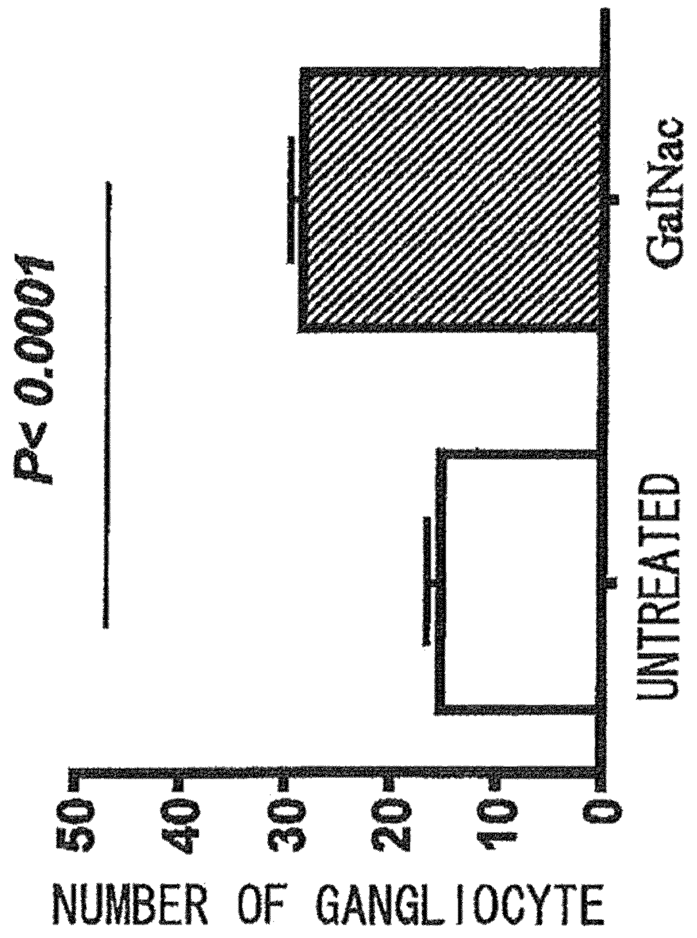

FIG. 50 depicts a graph showing the number of gangliocytes in a mouse diabetic retinopathy model. Counts show the number of gangliocytes in GGL. GalNac4S-6ST (G #1) siRNA significantly suppresses the reduction in gangliocyte number.

Figure 51:
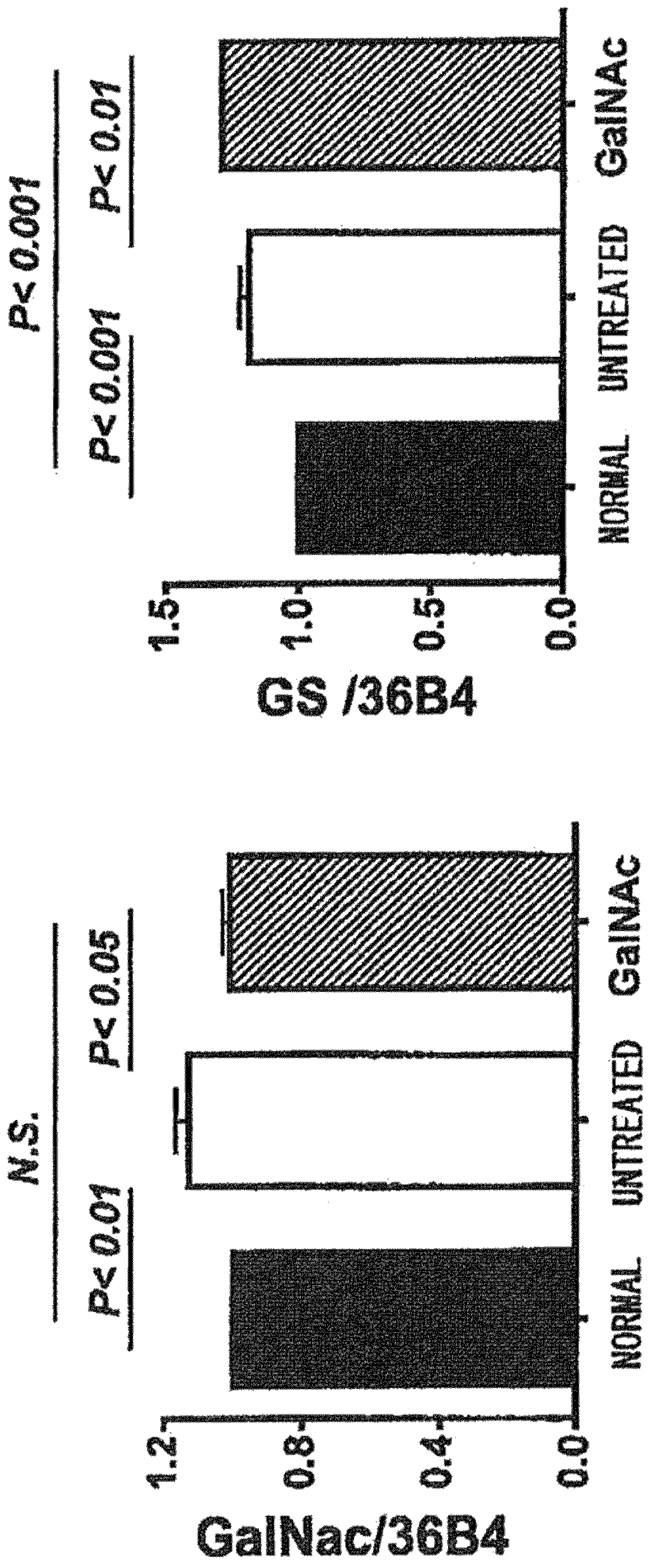

FIG. 51 depicts graphs showing the optic nerve regeneration effect in a mouse diabetic retinopathy model. GalNac4S-6ST (G #1) siRNA significantly increases the expression of GS in ocular tissues.

Figure 52:
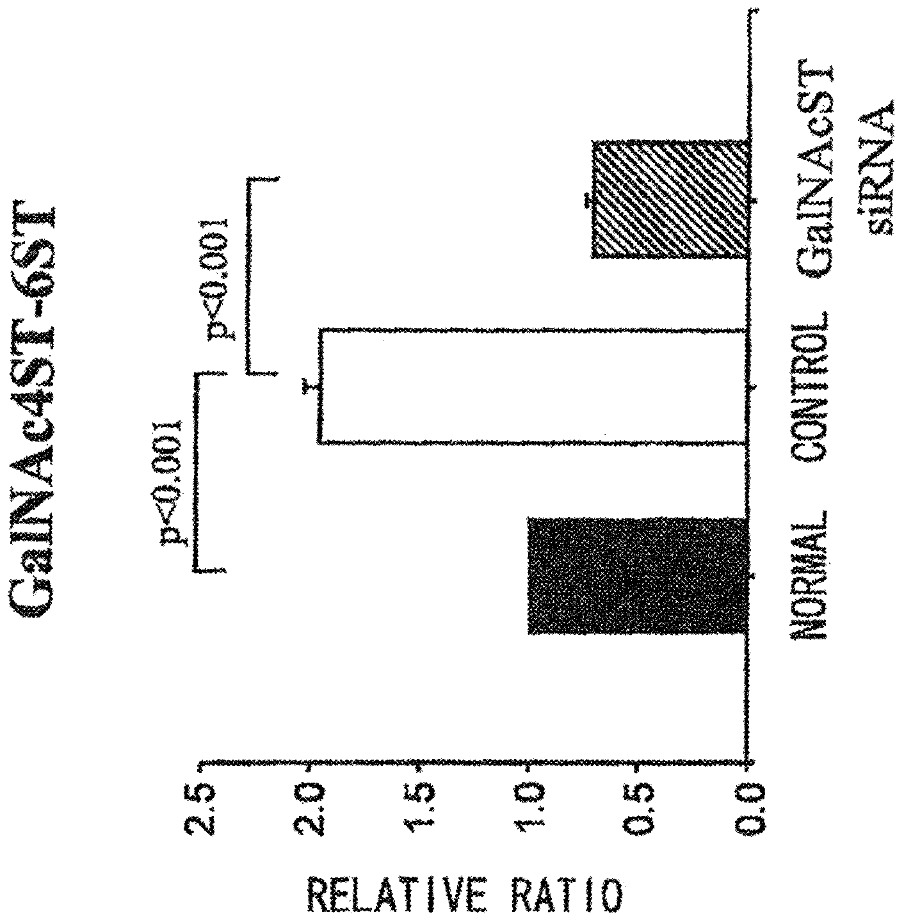

FIG. 52 depicts a graph showing gene expression in a mouse fatty liver injury model. The enhanced expression of GalNAc4S-6ST in liver tissues, and significant suppression of the expression by GalNAcST siRNA are shown.

Figure 53:
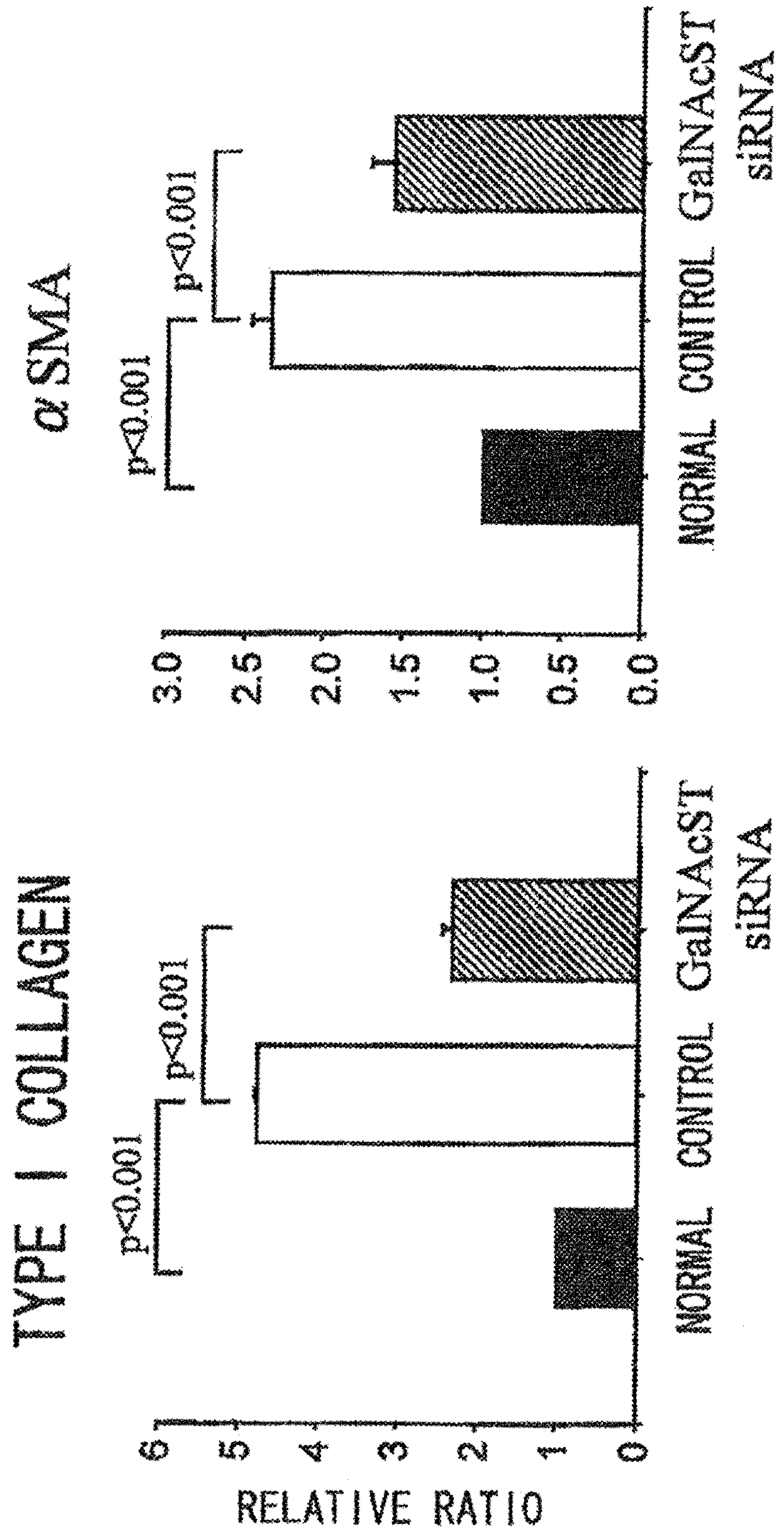

FIG. 53 depicts graphs showing the expression of fibrogenesis-related genes in a mouse fatty liver injury model. The enhanced expression of type I collagen and αSAM in liver tissues, and significant suppression of the expression by GalNAcST siRNA are shown.

Figure 54:
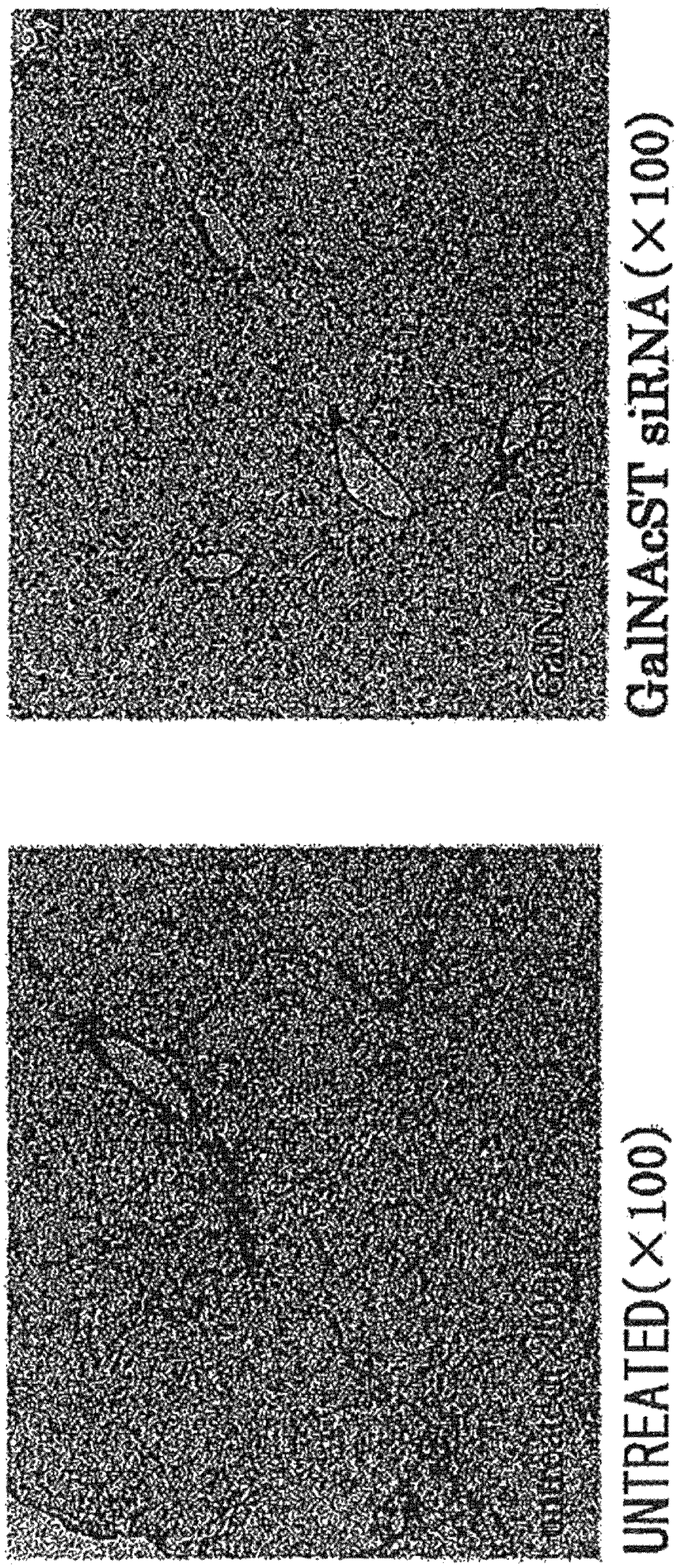

FIG. 54 depicts photographs showing the infiltration of fibrogenic cells in a mouse fatty liver injury model. GalNAcST siRNA suppresses the bridge-like accumulation of fibroblasts in liver tissues. Magnification: 100×.

Figure 55:
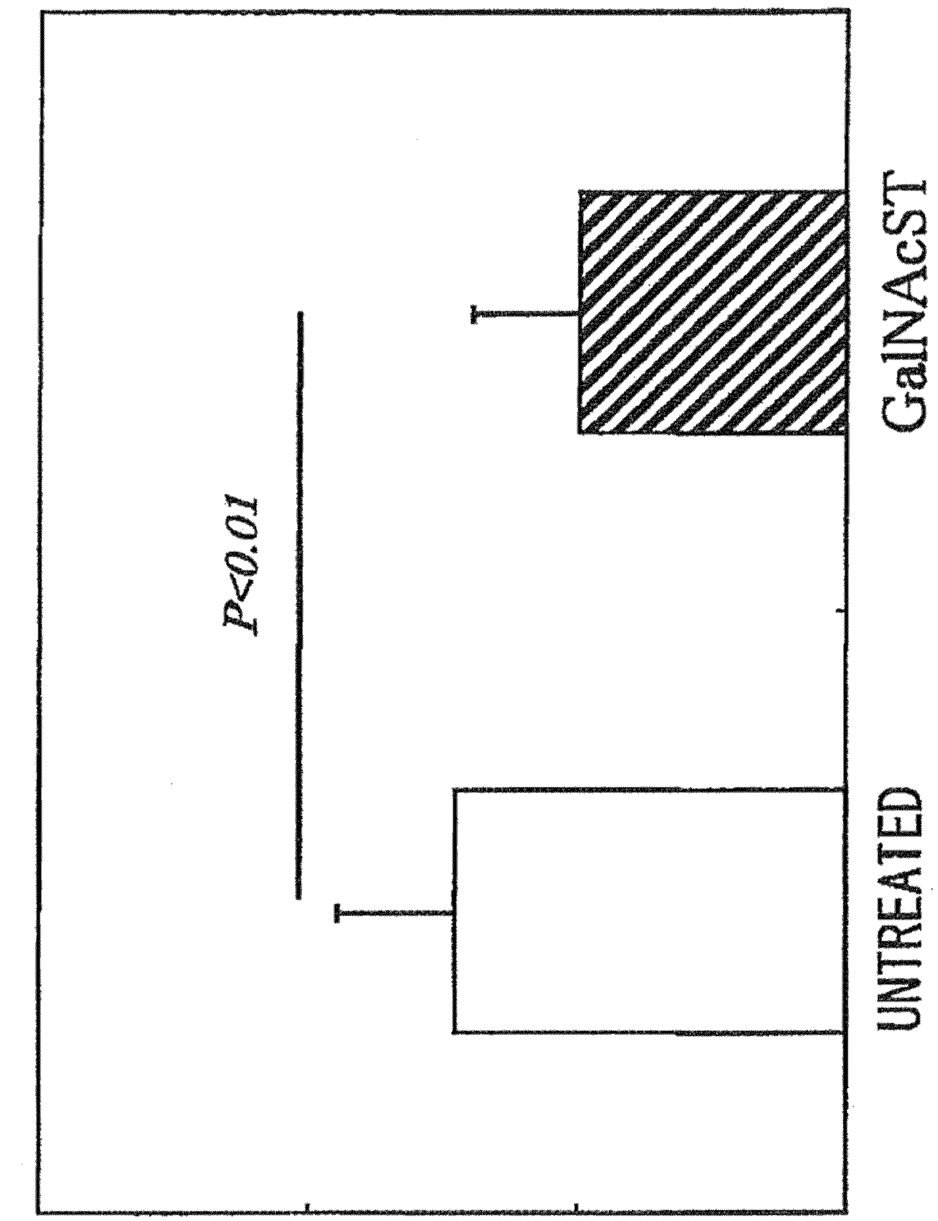

FIG. 55 depicts a graph showing clinical scores for fibrogenesis in a mouse fatty liver injury model. GalNAcST siRNA significantly suppresses the increase in the fibrogenesis score in liver tissues.

Figure 56:
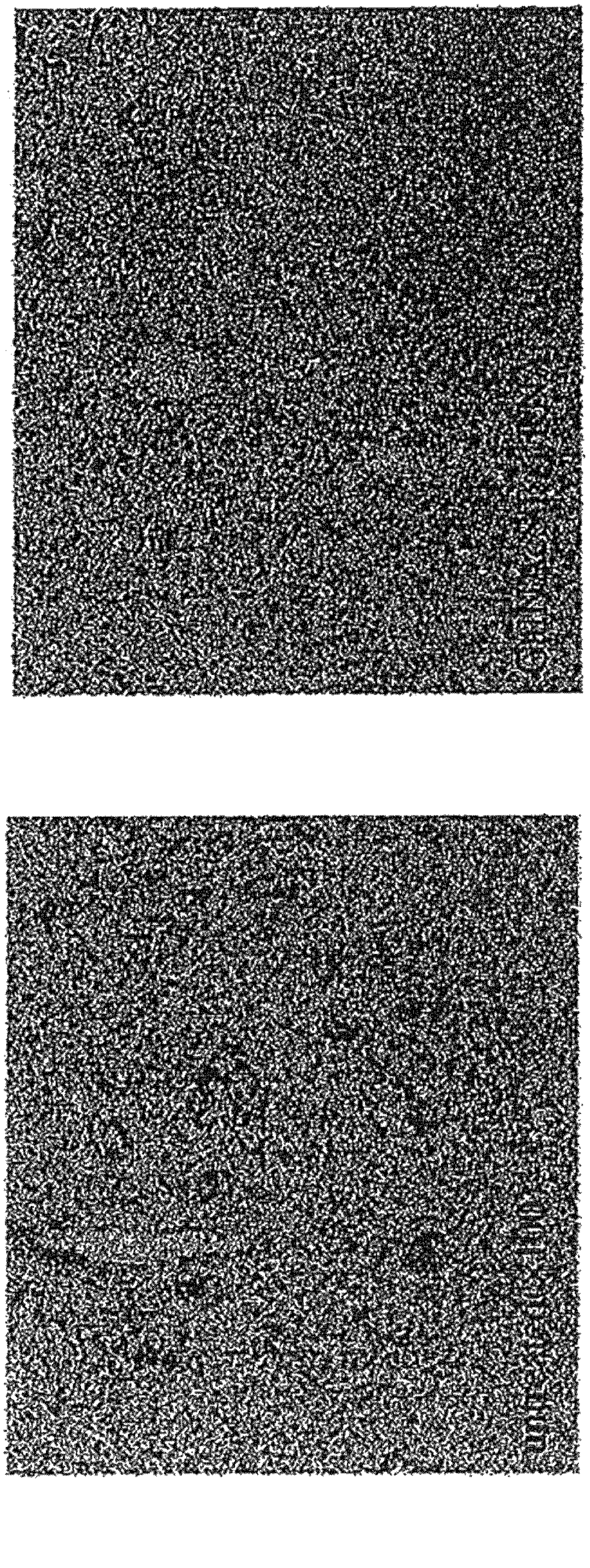

FIG. 56 depicts photographs showing macrophage infiltration in a mouse fatty liver injury model. GalNAcST siRNA significantly suppresses the accumulation of macrophages in liver tissues. Magnification: 100×.

Figure 57:
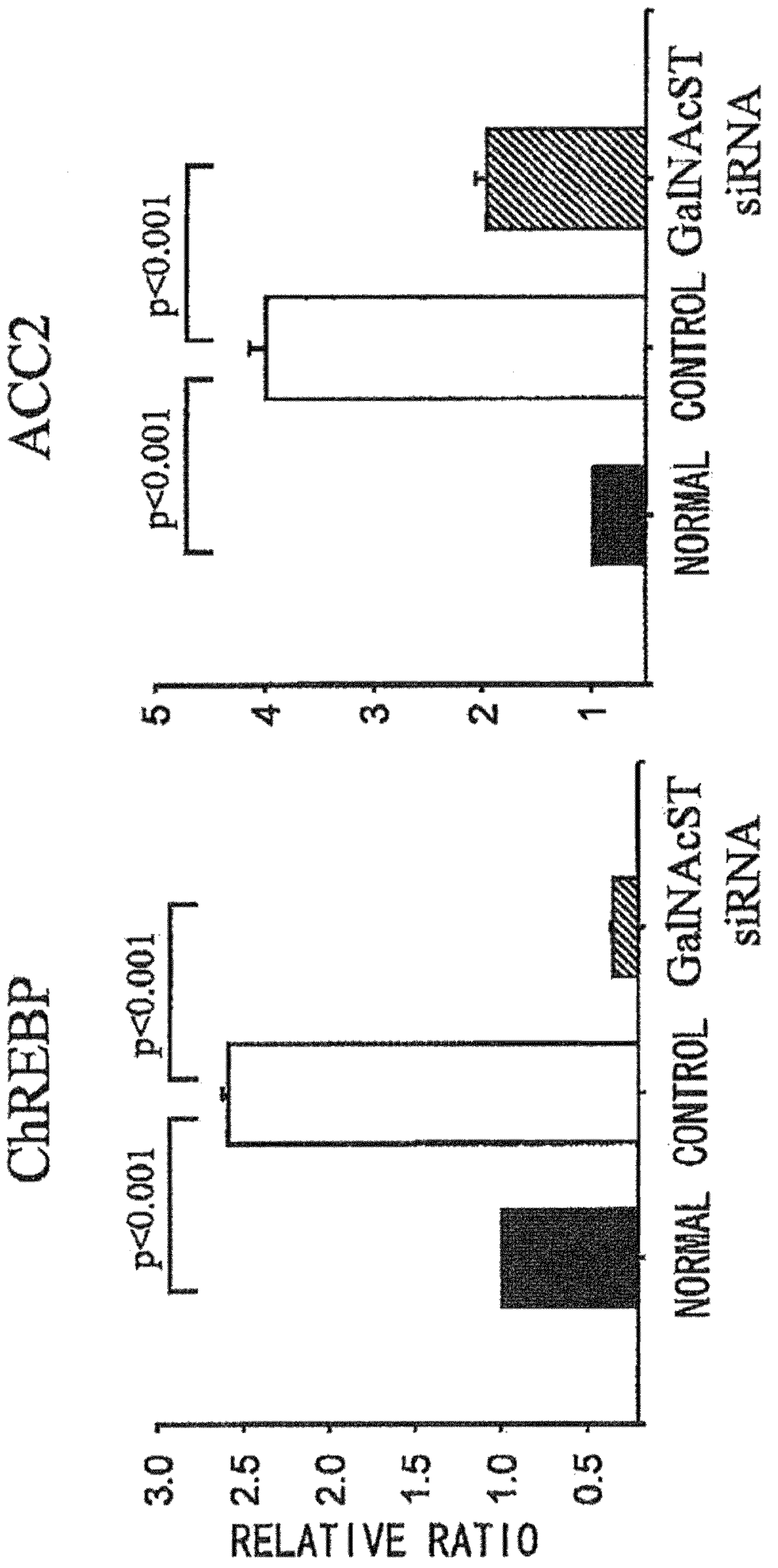

FIG. 57 depicts graphs showing the expression of lipid metabolism-related genes in a mouse fatty liver injury model. GalNAcST siRNA significantly suppresses the increased expression of ChREBP and ACC2 in liver tissues.

Figure 58:
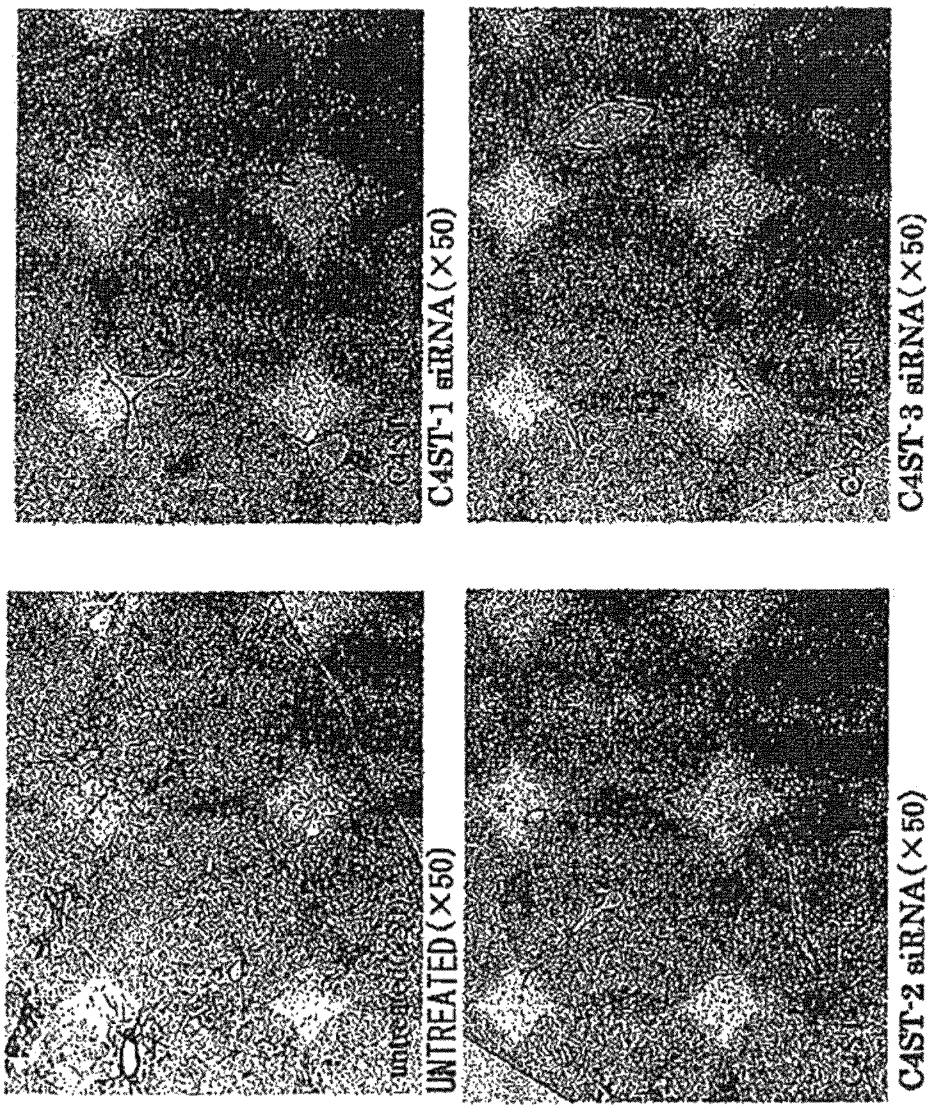

FIG. 58 depicts photographs showing the infiltration of fibrogenic cells in a mouse fatty liver injury model. C4ST-1, C4ST-2, and C4ST-3 siRNAs suppress the bridge-like accumulation of fibroblasts in liver tissues. Magnification: 100×.

Figure 59:
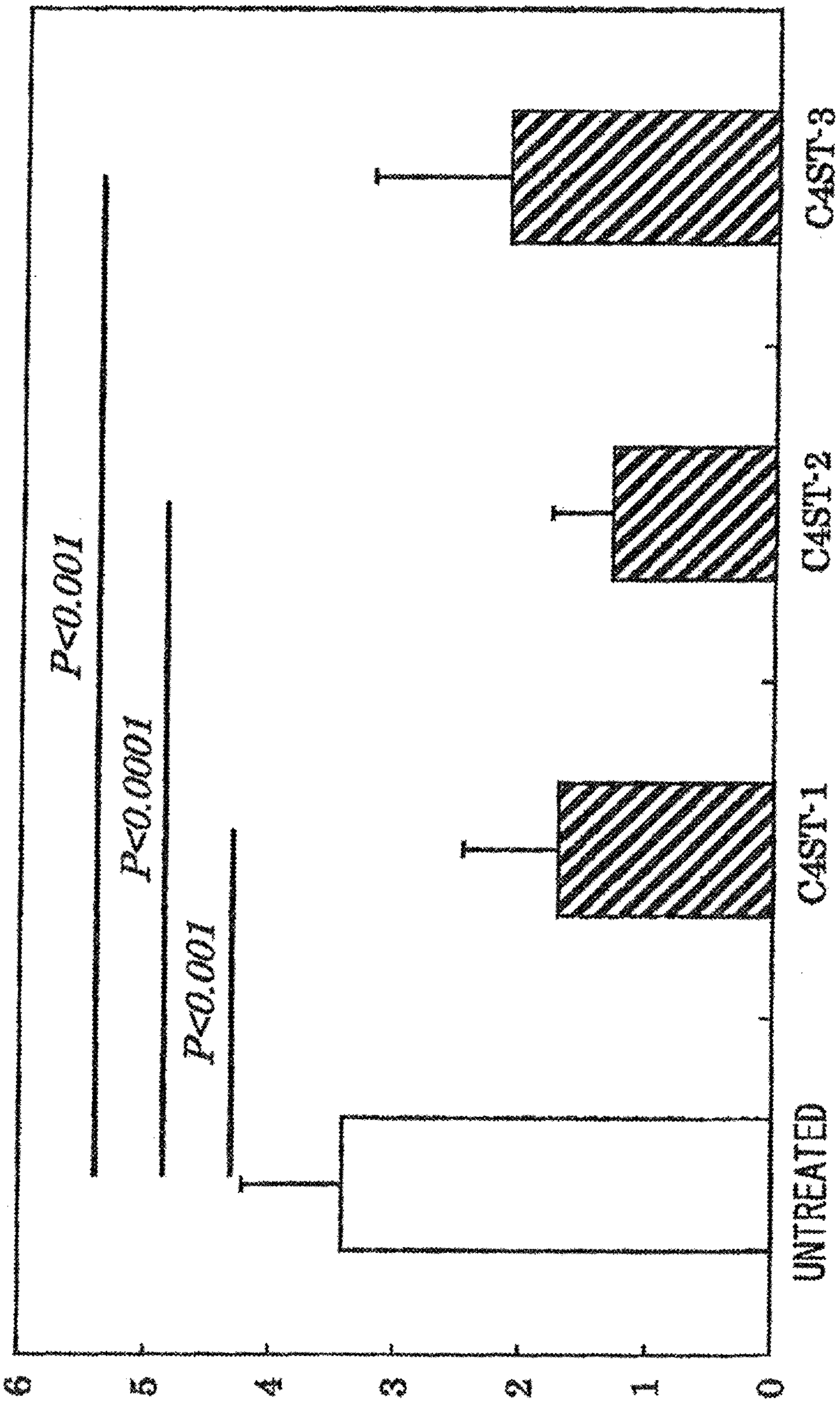

FIG. 59 depicts a graph showing clinical scores for fibrogenesis in a mouse fatty liver injury model. C4ST-1, C4ST-2, and C4ST-3 siRNAs significantly suppress the increase in the fibrogenesis score in liver tissues.

Figure 60:
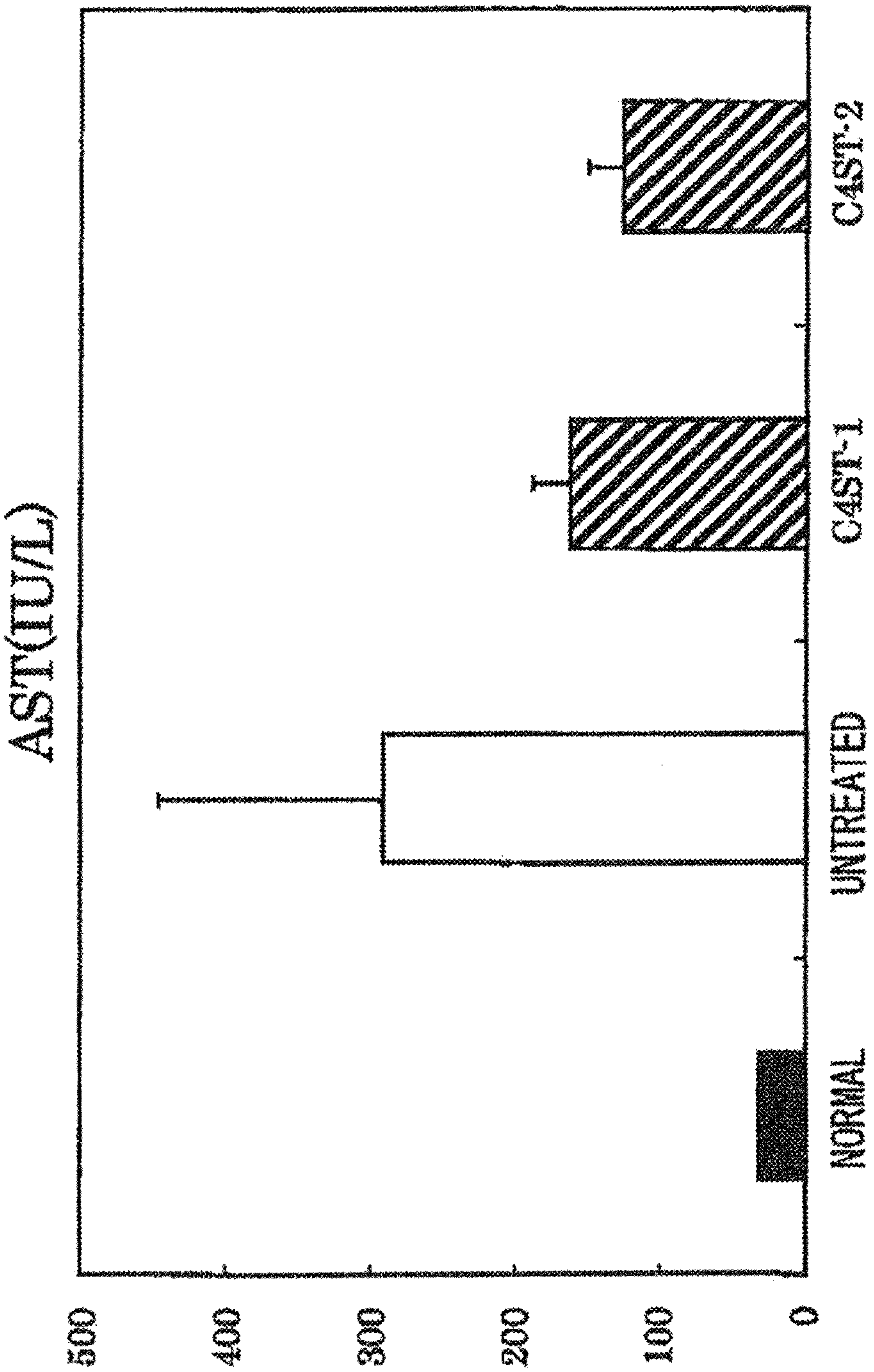

FIG. 60 depicts a graph showing clinical hepatic disorder in a mouse fatty liver injury model. C4ST-1, C4ST-2, and C4ST-3 siRNAs suppress the increase in ALT, which is an indicator of hepatocyte disorder.

Figure 61:
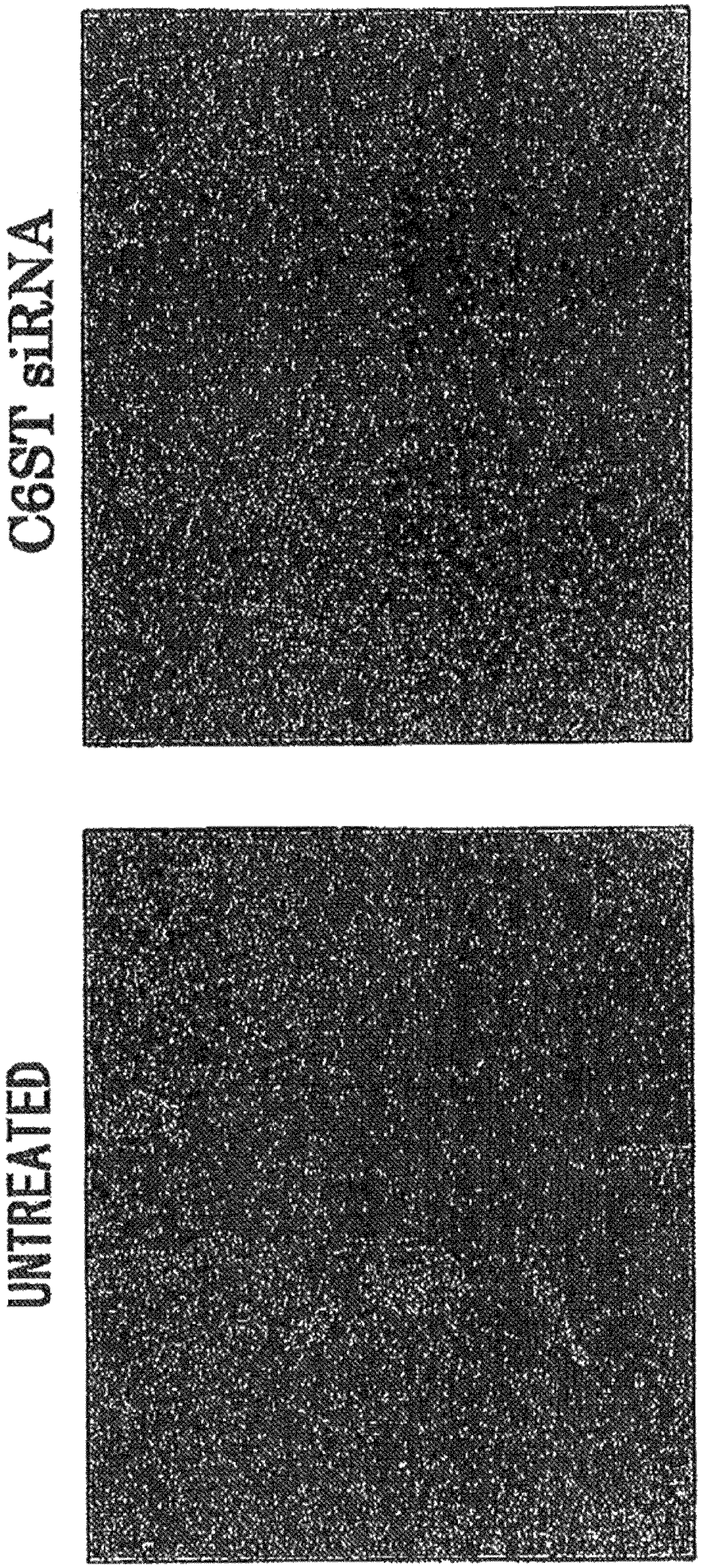

FIG. 61 depicts photographs showing the infiltration of fibroblasts in a mouse hepatic fibrosis model. C6ST siRNA significantly suppresses the accumulation of fibroblasts in liver tissues. Magnification: 50×.

Figure 62:
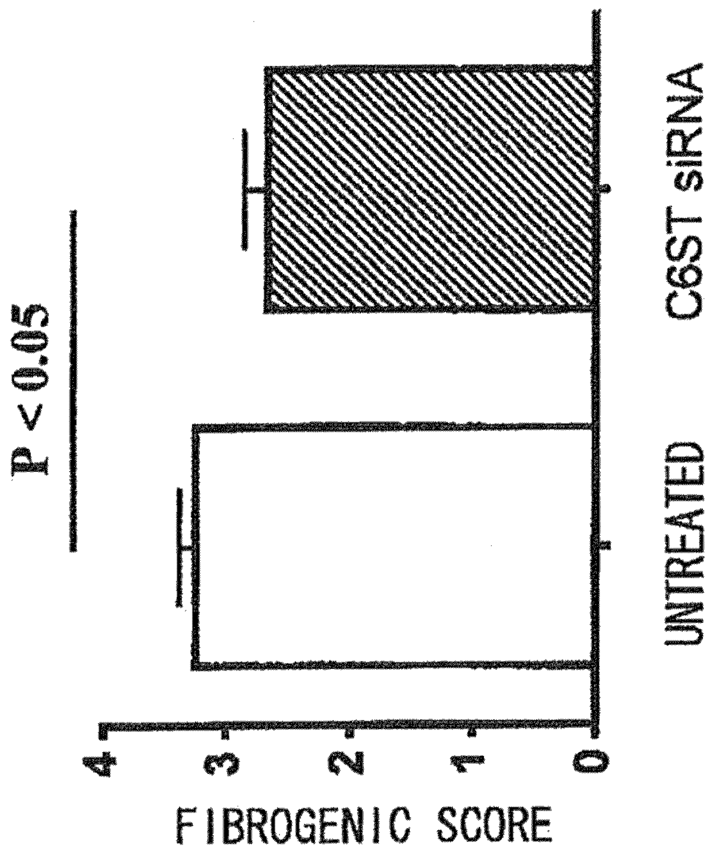

FIG. 62 depicts a graph showing clinical scores for fibrogenesis in a mouse hepatic fibrosis model. C6ST siRNA significantly suppresses the increase in the clinical fibrogenesis score in liver tissues.

Figure 63:
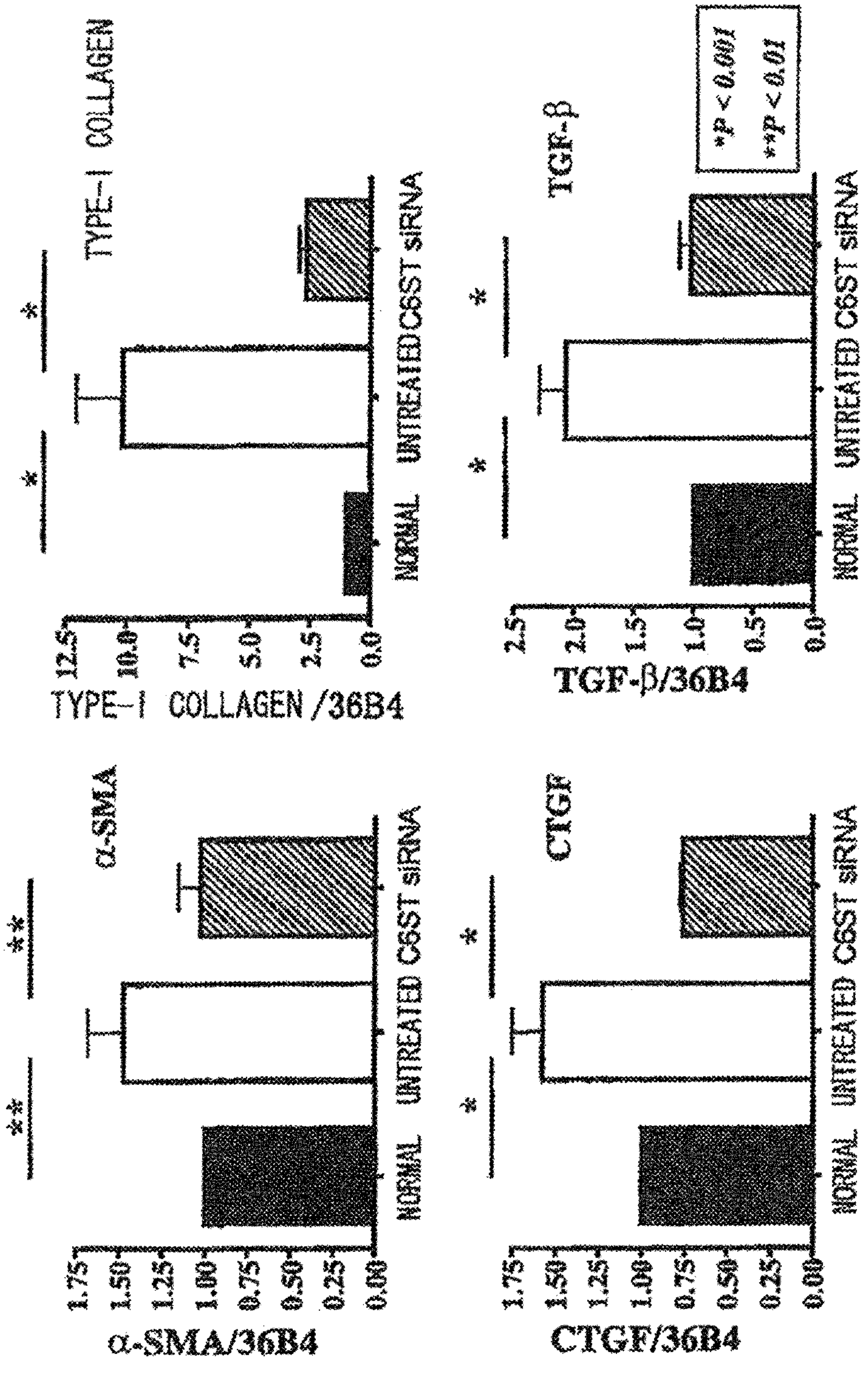

FIG. 63 depicts graphs showing the anti-fibrogenic effect in a mouse hepatic fibrosis model. C6ST siRNA significantly suppresses the expression of αSMA, type I collagen, CTGF, and TGFβ.

Figure 64:
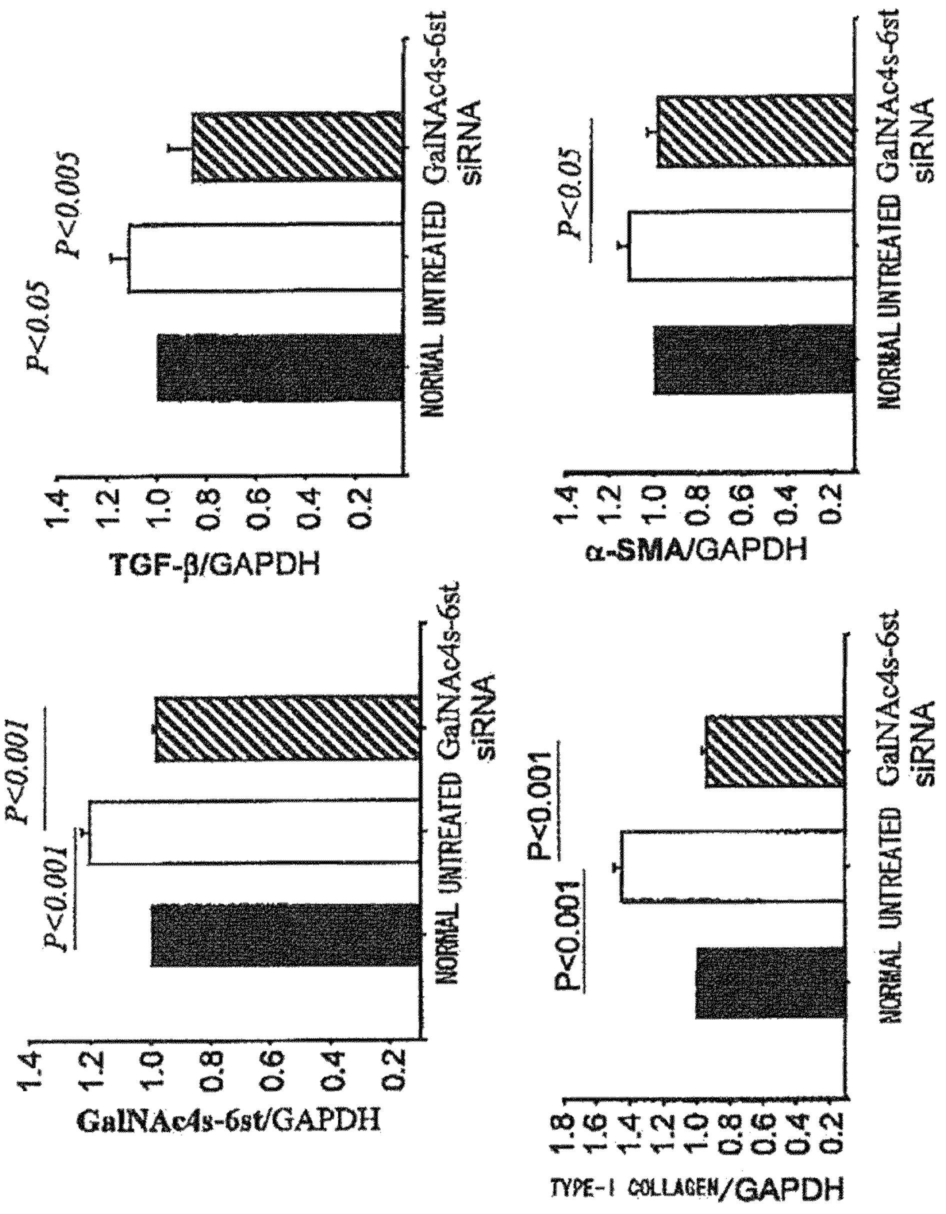

FIG. 64 depicts graphs showing the anti-fibrogenic effect in a mouse Parkinson's disease model. GalNAc4S-6ST siRNA significantly suppresses the expression of GalNAc4S-6ST, TGFβ, type I collagen, and αSMA in brain tissues.

Figure 65:
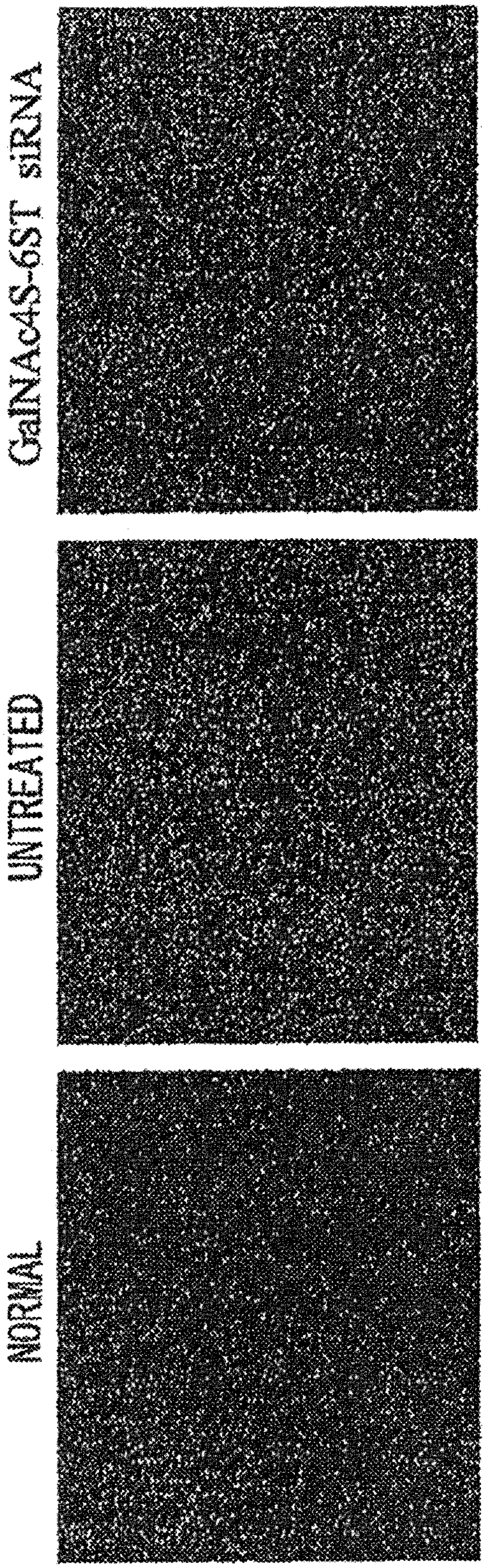

FIG. 65 depicts photographs showing the accumulation of fibroblasts in a mouse Parkinson's disease model. GalNAc4S-6ST siRNA drastically decreases the accumulation of fibroblasts in brain tissues. Magnification: 200×.

Figure 66:
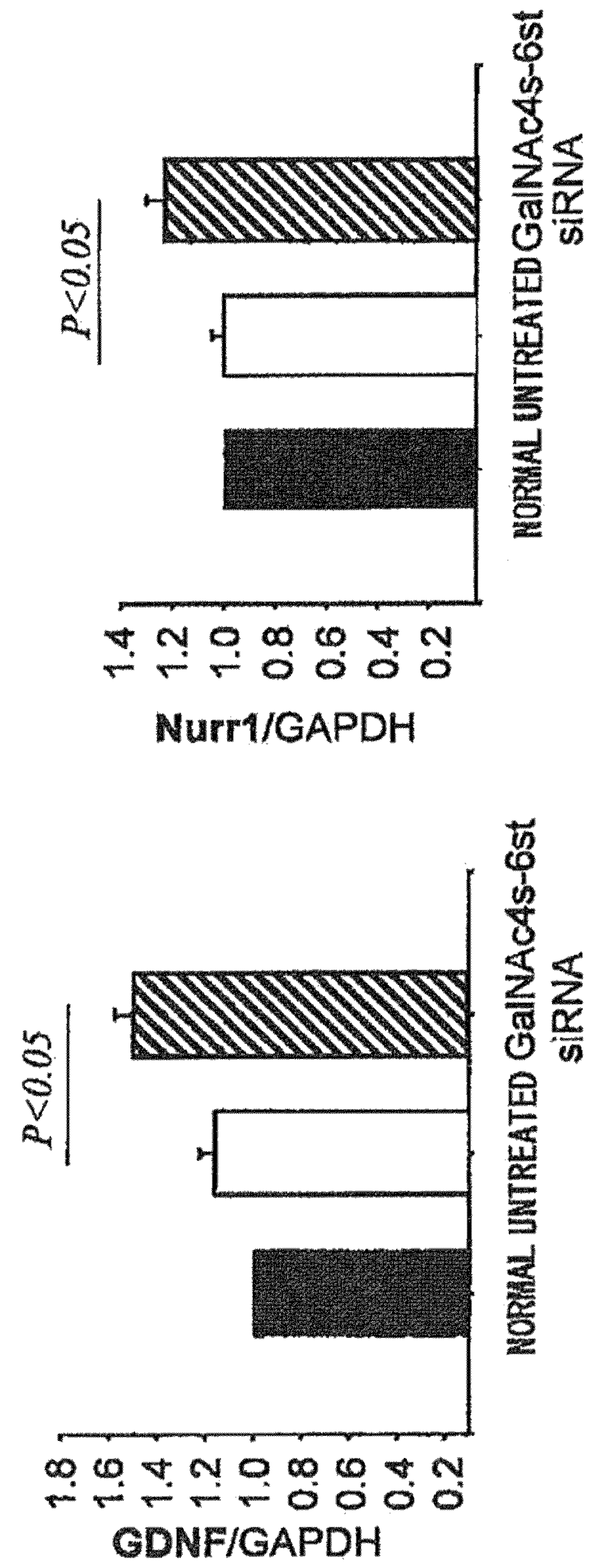

FIG. 66 depicts graphs showing the nerve protective effect in a mouse Parkinson's disease model. GalNAc4S-6ST siRNA significantly enhances the expression of GDNF and Nurr1.

Figure 67:
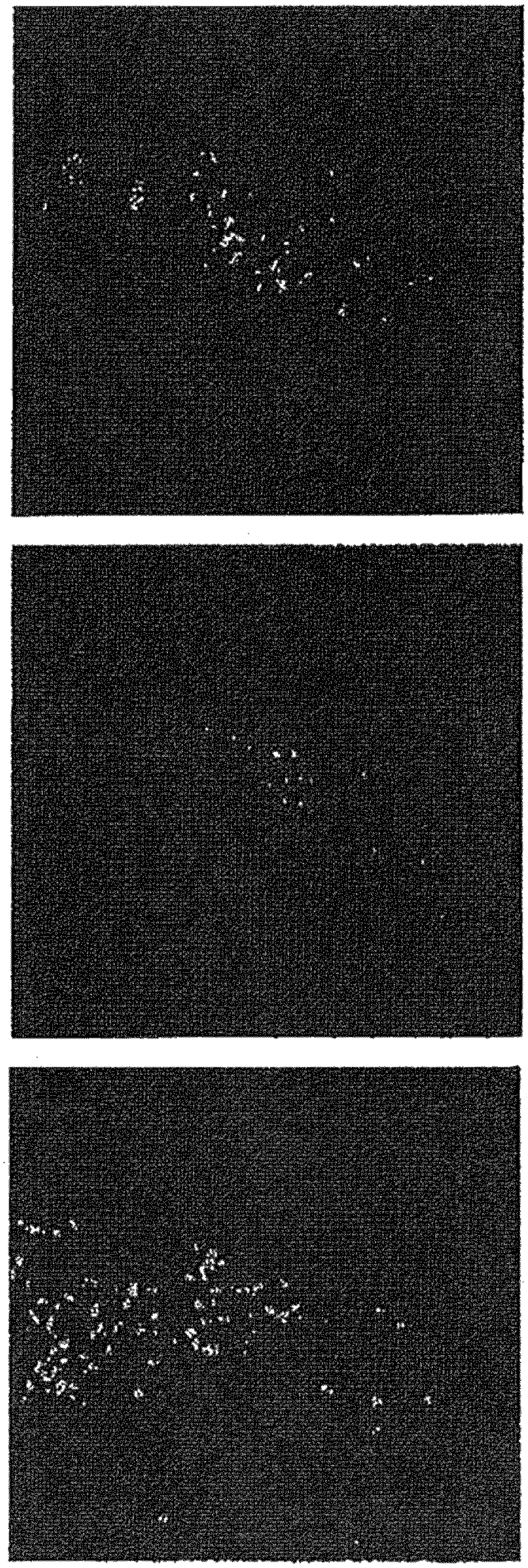

FIG. 67 depicts photographs showing the dopamine neuron regeneration effect in a mouse Parkinson's disease model. GalNAc4S-6ST siRNA suppresses the degeneration of TH-positive dopamine neurons. Magnification: 200×.

Figure 68:
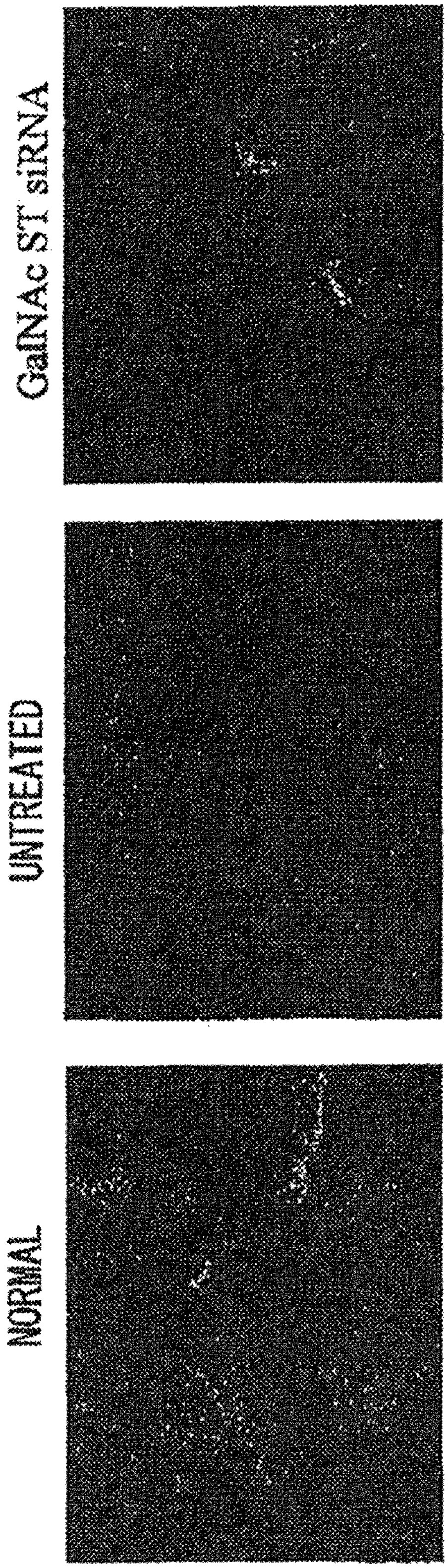

FIG. 68 depicts photographs showing the dopamine neuron regeneration effect in a mouse Parkinson's disease model. GalNAc4ST siRNA suppresses the degeneration of TH-positive dopamine neurons. Magnification: 200×.

Figure 69:
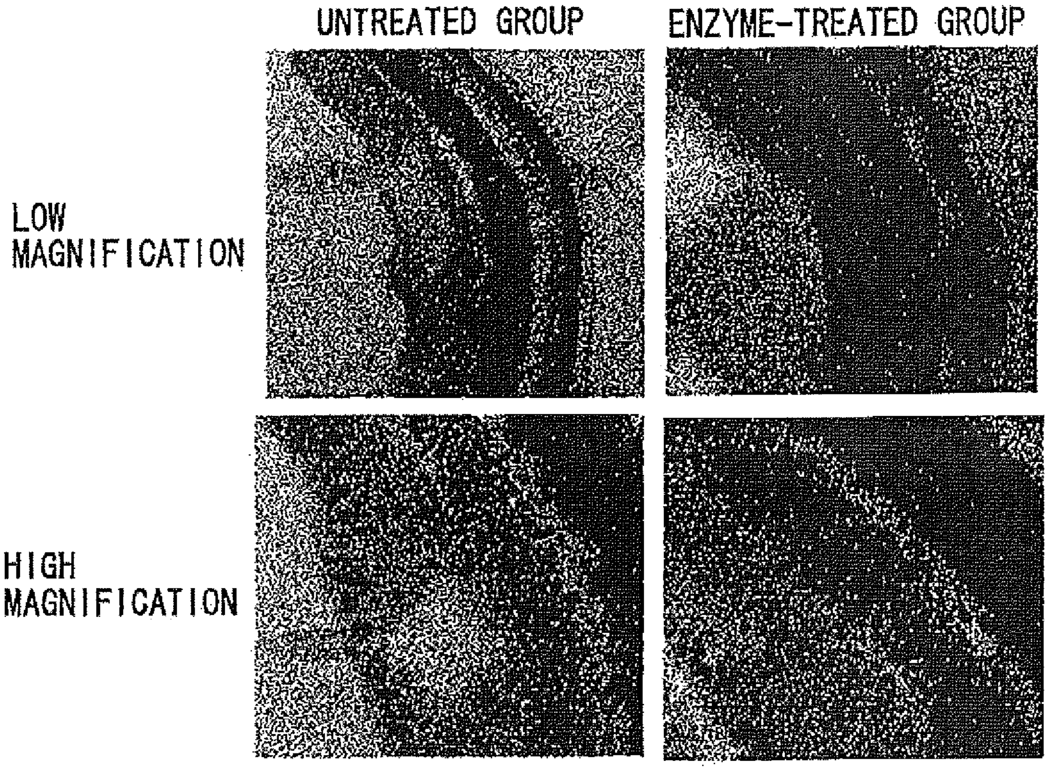

FIG. 69 depicts photographs showing the CSPG-reducing effect of C4-sulfatase in a mouse type 2 diabetic retinopathy model. The photographs show images of stained CSPG (CS56) (arrow) in the retina of type 2 diabetic retinopathy model mice.

Figure 70:
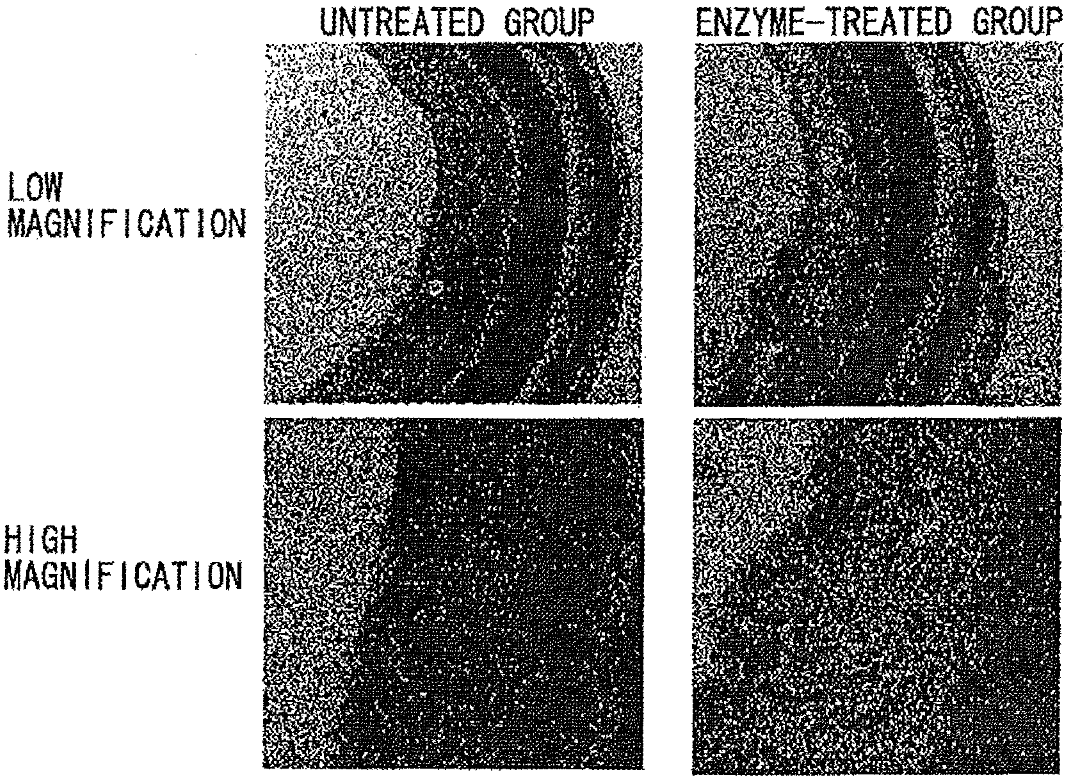

FIG. 70 depicts photographs showing the angiogenesis-suppressing effect of C4-sulfatase in a mouse type 2 diabetic retinopathy model. The photographs show images of stained vascular endothelial cells (CD31) (arrow) in the retina of type 2 diabetic retinopathy model mice.

Figure 71:
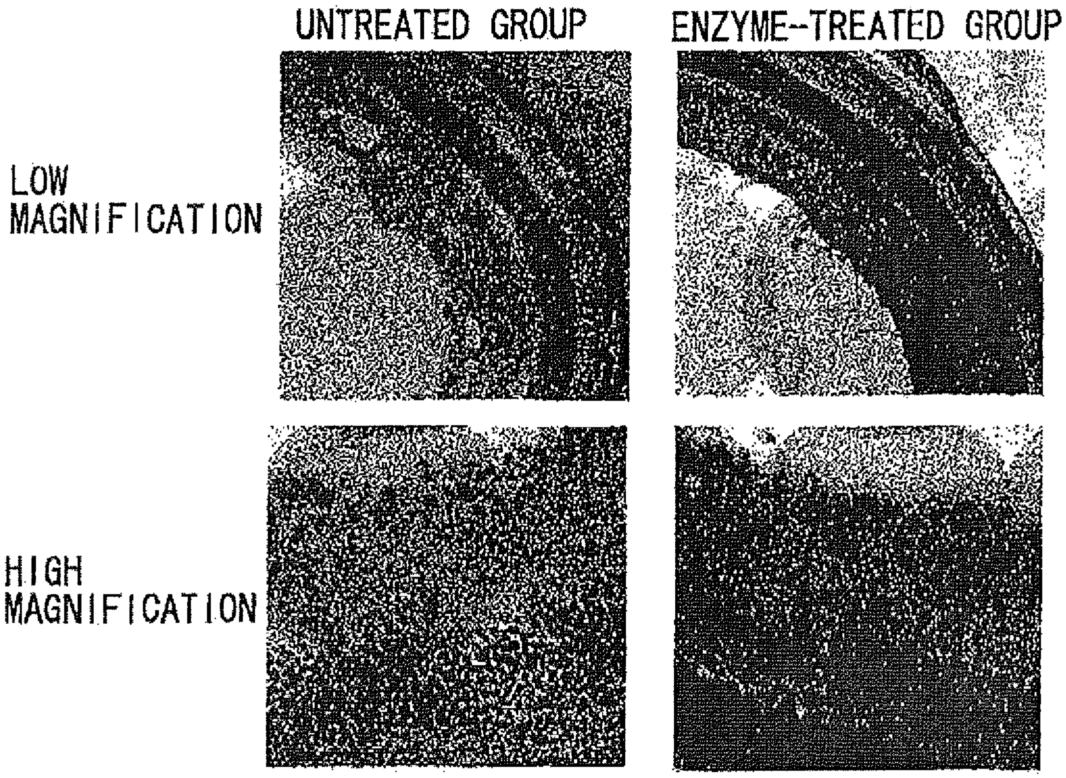

FIG. 71 depicts photographs showing the collagen augmentation-suppressing effect of C4-sulfatase in a mouse type 2 diabetic retinopathy model. The photographs show images of stained type IV collagen (arrow) in the retina of type 2 diabetic retinopathy model mice.

Figure 72:
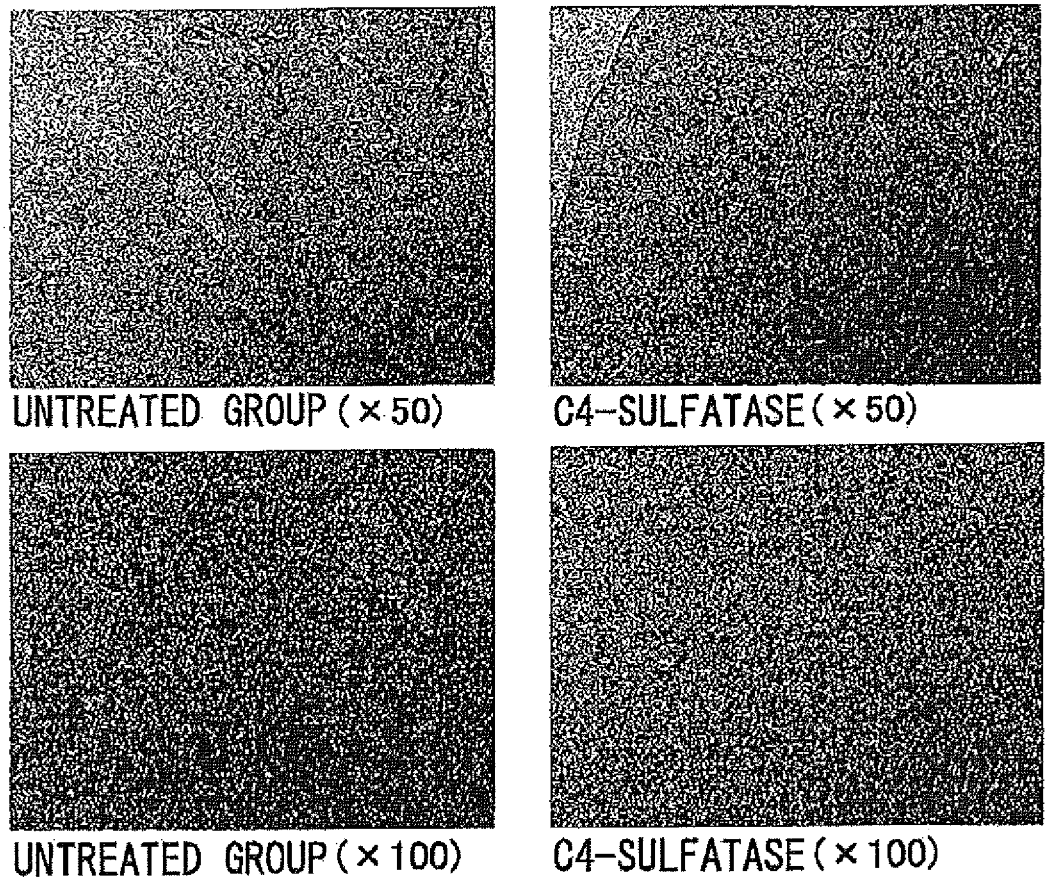

FIG. 72 depicts photographs showing the suppressive effect of C4-sulfatase on fibroblast accumulation in the liver of a mouse type 2 diabetes model. The magnification is 50 or 100 fold.

Figure 73:
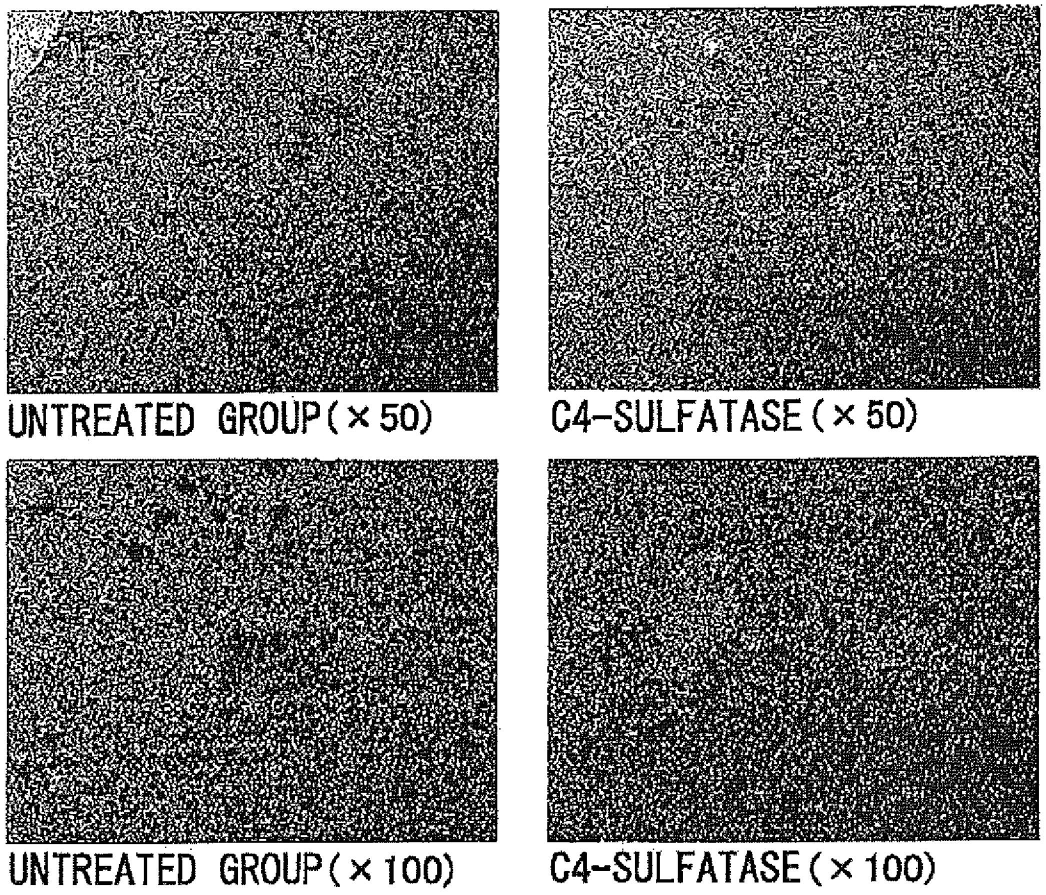

FIG. 73 depicts photographs showing the macrophage infiltration-suppressing effect in the liver of a mouse type 2 diabetes model. The magnification is 50 or 100 fold.

Figure 74:
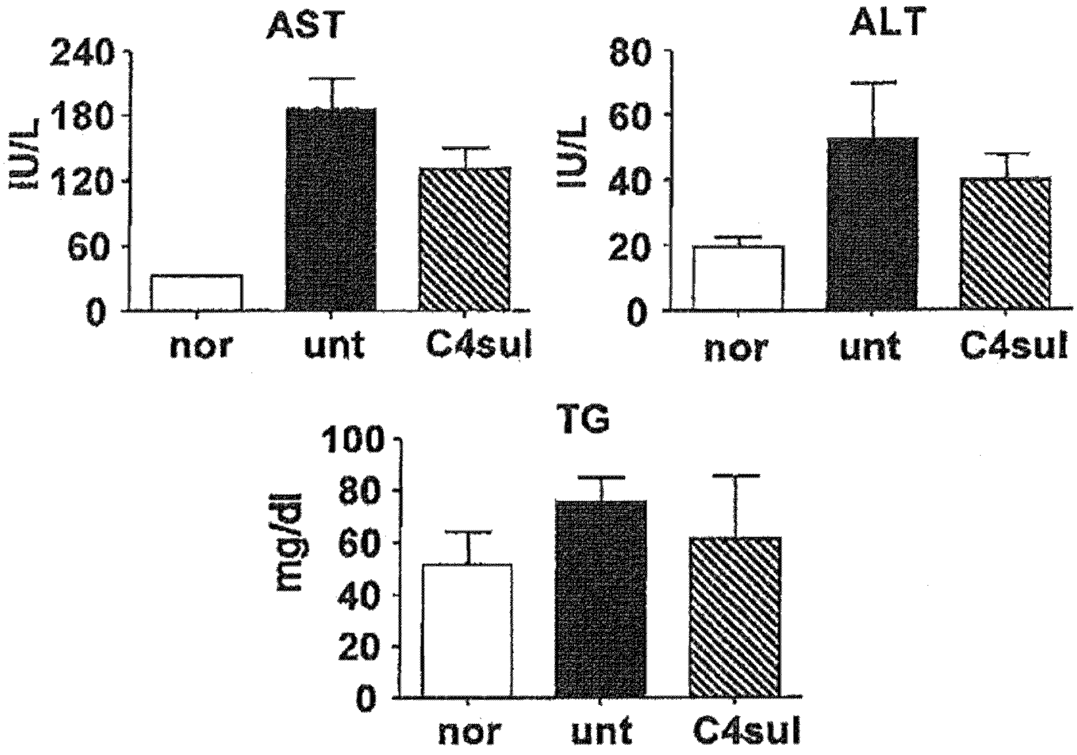

FIG. 74 depicts graphs showing the result of serum biochemical tests (AST, ALT, and TG) in a mouse type 2 diabetes model. In the graphs: unt, untreated group; nor, control group; C4sul, C4-sulfatase.

Figure 75:
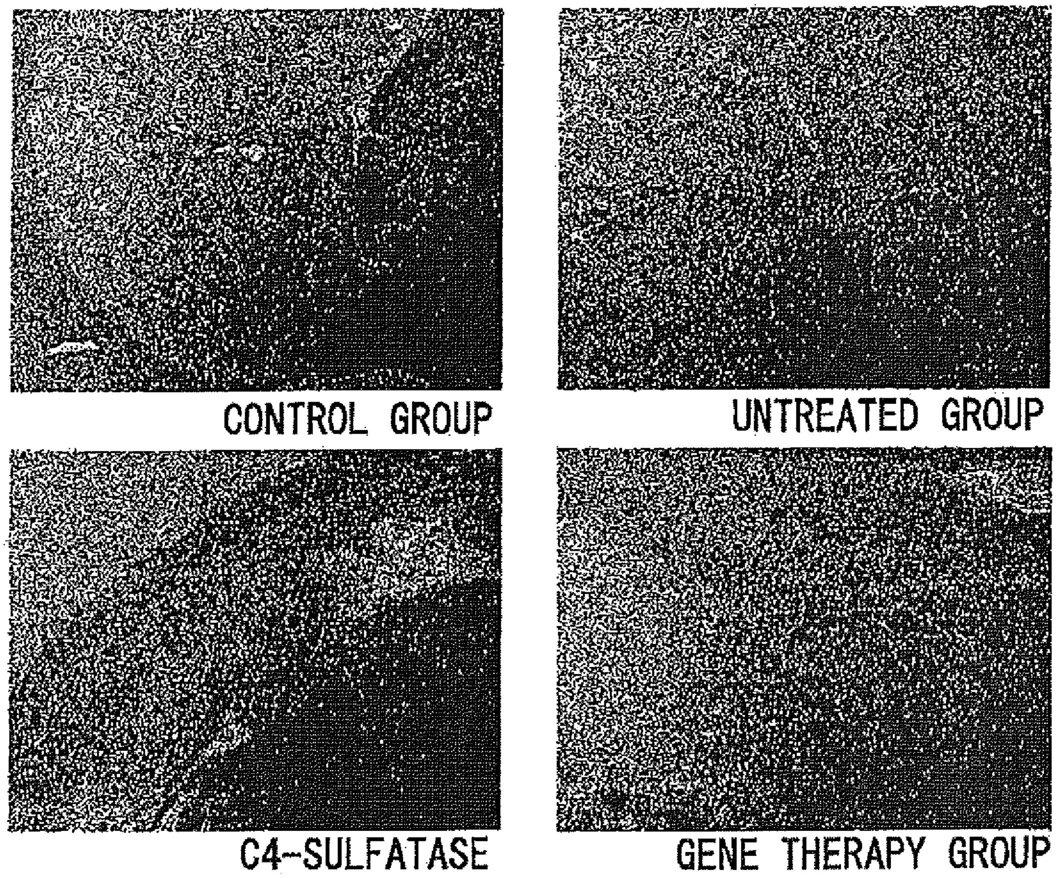

FIG. 75 depicts photographs showing the localization of CSPG in brain tissues. The photographs show the result of analyzing the dynamics of CSPG expression in brain tissues using an enzyme-antibody immunostaining method. Assay was carried out using CS-56 (Seikagaku Co.) for primary antibody and Mouse Stain Kit for staining.

Figure 76:
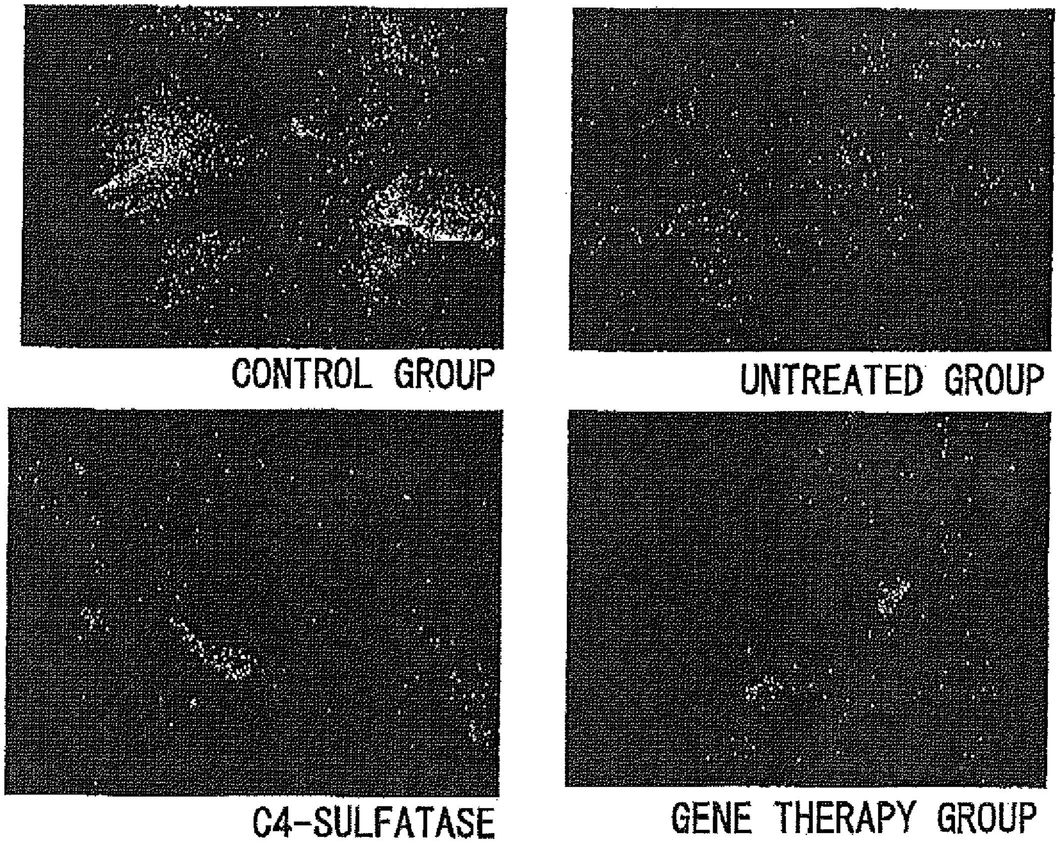

FIG. 76 depicts photographs showing the localization of dopaminergic neurons in brain tissues. The photographs show an analysis result obtained by a fluorescence immunostaining method.

Figure 77:
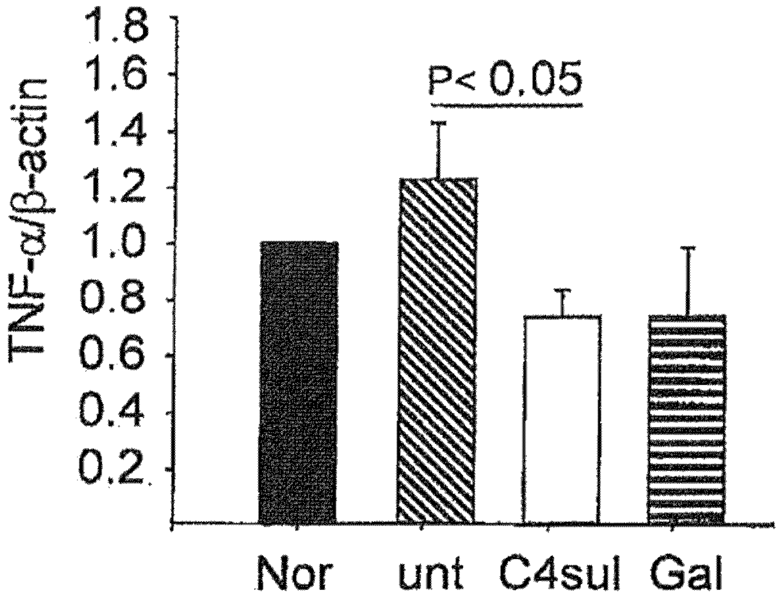

FIG. 77 depicts a graph showing the result of TNF-α gene expression analysis, which was obtained by Real-time PCR method. The graph shows the result of real-time PCR for the expression of TGF-β as a fibrosis marker, and TNF-α as an indicator for inflammation associated with macrophage infiltration.

Figure 78:
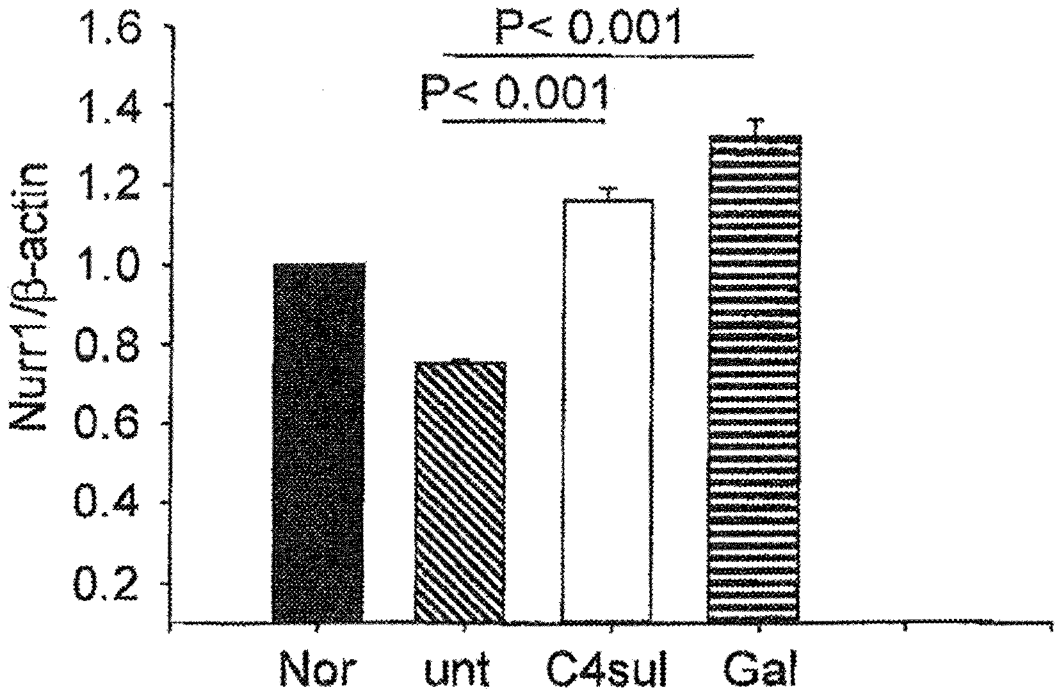

FIG. 78 depicts a graph showing the result of Nurr1 gene expression analysis by real-time PCR method. The graph shows the result for Nurr1 gene expression in brain tissues, which was obtained using Cyber premix kit (Takara Bio) and Real-time PCR thermal cycler DICE (Takara Bio). The graph indicates relative ratios between Nurr1 and a house keeping gene (β-actin).

MODE FOR CARRYING OUT THE INVENTION

The present invention will be specifically described below.

The present invention relates to tissue fibrogenesis inhibitors based on the mechanism of inhibiting sulfation at position 4 or 6 of N-acetylgalactosamine, a sugar constituting sugar chains.

Specifically, the present invention provides tissue fibrogenesis inhibitors comprising as an ingredient an inhibitor of sulfation at position 4 or 6 of N-acetylgalactosamine (herein sometimes also referred to as "inhibitors of the present invention" or simply as "inhibitors").

Herein, "N-acetylgalactosamine (GalNAc)" refers to the N-acetylated form of galactosamine, which is a hexosamine.

Furthermore, it is known that N-acetylgalactosamine can be chemically-modified at positions 1 to 6.

The present invention is characterized by inhibiting sulfation at position 4 or 6 of N-acetylgalactosamine.

Specifically, the sites where the sulfation is inhibited by the inhibitors of the present invention are indicated by arrow in the following formula of GalNAc.

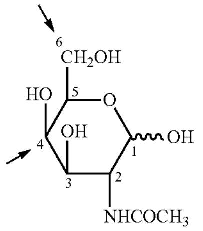

The sites where the sulfation is inhibited by the inhibitors of the present invention are positions 4 or 6 of GalNAc. In the present invention, the sulfation of GalNAc may be inhibited at both positions 4 and 6. In the present invention, preferred GalNAc is a sugar in chondroitin sulfate proteoglycan (CSPG).

Herein, the inhibition of sulfation refers to inhibition of transfer of a sulfate group to position 4 or 6 in GalNAc, elimination of a sulfate group from a site where GalNAc has been already sulfated, or substitution of a sulfate group with other chemically-modified group.

The agents for suppressing tissue fibrogenesis of the present invention (herein sometimes referred to as "agents of the present invention") preferably have an in vivo fibrogenesis-suppressing effect.

Tissues where fibrogenesis is suppressed by the agents of the present invention are not particularly limited. Such tissues include, for example, cardiac tissues, gastrointestinal tissues, lung tissues, pancreatic tissues, kidney tissues, ocular tissues, liver tissues, cranial nerve tissues, and skin tissues.

Herein, "fibrogenesis" may be referred to as "fibrosis". Alternatively, "fibrogenesis" may be synonymous with other phrases such as "fibrogenic lesion in tissues", "fibrogenic tissue alteration", and "neofibrogenesis".

The inhibitors of the present invention are not particularly limited as long as they are substances having the activity of inhibiting the sulfation at position 4 or 6 of N-acetylgalactosamine.

A preferred embodiment of inhibitors of the present invention includes, for example, substances having the activity of inhibiting the function of sulfotransferase that transfers a sulfate to position 4 or 6 of N-acetylgalactosamine.

Preferred embodiments of the above-described substances include, for example, compounds (nucleic acids) selected from the group consisting of:

(a) antisense nucleic acids against transcripts of the genes encoding the sulfotransferases that transfer a sulfate to position 4 or 6 of N-acetylgalactosamine, or portions thereof;

(b) nucleic acids with the ribozyme activity of specifically cleaving transcripts of genes encoding the sulfotransferases that transfer a sulfate to position 4 or 6 of N-acetylgalactosamine; and (c) nucleic acids with the activity of using RNAi effect to inhibit the expression of genes encoding the sulfotransferases that transfer a sulfate to position 4 or 6 of N-acetylgalactosamine (siRNAs that suppress the expression of sulfotransferase genes).

The "substances with the activity of inhibiting sulfation" also include, for example, compounds selected from the group consisting of:

(a) antibodies that bind to sulfotransferases that transfer a sulfate to position 4 or 6 of N-acetylgalactosamine;

(b) sulfotransferase variants for sulfotransferases that transfer a sulfate to position 4 or 6 of N-acetylgalactosamine; and (c) low-molecular-weight compounds that bind to sulfotransferases that transfer a sulfate to position 4 or 6 of N-acetylgalactosamine.

Another embodiment of inhibitors of the present invention includes, for example, substances having the activity of desulfating a sulfate group at position 4 or 6 of N-acetylgalactosamine. Such substances include, for example, enzymes that desulfate the sulfate group (desulfating enzymes) at position 4 or 6 of N-acetylgalactosamine.

The "desulfating" sulfate group at position 4 or 6 of N-acetylgalactosamine means that a sulfate group at position 4 or 6 is eliminated from N-acetylgalactosamine.

Such desulfating enzymes include, for example, chondroitin-4-sulfatase (C4-sulfatase) and chondroitin-6-sulfatase.

Sulfotransferases of the present invention are not particularly limited as long as enzymes have an activity of transferring a sulfate to position 4 or 6 of GalNAc, but include, for example:

1) GalNAc4ST-1: N-acetylgalactosamine 4-sulfotransferase-1

Alias CHST8:Carbohydrate (N-acetylgalactosamine 4-0) sulfotransferase 8

2) GalNAc4ST-2

Alias CHST9: Carbohydrate (N-acetylgalactosamine 4-0) sulfotransferase 9

3) C4ST-1: chondroitin-4-O-sulfotransferase-1

Alias CHST11: Carbohydrate (chondroitin 4) sulfotransferase 11

4) C4ST-2

Alias CHST12

5) C4ST-3

Alias CHST13

6) C6ST-1: chondroitin-6-O-sulfotransferase-1

Alias CHST3: Carbohydrate (chondroitin 6) sulfotransferase 3

7) GalNAc4S-6ST: N-acetylgalactosamine 4-sulfate 6-0 sulfotransferase

8) D4ST-1:dermatan 4 sulfotransferase 1

9) C6ST-2: chondroitin-6-O-sulfotransferase-2

Alias CHST7: Carbohydrate (chondroitin 6) sulfotransferase 7

Further, on a genomic DNA level, such groups of enzymes sharing features do not necessarily correspond to single genes. For example, both chondroitin-4-sulfatase and chondroitin-6-sulfatase can be retrieved from the public gene database GenBank as sequences referred to by multiple accession numbers (for example, GenBank accession Nos: NT_039500 (a portion thereof is shown under accession No: CAAA01098429 (SEQ ID NO: 1)), NT_078575, NT_039353, NW_001030904, NW_001030811, NW_001030796, and NW_000349).

Specifically, below are examples of sulfotransferases of the present invention with accession numbers in the public gene database GenBank, nucleotide sequences, and amino acid sequences:

GalNAc4ST-1 (Accession number NM_175140; nucleotide sequence: SEQ ID NO: 2; amino acid sequence, SEQ ID NO: 3)

GalNAc4ST-2 (Accession number NM_199055; nucleotide sequence: SEQ ID NO: 4; amino acid sequence, SEQ ID NO: 5)

C4ST-1 (Accession number NM_021439; nucleotide sequence: SEQ ID NO: 6, amino acid sequence, SEQ ID NO: 7)

C4ST-2 (Accession number NM_021528; nucleotide sequence: SEQ ID NO: 8; amino acid sequence, SEQ ID NO: 9)

C4ST-3 (Accession number XM_355798; nucleotide sequence: SEQ ID NO: 10; amino acid sequence, SEQ ID NO: 11)

D4ST (Accession number NM_028117; nucleotide sequence: SEQ ID NO: 12; amino acid sequence, SEQ ID NO: 13)

C6ST-1 (Accession number NM_016803; nucleotide sequence: SEQ ID NO: 14; amino acid sequence, SEQ ID NO: 15)

C6ST-2 (Accession number AB046929; nucleotide sequence: SEQ ID NO: 16; amino acid sequence, SEQ ID NO: 17)

GalNAc4S-6ST (Accession number NM_015892; nucleotide sequence: SEQ ID NO: 18; amino acid sequence, SEQ ID NO: 19)

In addition to the proteins listed above, the proteins of the present invention include those exhibiting high homology (typically 70% or higher, preferably 80% or higher, more preferably 90% or higher, and most preferably 95% or higher) to sequences shown in the Sequence Listing and having a function of the proteins listed above (for example, the function of binding to intracellular components). The proteins listed above are, for example, proteins comprising an amino acid sequence with an addition, deletion, substitution, or insertion of one or more amino acids in any of the amino acid sequences of SEQ ID NOs: 3, 5, 7, 9, 11, 13, 15, and 17, in which the number of altered amino acids is typically 30 amino acids or less, preferably ten amino acids or less, more preferably five amino acids or less, and most preferably three amino acids or less.

The above-described genes of the present invention include, for example, endogenous genes of other organisms which correspond to DNAs comprising any of the nucleotide sequences of SEQ ID NOs: 2, 4, 6, 8, 10, 12, 14, and 16 (homologues to the human genes described above, or the like).

Each of the endogenous DNAs of other organisms which correspond to DNAs comprising any of the nucleotide sequences of SEQ ID NOs: 2, 4, 6, 8, 10, 12, 14, and 16 are generally highly homologous to a DNA of any of SEQ ID NOs: 2, 4, 6, 8, 10, 12, 14, and 16. High homology means 50% or higher homology, preferably 70% or higher homology, more preferably 80% or higher homology, and still more preferably 90% or higher homology (for example, 95% or higher, or 96%, 97%, 98%, or 99% or higher).

Homology can be determined using the mBLAST algorithm (Altschul, et al. Proc. Natl. Acad. Sci. USA, 1990, 87, 2264-8; Karlin and Altschul, Proc. Natl. Acad. Sci. USA, 1993, 90, 5873-7). When the DNAs have been isolated from the body, each of them may hybridize under stringent conditions to a DNA of SEQ ID NO: 2, 4, 6, 8, 10, 12, 14, and 16. Herein, stringent conditions include, for example, "2×SSC, 0.1% SDS, 50° C.", "2×SSC, 0.1% SDS, 42° C.", and "1×SSC, 0.1% SDS, 37° C."; more stringent conditions include "2×SSC, 0.1% SDS, 65° C.", "0.5×SSC, 0.1% SDS, 42° C.", and "0.2×SSC, 0.1% SDS, 65° C.".

Those skilled in the art can appropriately obtain proteins functionally equivalent to the above-described proteins from the above-described highly homologous proteins by using methods for assaying the activity of desulfating or inhibiting the sulfation at position 4 or 6 of N-acetylgalactosamine.

Further, based on the nucleotide sequences of the above-described genes, those skilled in the art can appropriately obtain endogenous genes of other organisms that correspond to the above-described genes. In the present invention, the above-described proteins and genes in nonhuman organisms, which correspond to the above-described proteins and genes, or the above-described proteins and genes that are functionally equivalent to the above-described proteins and genes, may simply be referred to using the above-described names.

The proteins of the present invention can be prepared not only as natural proteins but also as recombinant proteins using genetic recombination techniques. The natural proteins can be prepared by, for example, methods of subjecting cell extracts (tissue extracts) that may express the above-described proteins to affinity chromatography using antibodies against the above-described proteins. On the other hand, the recombinant proteins can be prepared, for example, by culturing cells transformed with DNAs encoding the proteins described above. The above-described proteins of the present invention can be suitably used, for example, in the screening methods described herein below.

In the present invention, "nucleic acids" refer to both RNAs and DNAs. Chemically synthesized nucleic acid analogs, such as so-called "PNAs" (peptide nucleic acids), are also included in the nucleic acids of the present invention. PNAs are nucleic acids in which the fundamental backbone structure of nucleic acids, the pentose-phosphate backbone, is replaced by a polyamide backbone with glycine units. PNAs have a three-dimensional structure quite similar to that of nucleic acids.

Methods for inhibiting the expression of specific endogenous genes using antisense technology are well known to those skilled in the art. There are a number of causes for the action of antisense nucleic acids in inhibiting target gene expression, including:

- inhibition of transcription initiation by triplex formation;
- transcription inhibition by hybrid formation at a site with a local open loop structure generated by an RNA polymerase;
- transcription inhibition by hybrid formation with the RNA being synthesized;
- splicing inhibition by hybrid formation at an intron-exon junction;
- splicing inhibition by hybrid formation at the site of spliceosome formation;
- inhibition of transport from the nucleus to the cytoplasm by hybrid formation with mRNA;
- splicing inhibition by hybrid formation at the capping site or poly(A) addition site;
- inhibition of translation initiation by hybrid formation at the translation initiation factor binding site;
- inhibition of translation by hybrid formation at the ribosome binding site adjacent to the start codon;
- inhibition of peptide chain elongation by hybrid formation in the translational region of mRNA or at the polysome binding site of mRNA; and
- inhibition of gene expression by hybrid formation at the protein-nucleic acid interaction sites. Thus, antisense nucleic acids inhibit the expression of target genes by inhibiting various processes, such as transcription, splicing, and translation (Hirashima and Inoue, Shin Seikagaku Jikken Koza 2 (New Courses in Experimental Biochemistry 2), Kakusan (Nucleic Acids) IV: "Idenshi no Fukusei to Hatsugen (Gene replication and expression)", Ed. The Japanese Biochemical Society, Tokyo Kagakudojin, 1993, pp. 319-347).

The antisense nucleic acids used in the present invention may inhibit the expression and/or function of genes encoding any of the sulfotransferases described above, based on any of the actions described above.

In one embodiment, antisense sequences designed to be complementary to an untranslated region adjacent to the 5' end of an mRNA for a gene encoding an above-described sulfotransferase may be effective for inhibiting translation of the gene. Sequences complementary to a coding region or 3'-untranslated region can also be used. Thus, the antisense nucleic acids to be used in the present invention include not only nucleic acids comprising sequences antisense to the coding regions, but also nucleic acids comprising sequences antisense to untranslated regions of genes encoding the above-described sulfotransferases. Such antisense nucleic acids to be used are linked downstream of adequate promoters and are preferably linked with transcription termination signals on the 3' side. Nucleic acids thus prepared can be introduced into desired animals (cells) using known methods. The sequences of the antisense nucleic acids are preferably complementary to a gene or portion thereof encoding a sulfotransferase that is endogenous to the animals (cells) to be transformed with them. However, the sequences need not be perfectly complementary, as long as the antisense nucleic acids can effectively suppress expression of a gene. The transcribed RNAs preferably have 90% or higher, and most preferably 95% or higher complementarity to target gene transcripts. To effectively inhibit target gene expression using antisense nucleic acids, the antisense nucleic acids are preferably at least 15 nucleotides long, and less than 25 nucleotides long. However, the lengths of the antisense nucleic acids of the present invention are not limited to the lengths mentioned above, and they may be 100 nucleotides or more, or 500 nucleotides or more.

The antisense nucleic acids of the preset invention are not particularly limited, and can be prepared, for example, based on the nucleotide sequence of C4ST-1 (GenBank Accession No: NM_021439; SEQ ID NO: 6), C4ST-2 (GenBank Accession No: NM_021528; SEQ ID NO: 8), C4ST-3 (GenBank Accession No: XM_355798; SEQ ID NO: 10), or such.

Expression of the above-mentioned genes encoding sulfotransferases can also be inhibited using ribozymes or ribozyme-encoding DNAs. Ribozymes refer to RNA molecules with catalytic activity. There are various ribozymes with different activities. Among others, studies that focused on ribozymes functioning as RNA-cleaving enzymes have enabled the design of ribozymes that cleave RNAs in a site-specific manner. Some ribozymes have 400 or more nucleotides, such as group I intron type ribozymes and M1

RNA, which is comprised by RNase P, but others, called hammerhead and hairpin ribozymes, have a catalytic domain of about 40 nucleotides (Koizumi, M. and Otsuka E., Tanpakushitsu Kakusan Koso (Protein, Nucleic Acid, and Enzyme), 1990, 35, 2191).

For example, the autocatalytic domain of a hammerhead ribozyme cleaves the sequence G13U14C15 at the 3' side of C15. Base pairing between U14 and A9 has been shown to be essential for this activity, and the sequence can be cleaved when C15 is substituted with A15 or U15 (Koizumi, M. et al., FEBS Lett., 1988, 228, 228). Restriction enzyme-like RNA-cleaving ribozymes that recognize the sequence UC, UU, or UA in target RNAs can be created by designing their substrate-binding sites to be complementary to an RNA sequence adjacent to a target site (Koizumi, M. et al., FEBS Lett., 1988, 239, 285; Koizumi, M, and Otsuka, E., Tanpakushitsu Kakusan Koso (Protein, Nucleic Acid, and Enzyme), 1990, 35, 2191; and Koizumi, M. et al., Nucl Acids Res., 1989, 17, 7059).

In addition, hairpin ribozymes are also useful for the purposes of the present invention. Such ribozymes are found in, for example, the minus strand of satellite RNAs of tobacco ring spot viruses (Buzayan, J. M., Nature, 1986, 323, 349). It has been shown that target-specific RNA-cleaving ribozymes can also be created from hairpin ribozymes (Kikuchi, Y. and Sasaki, N., Nucl Acids Res., 1991, 19, 6751; and Kikuchi, Y. Kagaku to Seibutsu (Chemistry and Biology), 1992, 30, 112). Thus, the expression of the above-described genes encoding sulfotransferases can be inhibited by using ribozymes to specifically cleave the gene transcripts.

The expression of endogenous genes can also be suppressed by RNA interference (hereinafter abbreviated as "RNAi"), using double-stranded RNAs comprising a sequence the same as or similar to a target gene sequence.

A great many disease-related genes have been rapidly identified since the entire human nucleotide sequence was revealed upon the recent completion of the genome project, and currently specific gene-targeted therapies and drugs are being actively developed. Of these, the application to gene therapy of small interfering RNAs (siRNAs), which produce the effect of specific post-transcriptional suppression, has been drawing attention.

RNAi is a phenomenon discovered by Fire et al. in 1998 (Fire, A., Nature (1998) 391: 806-811), where double strand RNA strongly suppresses expression of homologous target genes. RNAi has been drawing attention recently as a method applicable in gene therapy, because it is simpler than conventional gene transfer methods using vectors or such, and its target specificity is high. Furthermore, in mammalian cells, RNAi can be induced using short dsRNAs (siRNAs) and has many advantages: compared to knockout mice, RNAi has a stable effect, is easy to experiment with, has a low cost, and so on.

Nucleic acids with inhibitory activity based on the RNAi effect are generally referred to as siRNAs or shRNAs. RNAi is a phenomenon in which, when cells or such are introduced with short double-stranded RNAs (hereinafter abbreviated as "dsRNAs") comprising sense RNAs that have sequences homologous to the mRNAs of a target gene, and antisense RNAs that comprise sequences homologous a sequence complementary thereto, the dsRNAs bind specifically and selectively to the target gene mRNAs, induce their disruption, and cleave the target gene, thereby effectively inhibiting (suppressing) target gene expression. For example, when dsRNAs are introduced into cells, the expression of genes with sequences homologous to the RNAs is suppressed (the genes are knocked down). As described above, RNAi can suppress the expression of target genes, and is thus drawing attention as a method applicable to gene therapy, or as a simple gene knockout method replacing conventional methods of gene disruption, which are based on complicated and inefficient homologous recombination.

In the present invention, the RNAs to be used in RNAi are not necessarily perfectly identical to the genes or portions thereof that encode an above-described sulfotransferase; however, the RNAs are preferably perfectly homologous to the genes or portions thereof. Furthermore, the terminal portion may include an overhang of about two bases.

The targets of the siRNAs to be designed are not particularly limited, as long as they are genes encoding an above-described sulfotransferase. Any region of the gene can be a candidate for a target.

For example, siRNAs may be prepared based on a nucleotide sequence of C4ST-1 gene (SEQ ID NO: 6), C4ST-2 gene (SEQ ID NO: 8), C4ST-3 gene (SEQ ID NO: 10), and such. More specifically, partial regions of such sequences may be used as candidates for the targets. For example, siRNAs may be prepared based on portions of the nucleotide sequences of C4ST-1 gene (SEQ ID NO: 20), C4ST-2 gene (SEQ ID NO: 21), C4ST-3 gene (SEQ ID NO: 22), C6ST-1 gene (SEQ ID NO: 23), C6ST-2 gene (SEQ ID NO: 24), or such. More specifically, examples of the siRNAs also include those targeted to the DNA sequences (SEQ ID NOs: 25, 26, 35 to 50, 55 to 65, and 82 to 88) specifically shown herein.

The siRNAs can be introduced into cells by adopting methods of introducing cells with plasmid DNAs linked with siRNAs synthesized in vitro or methods that comprise annealing two RNA strands.

The two RNA molecules described above may be closed at one end or, for example, may be siRNAs with hairpin structures (shRNAs). shRNAs refer to short hairpin RNAs, which are RNA molecules with a stem-loop structure, since a portion of the single strand constitutes a strand complementary to another portion. Thus, molecules capable of forming an intramolecular RNA duplex structure are also included in the siRNAs of the present invention.

In a preferred embodiment of the present invention, the siRNAs of the present invention also include, for example, double-stranded RNAs with additions or deletions of one or a few RNAs in an siRNA which targets a specific DNA sequence (SEQ ID NOs: 25, 26, 35 to 50, 55 to 65, and 82 to 88) shown herein and which can suppress the expression of C4ST-1, C4ST-2, C4ST-3, or such via RNAi effect, as long as the double-stranded RNAs have the function of suppressing the expression of a gene encoding an above-described sulfotransferase.

The RNAs used in RNAi (siRNAs) do not need to be perfectly identical (homologous) to the genes encoding the above proteins or portions thereof; however, the RNAs are preferably perfectly identical (homologous).

Some details of the RNAi mechanism still remain unclear, but it is understood that an enzyme called "DICER" (a member of the RNase III nuclease family) is contacted with a double-stranded RNA and degrades it in to small fragments, called "small interfering RNAs" or "siRNAs". The double-stranded RNAs of the present invention that have RNAi effect include such double-stranded RNAs prior to being degraded by DICER. Specifically, since even long RNAs that have no RNAi effect when intact can be degraded into siRNAs which have RNAi effect in cells, the length of the double-stranded RNAs of the present invention is not particularly limited.

For example, long double-stranded RNAs covering the full-length or near full-length mRNA of a gene encoding an above-described sulfotransferase can be pre-digested, for example, by DICER, and then the degradation products can be used as agents of the present invention. These degradation products are expected to contain double-stranded RNA (siRNA) molecules with an RNAi effect. With this method, it is not necessary to specifically select the mRNA regions expected to have RNAi effect. In other words, it is not necessary to accurately determine regions with RNAi effect in the mRNAs of the genes described above.

The above-described "double-stranded RNAs capable of suppression via RNAi effect" can be suitably prepared by those skilled in the art based on nucleotide sequences of the above-described sulfotransferases, which are targeted by the double-stranded RNAs. For example, the double-stranded RNAs of the present invention can be prepared based on the nucleotide sequence of SEQ ID NO: 25. In other words, it is within the range of ordinary experimentation for those skilled in the art to select an arbitrary consecutive RNA region in an mRNA that is a transcript of the nucleotide sequence of SEQ ID NO: 25, and prepare double-stranded RNA corresponding to the region. Those skilled in the art can also use known methods to properly select siRNA sequences with stronger RNAi effect from the mRNA sequence, which is the transcript of the nucleotide sequence of SEQ ID NO: 25. When one of the strands is already identified, those skilled in the art can readily determine the nucleotide sequence of the other strand (complementary strand). Those skilled in the art can appropriately prepare siRNAs using a commercially available nucleic acid synthesizer. Alternatively, general custom synthesis services may be used to synthesize desired RNAs.

The siRNAs of the present invention are not necessarily single pairs of double-stranded RNAs directed to target sequences, but may be mixtures of multiple double-stranded RNAs directed to regions that cover the target sequence. Herein, those skilled in the art can appropriately prepare the siRNAs as nucleic acid mixtures matched to a target sequence by using a commercially available nucleic acid synthesizer or DICER enzyme. Meanwhile, general custom synthesis services may be used to synthesize desired RNAs. The siRNAs of the present invention include so-called "siRNA cocktails".

All nucleotides in the siRNAs of the present invention do not necessarily need to be ribonucleotides (RNAs). Specifically, one or more of the ribonucleotides constituting the siRNAs of the present invention may be replaced with corresponding deoxyribonucleotides. The term "corresponding" means that although the sugar moieties are structurally differently, the nucleotide residues (adenine, guanine, cytosine, or thymine (uracil)) are the same. For example, deoxyribonucleotides corresponding to ribonucleotides with adenine refer to deoxyribonucleotides with adenine. The term "or more" described above is not particularly limited, but preferably refers to a small number of about two to five ribonucleotides.

Furthermore, DNAs (vectors) capable of expressing the RNAs of the present invention are also included in the preferred embodiments of compounds capable of suppressing the expression of the genes encoding the above-described proteins of the present invention. The DNAs (vectors) capable of expressing the double-stranded RNAs of the present invention are, for example, DNAs structured such that a DNA encoding one strand of a double-stranded RNA and a DNA encoding the other strand of the double-stranded RNA are linked with promoters so that each DNA can be expressed. The above DNAs of the present invention can be appropriately prepared by those skilled in the art using standard genetic engineering techniques. More specifically, the expression vectors of the present invention can be prepared by adequately inserting DNAs encoding the RNAs of the present invention into various known expression vectors.

Furthermore, the expression-inhibiting substances of the present invention also include compounds that inhibit the expression of the above-described sulfotransferases by binding to an expression regulatory region of a gene encoding the above-described sulfotransferases (for example, a promoter region). Such compounds can be obtained, for example, using a fragment of a promoter DNA of the gene encoding an above-described sulfotransferase to perform screening methods using as an indicator the activity of binding to the DNA fragment. Those skilled in the art can appropriately determine whether compounds of interest inhibit the expression of the above-described genes encoding sulfotransferases by using known methods, for example, reporter assays and such.

Furthermore, DNAs (vectors) capable of expressing the above-described RNAs of the present invention are also included in preferred embodiments of the compounds capable of inhibiting the expression of a gene encoding an above-described sulfotransferase of the present invention. For example, DNAs (vectors) capable of expressing the above-described double-stranded RNAs of the present invention are structured such that a DNA encoding one strand of a double-stranded RNA and a DNA encoding the other strand of the double-stranded RNA are linked to promoters so that both can be expressed. Those skilled in the art can appropriately prepare the above-described DNAs of the present invention using standard genetic engineering techniques. More specifically, the expression vectors of the present invention can be prepared by appropriately inserting DNAs encoding the RNAs of the present invention into various known expression vectors.

Preferred embodiments of the above-described vector of the present invention include vectors expressing RNAs (siRNAs) that can suppress the expression of C4ST-1, C4ST-2, C4ST-3, or the like by the RNAi effect.

Antibodies that bind to the above-described sulfotransferases can be prepared by methods known to those skilled in the art. Polyclonal antibodies can be obtained, for example, by the following procedure: small animals such as rabbits are immunized with an above-described natural protein or a recombinant protein expressed in microorganisms as a fusion protein with GST, or a partial peptide thereof. Sera are obtained from these animals and purified by, for example, ammonium sulfate precipitation, Protein A or G column, DEAE ion exchange chromatography, affinity column coupled with the sulfotransferase described above, synthetic peptide, or such, to prepare antibodies. Monoclonal antibodies can be obtained by the following procedure: small animals such as mice are immunized with an above-described sulfotransferase, or a partial peptide thereof. Spleens are removed from the mice and crushed to isolate cells. The cells are fused with mouse myeloma cells using a reagent such as polyethylene glycol. Clones producing antibodies that bind to an above-described sulfotransferase are selected from among the resulting fused cells (hybridomas). The obtained hybridomas are then transplanted into the peritoneal cavities of mice, and ascites collected. The obtained monoclonal antibodies can be purified by, for example, ammonium sulfate precipitation, Protein A or G columns, DEAE ion exchange chromatography, affinity columns coupled with an above-described sulfotransferase, synthetic peptides, or such.

The antibodies of the present invention are not particularly limited as long as they bind to an above-described sulfotransferase of the present invention. The antibodies of the present invention may be human antibodies, humanized antibodies created by gene recombination, fragments or modified products of such antibodies, in addition to the polyclonal and monoclonal antibodies described above.

The proteins of the present invention used as sensitizing antigens to prepare antibodies are not limited in terms of the animal species from which the proteins are derived. However, the proteins are preferably derived from mammals, for example, mice and humans. Human-derived proteins are particularly preferred. The human-derived proteins can be appropriately obtained by those skilled in the art using the gene or amino acid sequences disclosed herein.

In the present invention, the proteins to be used as sensitizing antigens may be whole proteins or partial peptides thereof. Such partial peptides of the proteins include, for example, amino-terminal (N) fragments and carboxyl-terminal (C) fragments of the proteins. Herein, "antibodies" refer to antibodies that react with a full-length protein or fragment thereof.

In addition to immunizing nonhuman animals with antigens to obtain the above hybridomas, human lymphocytes, for example, EB virus-infected human lymphocytes, can be sensitized in vitro with the proteins or with cells expressing the proteins, or with lysates thereof, and the sensitized lymphocytes can be fused with human-derived myeloma cells with the ability to divide permanently, for example, U266, to obtain hybridomas that produce desired human antibodies with binding activity to the proteins.

It is expected that antibodies against the above-described sulfotransferases of the present invention exhibit the effect of inhibiting protein expression or function by binding to the proteins. When using the prepared antibodies for human administration (antibody therapy), the antibodies are preferably human or humanized antibodies in order to reduce immunogenicity.

Furthermore, in the present invention, low-molecular-weight substances (low-molecular-weight compounds) that bind to the above-described sulfotransferases are also included in the substances capable of inhibiting the function of the above-described sulfotransferases. Such low-molecular-weight substances may be natural or artificial compounds. In general, the compounds can be produced or obtained by methods known to those skilled in the art. The compounds of the present invention can also be obtained by the screening methods described below.

In addition, the substances of the present invention capable of inhibiting the expression or function of the above-described sulfotransferases include dominant-negative mutants (dominant-negative proteins) for the above-described sulfotransferases. The "dominant-negative protein mutants for the above sulfotransferases that transfer a sulfate to position 4 or 6 of N-acetylgalactosamine" refer to proteins with the function of reducing or abolishing the activity of endogenous wild-type proteins by expressing the genes encoding the sulfotransferases that transfer a sulfate to position 4 or 6 of N-acetylgalactosamine.

The inhibitors of the present invention that inhibit sulfation at position 4 or 6 of N-acetylgalactosamine have therapeutic or preventive effect for fibrogenic disorders. Therefore, in a preferred embodiment, the agents of the present invention are therapeutic or preventive agents for fibrogenic disorders.

Herein, "therapeutic or preventive" does not necessarily refer to a perfect therapeutic or preventive effect on organs or tissues with tissue fibrogenesis, and may refer to a partial effect.

The tissue fibrogenesis-suppressing agents of the present invention have the activity of suppressing fibrogenesis through inhibiting the sulfation at position 4 or 6 of N-acetylgalactosamine, which is a cause of fibrogenesis. Thus, preferred embodiments of the present invention provide, for example, therapeutic or preventive agents for tissue fibrogenic disorders which comprise as an active ingredient a tissue fibrogenesis-suppressing agent of the present invention.

The "therapeutic agents for tissue fibrogenic disorders" of the present invention can also be referred to as "improving agents for tissue fibrogenic disorders", "anti-tissue fibrogenesis agents", or the like. Meanwhile, the agents of the present invention can also be referred to as "pharmaceutical agents", "pharmaceutical compositions", "therapeutic medicines", or the like.

The "treatments" of the present invention also comprise preventive effects that can suppress the onset of fibrogenesis in advance. The treatments are not limited to those producing a complete therapeutic effect on fibrogenic organs (tissues), and the effects may be partial.

The agents of the present invention can be combined with physiologically acceptable carriers, excipients, diluents and such, and orally or parenterally administered as pharmaceutical compositions. Oral agents may be in the form of granules, powders, tablets, capsules, solutions, emulsions, suspensions, or the like. The dosage forms of parenteral agents can be selected from injections, infusions, external preparations, inhalants (nebulizers), suppositories, and the like. Injections include preparations for subcutaneous, intramuscular, intraperitoneal, intracranial, and intranasal injections, and the like. The external preparations include nasal preparations, ointments, and such. Techniques for formulating the above-described dosage forms that contain the agents of the present invention as primary ingredients are known.

For example, tablets for oral administration can be produced by compressing and shaping the agents of the present invention in combination with excipients, disintegrants, binders, lubricants, and the like. Excipients commonly used include lactose, starch, mannitol, and the like. Commonly used disintegrants include calcium carbonate, carboxymethylcellulose calcium, and the like. Binders include gum arabic, carboxymethylcellulose, and polyvinylpyrrolidone. Known lubricants include talc, magnesium stearate, and such.

Known coatings can be applied to tablets comprising the agents of the present invention to prepare enteric coated formulations or for masking. Ethylcellulose, polyoxyethylene glycol, or such can be used as a coating agent.

Meanwhile, injections can be prepared by dissolving the agents of the present invention, which are chief ingredients, together with an appropriate dispersing agent, or dissolving or dispersing the agents in a dispersion medium. Both water-based and oil-based injections can be prepared, depending on the selection of dispersion medium. When preparing water-based injections, the dispersing agent is distilled water, physiological saline, Ringer's solution or such. For oil-based injections, any of the various vegetable oils, propylene glycols, or such is used as a dispersing agent. If required, a preservative such as paraben may be added at this time. Known isotonizing agents such as sodium chloride and glucose can also be added to the injections. In addition, soothing agents such as benzalkonium chloride and procaine hydrochloride can be added.

Alternatively, the agents of the present invention can be formed into solid, liquid, or semi-solid compositions to prepare external preparations. Such solid or liquid compositions can be prepared as the same compositions as described above and then used as external preparations. The semi-solid compositions can be prepared using an appropriate solvent, to which a thickener is added if required. Water, ethyl alcohol, polyethylene glycol, and the like can be used as the solvent. Commonly used thickeners are bentonite, polyvinyl alcohol, acrylic acid, methacrylic acid, polyvinylpyrrolidone, and the like. Preservatives such as benzalkonium chloride can be added to these compositions. Alternatively, suppositories can be prepared by combining the compositions with carriers, like oil bases such as cacao butter, or aqueous gel bases such as cellulose derivatives.

When the agents of the present invention are used as gene therapy agents, the agents may be directly administered by injection, or vectors carrying the nucleic acid may be administered. Such vectors include adenovirus vectors, adeno-associated virus vectors, herpes virus vectors, vaccinia virus vectors, retroviral vectors, and lentivirus vectors. These vectors allow efficient administration.

Alternatively, the agents of the present invention can be encapsulated into phospholipid vesicles such as liposomes, and then the vesicles can be administered. Vesicles carrying siRNAs or shRNAs are introduced into given cells by lipofection. The resulting cells are then systemically administered, for example, intravenously or intra-arterially. The cells can also be locally administered into tissues or such with fibrogenesis. siRNAs exhibit a quite superior and specific post-transcriptional suppression effect in vitro; however, in vivo they are rapidly degraded due to serum nuclease activity, and thus, their time was limited. There is therefore demand for the development of optimized and effective delivery systems. As one example, Ochiya et al. have reported that atelocollagen, a bio-affinity material, is a highly suitable siRNA carrier because it has the activity of protecting nucleic acids from nucleases in the body when mixed with the nucleic acids to form a complex (Ochiya, T. et al., Nat. Med., 1999, 5, 707-710; Ochiya, T. et al., Curr. Gene Ther., 2001, 1, 31-52); however, the methods for introducing drugs of the present invention are not limited thereto.

The agents of the present invention are administered to mammals including humans at required (effective) doses, within a dose range considered to be safe. Ultimately, the doses of the agents of the present invention can be appropriately determined by medical practitioners or veterinarians after considering the dosage form and administration method, and the patient's age and weight, symptoms, and the like. For example, adenoviruses are administered once a day at a dose of about $10^6$ to $10^{13}$ viruses every one to eight weeks, although the doses vary depending on the age, sex, symptoms, administration route, administration frequency, and dosage form.

Commercially available gene transfer kits (for example: AdenoExpress™, Clontech) may be used to introduce siRNAs or shRNAs into target tissues or organs.

Diseases to be treated or prevented by the agents of the present invention is not particularly limited as long as they are caused by tissue fibrogenesis, but preferably include, cardiac disorders, intestinal diseases, liver diseases, hepatic disorders, kidney disorders, cranial nerve diseases, eye disorders, pancreas disorders.

The "diseases caused by fibrogenesis" in the present invention is not particularly limited, and specifically include, for example, elastosis, scleroderma, chronic peritonitis, and retroperitoneal fibrosis in integumentary and epithelial tissues such as skin;

polymyositis, dermatomyositis, polyarteritis nodosa, soft tissue fibrosis, chronic rheumatoid arthritis, palmar fibromatosis, tendinitis, tenovaginitis, Achilles tendinitis, mycetoma pedis, and such in supportive tissues such as connective tissues and muscles;

myelofibrosis, hypersplenism, vasculitis, bradyarrhythmia, arteriosclerosis, obstructive thrombotic angiitis, nodular fibrosis, angina pectoris, dilated congestive cardiomyopathy, heart failure, restrictive cardiomyopathy, diffuse nonobstructive cardiomyopathy, obstructive cardiomyopathy, cor pulmonale, mitral stenosis, aortic valve stenosis, chronic pericarditis, endocardial fibrosis, endomyocardial fibrosis, and such in blood tissues and vascular system such as bone marrow and heart;

chronic pancreatitis, Crohn's disease, ulcerative colitis, alcoholic hepatitis, chronic hepatitis B, chronic hepatitis C, Wilson's disease, cirrhosis, viral hepatitis, Gaucher's disease, glycogen storage disease, alpha 1-antitrypsin deficiency, hemochromatosis, tyrosinemia, levulosemia, galactosemia, Zellweger syndrome, congenital hepatic fibrosis, portal hypertension, hepatic granulomatosis, Budd-Chiari syndrome, primary sclerosing cholangitis, fatty liver, nonalcoholic hepatitis, hepatic fibrosis, congenital hepatic fibrosis, alcoholic cirrhosis, viral cirrhosis, parasitic cirrhosis, toxic cirrhosis, trophopathic cirrhosis, congestive cirrhosis, hepatic sclerosis, Charcot's cirrhosis, Todd's cirrhosis, secondary biliary cirrhosis, unilobar cirrhosis, cirrhosis resulting from chronic nonsuppurative destructive cholangitis, obstructive cirrhosis, cholangiolitic cirrhosis, biliary cirrhosis, atrophic cirrhosis, postnecrotic cirrhosis, posthepatitic cirrhosis, nodular cirrhosis of the liver, mixed cirrhosis, micronodular cirrhosis, compensatory cirrhosis, decompensated cirrhosis, macronodular cirrhosis, septal cirrhosis, cryptogenic cirrhosis, periportal cirrhosis, portal cirrhosis, primary biliary cirrhosis, and such in the gastrointestinal system such as liver;

coccidioidomycosis, blastomycosis, allergic bronchopulmonary aspergillosis, Goodpasture's syndrome, pulmonary fibrosis associated with adult respiratory distress syndrome, chronic obstructive pulmonary disease, pulmonary atelectasis, pneumonia, chalicosis, asbestosis, hypersensitivity pneumonitis, lymphocytic interstitial pneumonia, Langerhans-cell granulomatosis, cystic fibrosis, pustular fibrosis, pulmonary fibrosis, idiopathic pulmonary fibrosis, fibrosing pulmonary alveolitis, interstitial fibrosis, diffuse pulmonary fibrosis, chronic interstitial pneumonia, bronchiectasis, bronchiolar fibrosis, peribronchial fibrosis, pleural fibrosis, and such in the respiratory system such as lung;

male hypogonadism, myotonic dystrophy, fibrosis such as associated with Peyronie's disease, chronic tubulointerstitial nephritis, autosomal recessive cystic kidney, myeloma kidney, hydronephrosis, rapidly progressive glomerulonephritis, nephrotoxic diseases, xanthogranulomatous pyelonephritis, sickle cell nephropathy, nephrogenic diabetes insipidus, autosomal dominant polycystic kidney disease, chronic glomerular nephritis, IgA nephropathy, renal sclerosis, focal glomerulosclerosis, membranous nephritis, membranoproliferative glomerulonephritis, chronic pyelonephritis, renal amyloidosis, polycystic kidney disease, retroperitoneal fibrosis, pathology in the kidney associated with a connective tissue disease such as lupus nephritis, diabetic nephropathy, chronic prostatitis, and urocystitis associated with schistosomiasis in the urogenital system such as kidney;

fibrotic breast disease, mammary fibroadenoma, and such;

congenital torticollis, ankylosing spondylitis, spinal cord disorders such as neurofibroma and neurological dysfunction after spinal cord injury, and cranial nerve diseases such as Parkinson's disease and Alzheimer's disease in the nervous system such as spinal cord;

retrolental fibrosis and proliferative retinopathy in the eyeball; and sarcoidosis that develops systemic involvement, fibrosis and systemic scleroderma associated with systemic lupus erythematosus, polymyositis, dermatomyositis, and such. However, in the present invention, the "disease caused by fibrogenesis" is not limited thereto, and includes diseases caused by fibrosis in each body tissue such as skin and organs.

The present invention also relates to methods of screening for agents for suppressing tissue fibrogenesis (herein sometimes referred to as "methods of the present invention"), which use as an indicator the degree of sulfation at position 4 or 6 of N-acetylgalactosamine.

A preferred embodiment of methods of the present invention is the methods comprising the step of selecting compounds that inhibit the sulfation at position 4 or 6 of N-acetylgalactosamine that constitute sugar chains.

Using the screening methods of the present invention, tissue fibrogenesis-suppressing agents or candidate compounds for agents for treating or preventing fibrogenic disorders can be efficiently acquired.

Preferred embodiments of the screening methods of the present invention are methods of screening for tissue fibrogenesis-suppressing agents that comprise the steps of (a) to (c):

(a) contacting test compounds with N-acetylgalactosamines or sugar chain having N-acetylgalactosamines;
(b) measuring a degree of sulfation at position 4 or 6 of N-acetylgalactosamines; and
(c) selecting compounds that reduce the degree of sulfation as compared with those without contacting with the test compounds.

Embodiments of the screening methods of the present invention are exemplified below. In the embodiments described below, N-acetylgalactosamines, sulfotransferases, desulfates, or such to be used include those derived from humans, mice, rats, and others, but are not particularly limited thereto.

The test compounds to be used in the embodiments described below are not particularly limited, but include, for example, single compounds, such as natural compounds, organic compounds, inorganic compounds, proteins, and peptides, as well as compound libraries, expression products of gene libraries, cell extracts, cell culture supernatants, products of fermenting microorganisms, extracts of marine organisms, and plant extracts.

In the methods of the present invention, the "contact" with test compounds is typically achieved by mixing the test compounds with N-acetylgalactosamines, sulfotransferases, or desulfates, but the "contact" is not limited to this methods. For example, the "contact" can also be achieved by contacting test compounds with cells expressing these proteins or portions thereof.

In the embodiments described below, the "cells" include those derived from humans, mice, rats, and such, but are not limited thereto. Cells of microorganisms, such as *Escherichia coli* and yeasts, which are transformed to express the proteins used in each embodiment, can also be used. For example, the "cells that express genes encoding sulfotransferases that transfer a sulfate to position 4 or 6 of N-acetylgalactosamine" include cells that express endogenous genes encoding sulfotransferases that transfer a sulfate to position 4 or 6 of N-acetylgalactosamine, or cells that express introduced foreign genes encoding sulfotransferases that transfer a sulfate to position 4 or 6 of N-acetylgalactosamine. Such cells that express foreign genes encoding sulfotransferases that transfer a sulfate to position 4 or 6 of N-acetylgalactosamine can typically be prepared by introducing host cells with expression vectors carrying a gene encoding a sulfotransferase that transfers a sulfate to position 4 or 6 of N-acetylgalactosamine as an insert. The expression vectors can be prepared using standard genetic engineering techniques.

In addition, the degree of sulfation in the methods of the present invention can be determined by methods known to those skilled in the art. For example, the degree of sulfation can be determined by measuring the amount of label using a labeled compound, antibody, or such that binds to a sulfated structure at position 4 or 6 of N-acetylgalactosamine, or a portion thereof. Alternatively, the degree of sulfation can be detected by chromatography, mass spectrometry, or the like.

Those skilled in the art can appropriately evaluate the degree of sulfation at position 4 or 6 of N-acetylgalactosamine, for example, by the following known methods:

(1) method based on quantitative dye binding using a labeling dye (1-9-dimethylene blue) (Nature. 1998 Feb. 26; 391 (6670): 908-11)
(2) method based on photo-affinity labeling using [$^{32}$P] 3',5'-ABP (Mandon, E. C., Milla, M. E., Kempner, E., and Hirschberg, C. B. (1994) Proc. Natl. Acad. Sci. USA, 91, 10707-10711)
(3) method based on photo-affinity labeling using 3'-[$^{32}$P]-β methyleneb PAPS (Ozeran, J. D., Wesley, J., and Schwarz, N. B. (1996) Biochemistry, 35, 3695-3703)
(4) method using anion exchange resins (method for isolating sulfated glycoproteins) (Vol. 16, No. 2 (19860430) pp. 69-72, Kitasato University, ISSN: 03855449)
(5) colorimetric staining of sGAG with Alcian blue (Anal Biochem. 1998 Feb. 15; 256(2): 229-37)

Furthermore, those skilled in the art can readily evaluate by the above-listed methods or the like whether a substance is an inhibitor of sulfation at position 4 or 6 of N-acetylgalactosamine of the present invention.

Another embodiment of screening methods of the present invention includes the methods comprising the step of selecting substances (compounds) which reduce the activity of sulfotransferases that transfer a sulfate to position 4 or 6 of N-acetylgalactosamine.

The above-described methods of the present invention comprise, for example, the steps of:

(a) contacting a test compound with sulfotransferases that transfer a sulfate to position 4 or 6 of N-acetylgalactosamine;

(b) measuring the sulfotransferase activity of the enzymes; and (c) selecting a compound that reduces the activity as compared to when the test compound is not contacted.

In the above-described methods, first, a test compound is contacted with a sulfotransferase that transfers a sulfate to position 4 or 6 of N-acetylgalactosamine.

Then, the sulfotransferase activity of the enzyme is measured. Next, a compound that reduces the activity as compared to without contact with the test compound is selected. Such a compound that reduces the activity can be used as a fibrogenesis inhibitor or a therapeutic agent for fibrogenic disorders.

Methods that enable evaluation (determination) of whether a test compound has the above-described sulfotransferase activity include, for example, the methods described below.

Various test compounds are mixed during a set period of culture of cells or cell lines that promote the sulfation at position 4 or 6 of N-acetylgalactosamine, and the degree of sulfation before and after the culture can be easily determined by, for example, using an antibody that recognizes sulfation at position 4 (clone: LY111, 2H6) or an antibody that recognizes sulfation at position 6 (clone: MC21C, M0225, and CS-56) (all from Seikagaku Co.). Fluorescence values may be compared between before and after the culture by using fluorescently labeled antibodies. Alternatively, the same detection method can be conducted using 2-B-6 or 3-B-3 antibodies before and after culture. Compounds that suppress an increase in the sulfation after cell culture (an increase in the fluorescence value for LY111 or MC21C), or compounds that promote the progression of desulfation after cell culture (an increase in the fluorescence value for 2-B-6 or 3-B-3) can be selected as a desired candidate compound in the methods of the present invention.

As a further option, cell lines that constitutively express sulfotransferase genes such as C4ST-1 and C6ST-1 can be prepared by introducing the genes into CHO cells, L cells, or such by well-known methods. The use of such cell lines that constitutively add sulfate groups allows a more clear determination of candidates for therapeutic compounds.

Another preferred embodiment of the screening methods for a tissue fibrogenesis inhibitor of present invention includes methods comprising the step of selecting compounds that reduce the expression of N-acetylgalactosamine sulfotransferase genes of the present invention.

The Above Methods of the Present Invention Comprise, for Example, the Steps of (a) contacting a test compound with cells expressing genes encoding sulfotransferases that transfer a sulfate to position 4 or 6 of N-acetylgalactosamine;

(b) measuring the gene expression level of the cells; and (c) selecting a compound that reduces the gene expression level as compared to when the test compound is not contacted.

In the above methods, test compounds are first contacted with cells expressing a gene encoding a sulfotransferase that transfers a sulfate to position 4 or 6 of N-acetylgalactosamine.

Next, the expression level of the gene encoding the sulfotransferases that transfer a sulfate to position 4 or 6 of N-acetylgalactosamine is measured. Herein, "expression of the gene" includes both transcription and translation. Gene expression level can be measured by methods known to those skilled in the art.

For example, mRNAs are extracted from cells expressing any one of the above-described proteins by conventional methods, and these mRNAs can be used as templates in Northern hybridization, RT-PCR, DNA arrays, or such to measure the transcription level of the gene. Alternatively, protein fractions are collected from cells expressing a gene encoding any of the above-described proteins, and expression of the protein can be detected by electrophoresis such as SDS-PAGE to measure the level of gene translation. Alternatively, the level of gene translation can be measured by detecting the expression of any of the above-described proteins by Western blotting using an antibody against the proteins. Such antibodies for use in detecting the proteins are not particularly limited, as long as they are detectable. For example, both monoclonal and polyclonal antibodies can be used.

Next, the expression level is compared with that in the absence of the test compounds (the control).

Then, compounds that reduce (suppress) the expression level of the gene as compared to when the test compounds are absent are selected. The compounds resulting in a reduction (suppression) can be agents for suppressing tissue fibrogenesis or candidate compounds for treating fibrogenic disorders.

Furthermore, an embodiment of the screening methods of the present invention includes methods of selecting the present invention's compounds that reduce the expression level of a gene encoding a sulfotransferase that transfers a sulfate to position 4 or 6 of N-acetylgalactosamine, using as an indicator, the amount (level) of reporter gene expression. The above-described methods comprise, for example, the steps of:

(a) contacting a test compound with cells or cell extracts containing a DNA structured such that a reporter gene is operably linked to a transcriptional regulatory region of a gene encoding a sulfotransferase that transfer a sulfate to position 4 or 6 of N-acetylgalactosamine;

(b) measuring the expression amount (level) of the reporter gene; and (c) selecting a compound that reduces the expression amount (level) of the reporter gene as compared to when the test compound is not contacted.

In the above methods, test compounds are first contacted with cells or cell extracts containing DNAs structured such that a reporter gene is operably linked with a transcriptional regulatory region of a gene encoding a sulfotransferase that transfers a sulfate to position 4 or 6 of N-acetylgalactosamine.

Herein, "operably linked" means that a reporter gene is linked with a transcriptional regulatory region of a gene encoding a sulfotransferase that transfers a sulfate to position 4 or 6 of N-acetylgalactosamine, such that expression of the reporter gene is induced upon binding of transcriptional factors to the transcriptional regulatory region. Therefore, the meaning of "operably linked" also includes cases where a reporter gene is linked with a different gene and produces a fusion protein with a different gene product, as long as expression of the fusion protein is induced upon the binding of transcriptional factors to the transcriptional regulatory region of the gene encoding the sulfotransferase that transfers a sulfate to position 4 or 6 of N-acetylgalactosamine. Those skilled in the art can obtain the transcriptional regulatory regions of genes encoding sulfotransferases that transfer a sulfate to position 4 or 6 of N-acetylgalactosamine that are present in the genome, based on the cDNA nucleotide sequences of the genes encoding the sulfotransferases that transfer a sulfate to position 4 or 6 of N-acetylgalactosamine.

The reporter genes for use in these methods are not particularly limited, as long as their expression is detectable. The reporter genes include, for example, the CAT gene, the lacZ gene, the luciferase gene, and the GFP gene. The "cells containing a DNA structured such that a reporter gene is operably linked with a transcriptional regulatory region of a gene encoding a sulfotransferase that transfers a sulfate to position 4 or 6 of N-acetylgalactosamine" include, for example, cells introduced with vectors carrying such structures as inserts. Such vectors can be prepared by methods well known to those skilled in the art. The vectors can be introduced into cells by standard methods, for example, calcium phosphate precipitation, electroporation, lipofection, and microinjection. The "cells containing a DNA structured such that a reporter gene is operably linked with a transcriptional regulatory region of a gene encoding a sulfotransferase that transfers a sulfate to position 4 or 6 of N-acetylgalactosamine" include cells in which the structure has been integrated into the chromosomes. A DNA structure can be integrated into chromosomes by methods generally used by those skilled in the art, for example, gene transfer methods using homologous recombination.

The "cell extracts containing a DNA structured such that a reporter gene is operably linked with a transcriptional regulatory region of a gene encoding a sulfotransferase that transfers a sulfate to position 4 or 6 of N-acetylgalactosamine" include, for example, mixtures of cell extracts included in commercially available in vitro transcription-translation kits and DNAs structured such that a reporter gene is operably linked with the transcriptional regulatory region of the gene encoding a sulfotransferase that transfers a sulfate to position 4 or 6 of N-acetylgalactosamine.

"Contact" can be achieved by adding test compounds to a culture medium of "cells containing a DNA structured such that a reporter gene is operably linked with a transcriptional regulatory region of a gene encoding a sulfotransferase that transfers a sulfate to position 4 or 6 of N-acetylgalactosamine", or by adding test compounds to the above-described commercially available cell extracts containing the DNAs. When the test compound is a protein, contact may also be achieved, for example, by introducing a DNA vector expressing the protein into the cells.

In the above methods, the expression level of the reporter gene is then measured. The expression level of the reporter gene can be measured by methods known to those skilled in the art, depending on the type of the reporter gene. When the reporter gene is the CAT gene, its expression can be determined, for example, by detecting the acetylation of chloramphenicol by the gene product. When the reporter gene is the lacZ gene, its expression level can be determined by detecting the color development of chromogenic compounds due to the catalytic action of the gene expression product. Alternatively, when the reporter gene is the luciferase gene, its expression level can be determined by detecting the fluorescence of fluorogenic compounds due to the catalytic action of the gene expression product. Furthermore, when the reporter gene is the GFP gene, its expression level can be determined by detecting the fluorescence of the GFP protein.

In the above methods, the expression amount (level) of the reporter gene is then compared with that in the absence of the test compounds (the control). Compounds that reduce (suppress) the expression level of the reporter gene as compared with a control are then selected, where the reporter gene is operably linked with a gene encoding a sulfotransferase that transfers a sulfate to position 4 or 6 of N-acetylgalactosamine. Compounds resulting in a reduction (suppression) can be agents for suppressing tissue fibrogenesis or candidate compounds for treating fibrogenic disorders.

The tissue fibrogenesis inhibitors that are found by the screening methods of the present invention are preferably therapeutic or preventive agents for fibrogenic disorders.

The present invention also provides methods of producing pharmaceutical compositions for treating or preventing fibrogenic disorders. The above-described production methods of the present invention comprise, for example, the steps of (a) selecting a tissue fibrogenesis inhibitor from test samples by the above-described methods of screening for tissue fibrogenesis inhibitors; and (b) combining the agent with a pharmaceutically acceptable carrier.

In these methods, first, a tissue fibrogenesis inhibitor is selected from test samples by the above-described methods of screening for tissue fibrogenesis inhibitors.

Then, the selected agent is combined with a pharmaceutically acceptable carrier. The pharmaceutically acceptable carrier includes, for example, those described above.

The present invention also provides kits comprising various agents, reagents, and the like, which are used to conduct the screening methods of the present invention.

The kits of the present invention can be prepared, for example, by selecting adequate reagents from the above-described various reagents, depending on the screening method to be conducted. The kits of the present invention may contain, for example, the sulfotransferases that transfer a sulfate to position 4 or 6 of N-acetylgalactosamine of the present invention. The kits of the present invention may further contain various reagents, vessels, and the like to be used in the methods of the present invention. The kits may appropriately contain, for example, antibodies, probes, various reaction reagents, cells, culture media, control samples, buffers, and instruction manuals containing a description of how to use the kits.

The present invention also provides therapeutic or preventive methods for fibrogenic disorders, which comprise the step of administering the agents of the present invention to individuals (for example, to patients and such).

The individuals subjected to the therapeutic or preventive methods of the present invention are not particularly limited, as long as they are organisms that can develop a fibrogenic disorder; however, humans are preferred.

In general, administration to individuals can be achieved, for example, by methods known to those skilled in the art, such as intraarterial injections, intravenous injections, and subcutaneous injections. The administered dose varies depending on the patient's weight and age, and the administration method or such; however, those skilled in the art (medical practitioners, veterinarians, pharmacists, and the like) can appropriately select a suitable dose.

The present invention also relates to the uses of agents of the present invention in producing tissue fibrogenesis inhibitors.

All prior art documents cited in this specification are incorporated herein by reference.

EXAMPLES

Herein below, the present invention will be specifically described with reference to Examples, but the technical scope of the present invention is not to be construed as being limited thereto.

Herein, occasionally, an siRNA structure (sequence) is presented by showing a DNA region of a target gene. Those skilled in the art can readily understand the structure of an siRNA comprising double-stranded RNA corresponding to the DNA sequence based on the information of DNA sequence described as a target sequence.

[Cardiac Tissue]

[Example 1] Assessment of the Target Sugar Chain-Related Gene Knockdown Effect of siRNAs and Anti-Fibrogenic Effect at the Gene Level in a Mouse Cardiomyopathy Model A model prepared by intraperitoneal administration of Doxorubicin hydrochloride (DOX; Kyowa Hakko), as a standard mouse cardiomyopathy model, was used in this Example and those below. This mouse model is classical, but highly reproducible and simple. Thus, the model has been widely used as a cardiomyopathy model for elucidating pathological conditions, experimenting new therapeutics, or such (Longhu Li, Circulation (2006) 113: 535-543; Xiaoming Yi, Am J Physiol Heart Circ Physiol (2006) 290: H1098-H1102; Kang Y J, J Biol Chem. 2000 May 5; 275(18): 13690-8; Nozaki N, Circulation (2004) 110: 2869-2874; Fisher P W, Circulation (2005) 111: 1601-1610).

The model mouse histologically develops fibrogenesis of the myocardial interstitium. This pathological findings is commonly observed in dilated cardiomyopathy, restrictive cardiomyopathy, hypertrophic cardiomyopathy, and arrhythmogenic right ventricular cardiomyopathy (ARVC), as well as left ventricular remodeling after acute myocardial infarction, stable angina pectoris, unstable angina pectoris, myocarditis, valvular heart disease, arrhythmia, or hypertension. The fibrogenesis is a pathological feature responsible for the myocardial dysfunction in chronic heart failure caused by the above-listed diseases (Jugdutt B I, Circulation. 108: 1395-1403, 2003).

First, the method of preparing the mouse model is described below. DOX (15 mg/kg; Kyowa Hakko) is administered to the peritoneal cavities of C57BL6/J mice (male, eight weeks old, CLEA Japan Inc.). The mice were reared for one week after administration, and then heart tissues were collected from them. As a control group, similar mice were also purchased and reared around the same time without DOX administration.

The GalNac4S-6ST siRNA agent was administered by the following procedure: 1 μg of GalNac4S-6ST siRNA (Hokkaido System Science, Co., Ltd.) was combined with 200 μl of 1% atelocollagen (Koken Co.) as a vehicle, and the mixture was intraperitoneally administered to each mouse 24 hours before DOX administration. The nucleotide sequence of the GalNac4S-6ST siRNA agent used in this Example is shown below, but the sequence is not limited to this Example.

[human GalNac4S-6ST siRNA](Gene Bank accession number NM_015892)

(Hokkaido System Science, Co., Ltd.)

```
                              (SEQ ID NO: 25)
5'-ggagcagagcaagaugaauacaauc-ag-3'

                              (SEQ ID NO: 26)
3'-ua-ccucgucucguucuacuuauguuag-5'
```

1 ml of RNA iso (TAKARA BIO INC.) was added to 50 mg each of organs (heart) excised from cardiomyopathy model mouse. The organs were crushed using an electrical homogenizer (DIGITAL HOMOGENIZER; AS ONE), then, 200 μl of chloroform (Sigma-Aldrich Japan) was added to the resulting suspension. The mixture was gently mixed and then cooled on ice for about five minutes, and centrifuged in a centrifuge (Centrifuge 5417R; Eppendorf) at 12,000 rpm and 4° C. for 15 minutes. After centrifugation, 500 μl of the supernatant was transferred to a fresh Eppendorf tube, and an equal volume of isopropanol (500 μl; Sigma-Aldrich Japan) was added thereto. The solution was mixed, and then 1 μl of glycogen (Invitrogen) was added thereto. The mixture was cooled on ice for 15 minutes, and then centrifuged at 12,000 rpm and 4° C. for 15 minutes. Next, RNA precipitate obtained after washing three times with 1,000 μl of 75% ethanol (Sigma-Aldrich Japan) was air-dried for 30 minutes to one hour, and then dissolved in Otsuka distilled water (Otsuka Pharmaceutical Co., Ltd). The solution was 100 times diluted with Otsuka distilled water. The RNA concentrations of extracted samples in UV plates (Corning Costar) were determined using a plate reader (POWER Wave XS; BIO-TEK).

Next, reverse transcription reaction (cDNA synthesis) is conducted by the following procedure. The concentrations of the obtained RNA samples were adjusted to 500 ng/20 μl. The samples were heated at 68° C. for three minutes in a BLOCK INCUBATOR (ASTEC), and cooled on ice for ten minutes. After cooling on ice, 80 μl of RT PreMix solution (composition: 18.64 μl of 25 mM $MgCl_2$ (Invitrogen), 20 μl of 5× Buffer (Invitrogen), 6.6 μl of 0.1 M DTT (Invitrogen), 10 μl of 10 mM dNTP mix (Invitrogen), 2 μl of RNase Inhibitor (Invitrogen), 1.2 μl of MMLV Reverse Transcriptase (Invitrogen), 2 μl of Random primer (Invitrogen), and 19.56 μl of sterile distilled water (Otsuka distilled water; Otsuka Pharmaceutical Co., Ltd.)), which had been prepared in advance, was added to the samples. The mixtures were heated in a BLOCK INCUBATOR (ASTEC) at 42° C. for one hour and at 99° C. for five minutes, and then cooled on ice. 100 μl of desired cDNAs were prepared and quantitative PCR reaction was carried out using the prepared cDNAs in the following composition. For quantitative PCR, SYBR Premix Kit (TAKARA BIO INC.) and Real-time PCR thermal cycler DICE (TAKARA BIO INC.) were used. Conditions of PCR reaction was: 95° C. for 10 seconds, 40 cycles of 95° C. for 5 seconds and 60° C. for 30 seconds, finally, melting curve analysis was conducted. Nucleotide sequences of primers used in the quantitative PCR were described below.

[Quantitative PCR Primer Sequences]

*mouse GalNAc4S-6ST (TAKARA BIO INC.)

```
Forward:
                              (SEQ ID NO: 27)
5'-GTGAGTTCTGCTGCGGTCCA-3'

Reverse:
                              (SEQ ID NO: 28)
5'-AGTCCATGCTGATGCCCAGAG-3'
```

*mouse procollagen Type 1 alpha 2 (TAKARA BIO INC.)

```
Forward:
                              (SEQ ID NO: 29)
5'-ACCCGATGGCAACAATGGA-3'

Reverse:
                              (SEQ ID NO: 30)
5'-ACCAGCAGGGCCTTGTTCAC-3'
```

*mouse α-SMA (TAKARA BIO INC.)

```
Forward:
                                (SEQ ID NO: 31)
5'-CATCCGTAAAGACCTCTATGCCAAC-3'

Reverse:
                                (SEQ ID NO: 32)
5'-ATGGAGCCACCGATCCACA-3'
```

*mouse rRibosome 18S (TAKARA BIO INC.)

```
Forward:
                                (SEQ ID NO: 33)
5'-TTCTGGCCAACGGTCTAGACAAC-3'

Reverse:
                                (SEQ ID NO: 34)
5'-CCAGTGGTCTTGGTGTGCTGA-3'
```

Figure 2:
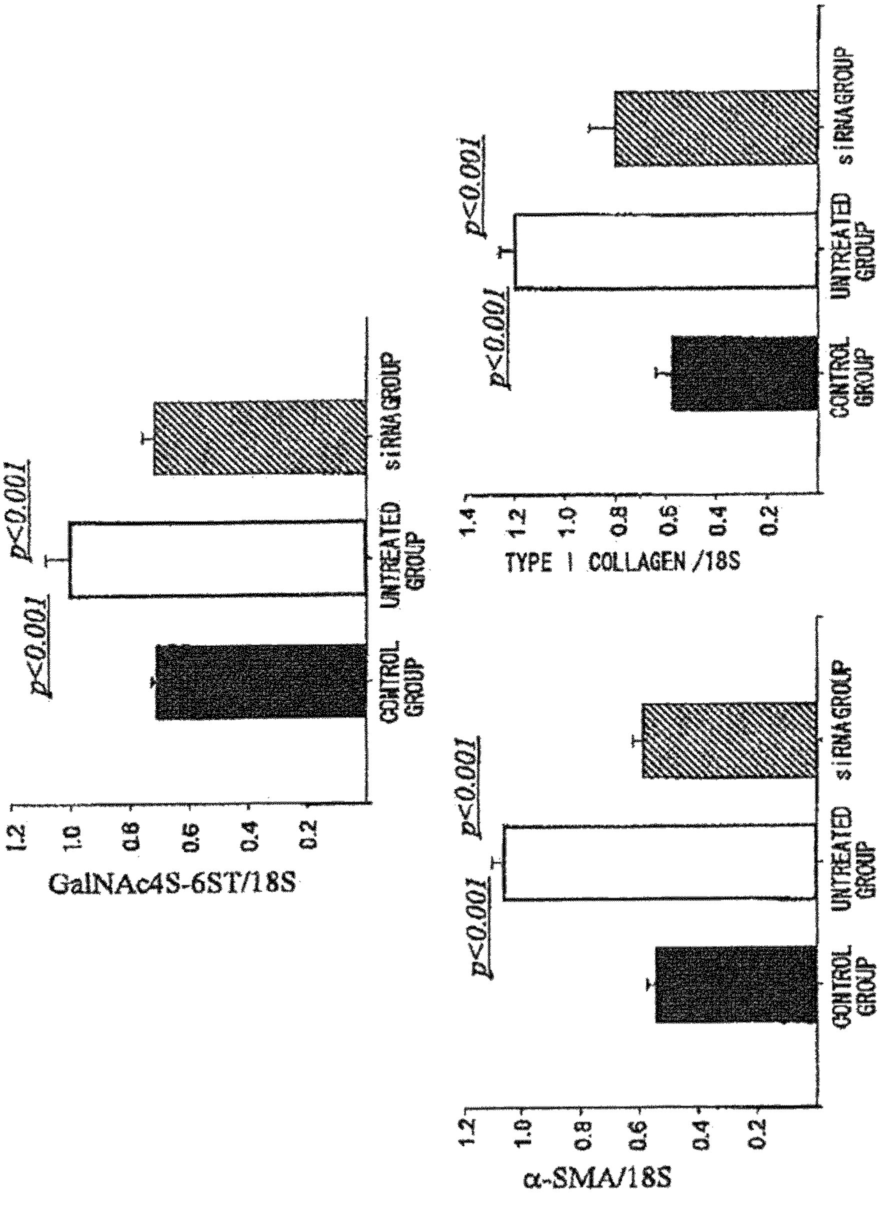
FIG. 2 shows the result analyzing the heart weight/body weight ratio of cardiomyopathy model mice in which cardiomyopathy was induced by intraperitoneal administration of Doxorubicin hydrochloride (DOX; Kyowa Hakko). $*P<0.05$ (t-test)

As shown in FIG. 2, the expressions of GalNAc4S-6ST, type I collagen, and α-SMA genes were determined, and the result showed that the expression of GalNac4S-6ST was significantly suppressed in the GalNAc4S-6ST siRNA-treated group as compared to the untreated group ($P<0.001$; when compared to the untreated group). Furthermore, the expressions of α-SMA and type I collagen genes were measured as indicators for fibrogenesis, which is an important pathological condition of cardiomyopathy. As a result, the significant reduction of expression were confirmed in the GalNAc4S-6ST siRNA-treated group as compared to the untreated group ($P<0.001$; when compared to the untreated group). This result demonstrates that the target knockdown effect of the GalNAc4S-6ST siRNA results in suppression of the progression of myocardial fibrogenesis at the gene expression level.

The agents of the present invention are thus useful, for example, as myocardial fibrogenesis inhibitors.

[Example 2] Cardiac Hypertrophy-Suppressing Effect of GalNAc4S-6ST siRNA in a Mouse Cardiomyopathy Model In this Example, the heart weights (mg) and body weights (g) of cardiomyopathy model mice were measured to calculate the heart/body weight ratio which is an indicator for cardiac hypertrophy. The cardiac hypertrophy-suppressing effect of the GalNAc4S-6ST (GalNac) siRNA was evaluated. Cardiac hypertrophy also serves as an indicator for tissue fibrotic change.

Figure 1:
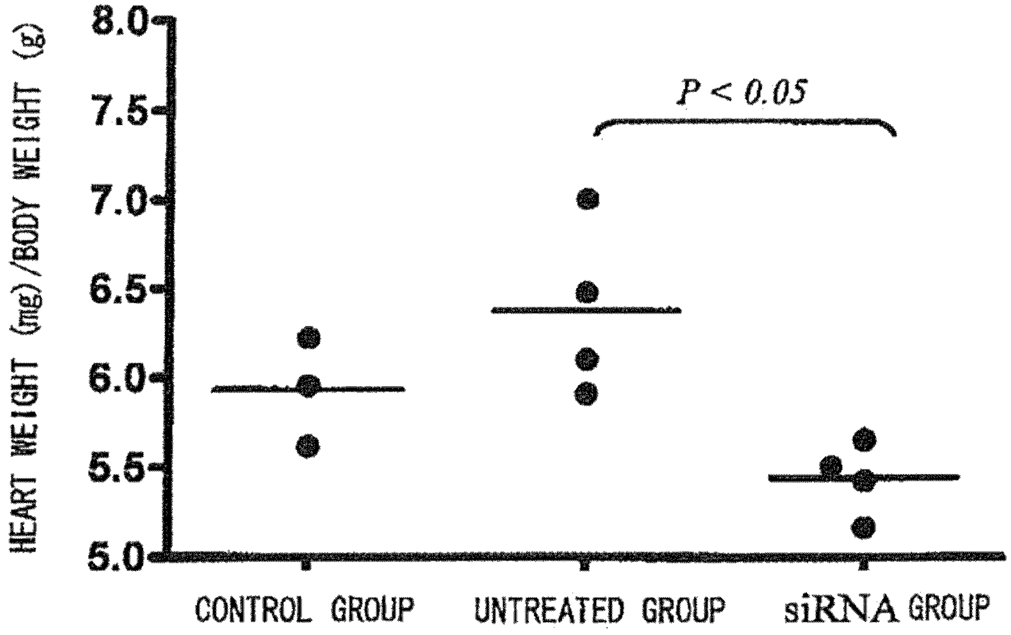
FIG. 1 shows the result of quantitative reverse transcription PCR method for gene expressions of cardiomyopathy model mice in which cardiomyopathy was induced by intratracheal administration of DOX. The examined items were GalNAc4S-6ST as an siRNA target gene, and α-SMA and type I collagen, both of which are fibrogenesis markers. The graph indicates relative ratios between a target gene and a house keeping gene (ribosome 18S). $*P<0.001$ (t-test)

FIG. 1 shows the result of calculating the heart weight (mg)/body weight (g) ratios in the siRNA-treated group (n=4) and untreated group (n=4). The result showed that the ratio was 6.376±0.484 and 5.442±0.203 in the untreated and siRNA-treated groups, respectively. Thus, the significant reduction of the ratio was found in the siRNA-treated group as compared to the untreated group ($p<0.05$; t-test). This suggests that GalNac4S-6ST siRNA has the effect of suppressing pathological cardiac hypertrophy.

The agents of the present invention are thus useful, for example, as cardiac hypertrophy-suppressing agents (therapeutic agents for cardiac hypertrophy).

[Example 3] Assessment of Type I Collagen Deposition-Suppressing Effect of GalNAc4S-6ST siRNA in a Mouse Cardiomyopathy Model In this Example, the type I collagen deposition (an indicator of fibrogenesis)-suppressing effect of GalNac4S-6ST siRNA was assessed using heart samples of cardiomyopathy model mice. Cardiac tissue samples were collected from the same mice as described in Example 1, and embedded in OCT compound (Miles), an embedding medium for cryo-sectioning. The samples were sliced into thin sections using Cryostat (Carl Zeiss). The resulting sections were fixed with acetone (Sigma Aldrich Japan) for ten minutes, and then washed with phosphate buffer. A rabbit antiserum anti-type I collagen (rabbit polyclonal antibody, 1:2,000 dilution; LSL) was added as the primary antibody, and the sections were incubated at room temperature for one hour. Then, a peroxidase-labeled goat anti-rabbit IgG antibody (1:200 dilution; Cappel) was added as the secondary antibody, and the sections were incubated at room temperature for 30 minutes. After incubation, DAB substrate (Nichirei) was added to the samples. The samples were observed under a light microscope (Leica Microsystems).

Figure 3:
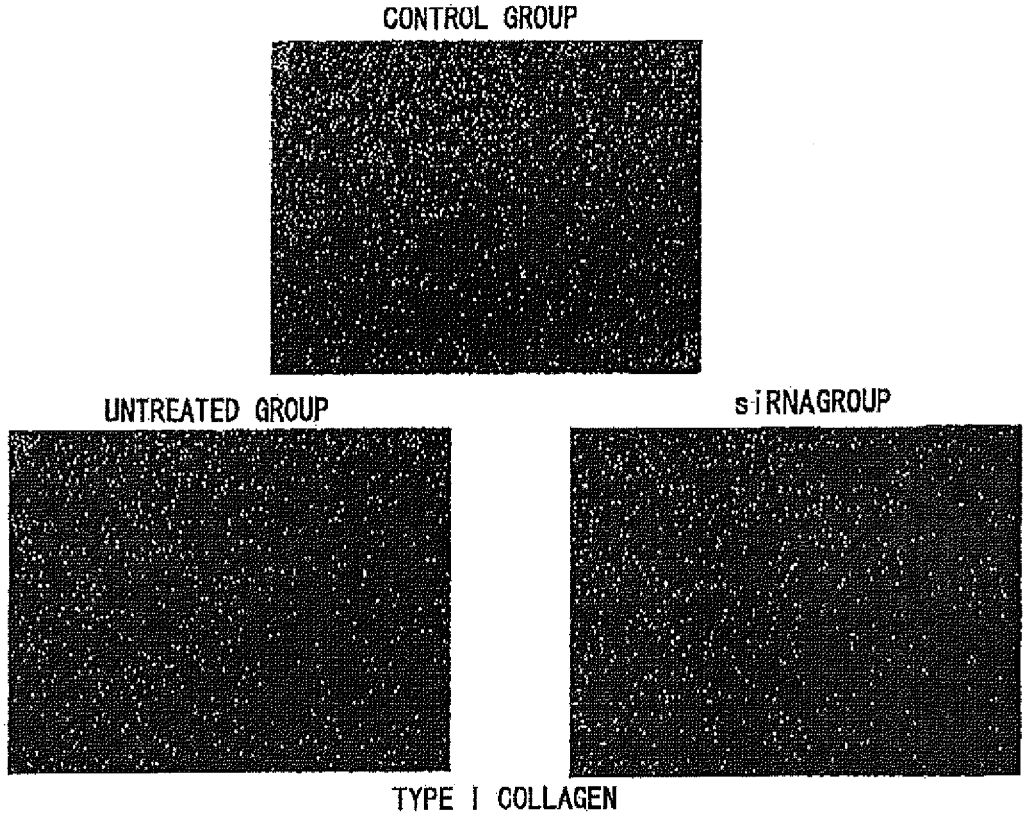
FIG. 3 depicts photographs showing histological observations indicating the suppressive effect on type I collagen deposition in an siRNA-treated group of cardiomyopathy model mice in which cardiomyopathy was induced by intratracheal administration of DOX. The magnification is 100 fold.

The histological findings were shown in FIG. 3. Very intense positive signals for type I collagen were observed between myocardial fibers in the untreated group. Meanwhile, in the siRNA-treated group, the type I collagen-positive signals were considerably weaker than those of the untreated group. The above-described type I collagen immunostaining result demonstrates that the GalNac4S-6ST siRNA has the effect of suppressing the excessive deposition of type I collagen in myocardial tissues. This result correlates with the result of quantitative PCR described in Example 1.

The agents of the present invention are thus useful, for example, as agents for suppressing type I collagen deposition in myocardial tissues.

[Example 4] Assessment of Type III Collagen Deposition-Suppressing Effect of GalNAc4S-6ST siRNA in a Mouse Cardiomyopathy Model In this Example, the type III collagen deposition (an indicator of fibrogenesis activity)-suppressing effect of GalNac4S-6ST siRNA was assessed using heart samples of cardiomyopathy model mice. Tissue sections obtained by the same method as described in Example 3 were fixed with acetone (Sigma Aldrich Japan) for ten minutes, and then washed with phosphate buffer. A rabbit antiserum anti-type III collagen (rabbit polyclonal antibody, 1:2000 dilution; LSL) was added as the primary antibody, and the sections were incubated at room temperature for one hour. Then, a peroxidase-labeled goat anti-rabbit IgG antibody (1:200 dilution; Cappel) was added as the secondary antibody, and the sections were incubated at room temperature for 30 minutes. After incubation, DAB substrate (Nichirei) was added to the samples. The samples were observed under a light microscope (Leica Microsystems).

Figure 4:
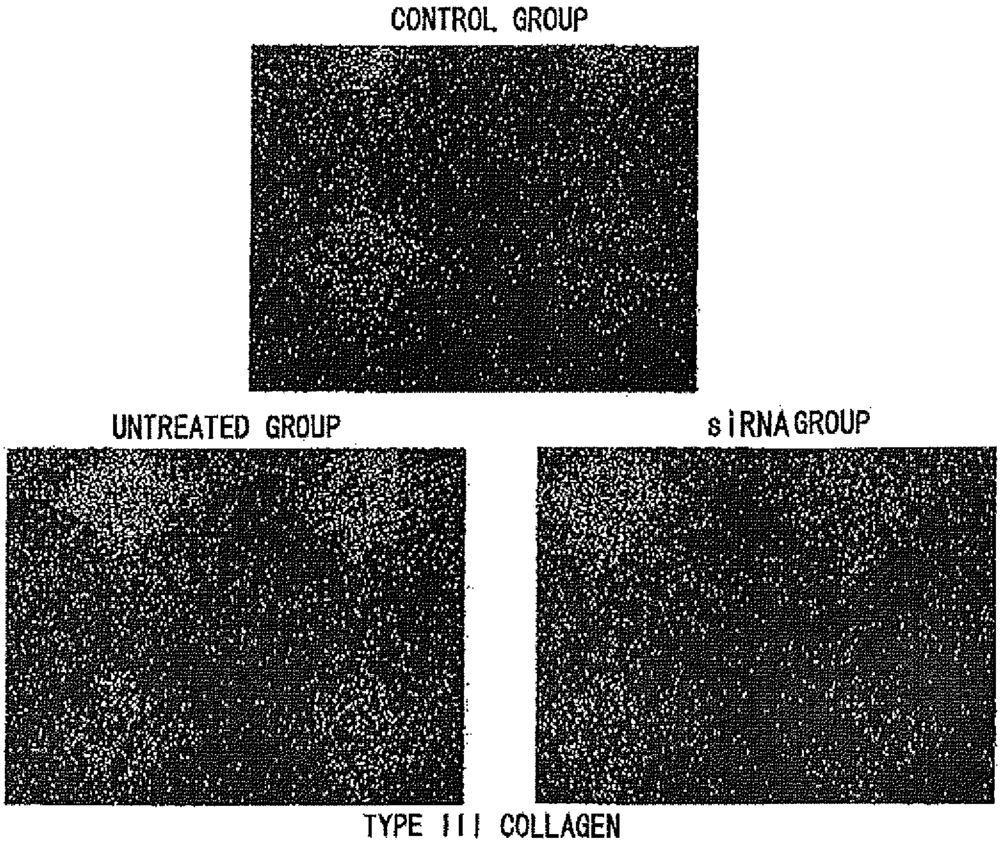
FIG. 4 depicts photographs showing histological observations indicating the suppressive effect on type III collagen deposition in an siRNA-treated group of cardiomyopathy model mice in which cardiomyopathy was induced by intratracheal administration of DOX. The magnification is 100 fold.

The histological findings are shown in FIG. 4. Moderately strong positive signals for type III collagen were observed between myocardial fibers in the untreated group. Meanwhile, in the siRNA-treated group, the type III collagen-positive signals were comparable to those of the control group. The above-described result of type III collagen immunostaining demonstrates that the GalNac4S-6ST siRNA has the effect of suppressing the type III collagen deposition in heart tissues, implying that the siRNA is also effective in suppressing active collagen deposition.

The agents of the present invention are thus useful, for example, as agents for suppressing type III collagen deposition in myocardial tissues.

[Example 5] Assessment of Fibroblast Infiltration-Suppressing Effect of GalNAc4S-6ST siRNA in a Mouse Cardiomyopathy Model This Example assesses the pharmacological effect of GalNAc4S-6ST siRNA on the kinetics of fibroblasts that infiltrate into cardiac tissues of cardiomyopathy model mice due to DOX administration. Tissue sections obtained by the same method as described in Example 3 were fixed with acetone (Sigma Aldrich Japan) for ten minutes, and then washed with phosphate buffer. An anti-mouse fibroblast antibody (ER-TR7, rat monoclonal antibody, 1:400 dilution; BMA Biomedicals Ltd.) was added as the primary antibody, and the sections were incubated at room temperature for one hour. Then, a peroxidase-labeled goat anti-rat immunoglobulin antibody (1:200 dilution; Biosource International, Inc.) was added as the secondary antibody, and the sections were incubated at room temperature for 30 minutes. After incubation, DAB substrate (Nichirei Biosciences) was added to the samples. The samples were observed under a light microscope (Leica Microsystems).

Figure 5:
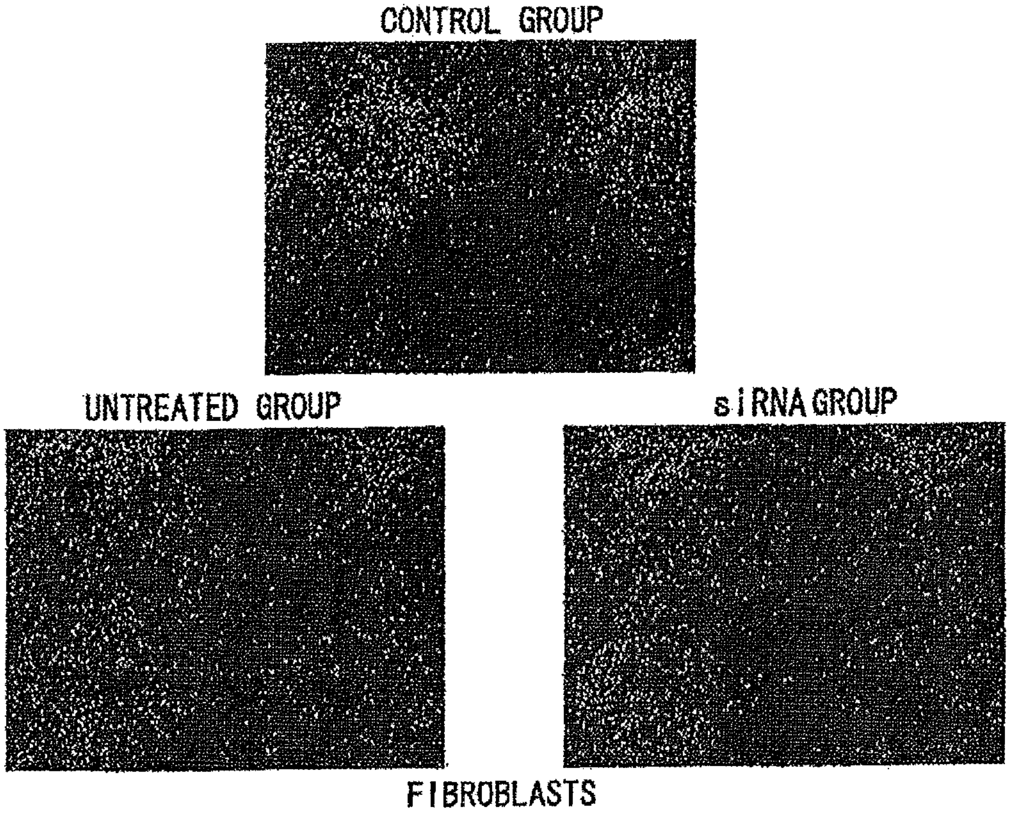
FIG. 5 depicts photographs showing the suppressive effect on fibroblast accumulation in an siRNA-treated group of cardiomyopathy model mice in which cardiomyopathy was induced by intratracheal administration of DOX. The magnification is 50 fold.

The histological findings were shown in FIG. 5. The photograph focuses on the ventricular septum. Infiltration of numerous fibroblasts was observed in the untreated group as compared to the control group. In contrast, the degree of fibroblast infiltration in the siRNA-treated group was less as compared to the untreated group. The above-described result shows that GalNac4S-6ST siRNA has the pharmacological effect of suppressing the fibroblast infiltration into myocardial tissues and this activity contributes to the anti-fibrogenic effect.

The agents of the present invention are thus useful, for example, as agents for suppressing fibroblast infiltration into myocardial tissues.

[Gastrointestinal Tissue]

[Example 6] Clinical Fibrogenesis-Suppressing Effect of GalNAc4S-6ST in a Mouse Intestinal Fibrosis Model The colitis model mice were prepared by allowing C57BL/6J mice (female, six weeks old; CLEA Japan Inc.) to freely drink high-concentration chlorine water containing 3% dextran sulfate sodium (DSS; Wako Pure Chemical Industries Ltd.) for eight days. The DSS-induced colitis model has excellent reproducibility, and is thus widely used as a typical experimental mouse model for inflammatory bowel diseases such as ulcerative colitis or Crohn's disease, as well as a model with full-thickness inflammation and fibrotic changes, and muscle layer thickening, which are histological characteristics of the narrowing of colon lumen (Sasaki N, J Inflamm. 2005 2: 13, Review: Pucilowska J B et al. Am J Physiol Gastroenterol Liver Physiol. 279: G653-G659, 2000). Therefore, the histological findings are commonly and widely observed in inflammatory bowel diseases as well as pathological conditions with the histological narrowing of the intestinal lumen, specifically diseases such as intestinal Behcet's disease (simple ulcer), irritable bowel syndrome, ischemic enteritis, drug-induced enteritis, radiation enteritis, esophagus achalasia, esophago stenosis associated with scleroderma, narrowing of the colon lumen associated with systemic lupus erythematosus (SLE), Hirschsprung's disease, stenosis after removal of intestine (postoperative stricture), narrowing of the intestinal lumen after endoscopic mucosal resection for gastrointestinal cancer (tongue cancer, epipharynx carcinoma, pharyngeal cancer, esophageal cancer, stomach cancer, small intestinal cancer, colon cancer, and rectal cancer), and ileus.

Simultaneously to feeding mice with 3% DSS water, the same GalNAc4S-6ST siRNA (1 μg/head) as described in Example 1 was combined with atelocollagen (Koken Co.) prediluted 10-fold with PBS and 200 μl of the mixture was injected to the peritoneal cavities of the mice. The group of mice treated as described above was named "GalNAc4S-6ST siRNA group", while a group treated with atelocollagen alone without combining GalNAc4S-6ST siRNA was named the "control group". The body weight and the disease activity index (DAI) score were recorded during seven days of 3% DSS water feeding (Kihara M., Gut. 2003, 52, 713-9). The evaluation criteria for DAI are shown below.

TABLE 1

| Index | Weight loss | Stool consistency | Fecal blood |
|---|---|---|---|
| 0 | None | Normal | Normal |
| 1 | 1-5% | | Hem occult (+) |
| 2 | 5-10% | Loose stools | Hem occult (++) |
| 3 | 10-20% | | Hem occult (+++) |
| 4 | >20% | Diarrhea | Gross bleeding |

Figure 6:
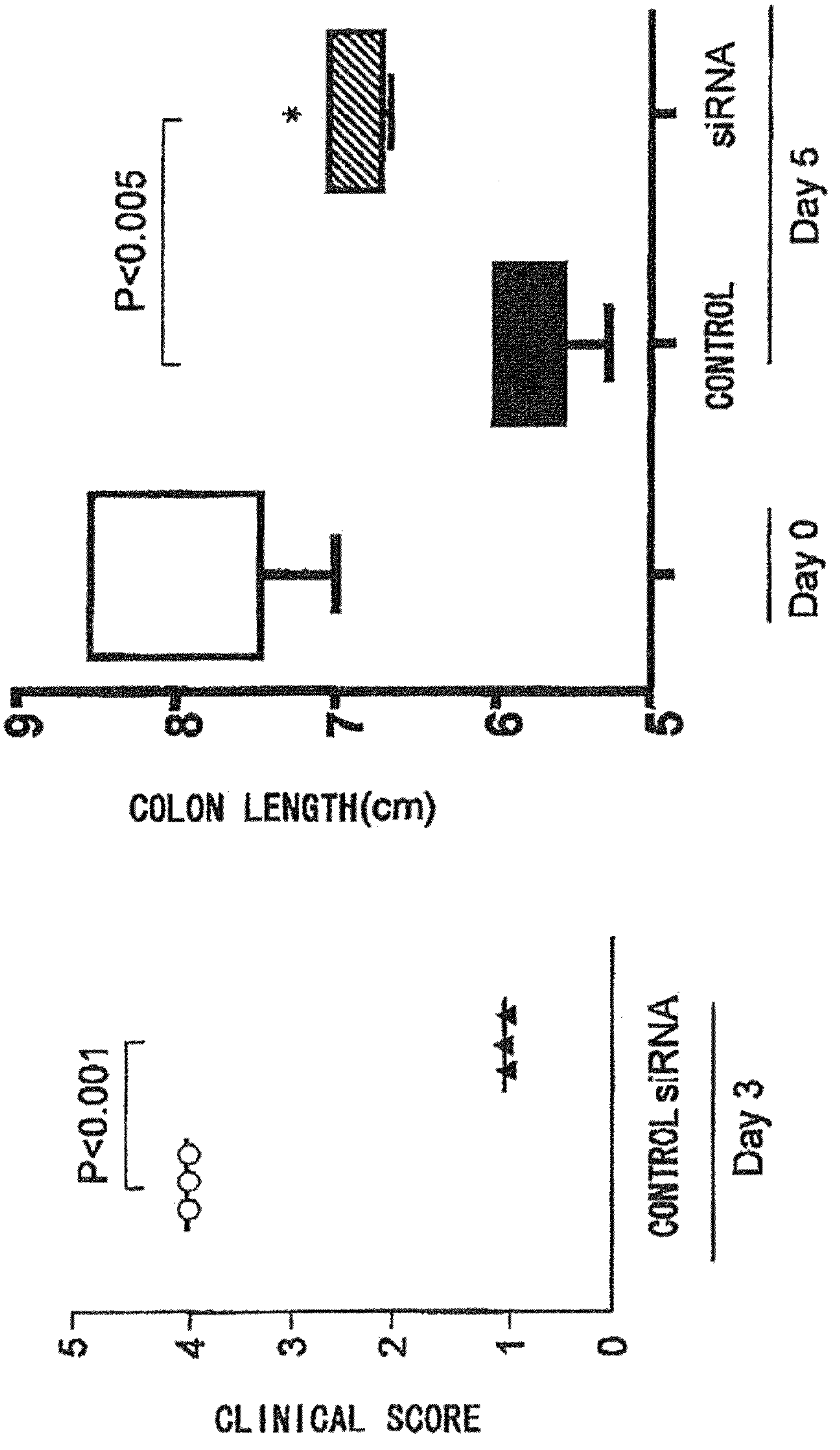
FIG. 6 depicts graphs showing clinical features of a mouse intestinal fibrogenesis model, in which intestinal fibrogenesis was induced by DSS. The administration of GalNAc4S-6ST siRNA resulted in significant reduction of clinical score (left) and colon shortening (right).

The result of scoring the DAI of each mouse, setting the score on the first day of DSS water feeding (day 0) as 1, is shown in FIG. 6. On the third day, the GalNAc4S-6ST siRNA-administered group exhibited a significantly lower score as compared to the control group ($p<0.001$; t-test). This result suggests that suppression of GalNAc4S-6ST gene expression produces the effect of suppressing inflammatory activity at relatively earlier stages.

Furthermore, the mice were sacrificed and their colon lengths were measured on the fifth day. The colon shortening was significantly suppressed in the GalNAc4S-6ST siRNA-administered group ($p<0.005$; t-test) (FIG. 6). The colon length is a definitive indicator that reflects intestinal fibrogenesis or stenosis. Thus, it was also clinically demonstrated that the fibrotic change of intestine was suppressed in the GalNAc4S-6ST siRNA-administered group.

The agents of the present invention are thus useful, for example, as agents for suppressing fibrotic changes of the intestine.

[Example 7] Intestinal Fibrogenesis-Suppressing Effect of GalNAc4S-6ST siRNA in a Mouse Intestinal Fibrosis Model In this Example, the expression of fibrogenesis-related genes in the colon after GalNAc4S-6ST siRNA administration was assessed by the quantitative real-time PCR method.

The intestinal fibrogenesis model was prepared by the same method as described in Example 6. The mice were sacrificed on day 7. A part of the collected colon was placed in 1.5-ml tubes, and frozen with liquid nitrogen. cDNA was synthesized by the same method as that described in Example 1, and quantitative PCR was carried out. The primer sequences and the number of PCR cycle conditions were the same as those described in Example 1.

Figure 7:
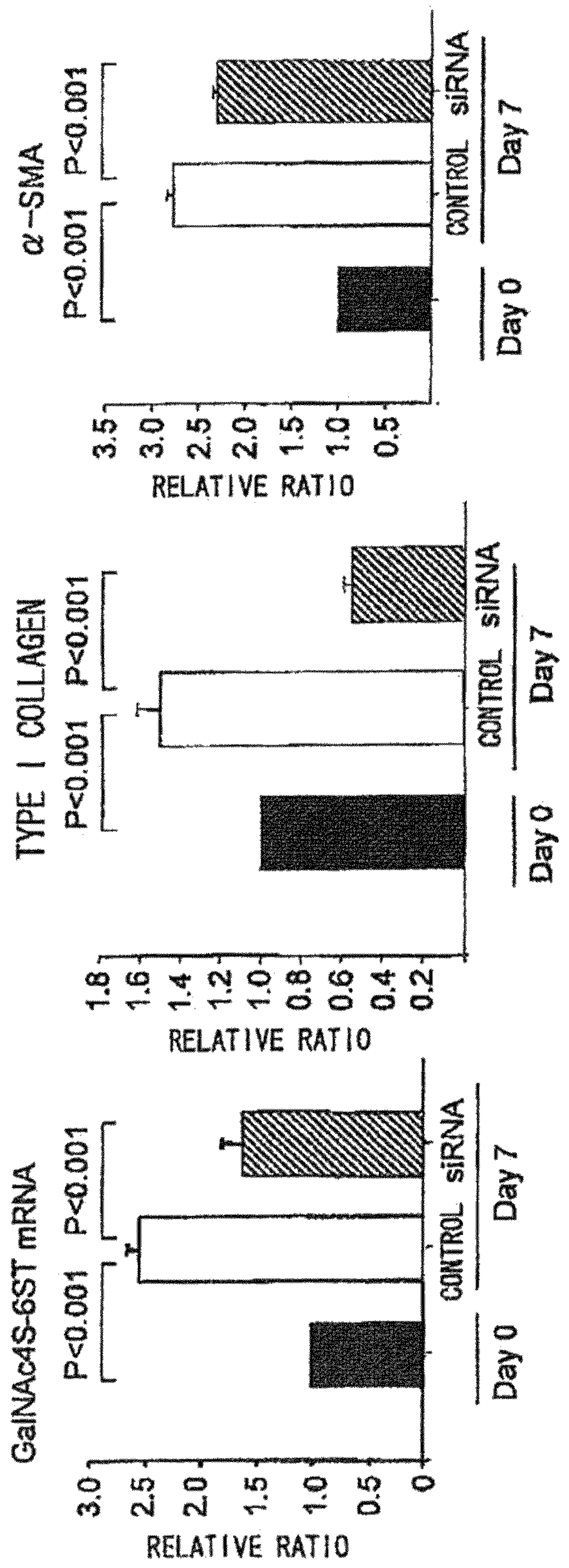
FIG. 7 depicts graphs showing the expression of fibrogenesis-related genes in a mouse intestinal fibrogenesis model. GalNAc4S-6ST, and α-SMA and type I collagen, both of which are fibrogenesis markers, were assessed for the expression in colonic tissue. The graphs indicate relative ratios between a target gene and a house keeping gene (ribosome 18S). The enhanced expression of type I collagen (left, bottom) and α-SMA (right, bottom) is significantly suppressed due to the silencing effect of GalNAc4S-6ST siRNA (upper).

The result is shown in FIG. 7. The expression of GalNAc4S-6ST gene was enhanced in this model. The significant knockdown of the gene was confirmed by GalNAc4S-6ST siRNA treatment ($p<0.001$; t-test). Furthermore, the enhanced expression of type I collagen and α-SMA as indicators of fibrogenesis were significantly suppressed by GalNAc4S-6ST siRNA (for both genes, $p<0.001$; t-test). The result suggests that the enhanced fibrotic changes of the colon can be effectively suppressed by suppressing the expression of GalNAc4S-6ST.

The agents of the present invention are thus useful, for example, as agents for suppressing the fibrotic changes of the colon.

Figure 8:
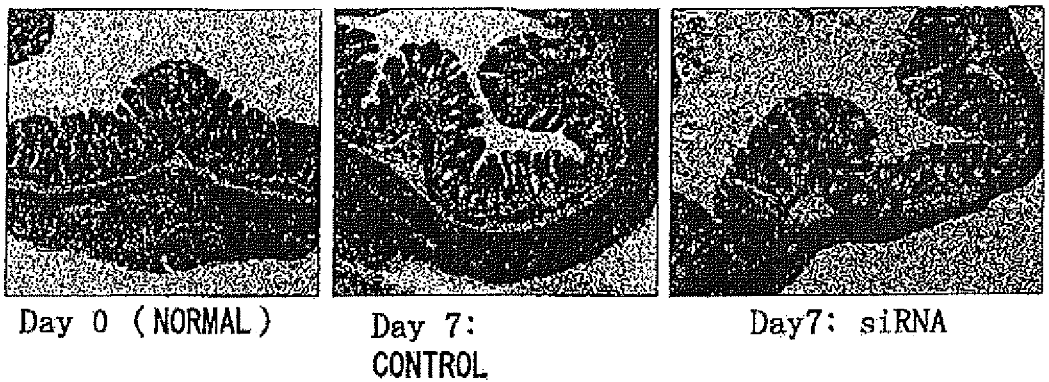
FIG. 8 depicts photographs showing collagen deposition in a mouse intestinal fibrogenesis model. Images of Masson-stained colonic tissues. The magnification is 100 fold. GalNAc4S-6ST siRNA reduces the collagen deposition in tissues.

[Example 8] Tissue Fibrogenesis-Suppressing Effect of GalNAc4S-6ST siRNA in a Mouse Intestinal Fibrosis Model The intestinal fibrogenesis model was prepared by the same method as described in Example 6. The mice were sacrificed on day 7. Cryoblocks and tissue sections were prepared from the collected colon by the same method as described in Example 3. Masson-stained images of colonic tissue sections are shown in FIG. 8. Masson staining serves as an indicator to assess fibrotic change of tissues by visualizing collagen fibers. In the GalNAc4S-6ST siRNA-administered group, the full-thickness (lamina propria mucosae, submucosa, and muscle layer) collagen fiber deposition was significantly suppressed as compared to the control group.

The agents of the present invention are thus useful, for example, as agents for suppressing the full-thickness (lamina propria mucosae, submucosa, and muscle layer) collagen fiber deposition.

[Example 9] Histological Fibroblast Infiltration-Suppressing Effect of GalNAc4S-6ST siRNA in a Mouse Intestinal Fibrosis Model The intestinal fibrogenesis model was prepared by the same method as described in Example 6. The mice were sacrificed on day 7. Cryoblocks and tissue sections were prepared from the collected colon by the same method as described in Example 3. The resulting sections were fixed with acetone (Wako Pure Chemical Industries) for ten minutes, and then washed with phosphate buffer. An anti-ER-TR7 antibody (rat monoclonal antibody, 1 μg/ml; BMA) was added as the primary antibody, and the sections were incubated at room temperature for one hour. Then, the secondary antibody reaction was carried out by adding a peroxidase-labeled anti-rat IgG antibody (1:200 dilution), which was followed by color development by adding DAB substrate (Nichirei Biosciences). Then, the nucleus was stained by Lillie-Mayer hematoxylin (Muto Pure Chemicals Co.). The samples were observed under a light microscope (Leica Microsystems). The antibody binding was detected by visualizing it as signals.

Figure 9:
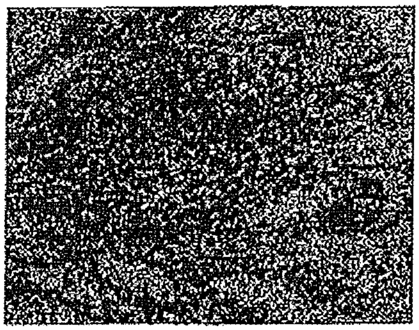
FIG. 9 depicts photographs showing fibroblast infiltration in a mouse model for intestinal fibrogenesis. Images of stained fibroblasts in colonic tissues. The magnification is 100 fold. GalNAc 4S-6ST siRNA suppresses the full-thickness infiltration of fibroblasts.
Figure 9:
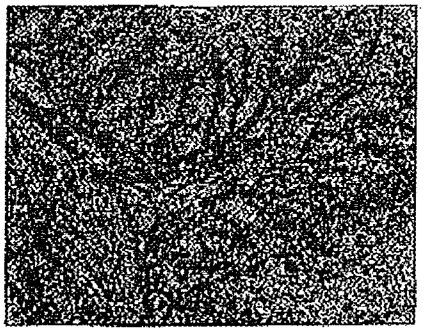

As a result, the full-thickness infiltration of fibroblasts was significantly suppressed in the GalNAc4S-6ST siRNA-treated group as compared to the control group (FIG. 9). This result demonstrates that the inhibition of GalNAc4S-6ST gene expression results in suppression of the infiltration and retention of fibroblasts in focal tissue lesion and thereby reduces the enhanced fibrotic change.

The agents of the present invention are thus useful, for example, as agents for suppressing the infiltration or retention of fibroblasts.

[Example 10] Histological Macrophage Infiltration-Suppressing Effect of GalNAc4S-6ST siRNA in a Mouse Intestinal Fibrosis Model The intestinal fibrogenesis model was prepared by the same method as described in Example 6. The mice were sacrificed on day 7. Cryoblocks and tissue sections were prepared from the collected colon by the same method as described in Example 3. The resulting sections were fixed with acetone (Wako Pure Chemical Industries) for ten minutes, and then washed with phosphate buffer. An anti-F4/80 antibody (clone A3-1, rat monoclonal antibody, 2 μg/ml: CALTAG LABORATORIES) was added as the primary antibody, and the sections were incubated at room temperature for one hour. Then, the secondary antibody reaction was carried out by adding a peroxidase-labeled anti-rat IgG antibody (1:200 dilution), which was followed by color development by adding DAB substrate (Nichirei Biosciences). Then, the nucleus was stained by Lillie-Mayer hematoxylin (Muto Pure Chemicals Co.). The samples were observed under a light microscope (Leica Microsystems). The antibody binding was detected by visualizing it as signals.

Figure 10:
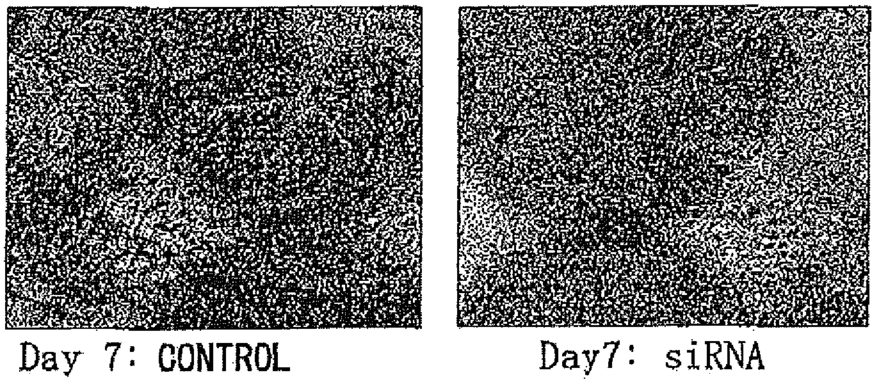
FIG. 10 depicts photographs showing images of macrophage infiltration in a mouse intestinal fibrogenesis model. Images of stained macrophages in colonic tissues. Magnification: 100×. GalNAc4S-6ST siRNA suppresses the full-thickness infiltration of macrophages.

The result showed that the full-thickness macrophage infiltration was significantly suppressed in the GalNAc4S-6ST siRNA-treated group as compared to the control group (FIG. 10). This result demonstrates that the inhibition of GalNAc4S-6ST gene expression resulted in suppression of the infiltration of macrophages and fibroblasts, which are cell groups responsible for the persistent or enhanced fibrotic changes, and thereby comprehensively suppressed the tissue fibrotic changes.

The agents of the present invention are thus useful, for example, as agents for suppressing the infiltration of macrophages or fibroblasts.

[Example 11] Histological Macrophage Infiltration-Suppressing Effect of GalNAcST siRNA in a Mouse Intestinal Fibrosis Model GalNAc4S-6ST is an enzyme that transfers a sulfate group to position 6 in N-acetylgalactosamine sulfated at position 4. GalNAc-4ST1 and GalNAc-4ST2, which belong to the 4-O-sulfotransferase family, were assessed in this Example. The intestinal fibrogenesis model was prepared by the same method as described in Example 6. The mice were sacrificed on day 7. In this Example, GalNAc4S-6ST siRNA, GalNAc4ST-1, and GalNAc4ST-2 (GeneWorld) were combined together; 1 μg of the mixture was combined with 200 μl of 1% atelocollagen (Koken Co.), which is a vehicle, and administered intraperitoneally to each mouse. A group administered with the siRNA is referred to as "GalNAc ST siRNA-administered group". The control group is the same as described in Example 6. The siRNA nucleotide sequences of GalNAc4S-6ST, GalNAc4ST-1, and GalNAc4ST-2 used in this Example are shown below, but the sequence are not limited the Example.

[GalNAc4ST-1 siRNA cocktail sequences](GenBank accession number NM_175140)

(GeneWorld)

```
                                    (SEQ ID NO: 35)
5'-ACCCCCAACTCGGAACGATGCGGCT-3'

                                    (SEQ ID NO: 36)
5'-TGCATGTTCTCGTCCATCCTGCTG-3'

                                    (SEQ ID NO: 37)
5'-CGCCACCGTGTACTGTACTGTGAAGT-3'

                                    (SEQ ID NO: 38)
5'-AGGCT GCTCCAACTG GAAGAGGGTG-3'
```

[GalNAc4ST-2 siRNA cocktail sequences](GenBank accession number NM_199055)
(GeneWorld)

(SEQ ID NO: 39)
5'-ATATAGTATCTAGGATATATGTAG-3'

(SEQ ID NO: 40)
5'-GAAGTACCAAAAGCTGGCTGCTCTA-3'

(SEQ ID NO: 41)
5'-TTCTATCACTTGGACTATTTGATGTT-3'

(SEQ ID NO: 42)
5'-TACACAACTCCACATTTGTAATTTG-3'

[GALNac4S-6ST siRNA cocktail sequences](GenBank accession number NM_029935)
(GeneWorld)

(SEQ ID NO: 43)
5'-CCAGAAGCCAAGCTCATTGTTATG-3'

(SEQ ID NO: 44)
5'-CTGTGGAGAGGTTGTACTCAGACTA-3'

(SEQ ID NO: 45)
5'-ATTTGCCTGGAAGACAACGTGAGAGC-3'

(SEQ ID NO: 46)
5'-GTCCCTTCTGCAGAAGCTGGGCCCACT-3'

Figure 11:
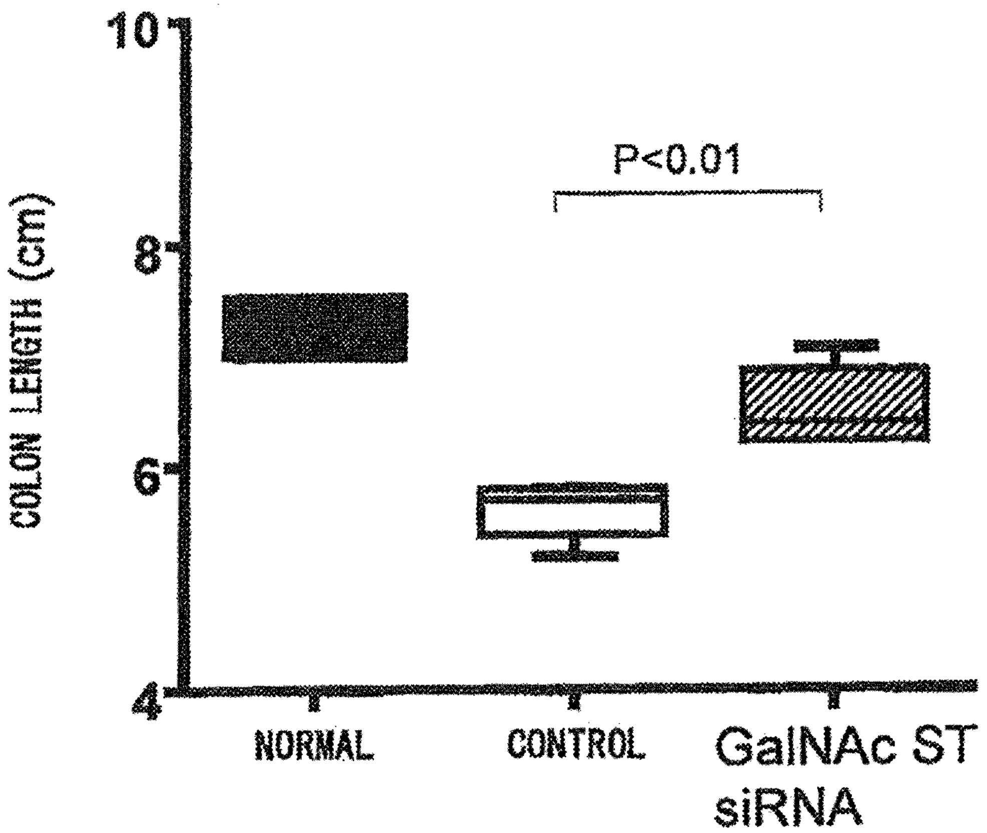
FIG. 11 depicts a graph showing colon lengths in a mouse intestinal fibrogenesis model. GalNAc4ST siRNA significantly suppresses colon shortening.

As investigated in detail in Examples 6 to 10, the tissue fibrotic changes in the mouse intestinal fibrogenesis model can be assessed representatively by the colon length. Accordingly, the colon length on day 7 is shown as an essential evaluation item in this Example. In the GalNAc ST siRNA-administered group, the shortening of colon was significantly suppressed as compared to the control group ($p<0.01$; t-test) (FIG. 11). It was thus demonstrated that the intestinal fibrogenesis was inhibited by suppressing the expression of the GalNAc4ST-1 and GalNAc4ST-2 genes.

The agents of the present invention are thus useful, for example, as intestinal fibrogenesis inhibitors.

[Lung Tissue]

[Example 12] Effect of C6ST-1 siRNA on Pulmonary Alveolar Interstitium in a Mouse Pulmonary Emphysema Model A basic mouse pulmonary emphysema model, which is prepared by intratracheal administration of porcine pancreatic elastase (PPE), is used in this Example. This mouse model is classical, but highly reproducible and simple. Thus, this mouse model has been used commonly as a pulmonary emphysema model. Inflammatory cell infiltration to the pulmonary alveolar interstitium is observed as a histological feature. This histological finding is commonly detected in chronic obstructive pulmonary disease (COPD) such as emphysema and chronic bronchitis as well as diseases causing chronic respiratory failure, such as idiopathic interstitial pneumonias (IIPs), coniosis, and pulmonary tuberculosis sequelae (Karlinsky J B et al., Am Rev Respir Dis 1978; 117: 1109-1133; Otto-Verbeme C J et al., Protective effect of pulmonary surfactant on elastase-induced emphysema in mice. Eur Respir J 1992; 5: 1223-1230; Janoff A et al., Prevention of elastase-induced experimental emphysema by oral administration of a synthetic elastase inhibitor. Am Rev Respir Dis 1980; 121: 1025-1029; Christensen T G, et al., Irreversible bronchial goblet cell metaplasia in hamsters with elastase-induced pan acinar emphysema. J Clin Invest 1977; 59: 397-404; Lucey E C, et al., Remodeling of alveolar walls after elastase treatment of hamsters: results of elastin and collagen mRNA in situ hybridization. Am J Respir Crit Care Med 1998; 158: 555-564; Snider G L, Lucey E C, Stone P J. Animal models of emphysema. Am Rev Respir Dis 1986; 133: 149-169).

In this Example, the effect of C6ST-1 siRNA in suppressing emphysematous lesions was examined by hematoxylin-eosin staining (HE staining) of lung tissue samples from pulmonary emphysema model mice.

First, the model mice were prepared. PPE (4 units; Calbiochem-Novabiochem) was administered intratracheally to C57BL6/J mice (female, 5- to 6-weeks old; CLEA Japan). The mice were grown for three weeks after administration, and then lung tissues were collected from them. Mice that did not have PPE administration were used as the control group.

The C6ST-1 siRNA was administered by the same procedure as shown in Example 1: 1 μg of C6ST-1 siRNA (Ambion) was combined with 1% atelocollagen (Koken Co.), which is an siRNA vehicle, and administered to the peritoneal cavities once a week after PPE administration. The dose was 200 μl/head.

*[C6ST-1 siRNA cocktail sequences]
(GenBank accession number NM 016803)

(SEQ ID NO: 47)
5'-gcgccccctctccccatggagaaag-3'

(SEQ ID NO: 48)
5'-gctttgcctcaggatttccgggacc-3'

(SEQ ID NO: 49)
5'-ggttcagccttggtctaccgtgatgtc-3'

(SEQ ID NO: 50)
5'-gcagttgttgctatgcgacctgtat-3'

The collected right lung tissues were embedded in the OCT compound (Miles), an embedding medium for cryosectioning, and cryoblocks were prepared using liquid nitrogen. The cryoblocks were sliced into 6-μm sections using cryostat (Microm).

The resulting sections were fixed with 1% glutaraldehyde (Nacalai Tesque) for 10 minutes, and further fixed with formol-calcium solution for 10 minutes. The sections were washed with phosphate buffer, and then stained with Lillie-Mayer's hematoxylin solution (Sigma Aldrich Japan) at room temperature for 5 minutes. The sections were washed gently with a decolorizing solution (70% ethanol containing 0.5% HCl; prepared using reagents from Nacalai Tesque), and then washed with water for 10 minutes. The sections were stained with eosin-alcohol at room temperature for 5 minutes, and then washed with water for 10 minutes. The sections were washed gently with 100% ethanol, and then allowed to stand for 3 minutes. The sections were further washed gently with xylene (Nacalai Tesque), and allowed to stand for 10 minutes. This sample was histologically observed using a light microscope (Leica Microsystems).

Figure 12:
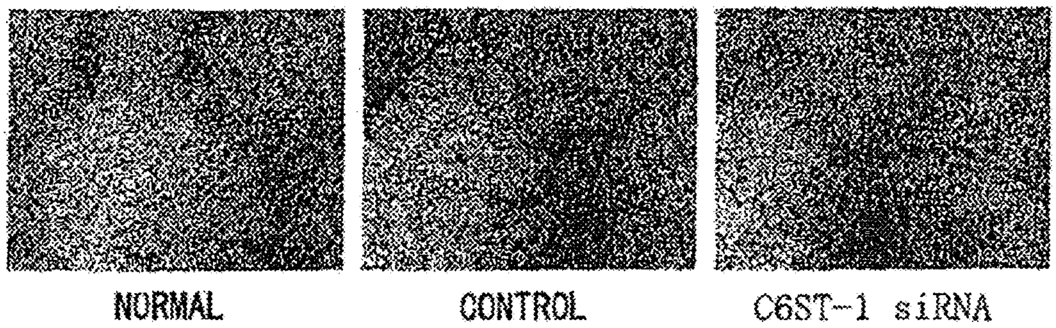
FIG. 12 depicts photographs showing clinical images of a mouse emphysema model, in which emphysema was induced by PPE. C6ST-1 siRNA administration significantly suppresses the histological disruption of the pulmonary alveolar wall. Magnification: 100×.

The obtained histological images are shown in FIG. 12. The histological features of a normal lung parenchyma with characteristic faveolate alveolar septal walls are found in the control group (PPE non-administered mice). Meanwhile, emphysematous lesions due to destruction and abolishment of alveolar septal walls and enlargement of air space (characteristics of pulmonary emphysema) can be observed in the untreated group (administered with PPE but not with C6ST-1 siRNA) shown in the middle photograph. On the other hand, in the enzyme-treated group (administered with PPE and C6ST-1 siRNA), slight abolishment of alveolar septal walls and emphysematous lesions can be observed; however, their levels are significantly improved.

[Example 13] Pulmonary Interstitial Fibrosis-Suppressing Effect of C6ST-1 siRNA in a Mouse Pulmonary Emphysema Model In this Example, the expression of fibrosis-related genes in the pulmonary alveolar interstitium after C6ST-1 siRNA administration is assessed by quantitative real-time PCR method.

The COPD model was prepared by the same method as described in Example 12. A part of the collected lung tissue were placed in 1.5-ml tubes, and frozen with liquid nitrogen. cDNA synthesis was carried out by the same method as described in Example 1, and quantitative PCR was conducted. The primer sequences for type I collagen and α-SMA and PCR conditions were also the same as described in Example 1. The sequences of C6ST-1 primers are shown below.

[Quantitative PCR Primer Sequences]

*mouse C6ST-1 (Takara Bio)

```
Forward:
                                     (SEQ ID NO: 51)
5'-TGTTCCTGGCATTTGTGGTCATA-3'

Reverse:
                                     (SEQ ID NO: 52)
5'-CCAACTC GCTCAGGGACAAGA-3'
```

Figure 13:
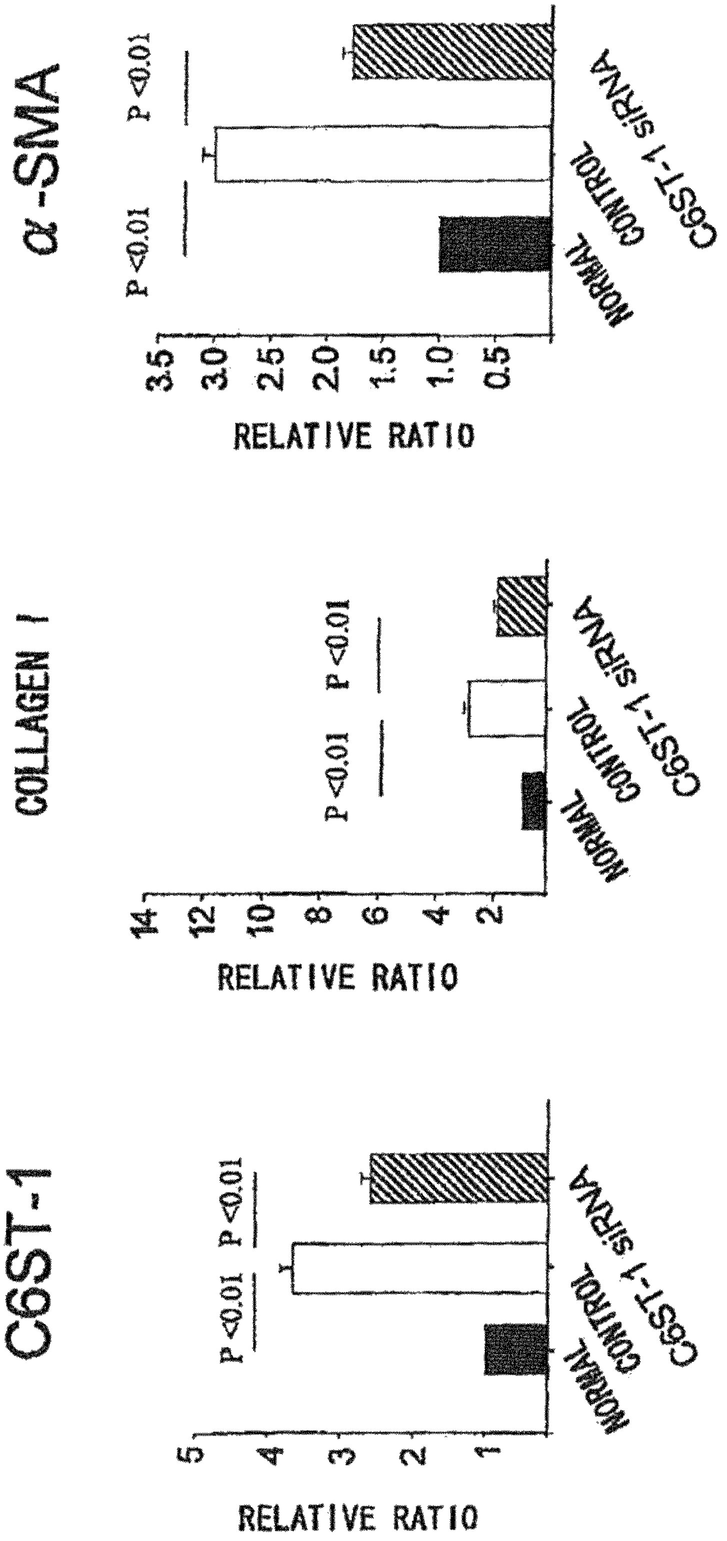
FIG. 13 depicts graphs showing the expression of fibrogenesis-related genes in a mouse emphysema model. GalNAc4S-6ST, and α-SMA and type I collagen, both of which are fibrogenesis markers, were assessed for the expression in pulmonary tissues. The graphs indicate relative ratios between a target gene and a house keeping gene (ribosome 18S). The enhanced expression of type I collagen (middle) and α-SMA (right) is significantly suppressed due to the silencing effect of C6ST-1 siRNA (left).

The result is shown in FIG. 13. The expression of C6ST-1 gene is enhanced in this model. Significant knockdown of the C6ST-1 gene was confirmed by C6ST-1 siRNA treatment ($p<0.01$; t-test). Furthermore, the enhanced expression of type I collagen and α-SMA as indicators for fibrogenesis were significantly suppressed by C6ST-1 siRNA (for both genes, $p<0.01$; t-test). This result suggests that the enhanced fibrotic changes of pulmonary interstitium can be effectively suppressed by inhibiting the expression of C6ST-1.

The agents of the present invention are thus useful, for example, as agents for suppressing fibrotic changes of the pulmonary interstitium.

[Example 14] Histological Fibroblast Cell Infiltration-Suppressing Effect of C6ST-1 siRNA in a Mouse Pulmonary Emphysema Model The intestinal fibrogenesis model was prepared by the same method as described in Example 12. Cryoblocks and tissue sections were prepared from the collected lung tissues by the same method as described in Example 3. The resulting sections were fixed with acetone (Wako Pure Chemical Industries) for ten minutes, and then washed with phosphate buffer. An anti-ER-TR7 antibody (rat monoclonal antibody, 1 μg/ml; BMA) was added as the primary antibody, and the sections were incubated at room temperature for one hour. Then, the secondary antibody reaction was carried out by adding a peroxidase-labeled anti-rat IgG antibody (1:200 dilution), which was followed by color development by adding DAB substrate (Nichirei Biosciences). Then, the nucleus was stained by Lillie-Mayer hematoxylin (Muto Pure Chemicals Co.). The samples were observed under a light microscope (Leica Microsystems). The antibody binding was detected by visualizing it as signals.

Figure 14:
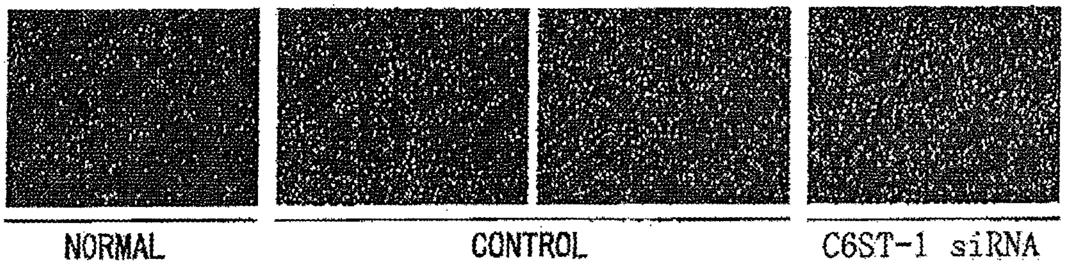
FIG. 14 depicts photographs showing fibroblast infiltration in a mouse emphysema model. Images of stained fibroblasts in pulmonary tissues. Magnification: 200×. C6ST-1 siRNA suppresses fibroblast infiltration into the pulmonary alveolar interstitium.

As a result, a strong accumulation of fibroblasts was observed in the interstitium with damaged alveolar septa in the control group (FIG. 14; left panel for the control group). Furthermore, accumulation of many fibroblasts was also observed in the interstitium where the alveolar septa were being damaged (FIG. 14; right panel for the control group). Thus, the present inventors obtained the unexpected result that excessive accumulation of fibroblasts lead to the alveolar wall damaging process in pathological conditions such as COPD. Meanwhile, fibroblast infiltration to the interstitium of alveolar tissue was obviously suppressed in the C6ST-1 siRNA-treated group (FIG. 14). It was thus demonstrated that the suppression of C6ST-1 gene expression resulted in inhibition of fibroblast infiltration and retention in the interstitium of alveolar tissue and thereby reduced the enhanced fibrotic changes.

The agents of the present invention are thus useful, for example, as agents for suppressing fibroblast infiltration and retention in the interstitium of alveolar tissue.

[Example 15] Histological Macrophage Infiltration-Suppressing Effect of C6ST-1 siRNA in a Mouse Pulmonary Emphysema Model The COPD model was prepared by the same method as described in Example 12. The collected lung tissues were processed by the same method as described in Example 3 to prepare tissue cryoblocks and sections. The resulting sections were fixed with acetone (Wako Pure Chemical Industries) for ten minutes, and then washed with phosphate buffer. An anti-F4/80 antibody (clone A3-1, rat monoclonal antibody, 2 μg/ml; CALTAG LABORATORIES) was added as the primary antibody, and the sections were incubated at room temperature for one hour. Then, the secondary antibody reaction was carried out by adding a peroxidase-labeled anti-rat IgG antibody (1:200 dilution), which was followed by color development by adding DAB substrate (Nichirei Biosciences). Then, the nucleus was stained by Lillie-Mayer hematoxylin (Muto Pure Chemicals Co.). The samples were observed under a light microscope (Leica Microsystems). The antibody binding was detected by visualizing it as signals.

Figure 15:
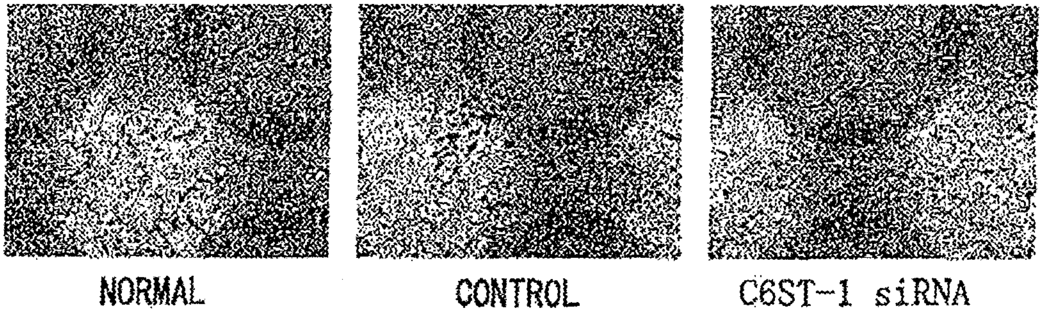
FIG. 15 depicts photographs showing images of macrophage infiltration in a mouse emphysema model. Images of stained macrophages in pulmonary tissues. Magnification: 200×. C6ST-1 siRNA suppresses macrophage infiltration into the pulmonary alveolar interstitium.

The result showed that the macrophage infiltration to the pulmonary alveolar interstitium was clearly suppressed in the C6ST-1 siRNA-treated group as compared to the control group (FIG. 15). It was thus demonstrated that the suppression of C6ST-1 gene expression resulted in suppression of the infiltration of macrophages and fibroblasts, which are cell groups responsible for the persistent or enhanced fibrotic changes, and thereby comprehensively suppressed the tissue fibrotic changes.

The agents of the present invention are thus useful, for example, as agents for suppressing the infiltration of macrophages to the pulmonary alveolar interstitium.

[Example 16] Respiratory Function-Preserving Effect of C6ST-1 siRNA in a Mouse Pulmonary Emphysema Model In this Example, C6ST-1 siRNA was assessed for its influence on respiratory function using static lung compliance (static compliance (Cst)) as an indicator to evaluate the clinical effect of C6ST-1 siRNA in pulmonary emphysema model mice. Cst represents a measure of lung tissue flexibility. Cst is increased in pulmonary emphysema, which is a disease with alveolar tissue damage.

Pulmonary emphysema model mice were prepared by the same procedure described in Example 12, and then treated with C6ST-1 siRNA. An anesthetic agent was given to the mice to stop spontaneous respiration, and then their Cst was monitored using FlexiVent (SCIREQ) respiratory function analyzer in the PV loop mode. Mice were connected to the FlexiVent by the following procedure: a median incision was performed after stopping spontaneous respiration, and then a special cannula was inserted into the trachea, which was followed by peribronchial ligation.

Figure 16:
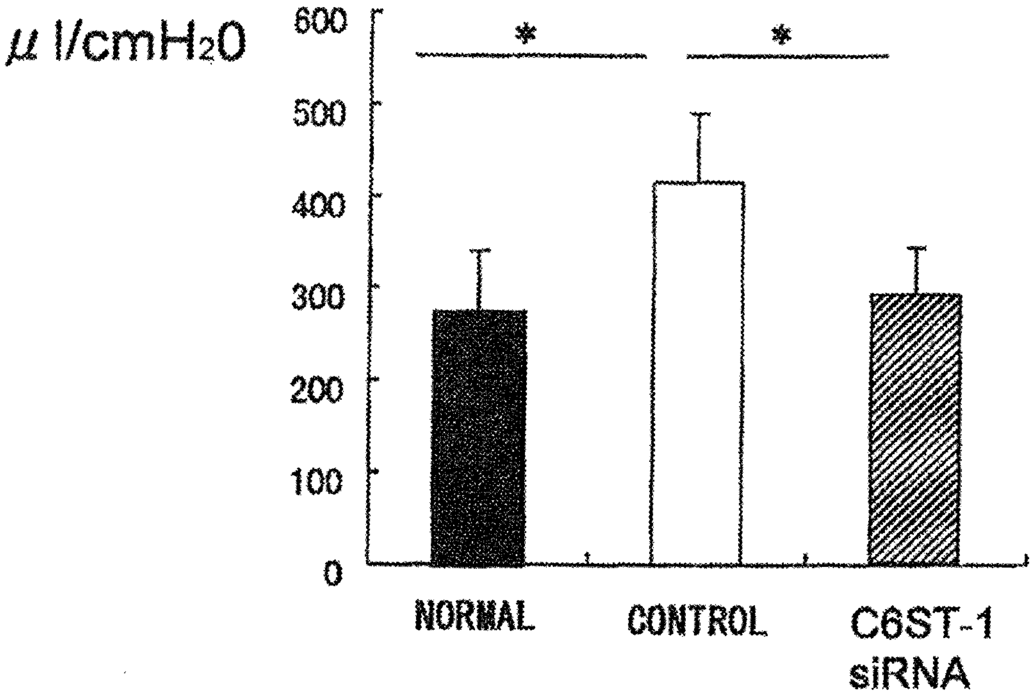
FIG. 16 depicts a graph showing static lung compliance (Cst) in a mouse emphysema model. C6ST-1 siRNA significantly reduces Cst.

The result of this Example is shown in FIG. 16. Cst was 42.62±2.25 μl/cm H2O in the control group, while it was 51.22±5.2 μl/cm H2O in the untreated group (when compared to the control group, P=0.03; t-test). Thus, a statistically significant increase was observed in the untreated group. In contrast, Cst was 42.92±1.82 μl/cm H2O (when compared to the untreated group, P=0.03; t-test) and thus significantly decreased in the C6ST-1 siRNA-administered group when compared to the untreated group.

It was thus demonstrated that the C6ST-1 siRNA-administered group significantly suppressed the increase in Cst caused by pulmonary emphysema induced by intratracheal administration of PPE. Furthermore, the result described in this Example suggests that the suppression of C6ST-1 gene expression not only suppresses the alveolar damage caused by fibrotic changes of the interstitium of lung tissue but also improves the actual clinical symptoms (respiratory conditions).

The agents of the present invention are thus useful, for example, as agents for suppressing alveolar damage.

[Example 17] Tissue-Preserving Effect of C6ST-1 siRNA in a Mouse Pulmonary Emphysema Model In pulmonary emphysema, whose characteristic pathological feature is enlarged alveolar air space, the lung capacity is increased with progression of emphysematous lesions. The purpose of this Example is to prove that the therapeutic effect of C6ST-1 siRNA is not only suppression of damage at the cell level but also the effect of morphological maintenance and preservation of the organ.

The pulmonary tissues used in this Example were the right lungs of the same lung tissues as used in Example 12. The lung tissues isolated from mice were gently washed with phosphate buffer and then immersed into phosphate buffer saturated in a glass container. The glass container filled with phosphate buffer was weighed in advance. After the lung tissues were added to the container, lung capacity was calculated by converting the increased weight into a liquid volume.

Figure 17:
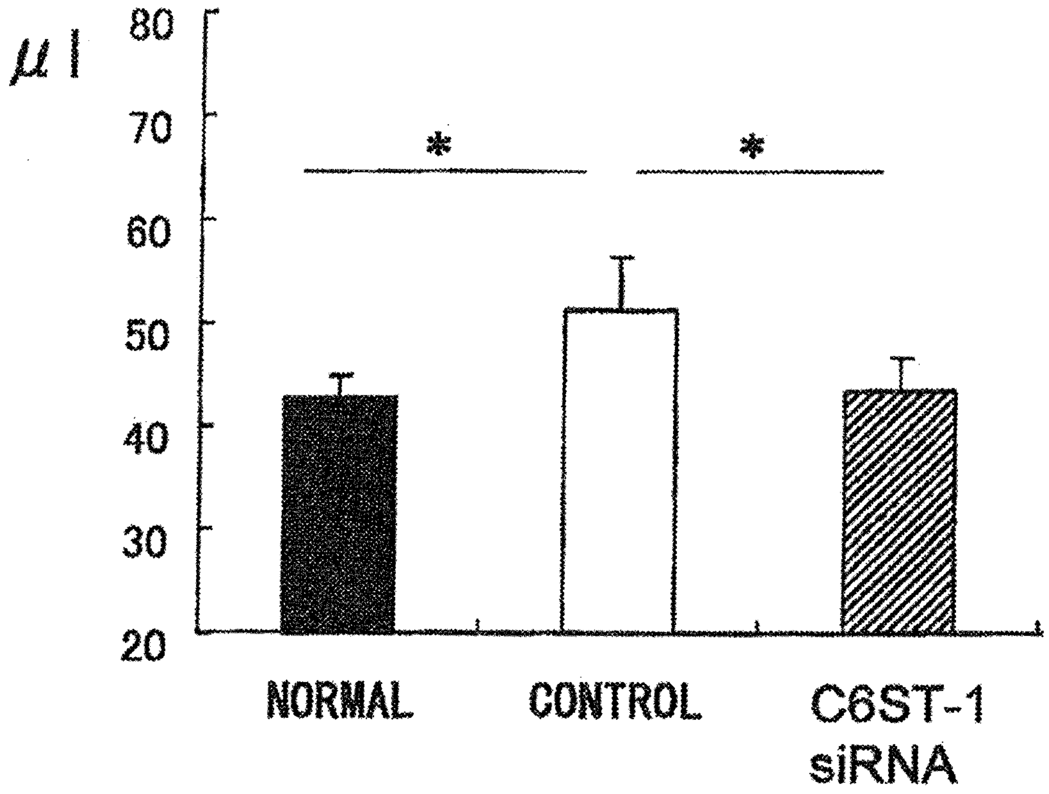
FIG. 17 depicts a graph showing the right lung volume (μl) in a mouse emphysema model. C6ST-1 siRNA significantly reduces lung volume.

The result of this Example is shown in FIG. 17. The lung capacity was 277.5±61.85 μl in the control group, while it was 413.33±77.67 μl in the untreated group (when compared to the control group, P=0.024; t-test). Thus, a statistically significant increase of lung capacity was observed in the untreated group. In contrast, the lung capacity was 292.5±51.23 μl and thus significantly decreased in the C6ST-1 siRNA-treated group (when compared to the untreated group P=0.027; t-test) when compared to the untreated group.

These results revealed that the inhibition of C6ST-1 gene expression effectively suppresses the increase in the lung capacity associated with pulmonary emphysema induced by intratracheal administration of PPE. This suggests that the effect is not only the suppression of the damage at the cell level but also the effect of morphological maintenance and preservation of the organ or effect of repairing damaged tissues.

The agents of the present invention are thus useful, for example, as agents for suppressing the increase of lung capacity caused by pulmonary emphysema.

[Example 18] Pulmonary Interstitial Fibrosis-Suppressing Effect of GalNAcST siRNA in a Mouse Pulmonary Emphysema Model The importance of sulfation at position 4 and 6 is demonstrated with an additional Example. In this Example, the expression of fibrosis-related genes in the pulmonary alveolar interstitium after GalNAcST siRNA administration was assessed by quantitative real-time PCR method using the same method as described in Example 11. The siRNA sequences are the same as shown in Example 11.

The pulmonary emphysema model was prepared by the same method as described in Example 12. A part of the collected lung tissues were placed into 1.5-ml tubes, and frozen with liquid nitrogen. cDNA synthesis was carried out by the same method as described in Example 1, and assessed by quantitative PCR method. The primer sequences and of PCR conditions were the same as described in Examples 1 and 13. The primer sequences for TGF-β are shown below.

[Primer Sequences Used in Quantitative PCR]

*mouse TGF-β (Takara Bio Inc.)

```
Forward:
                                  (SEQ ID NO: 53)
5'-GTGTGGAGCAACATGTGGAACTCTA-3'

Reverse:
                                  (SEQ ID NO: 54)
5'-TTGGTTCAGCCACTGCCGTA-3'
```

Figure 18:
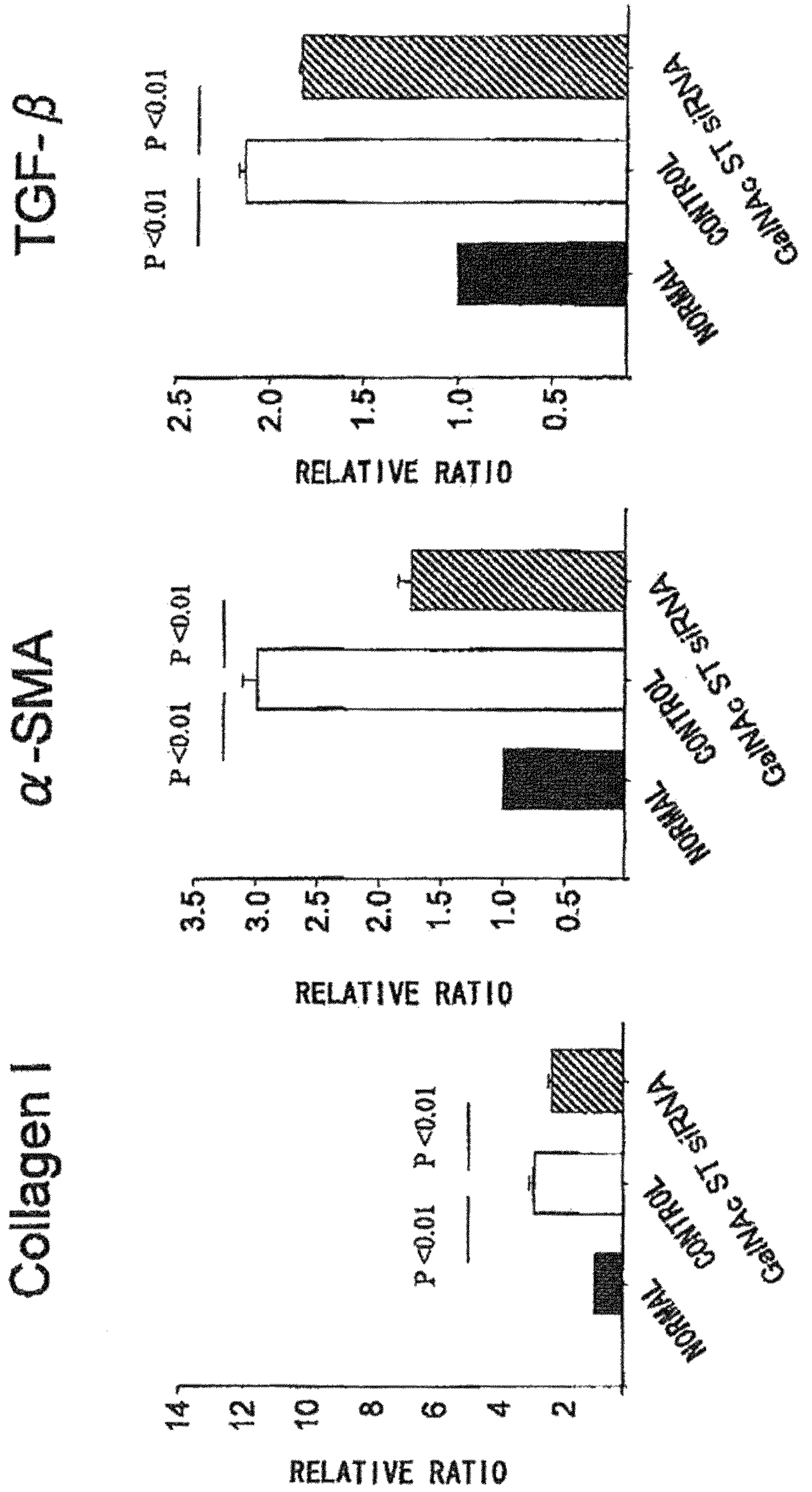
FIG. 18 depicts graphs showing the expression of fibrogenesis-related genes in a mouse emphysema model. α-SMA, type I collagen, and TGF-β, which are fibrogenesis markers, were assessed for the expression in pulmonary tissues. The graphs indicate relative ratios between a target gene and a house keeping gene (ribosome 18S). The enhanced expression of each fibrogenesis marker is significantly suppressed due to the silencing effect of GalNAcST siRNA.
Figure 19:
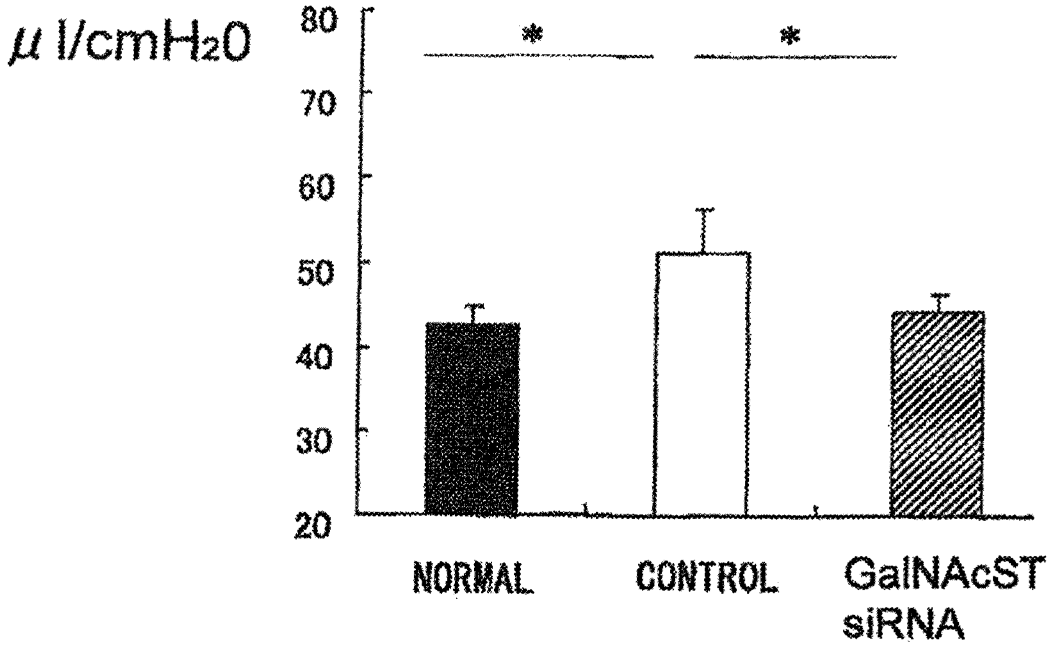
FIG. 19 depicts a graph showing static lung compliance (Cst) in a mouse emphysema model. GalNAcST siRNA significantly reduces Cst.

The result is shown in FIG. 18. The enhanced expression of type I collagen, α-SMA, and TGF-β as indicators for fibrogenesis were also significantly suppressed by GalNAcST siRNA (for all genes, p<0.01; t-test) in this Example. This result demonstrates that the suppression of GAlNAc4ST-1, GAlNAc4ST-2, and GAlNAc4S-6ST expression can effectively inhibit the enhanced fibrotic changes of pulmonary interstitium.

The agents of the present invention are thus useful, for example, as agents for suppressing fibrotic changes in lung interstitium.

[Example 19] Respiratory Function-Preserving Effect of GalNAcST siRNA in a Mouse Pulmonary Emphysema Model In this Example, GAlNAcST siRNA was assessed for its influence on respiratory function using static lung compliance (static compliance (Cst)) as an indicator to evaluate the clinical effect of GAlNAcST siRNA in pulmonary emphysema model mice.

Pulmonary emphysema model mice were prepared by the same procedure described in Example 12, and then treated with GAlNAcST siRNA. The spontaneous respiration of mice was ceased by an anesthetic agent, and then their Cst was monitored using FlexiVent (SCIREQ) respiratory function analyzer in the PV loop mode. Mice were connected to the FlexiVent by the following procedure: a median incision was performed after stopping spontaneous respiration, and then a special cannula was inserted into the trachea, which was followed by peribronchial ligation.

The result of this Example is shown in FIG. 18. Cst was 42.62±2.25 μl/cm H2O in the control group, while it was 51.22±5.2 μl/cm H2O in the untreated group (when compared to the control group, P=0.03; t test). Thus, a statistically significant increase was observed in the untreated group. In contrast, Cst was 44.15±2.29 μl/cm H2O (when compared to the untreated group, P=0.0018; t-test) and thus significantly decreased in the C6ST-1 siRNA-administered group when compared to the untreated group.

It was thus demonstrated that the increase in Cst caused by pulmonary emphysema induced by intratracheal administration of PPE was significantly suppressed in the GalNAcST siRNA-administered group. Furthermore, the result described in this Example suggests that the inhibition of GAlNAc4ST-1, GAlNAc4ST-2, and GAlNAc4S-6ST gene expression not only suppresses the alveolar damage caused by the fibrotic change of interstitium of lung tissue but also improves the actual clinical symptom (respiratory condition).

The agents of the present invention are thus useful, for example, as agents for suppressing alveolar damage or as an agent for improving respiratory conditions.

[Example 20] Tissue-Preserving Effect of GalNAcST siRNA in a Mouse Pulmonary Emphysema Model The objective of this Example is to prove that the therapeutic effect of GalNAcST siRNA is not only the suppression at the cell level but also the effect of morphological maintenance and preservation of the organ.

The pulmonary tissues used in this Example were the right lungs of the same lung tissues as used in Example 12. The lung tissues isolated from mice were gently washed with phosphate buffer and then immersed in phosphate buffer saturated in a glass container. The glass container filled with phosphate buffer was weighed in advance. After the lung tissues were added to the container, lung capacity was calculated by converting the increased weight into a liquid volume.

Figure 20:
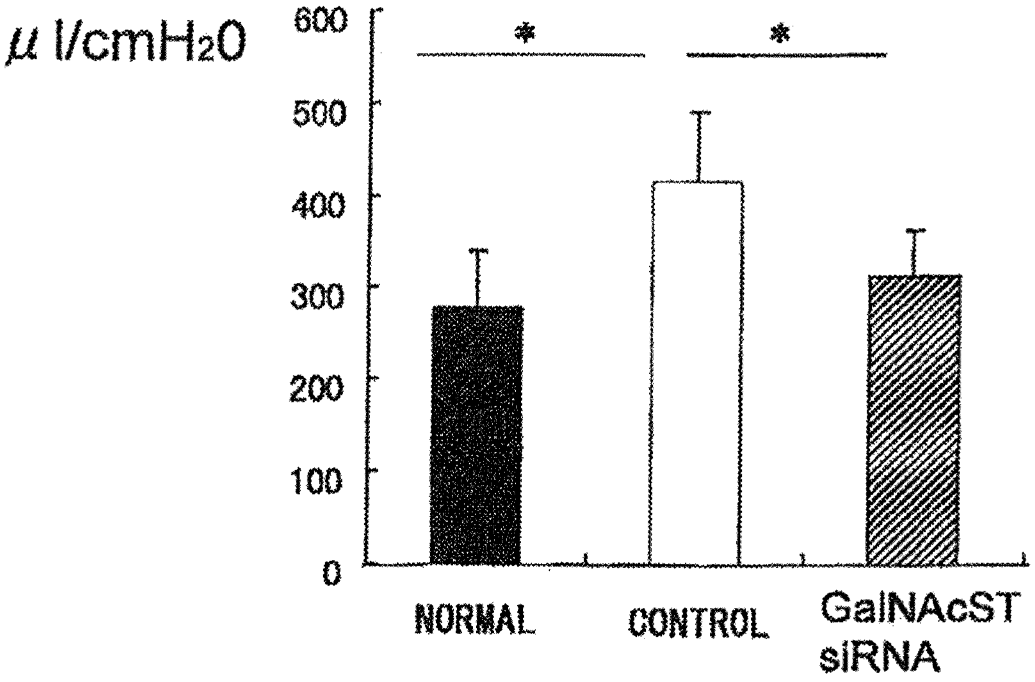
FIG. 20 depicts a graph showing the right lung volume (μl) in a mouse emphysema model. GalNAcST siRNA significantly reduces lung volume.

The result of this Example is shown in FIG. 20. The lung capacity was 277.5±61.85 μl in the control group, while it was 413.33±77.67 μl in the untreated group (when compared to the control group, P=0.024; t-test). Thus, a statistically significant increase of lung capacity was observed in the untreated group. In contrast, the lung capacity was 315±51.96 μl and thus significantly decreased in the GalNAcST siRNA-treated group (when compared to the untreated group P=0.049; t-test).

When taken together, these results reveal that the inhibition of GAlNAc4ST-1, GAlNAc4ST-2, and GAlNAc4S-6ST gene expressions effectively suppresses the increase in the lung capacity associated with pulmonary emphysema induced by intratracheal administration of PPE. This suggests that the effect is not only the suppression of the damage at the cell level but also the effect of maintaining and preserving the morphology of the organ or the effect of repairing damaged tissues.

The agents of the present invention are thus useful, for example, as agents for maintaining or preserving lung morphology.

[Pancreatic Tissue]

The Examples below describe preparation of a type 2 diabetes model by administration of Streptozotocin to C57BL/6JcL mice (female; CLEA Japan Inc.) on day 2 after birth and assessment of the mice for weight and blood glucose changes, gene expression, and fibrotic change of pancreatic tissues caused by treatment with chondroitin D-N-acetylgalactosamine-4-O-sulfotransferase 1 (C4ST-1) siRNA, chondroitin D-N-acetylgalactosamine-4-O-sulfotransferase 2 (C4ST-2) siRNA, and chondroitin D-N-acetylgalactosamine-4-O-sulfotransferase 3 (C4ST-3) siRNA. Each siRNA was administered by the same method as described in Example 1. Sequences are shown below.

*[C4ST-1 siRNA cocktail sequences]

C4ST1 (Chondroitin D-N-acetylgalactosamine-4-O-sulfotransferase 1)

(GenBank accession number NM_021439)

```
                                      (SEQ ID NO: 55)
5'-ACAAAGCCATGAAGCCGGCGCTGCTGGAAGTGATGAGGATGAACAGAA
TT-3'

                                      (SEQ ID NO: 56)
5'-CAACCTGAAGACCCTTAACCAGTACA-3'

                                      (SEQ ID NO: 57)
5'-GCATCCCAGAGATCAACCACCGCTTG-3'
```

*[C4ST-2 siRNA cocktail sequences]

C4ST2 (Chondroitin D-N-acetylgalactosamine-4-O-sulfotransferase 2)

(GenBank accession number NM_021528)

```
                                      (SEQ ID NO: 58)
5'-GCCAGGAGTGGGCCCAGCCCAGGGC -3'

                                      (SEQ ID NO: 59)
5'-ATGACCAAGCCGCGGCTCTTCCGGCTG -3'

                                      (SEQ ID NO: 60)
5'-AGAGCCTGCTGGACCGGGGCAGCCCCTA -3'

                                      (SEQ ID NO: 61)
5'-GAGACCCCCTGGACATCCCCCGGGAACA-3'
```

*[C4ST-3 siRNA cocktail sequences]

C4ST3 (Chondroitin D-N-acetylgalactosamine-4-O-sulfotransferase 3)

(GenBank accession number XM_355798)

```
                                      (SEQ ID NO: 62)
5'-ATGACTGTCGCCTGCCACGCGTGCCA -3'

                                      (SEQ ID NO: 63)
5'-CAGCATGGGAAGACGCTCCTGTTGCA -3'

                                      (SEQ ID NO: 64)
5'-TCCAAGCGCAATCCCTGCGCACGAGGCG -3'

                                      (SEQ ID NO: 65)
5'-GCCTGGCCTGCTGCCCTCGCTGGCC -3'
```

First, sample preparation was conducted as described below.

[Example 21] Assessment of Anti-Obesity Effect of C4ST-1. C4ST-2, and C4ST-3 siRNA Treatment in Streptozocin-Induced C57BL/6JcL Type 2 Diabetes Model Mice Gestational Day 14 C57BL/6JcL mice (CLEA Japan Inc.) were reared and allowed to deliver. 10 mg/ml Streptozocin (SIGMA) was subcutaneously administered at 20 μl/head to Day 2 postnatal female C57BL/6JcL mice. The mice were reared with sterile water and CE-2 Diet (CLEA Japan Inc.) until they were four weeks old, and then on sterile water and a High Fat Diet (CLEA Japan Inc.) for the next two weeks. On the second week, 1 μg of a mixture of chondroitin D-N-acetylgalactosamine-4-O-sulfotransferase 1 (C4ST-1), chondroitin D-N-acetylgalactosamine-4-O-sulfotransferase 2 (C4ST-2), and chondroitin D-N-acetylgalactosamine-4-O-sulfotransferase 3 (C4ST-3) siRNAs (GeneWorld) were combined with 1% atelocollagen (Koken Co.), which is a vehicle for siRNA, and 200 μl of the mixture was administered into peritoneal cavities once a week, twice in total (for two weeks). On Day 14 of this experiment, 100 μl of 5 mg/ml BrdU (ZyMED Laboratory Inc.) was administered into the tail vein, and one hour after administration the mice were dissected and the liver, pancreas, kidney, testis, ovary, and muscle were isolated to obtain samples for immunostaining and gene expression analysis. The body weight change was monitored over time for 14 days of this Example.

Figure 21:
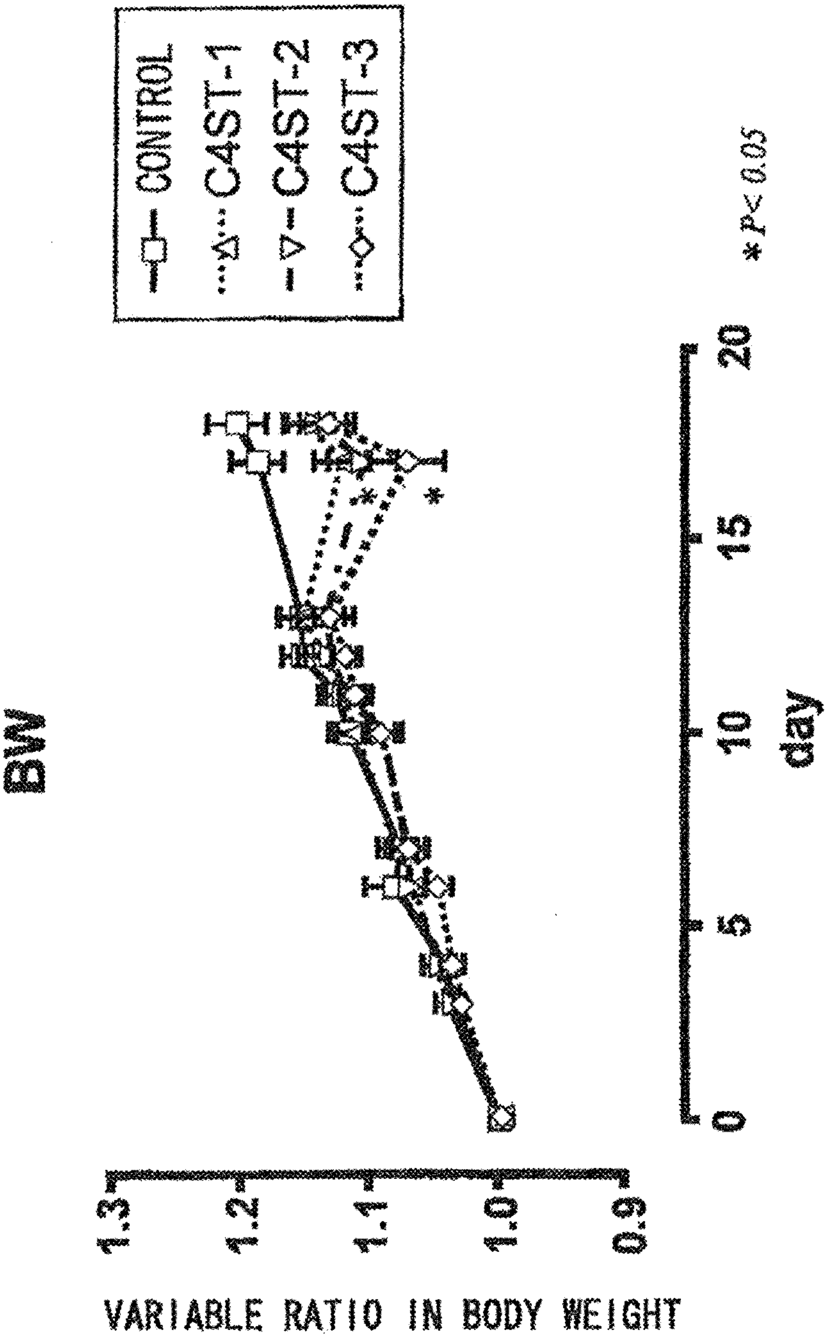
FIG. 21 depicts a graph showing obesity changes in a mouse type 2 diabetes model. C4ST-1, C4ST-2, and C4ST-3 siRNAs tends to suppress obesity. C4ST-2 and C4ST-3 siRNAs produce a significant anti-obesity effect.

The result is shown in FIG. 21. The vertical axis indicates the body weight (g), while the horizontal axis indicates the monitoring days. FIG. 21 shows that the weight increase tended to be suppressed 10 days after treatment in the C4ST-1 siRNA-treated group, C4ST-2 siRNA-treated group, and C4ST-3 siRNA-treated group as compared to the control group. The weight increase was significantly suppressed on day 18 in the C4ST-2 siRNA-treated group and C4ST-3 siRNA-treated group (both groups; $p<0.05$). This result suggests that obesity associated with type 2 diabetes can be suppressed by inhibiting the expression of C4ST-1, C4ST-2, and C4ST-3.

The agents of the present invention are thus useful, for example, as agents for suppressing body weight increase, or as agents for suppressing obesity associated with type 2 diabetes.

Figure 22:
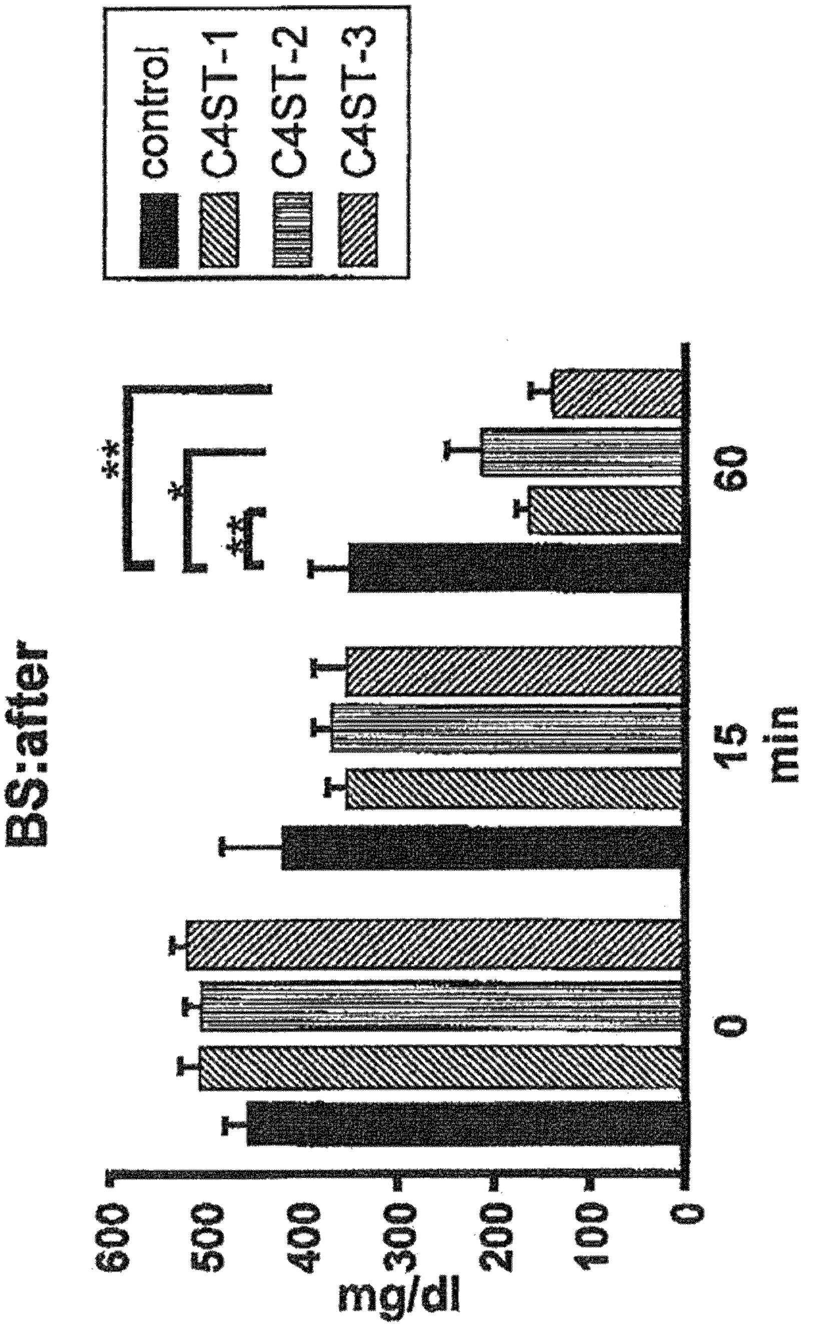
FIG. 22 depicts a graph showing insulin resistance in a mouse type 2 diabetes model. C4ST-1, C4ST-2, and C4ST-3 siRNAs significantly improve insulin resistance.

[Example 22] Assessment of Insulin Resistance after Treatment with C4ST-1. C4ST-2, and C4ST-3 siRNAs in Streptozocin-Induced C57BL/6JcL Type 2 Diabetes Model Mice As an insulin-tolerance test, human crystalline insulin (0.75 U/kg) was administered into peritoneal cavities the day before dissection, and 0, 15, and 60 minutes after administration, the blood glucose levels were measured and evaluated using a blood glucose monitor, Glu-Test Ace (BOMBYX Medicine co.). The blood glucose level changes monitored at 0, 15, and 60 minutes after siRNA treatment are shown in FIG. 22. The vertical axis indicates the blood glucose level (mg/dl), while the horizontal axis indicates 0, 15, and 60 minutes after insulin-tolerance test.

FIG. 22 shows that the blood glucose level was not significantly decreased 0 and 15 minutes after treatment in any of the C4ST-1 siRNA-treated group, C4ST-2 siRNA-treated group, and C4ST-3 siRNA-treated group as compared to the control group, while it significantly decreased 60 minutes after treatment in each of the C4ST-1 siRNA-treated group, C4ST-2 siRNA-treated group, and C4ST-3 siRNA-treated group. This result suggests that insulin resistance, which is an essential functional disorder in type 2 diabetes, can be effectively improved by suppressing the expression of C4ST-1, C4ST-2, and C4ST-3.

The agents of the present invention are thus useful, for example, as agents for improving insulin resistance in type 2 diabetes.

[Example 23] Assessment of Gene Expression in Pancreatic Tissues after Treatment with C4ST-1, C4ST-2, and C4ST-3 siRNAs in Streptozocin-Induced C57BL/6JcL Type 2 Diabetes Model Mice cDNA was prepared by the same method as described in Example 1 from 50 mg of each organ (pancreas) isolated from Streptozocin-induced female C57BL/6JcL mice. PCR was conducted in the following composition.

2 μl of PCR Buffer [composition: 166 mM $(NH_4)_2SO_4$ (Sigma Aldrich Japan), 670 mM Tris pH8.8 (Invitrogen), 67 mM $MgCl_2 \cdot 6H2O$ (Sigma Aldrich Japan), 100 mM 2-mercaptoethanol (WAKO)], 0.8 μl of 25 mM dNTP mix (Invitrogen), 0.6 μl of DMSO (Sigma Aldrich Japan), 0.2 μl of Primer Forward (GeneWorld), 0.2 μl of Primer Reverse (GeneWorld), 15.7 μl of Otsuka distilled water (Otsuka Pharmaceuticals, Inc.), 0.1 μl of Taq polymerase (Perkin Elmer), and 1 μl of cDNA obtained as described above were combined, and reacted using Authorized Thermal Cycler (eppendorf) at 35 cycles of 94° C. for 45 seconds, 56° C. for 45 seconds, and 72° C. for 60 seconds. After the reaction, the obtained PCR products were combined with 2 μl of Loading Dye (Invitrogen). 1.5% agarose gel was prepared using UltraPure Agarose (Invitrogen), and the samples were electrophoresed in a Mupid-2 plus (ADVANCE) at 100 V for 20 minutes. After electrophoresis, the gel was shaken for 20-30 minutes in a stain solution prepared by 10,000 times diluting Ethidium Bromide (Invitrogen) with 1×LoTE (composition: 3 mM Tris-HCl (pH 7.5) (Invitrogen), 0.2 mM EDTA (pH 7.5) (Sigma Aldrich Japan)). The gel was photographed with EXILIM (CASIO) positioned on I-Scope WD (ADVANCE) and the gene expression was confirmed.

Primers (Forward and Reverse) (GeneWorld) used are described in the following.

[Primer Sequences]

*GAPDH

```
Forward:
                                    (SEQ ID NO: 66)
5'-CTGCCAAGTATGACATCA -3'

Reverse:
                                    (SEQ ID NO: 67)
5'-TACTCCTTGGAGGCCATGTAG -3'
```

*C4ST1 (Chondroitin D-N-acetylgalactosamine-4-O-sulfotransferase 1)

```
Forward:
                                    (SEQ ID NO: 68)
5'-gtggatgaggaccacgaact-3'

Reverse:
                                    (SEQ ID NO: 69)
5'-cttttcaagcggtggttgat-3'
```

*C4ST2 (Chondroitin D-N-acetylgalactosamine-4-O-sulfotransferase 2)

```
Forward:
                                    (SEQ ID NO: 70)
5'-acctcctagacccacacacg-3'

Reverse:
                                    (SEQ ID NO: 71)
5'-ggatgttggcaaaccagtct-3'
```

*C4ST3 (Chondroitin D-N-acetylgalactosamine-4-O-sulfotransferase 3)

```
Forward:
                                     (SEQ ID NO: 72)
5'-atgagcccttcaacgaacac-3'

Reverse:
                                     (SEQ ID NO: 73)
5'-tggtagaaggggctgatgtc-3'
```

Figure 23:
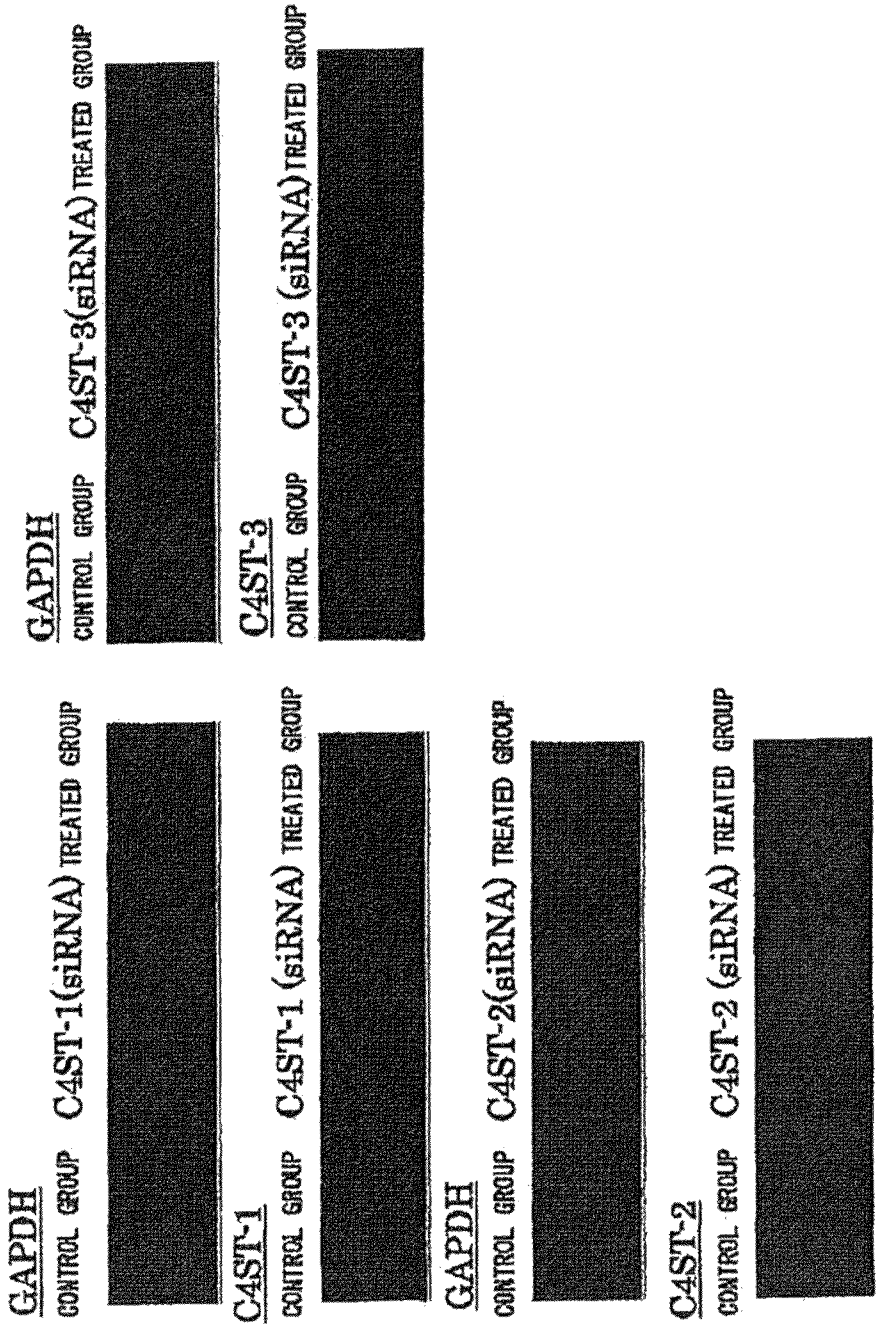
FIG. 23 depicts photographs showing gene expressions in pancreatic tissues in a mouse type 2 diabetes model. C4ST-1, C4ST-2, and C4ST-3 siRNAs suppress the expression of C4ST-1, C4ST-2, and C4ST-3 genes in pancreatic tissues.

Result is shown in FIG. 23. GAPDH expression, which is used as a positive control, was confirmed by RT-PCR in the control group, C4ST1 (Chondroitin D-N-acetylgalactosamine-4-O-sulfotransferase 1), C4ST2 (Chondroitin D-N-acetylgalactosamine-4-O-sulfotransferase 2), and C4ST3 (Chondroitin D-N-acetylgalactosamine-4-O-sulfotransferase 3). Compared to the control group, expression was reduced in C4ST1 (Chondroitin D-N-acetylgalactosamine-4-O-sulfotransferase 1) siRNA-, C4ST2 (Chondroitin D-N-acetylgalactosamine-4-O-sulfotransferase 2) siRNA-, C4ST3 (Chondroitin D-N-acetylgalactosamine-4-O-sulfotransferase 3) siRNA-treated groups, and C4ST1 (Chondroitin D-N-acetylgalactosamine-4-O-sulfotransferase 1), C4ST2 (Chondroitin D-N-acetylgalactosamine-4-O-sulfotransferase 2), C4ST3 (Chondroitin D-N-acetylgalactosamine-4-O-sulfotransferase 3) gene knockdown was confirmed by administration of Atelocollagen-mediated C4ST1 (Chondroitin D-N-acetylgalactosamine-4-O-sulfotransferase 1) siRNA, C4ST2 (Chondroitin D-N-acetylgalactosamine-4-O-sulfotransferase 2) siRNA, C4ST3 (Chondroitin D-N-acetylgalactosamine-4-O-sulfotransferase 3) siRNA.

[Example 24] Assessment of Accumulation of Amyloid Precursor Protein in Pancreas after Treatment with C4ST-1. C4ST-2, and C4ST-3 siRNAs in Streptozocin-Induced C57BL/6JcL Type 2 Diabetes Model Mice In this Example, the amyloid precursor protein (APP) deposition-suppressing effect of C4ST-1, C4ST-2, and C4ST-3 siRNAs was assessed using pancreatic tissue samples of type 2 diabetes model mice. The deposition of APP and amyloid fibers in islets including R cells has long been known to be an important histopathological feature of type 2 diabetes. In recent years, APP has been demonstrated to be involved in Alzheimer's disease (Johnson K H et al. N Eng J Med 321: 513, 1989; Rhodes C J. Science 307: 380, 2005; Haan M N. Nat Clin Pract Neurol 3: 159, 2006; Prentki M et al. J Clin Invest 116: 1802, 2006).

Figure 24:
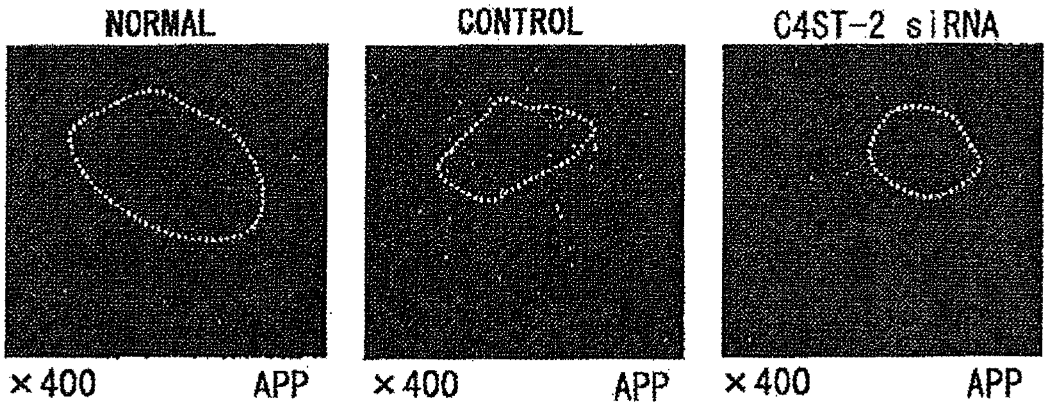
FIG. 24 depicts photographs showing APP deposition in pancreatic islets in a mouse type 2 diabetes model. C4ST-2 siRNA suppresses the deposition of APP in islets. Cell nucleus; magnification: 400×.

The prepared sections of tissue samples were stained with a goat anti-amyloid precursor protein antibody (Calbiochem) by the same method as described in Example 3 to assess its expression at the tissue level. FIG. 24 shows histological images of the normal mouse group, control group, and C4ST-2 siRNA-treated group. The APP deposition is enhanced in the islets of type 2 diabetes model mice. The deposition was demonstrated to be clearly suppressed in the C4ST-2 siRNA-treated group as compared to the control group.

The agents of the present invention are thus useful, for example, as agents for suppressing amyloid fiber deposition.

[Example 25] Histological Fibroblast Infiltration-Suppressing Effect of C4ST-1, C4ST-2, and C4ST-3 siRNA Treatment in Streptozocin-Induced C57BL/6JcL Type 2 Diabetes Model Mice Cryoblocks and tissue sections were prepared from the collected pancreatic tissues by the same method as described in Example 3. The resulting sections were fixed with acetone (Wako Pure Chemical Industries) for ten minutes, and then washed with phosphate buffer. An anti-ER-TR7 antibody (rat monoclonal antibody, 1 μg/ml; BMA) was added as the primary antibody, and the sections were incubated at room temperature for one hour. Then, the secondary antibody reaction was carried out by adding a peroxidase-labeled anti-rat IgG antibody (1:200 dilution), and color development was performed by adding DAB substrate (Nichirei Biosciences). Then, the nucleus was stained by Lillie-Mayer hematoxylin (Muto Pure Chemicals Co.). The samples were observed under a light microscope (Leica Microsystems). The antibody binding was detected by visualizing it as signals.

Figure 25:
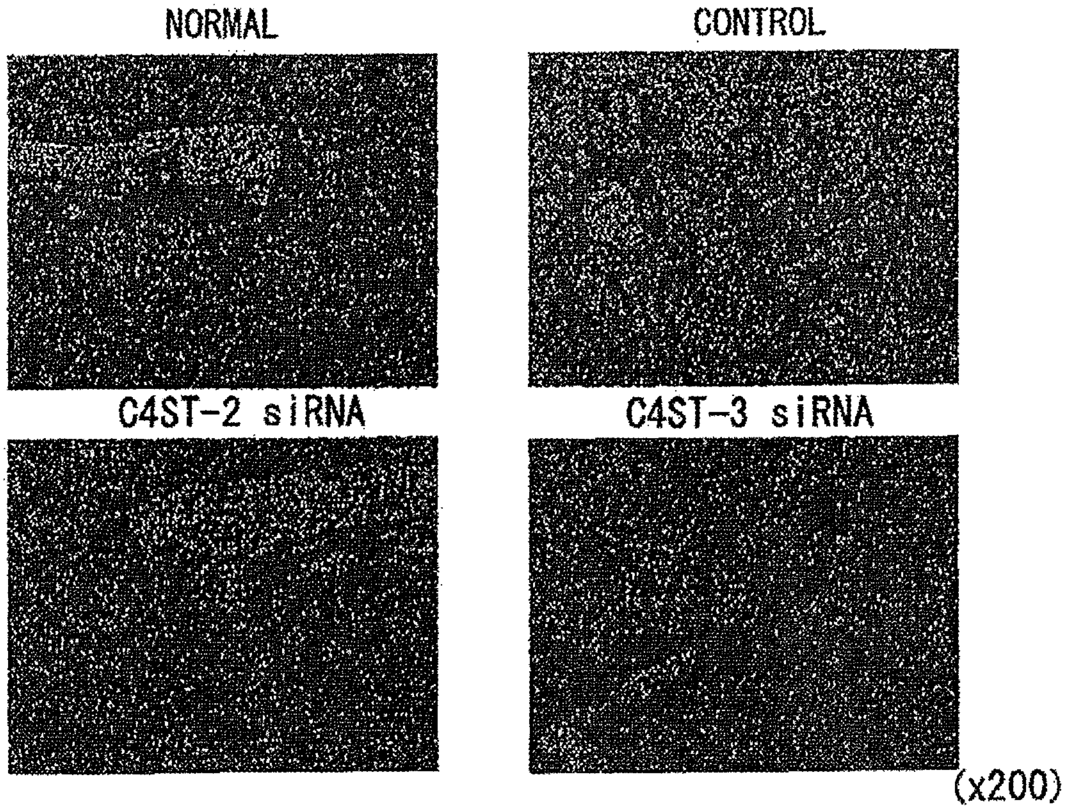
FIG. 25 depicts photographs showing fibroblast infiltration in pancreatic islets in a mouse type 2 diabetes model. C4ST-1, C4ST-2, C4ST-3 siRNAs suppress fibroblast infiltration into islets. Magnification: 200×.

The result showed that the fibroblast infiltration to pancreatic islets was significantly suppressed in each of the C4ST-1 siRNA-, C4ST-2 siRNA-, and C4ST-3 siRNA-treated groups as compared to the control group (FIG. 25). This result demonstrates that the inhibition of C4ST-1, C4ST-2, and C4ST-3 gene expression reduces the enhanced tissue fibrotic change by suppressing the fibroblast infiltration and retention in islets containing R cells.

The agents of the present invention are thus useful, for example, as agents for suppressing fibroblast infiltration to islets.

[Example 26] Histological Macrophage Infiltration-Suppressing Effect of Treatment with C4ST-1, C4ST-2, and C4ST-3 siRNAs in Streptozocin-Induced C57BL/6JcL Type 2 Diabetes Model Mice Cryoblocks and tissue sections were prepared from the collected pancreatic tissues by the same method as described in Example 3. The resulting sections were fixed with acetone (Wako Pure Chemical Industries) for ten minutes, and then washed with phosphate buffer. An anti-F4/80 antibody (clone A3-1, rat monoclonal antibody, 2 μg/ml; CALTAG LABORATORIES) was added as the primary antibody, and the sections were incubated at room temperature for one hour. Then, the secondary antibody reaction was carried out by adding a peroxidase-labeled anti-rat IgG antibody (1:200 dilution), and color development was performed by adding DAB substrate (Nichirei). Then, the nucleus was stained by Lillie-Mayer hematoxylin (Muto Pure Chemicals Co.). The samples were observed under a light microscope (Leica Microsystems). The antibody binding was detected by visualizing it as signals.

Figure 26:
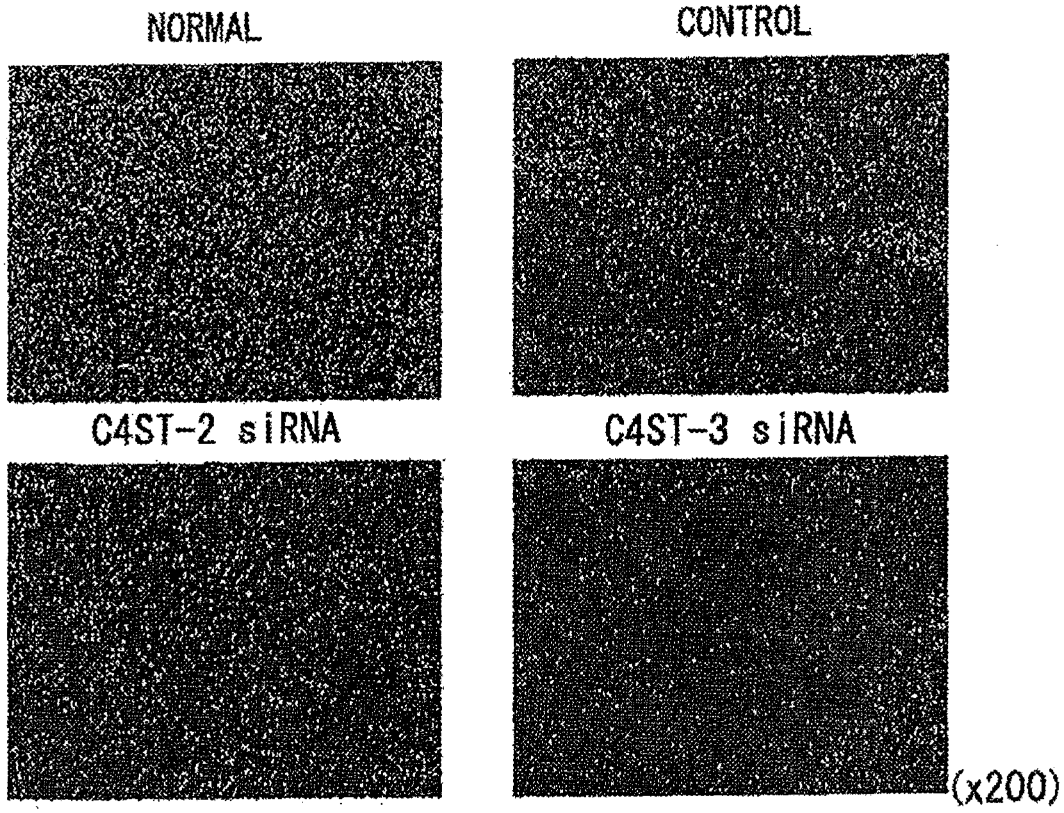
FIG. 26 depicts photographs showing macrophage infiltration into pancreatic islets in a mouse type 2 diabetes model. C4ST-1, C4ST-2, and C4ST-3 siRNAs suppress macrophage infiltration into islets. Magnification: 200×.

The result showed that the macrophage infiltration to the pancreatic islets was significantly suppressed in each of the C4ST-1 siRNA-, C4ST-2 siRNA-, and C4ST-3 siRNA-treated groups as compared to the control group (FIG. 26). This finding demonstrates that the suppression of C4ST-1, C4ST-2, and C4ST-3 gene expressions resulted in general inhibition of the tissue fibrotic changes via suppression of the infiltration of macrophages and fibroblasts, which are cell groups responsible for the persistent or enhanced fibrotic changes.

The agents of the present invention are thus useful, for example, as agents for suppressing the infiltration of macrophages to the pancreatic islets.

Figure 27:
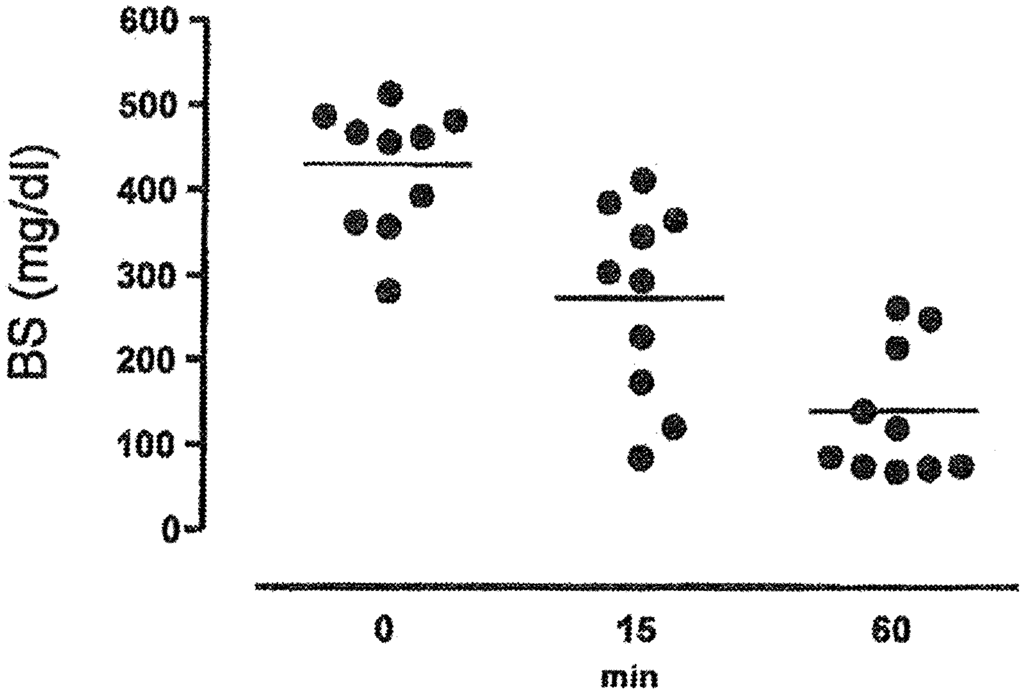
FIG. 27 depicts a graph showing insulin resistance in a mouse type 2 diabetes model. GalNAcST siRNA administration decreases the blood glucose level well after insulin loading. Specifically, this shows the improvement of insulin resistance.

[Example 27] Assessment of Insulin Resistance after GalNAcST siRNA Treatment in Streptozocin-Induced C57BL/6JcL Type 2 Diabetes Model Mice The importance of sulfation at position 4 and 6 is demonstrated with an additional Example. In this Example, the improvement of insulin resistance by GalNAcST siRNA administration is assessed using the same methods as described in Examples 11 and 18. The type 2 diabetes model was prepared by the same method as described in Example 21, and the insulin resistance was tested by the same method as described in Example 22. The result is shown in FIG. 27.

GalNAcST siRNA administration exhibited a good anti-hyperglycemic effect after insulin loading. This result suggests that the insulin resistance arising from fibrotic changes in islets of pancreatic tissues can be effectively improved by suppressing the expression of GalNAc4ST-1, GalNAc4ST-2, and GalNAc4S-6ST.

The agents of the present invention are thus useful, for example, as hypoglycemic agents or as agents for improving the insulin resistance of pancreatic tissue.

[Kidney Tissue]

Fibrotic changes of kidney tissue are thought to be the endpoints of various kidney diseases. (1) From a classical point of view, tubulointerstitial disease is understood as a representative disease caused by renal fibrogenesis. This disease includes Sjogren's syndrome, transplant rejection (chronic allograft nephropathy, etc.), and graft-versus-host reaction (graft-versus-host disease, etc.), in addition to drug-induced, infective, radiation-induced, and heavy metal-induced interstitial renal disorders. (2) Renal fibrogenesis also includes renovascular disease. Renovascular disease includes nephrosclerosis associated with hypertension. In recent years, this disease also includes fibrogenesis associated with arteriosclerosis and metabolic syndrome. Furthermore, interstitial fibrogenesis also occurs as a result of proteinuria or the like in primary glomerular disease, which leads to renal failure. Thus, renal fibrotic changes can also be developed in: (3) primary glomerular disease and (4) secondary glomerular diseases. The diseases of (3) include IgA nephropathy, minimal lesion nephrotic syndrome, membranous nephropathy, membranoproliferative glomerulonephritis, and focal segmental glomerulosclerosis (FGFS). The diseases of (4) include diabetic nephropathy, lupus nephritis associated with systemic lupus erythematosus (SLE), nephropathy associated with chronic rheumatoid arthritis, amyloid nephropathy, and nephropathy associated with type B or C hepatitis. (5) Finally, renal fibrogenesis also includes interstitial kidney diseases caused by urinary obstruction, including urinary lithiasis, tumors, and neurogenic bladder dysfunctions.

Recently, the group of diseases listed above has been collectively named "chronic kidney disease (CKD)" as a clinical concept which is classified and diagnosed based on the decree of kidney function. CKD gradually progresses through interstitial fibrotic changes, leading to chronic renal failure, and then end-stage renal disease (ESRD). Conventionally, only dialysis has been a definitive treatment for ESRD. Although the possibility of slowing down progression to ESRD has been suggested by using an antihypertensive agent that act on the angiotensin system, therapeutic methods that target renal fibrogenesis itself have not been established. There is a desperate need for new CKD treatment. In terms of the progression process of pathological conditions, treatment targeting fibrotic changes is of the greatest significance as a common therapeutic strategy regardless of the type of primary disease. It has been reported that there are 500 million CKD patients worldwide. It is predicted that the number of patients will continue to increase in the future due to altered lifestyle habits. In addition, a large-scale trial revealed the very high risk of death from a cardiovascular disorder before receiving dialysis. Thus, considering CKD as a disease of the 21st century, active treatment of CKD is a significant challenge in the medical community (Sergio A et al., Hypertension 38: 635, 2001; Weiner D E et al., JASN 15: 1307, 2004; Anavekar N S et al., N Eng J Med 351: 1285, 2004; Remuzzi G et al., J Clin Invest 116: 288, 2006; Tonelli M et al., BMJ 332: 1426, 2006; Khwaja A et al., Kidney International doi:10.1038/sj.ki.5002489).

In the next Examples, the inhibition of sugar chain-related genes that modify the sulfate group at position 4 or 6 was assessed for the effect on histological fibrotic changes in the renal interstitium.

[Example 28] Assessment of Anti-Fibrogenic Effect of C4ST-1 siRNA in a Mouse Diabetic Nephropathy Model A type 2 diabetes model was prepared by the same method as described in Example 21. Gestational Day 14 of C57BL/6JcL mice (CLEA Japan Inc.) were reared and allowed to deliver. Streptozotocin (STZ; Sigma) was administered to Day 2 postnatal C57BL/6JcL mice to prepare a STZ-induced diabetes model. The mice were subcutaneously injected with 20 μl of STZ (10 mg/ml) three times for two days. Thus, a total of 60 μl was administered to the mice. Together with their mothers, the mice were fed with a normal diet until they are four weeks old. After weanling at the age of four completed weeks, the mice were fed with a High Fat Diet (CLEA Japan Inc.) for two weeks. In the second week, 1 μg of chondroitin D-N-acetylgalactosamine-4-O-sulfotransferase 1 (C4ST-1) siRNA (GeneWorld) was combined with 0.1% atelocollagen (Koken Co.), which is a vehicle for siRNA, and 200 μl of the resulting mixture was administered into peritoneal cavities once a week (one shot/week) twice in total (for two weeks). On day 14 of this experiment, the mice were dissected and their kidneys were isolated to obtain samples for immunostaining. Gene expression, body weight, and effect on insulin resistance are described in Examples 21, 22, and 23.

The prepared sections of kidney tissue samples were fixed with acetone (Wako Pure Chemical Industries) for ten minutes, and then washed with phosphate buffer. An anti-F4/80 antibody (clone A3-1, rat monoclonal antibody, 2 g/ml, CALTAG LABORATORIES) was added as the primary antibody, and the sections were incubated at room temperature for one hour. Then, the secondary antibody reaction was carried out by adding a peroxidase-labeled anti-rat IgG antibody (1:200 dilution), and color development was performed by adding DAB substrate (Nichirei Biosciences). Then, the nucleus was stained by Lillie-Mayer hematoxylin (Muto Pure Chemicals Co.). The samples were observed under a light microscope (Leica Microsystems). The antibody binding was detected by visualizing it as signals.

Figure 28:
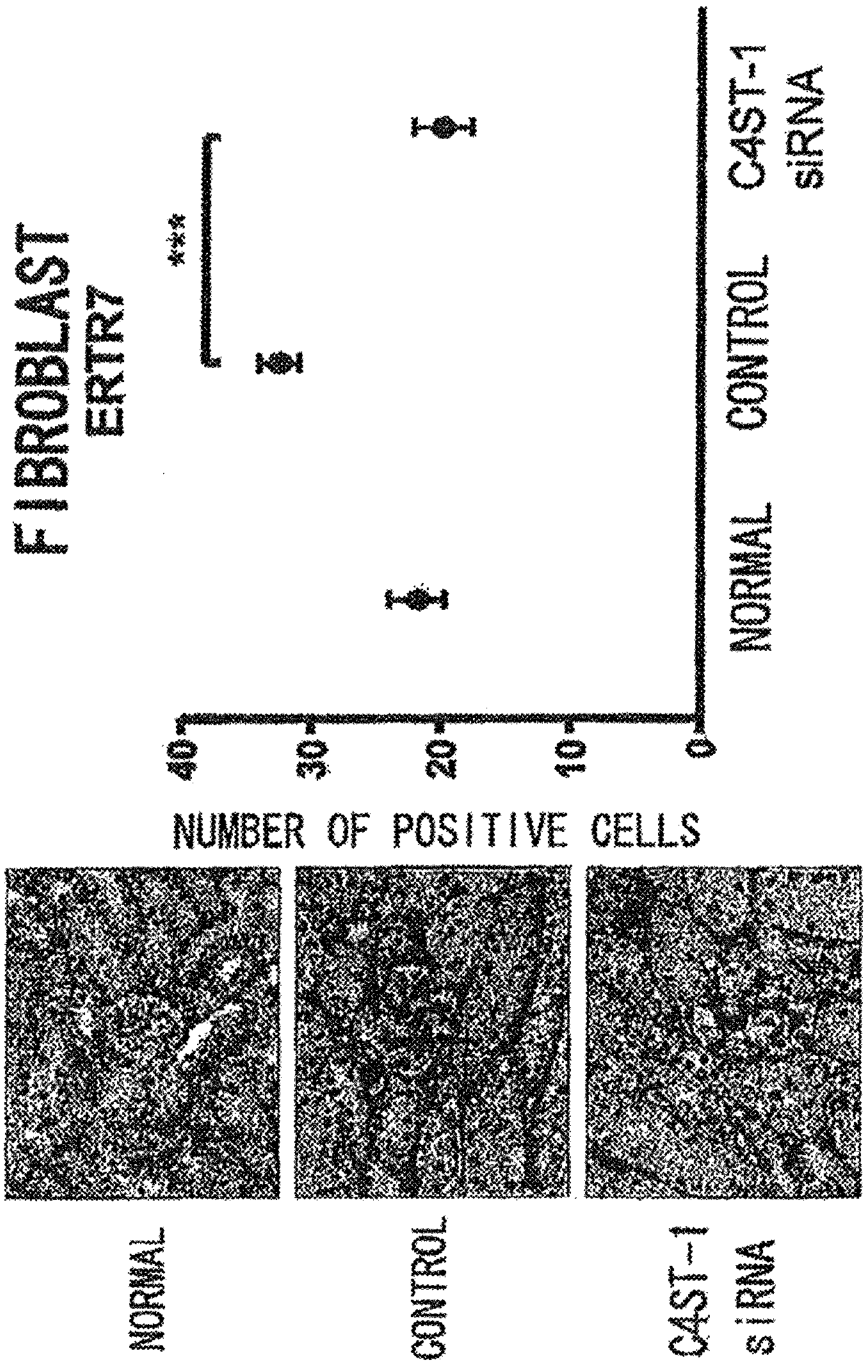
FIG. 28 depicts a graph and photographs showing the accumulation of fibroblasts in the interstitium of kidney tissue in a mouse diabetic nephropathy model. C4ST-1 siRNA significantly suppresses the accumulation of fibroblasts. Magnification: 200×.

The result showed that the infiltration of fibroblasts (ER-TR7-positive cells) in the renal cortex and medulla was less in the C4ST-1 siRNA-treated group as compared to that in the control group (FIG. 28; the original images are in color).

The ER-TR7-positive cells were counted to quantify the fibrogenesis in inflammatory cells. Each sample was observed with ten microscopic optical fields under a microscope at a magnification of 400 fold, and the number of positive cell were counted and compared between the control group and C4ST-1 siRNA-treated group. The result showed that the ER-TR7 positivity ratio was significantly reduced in the C4ST-1 siRNA-treated group as compared to the control group ($p<0.001$).

[Example 29] Assessment of C4ST-1 siRNA for its Effect on Macrophage Infiltration in a Mouse Diabetic Nephropathy Model The prepared sections of kidney tissue samples were fixed with acetone (Wako Pure Chemical Industries) for ten minutes, and then washed with phosphate buffer. An anti-ER-TR7 antibody (rat monoclonal antibody, 1 μg/ml; BMA) was added as the primary antibody, and the sections were incubated at room temperature for one hour. Then, the secondary antibody reaction was carried out by adding a peroxidase-labeled anti-rat IgG antibody (1:200 dilution), and color development was performed by adding DAB substrate (Nichirei Biosciences). Then, the nucleus was stained by Lillie-Mayer hematoxylin (Muto Pure Chemicals Co.). The samples were observed under a light microscope (Leica Microsystems). The antibody binding was detected by visualizing it as signals.

Figure 29:
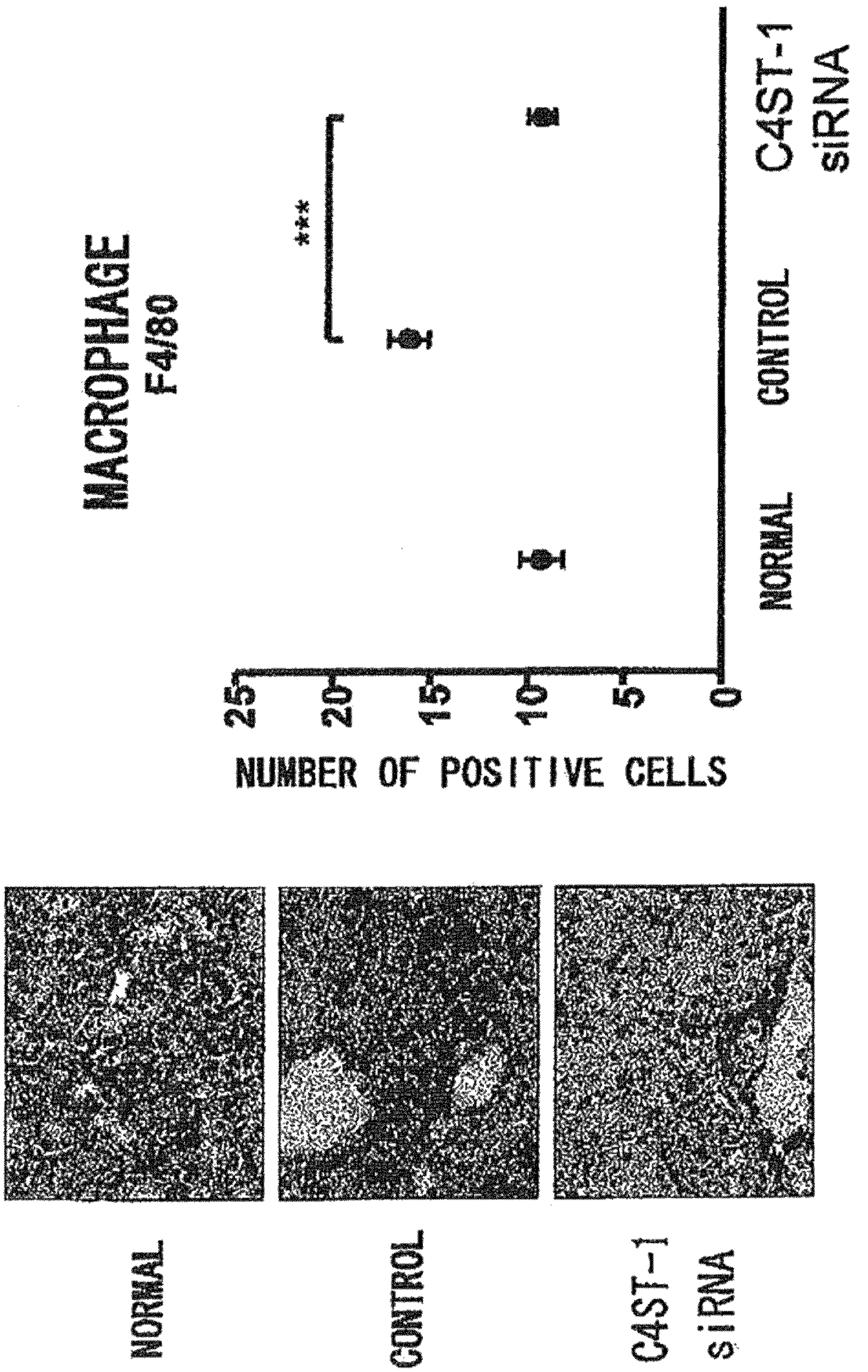
FIG. 29 depicts a graph and photographs showing the accumulation of macrophages in the interstitium of kidney tissue in a mouse model for diabetic nephropathy. C4ST-1 siRNA significantly suppresses the accumulation of macrophages. Magnification: 200×.

The result showed that the infiltration of macrophages (F4/80-positive cells) in the renal cortex and medulla was less in the C4ST-1 siRNA-treated group as compared to that in the control group (FIG. 29; the original images are in color). Furthermore, the tissue lesions were quantified by the same method as described in Example 28. The result showed that the macrophage positivity ratio was significantly reduced in the C4ST-1 siRNA-treated group as compared to the control group ($p<0.001$).

[Example 30] Assessment of C4ST-1 siRNA for Fibroblast Activation in Tissues in a Mouse Diabetic Nephropathy Model The sections of kidney tissue samples were fixed with acetone (Wako Pure Chemical Industries) for ten minutes, and washed with phosphate buffer. An anti-human smooth muscle actin antibody (αSMA: mouse monoclonal antibody, 1:100; DACO) was added as the primary antibody, and the sections were incubated at room temperature for one hour. Then, the secondary antibody reaction was carried out using Histofine Mouse Stain kit (Nichirei), and color development was performed by adding DAB substrate (Nichirei Biosciences). Then, the nucleus was stained by Lillie-Mayer hematoxylin (Muto Pure Chemicals Co.). The samples were observed under a light microscope (Leica Microsystems). The antibody binding was detected by visualizing it as signals.

Figure 30:
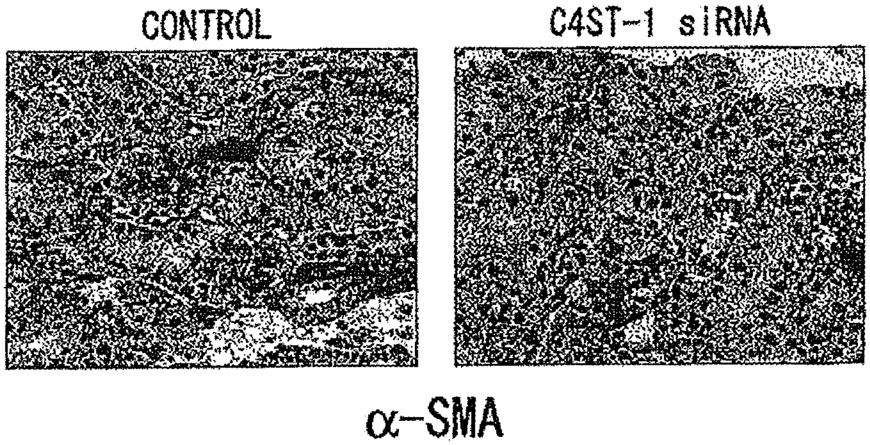
FIG. 30 depicts photographs showing the accumulation of αSMA-positive cells in the interstitium of kidney tissue in a mouse diabetic nephropathy model. C4ST-1 siRNA significantly suppresses the accumulation of αSMA-positive cells. Magnification: 200×.

The result showed that αSMA-positive cells retained in juxtaglomerular and interstitial areas were significantly reduced in the C4ST-1 siRNA-treated group as compared to the control group (FIG. 30; the original images are in color). αSMA serves as a functional marker for fibroblast activation. This result demonstrates that inhibition of C4ST-1 gene expression suppress activation of fibroblasts infiltrating in the tissue.

The agents of the present invention are thus useful, for example, as fibroblast activation inhibitors.

[Example 31] Assessment of GalNAc4S-6ST siRNA for Tissue Fibrogenic Alteration in a Mouse Diabetic Nephropathy Model The diabetic nephropathy model was prepared by the same method as described in Example 28 to assess the effect of GalNAc4S-6ST siRNA. In this Example, the follow-up examination was carried out over a longer period of time. The sequence of GalNAc4S-6ST siRNAs was the same as shown in Example 1. The siRNAs were administered into peritoneal cavities once at the age of eight weeks and once again at age of nine weeks. Furthermore, as a control for comparison, Valsartan, an angiotensin II receptor blocker (ARB), was orally administered at a dose of 30 mg/kg on the same schedule. Kidney tissues were collected at the age of ten weeks to conduct immunohistochemical and gene expression tests. To assess the gene expression in the kidney tissues, quantitative PCR was carried out by the same method as described in Example 1. In this Example, 36B4 was used as an internal control. The sequence of 36B4 is shown below.

[Primer Sequences Used in Quantitative PCR]

*mouse 36B4 (Takara Bio)

```
Forward:
                              (SEQ ID NO: 74)
5'-TTCCAGGCTTTGGGCATCA-3'

Reverse:
                              (SEQ ID NO: 75)
5'-ATGTTCAGCATGTTCAGCAGTGTG-3'
```

Figure 31:
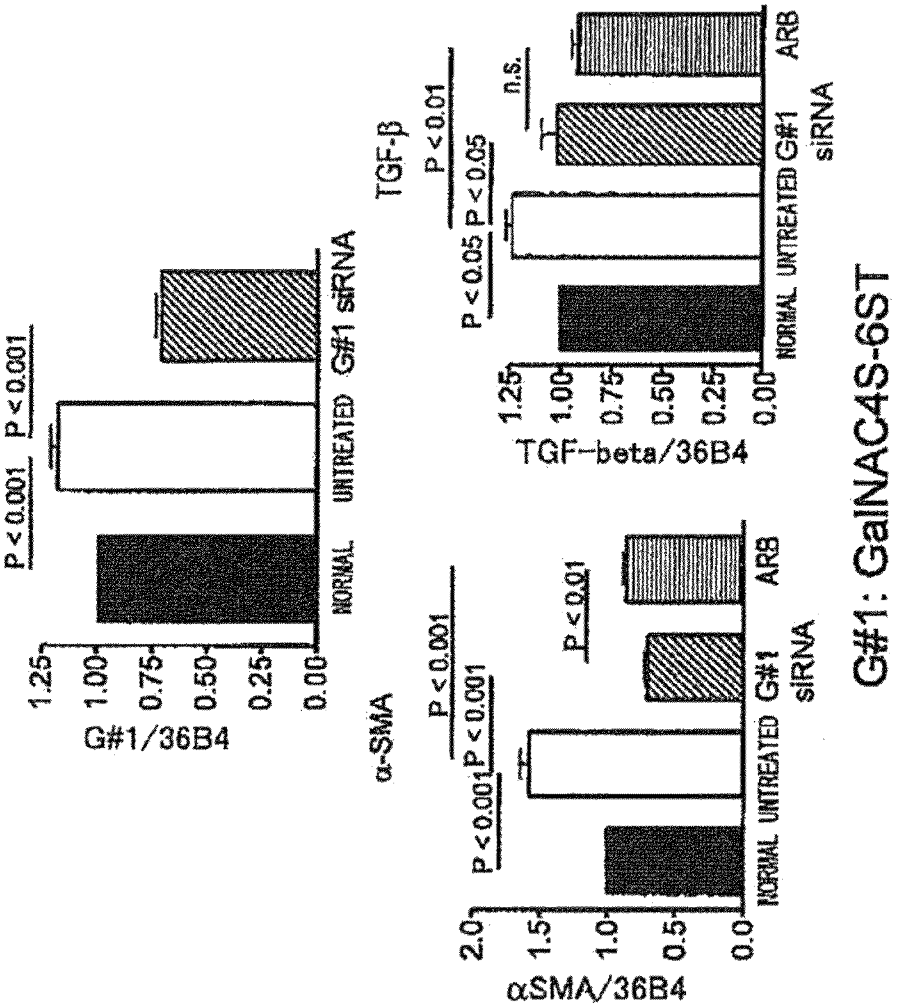
FIG. 31 depicts graphs showing an anti-fibrogenic effect in a mouse diabetic nephropathy model. GalNAc4S-6ST (G #1) siRNA administration significantly suppresses the enhanced expression of GalNAc4S-6ST (G #1), αSMA, and TGFβ in kidney tissues. ARB; angiotensin receptor antagonist (Valsartan).

The result is shown in FIG. 31 (GalNAc4S-6ST is abbreviated as G #1 in this figure). In the diabetic nephropathy model, the expression of GalNAc4S-6ST in kidney tissues is enhanced. The administration of GalNAc4S-6ST siRNA significantly suppressed not only the expression of GalNAc4S-6ST gene in kidney tissues but also the enhanced expression of αSMA and TGFβ, which are fibrosis markers. The therapeutic effect was evaluated by comparing with that of ARB, and the result showed that the TGFβ-suppressing effect was observed in both groups and there was no significant difference between the two while the αSMA-suppressing effect was significant in the GalNAc4S-6ST siRNA-administered group as compared to the ARB-administered group. This result suggests that the markers for fibrotic changes in kidney tissues can be suppressed by inhibiting the expression of GalNAc4S-6ST gene. The result also demonstrates that GalNAc4S-6ST siRNA showed a markedly superior effect in terms of fibroblast activation (enhancement of αSMA).

Figure 32:
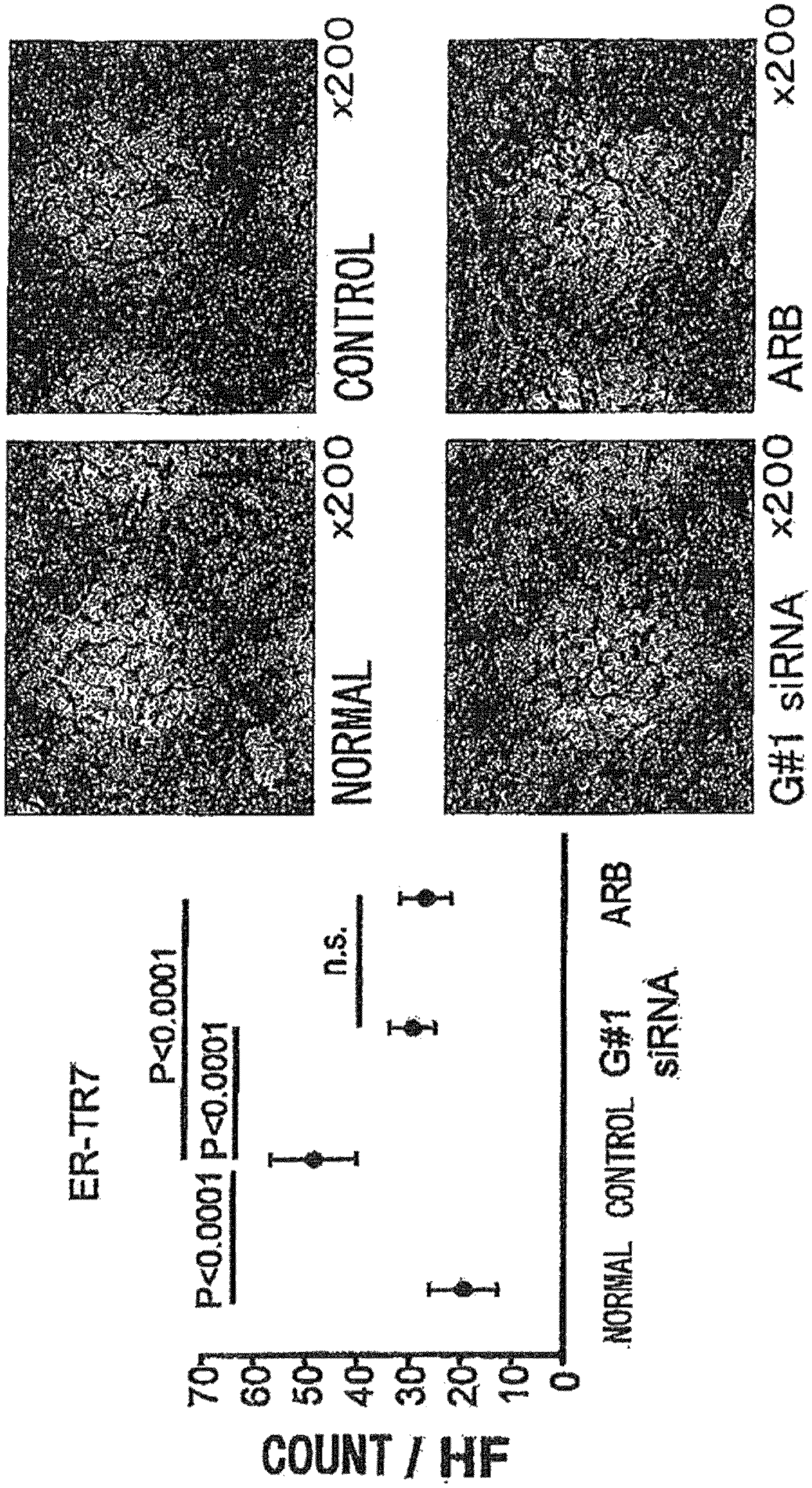
FIG. 32 depicts a graph and photographs showing fibroblast accumulation in the interstitium of kidney tissue in a mouse diabetic nephropathy model. GalNAc4S-6ST (G #1) siRNA significantly suppresses the accumulation of fibroblasts. Magnification: 200×.

[Example 32] Assessment of GalNAc4S-6ST siRNA for Fibroblast Infiltration in a Mouse Diabetic Nephropathy Model The degree of fibroblast infiltration into kidney tissues was quantitatively evaluated by conducting an immunohistochemical study using the same method as described in Example 28. The result is shown in FIG. 32. Fibroblast infiltration to kidney tissues was significantly suppressed by GalNAc4S-6ST siRNA administration. A quantitative evaluation over the entire interstitium did not show any significant difference between GalNAc4S-6ST siRNA administration and ARB treatment. Meanwhile, when the evaluation was restricted to fibroblasts infiltrating in juxtaglomerular areas, a significant suppressing effect was observed in the GalNAc4S-6ST siRNA-administered group, as shown in the figure.

The agents of the present invention are thus useful, for example, as agents for suppressing fibroblast infiltration into renal interstitium.

Figure 33:
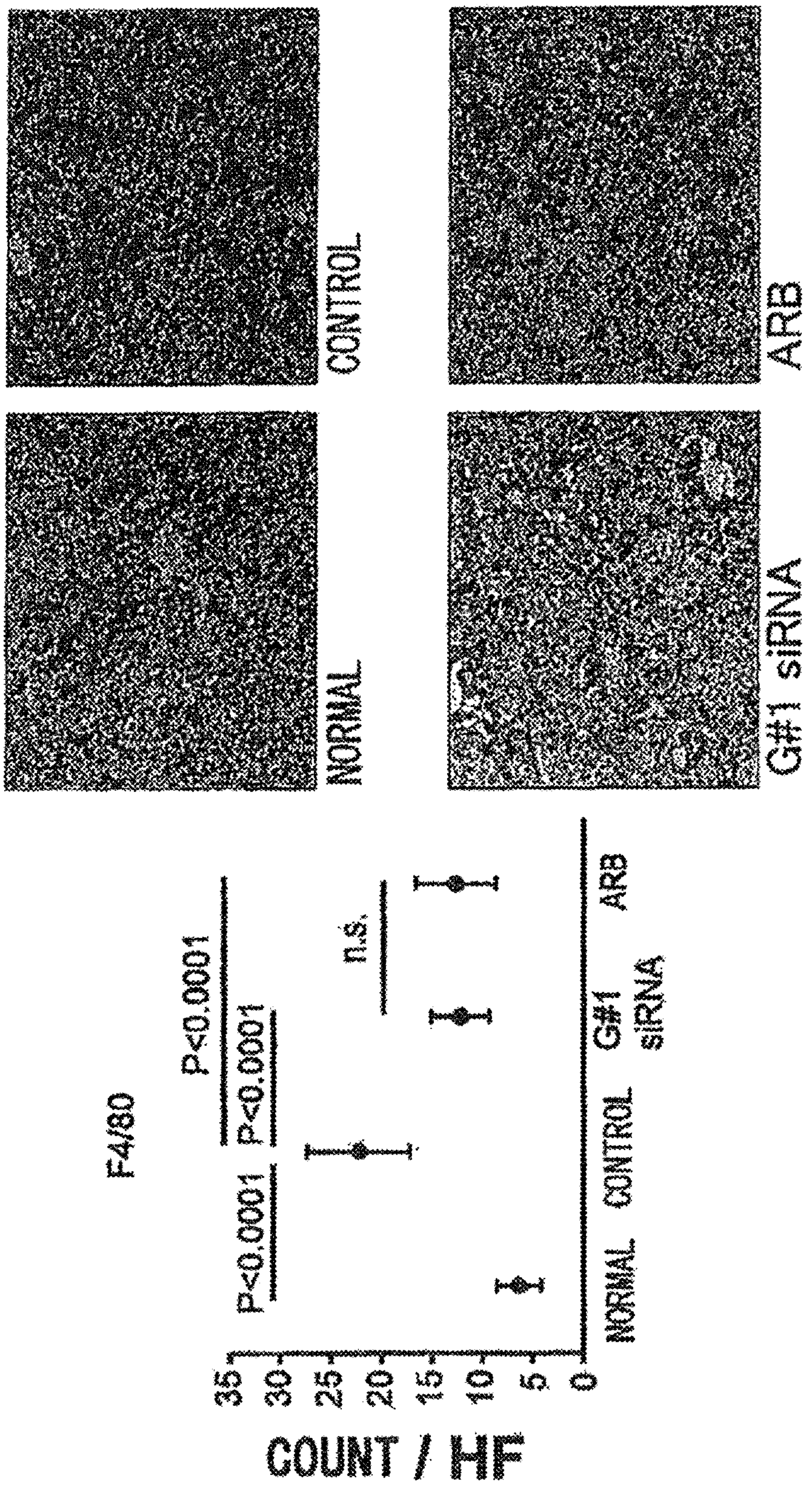
FIG. 33 depicts a graph and photographs showing macrophage accumulation in the interstitium of kidney tissue in a mouse diabetic nephropathy model. GalNAc4S-6ST (G #1) siRNA significantly suppresses the accumulation of macrophages. Magnification: 200×.

[Example 33] Assessment of GalNAc4S-6ST siRNA in Macrophage Infiltration in a Mouse Diabetic Nephropathy Model The degree of fibroblast infiltration into kidney tissues was quantitatively evaluated by conducting an immunohistochemical study using the same method as described in Example 29. The result is shown in FIG. 33. Macrophage infiltration into kidney tissues was significantly suppressed by GalNAc4S-6ST administration. A quantitative evaluation over the entire interstitium did not show any significant difference between GalNAc4S-6ST siRNA administration and ARB treatment. Meanwhile, when the evaluation was restricted to macrophages infiltrating in juxtaglomerular areas, a significant suppressing effect was observed in the GalNAc4S-6ST siRNA-administered group, as shown in the figure.

The agents of the present invention are thus useful, for example, as agents for suppressing macrophage infiltration to renal interstitium.

[Example 34] Assessment of GalNAc4S-6ST siRNA in Glomerular Basement Membrane Thickening in a Mouse Diabetic Nephropathy Model Type IV collagen was immunostained by the same method as described in Examples 32 and 33. A rabbit anti-mouse type IV collagen antiserum (LSL) was added as the primary antibody, and the sections were incubated at room temperature for one hour. Then, the secondary antibody reaction was carried out by adding a peroxidase-labeled anti-rabbit IgG antibody (1:200 dilution), and color development was performed by adding DAB substrate (Nichirei Biosciences). Then, the nucleus was stained by Lillie-Mayer hematoxylin (Muto Pure Chemicals Co.). The samples were observed under a light microscope (Leica Microsystems). The antibody binding was detected by visualizing it as signals.

Figure 34:
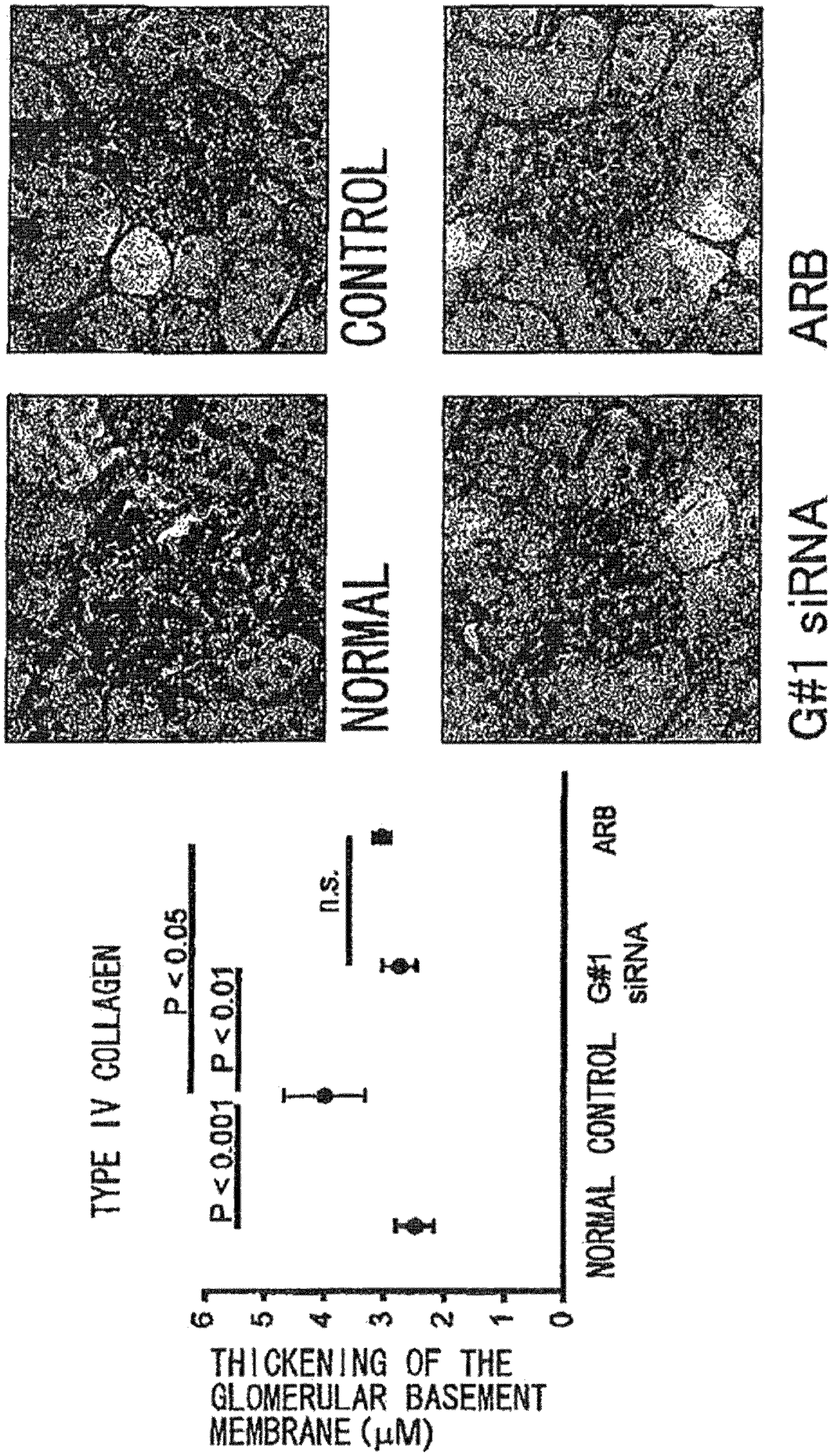
FIG. 34 depicts a graph and photographs showing the accumulation of type IV collagen in a mouse diabetic nephropathy model. GalNAc4S-6ST (G #1) siRNA significantly suppresses the thickening of glomerular basement membrane, which can be confirmed by the positivity for type IV collagen. Magnification: 400×.

The thickness of collagen visualized as signals surrounding glomeruli was measured to quantify the accumulation of type IV collagen. 15 to 20 glomeruli were assessed for each sample. The thickness of the thickest portion around a glomerulus was measured on a display monitor using vernier calipers. The result showed that glomerular basement membrane (GBM) thickening was significantly suppressed in the GalNAc4S-6ST siRNA-administered group as compared to the control group (FIG. 34). The thickening tended to be suppressed more markedly in the GalNAc4S-6ST siRNA-administered group as compared to ARB.

The agents of the present invention are thus useful, for example, as agents for suppressing glomerular basement membrane thickening.

Figure 35:
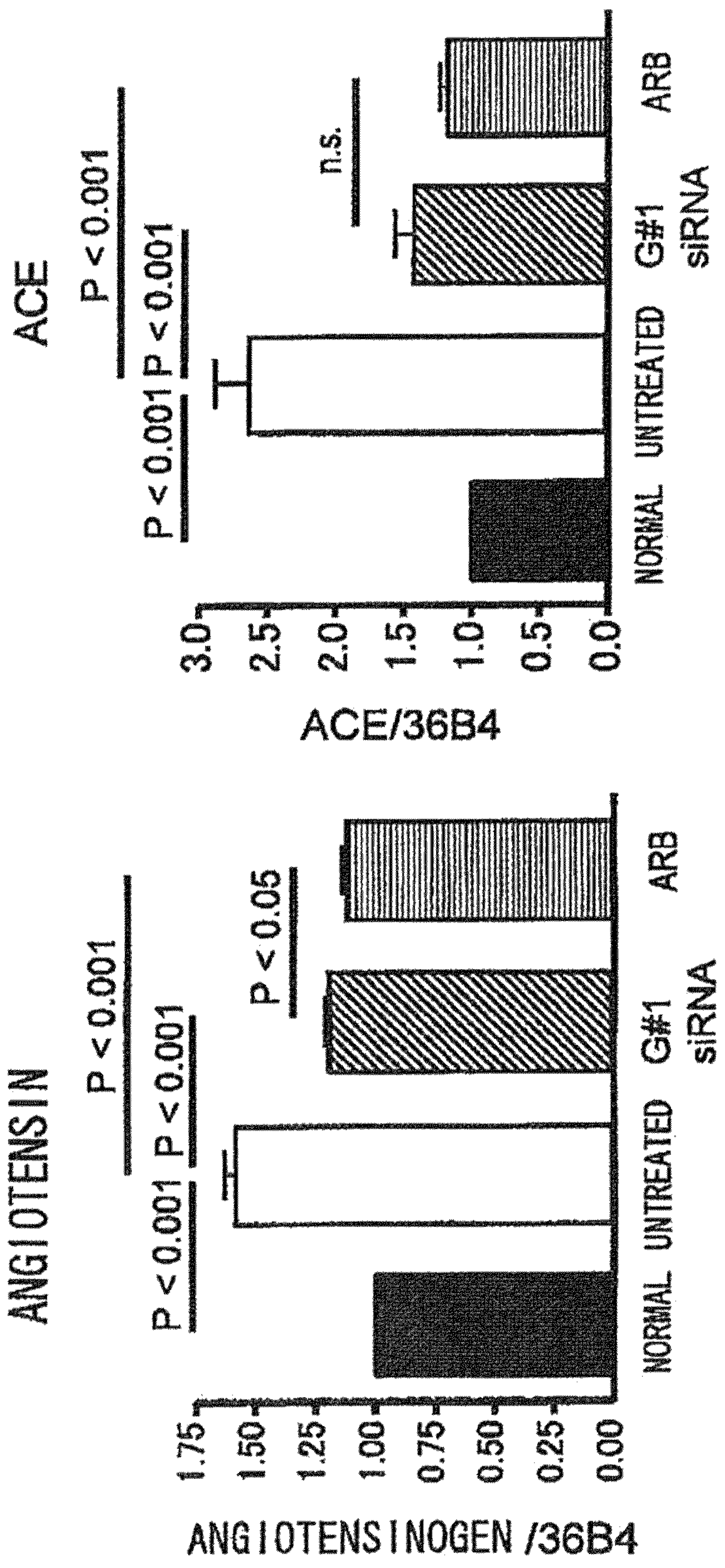
FIG. 35 depicts graphs showing the renal protective effect in a mouse diabetic nephropathy model. GalNAc4S-6ST (G #1) siRNA significantly suppresses the enhanced expression of angiotensinogen and ACE in kidney tissues.

[Example 35] Assessment of GalNAc4S-6ST siRNA in the Angiotensin Pathway in a Mouse Diabetic Nephropathy Model Angiotensin II has been reported to be involved in fibrogenesis in diabetic nephropathy. In this Example, the angiotensin pathway in kidney tissues was assessed by quantitative PCR. The expression of angiotensinogen and angiotensin converting enzyme (ACE) is enhanced in this model (FIG. 35). The enhanced expression was speculated to be a factor responsible for the renal enhancement of angiotensin II. The effect on suppressing angiotensinogen and ACE was observed in the GalNAc4S-6ST siRNA-administered group (FIG. 35). The result demonstrates that GalNAc4S-6ST siRNA also produces an improving effect on the angiotensin pathway through suppression of fibroblast infiltration and activation by suppressing the GalNAc4S-6ST gene.

The agents of the present invention are thus useful, for example, as agents for suppressing the expression of angiotensinogen or as an angiotensin converting enzyme inhibitor.

[Example 36] Assessment of GalNAc4S-6ST siRNA in Serum Creatinine Concentration in a Mouse Diabetic Nephropathy Model Serum creatinine is a most commonly used clinical marker for renal function. The serum creatinine concentration is elevated due to impaired renal function during the process from diabetic nephropathy to ESRD. However, it has been revealed that functional nephrons are already functionally impaired by 50% when the serum creatinine level is elevated. Protecting renal function before the creatinine level increases is a clinically important challenge.

Figure 36:
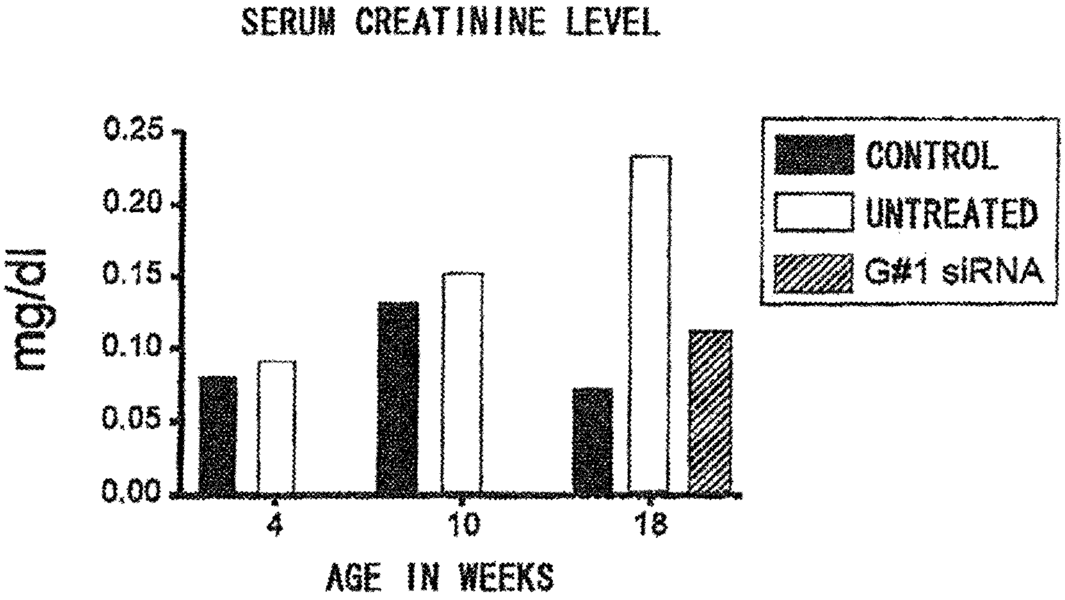
FIG. 36 depicts a graph showing the renal function protective effect in a mouse diabetic nephropathy model.

In this model as well, elevation of serum creatinine level was observed eventually at the age of 18 weeks when histological fibrogenesis had already progressed (FIG. 36). The elevation of serum creatinine was suppressed in the GalNAc4S-6ST siRNA-administered group as compared to the control group (FIG. 36). This result suggests that inhibition of the GalNAc4S-6ST gene results in suppression of fibrotic changes of renal tissue and thereby suppresses the elevation of serum creatinine, i.e., the deterioration of renal function. Thus, suppression of the GalNAc4S-6ST gene produces a very beneficial renal protective effect.

The agents of the present invention are thus useful, for example, as agents for suppressing the deterioration of renal function, or as a renal protective agent.

[Example 37] Assessment of Anti-Fibrogenic Effect of GalNAcST siRNA in a Mouse Diabetic Nephropathy Model The importance of sulfation at position 4 and 6 is shown with an additional Example. The effect of GalNAcST siRNA administration on fibrotic changes in the renal interstitium was assessed by the same method as described in Example 11. The schedule of GalNAcST siRNA administration is the same as described in Example 28. Quantitative PCR was carried out using kidney tissues by the same method as described Example 31. In this Example, β-actin was used as an internal control. The sequence of β-actin is shown below.

[Quantitative PCT Primer Sequences]

*mouse β actin (Takara Bio)

```
Forward:
                                    (SEQ ID NO: 76)
5'-CATCCGTAAAGACCTCTATGCCAAC-3'

Reverse:
                                    (SEQ ID NO: 77)
5'-ATGGAGCCACCGATCCACA-3'
```

As shown in FIG. 37, the expression of GalNAc4ST-1, GalNAc4ST-2, and GalNAc4S-6ST was enhanced in kidney tissues in the diabetic nephropathy model. The expression of all the genes was significantly suppressed by administering GalNAcST siRNA.

[Example 38] Assessment of Anti-Fibrogenic and Kidney-Protecting Effects of GalNAcST siRNA In a Mouse Diabetic Nephropathy Model The enhanced expression of αSMA, TGFβ, and CTGF, which are fibrogenesis markers for kidney tissue fibrogenesis, was significantly suppressed in the GalNAcST siRNA-administered group as compared to the control group (FIG. 38). The enhanced expression of ACE was also significantly suppressed in the GalNAcST siRNA-administered group. This result demonstrates that inhibition of GalNAc4ST-1, GalNAc4ST-2, and GalNAc4S-6ST expression results in suppression of kidney tissue fibrogenesis and renal protection. Together with the result of Example 35, the fact that ACE was markedly reduced by suppressing any of the genes demonstrates that they have a hypotensive effect.

The agents of the present invention are thus useful, for example, as antihypertensive agents.

[Example 39] Assessment of GalNAc4S-6ST siRNA for Gene Expression in a Mouse Drug-Induced Interstitial Nephritis Model This Example assesses the effect of GalNAc4S-6ST siRNA on a typical drug-induced interstitial nephritis. First, the mouse model is prepared as described below. Adriamycin (15 mg/kg; Kyowa Hakko) was administered to the peritoneal cavities of C57BL6/J mice (male, eight weeks old, CLEA Japan Inc.). The mice were reared for one week after administration, and then kidney tissues were collected from them. As a control group, mice of the same lineage and age were also purchased and reared in the same period, but Adriamycin was not given to them.

GalNac 4S-6ST siRNA was administered by the same method as described in Example 1: 1 μg of GalNac 4S-6ST siRNA (Hokkaido System Science Co.) was combined with 200 μl of 1% atelocollagen (Koken Co.), which is a vehicle, and the resulting mixture was administered intraperitoneally to each mouse 24 hours before Adriamycin administration. The expression of GalNac4S-6ST is also enhanced in kidney tissues in the typical drug-induced interstitial nephritis model described in this Example (FIG. 39). The expression was significantly suppressed by administering GalNac4S-6ST siRNA.

[Example 40] Assessment of GalNAc4S-6ST siRNA in Gene Expression in a Mouse Drug-Induced Interstitial Nephritis Model In this Example, immunostaining of type I collagen was carried out by the same method as described in Example 34. A rabbit anti-rat type I collagen antiserum (LSL) was added as the primary antibody, and the sections were incubated at room temperature for one hour. Then, the secondary antibody reaction was carried out by adding a peroxidase-labeled anti-rabbit IgG antibody (1:200 dilution), and color development was performed by adding DAB substrate (Nichirei Biosciences). Then, the nucleus was stained by Lillie-Mayer hematoxylin (Muto Pure Chemicals Co.). The samples were observed under a light microscope (Leica Microsystems). The antibody binding was detected by visualizing it as signals.

The result is shown in FIG. 40. Diffuse deposition of type I collagen was observed over juxtaglomerular and interstitial areas in the control group, while the deposition was markedly suppressed in the GalNac4S-6ST-administered group. This result suggests that fibrotic changes in kidney tissues can also be suppressed by suppressing the expression of GalNac4S-6ST in the drug-induced interstitial nephritis.

The agents of the present invention are thus useful, for example, as agents for suppressing fibrotic changes in kidney tissues.

[Example 41] Assessment of Anti-Fibrosis Effect of C6ST siRNA in Renal Fibrosis Model Mice Induced by Unilateral Ureteral Obstruction (UUO)

First, a mouse model for renal fibrosis is prepared as described below. Renal fibrosis model mouse was prepared by conducting unilateral ureteral obstruction (UUO) to C57BL/6JcL mice (female, eight weeks old; CLEA Japan Inc.). This model has excellent reproducibility, and is thus widely used as an experimental mouse renal fibrosis model (American Journal of Pathology 2003 163 (4): 1261-1273). Mice were subjected to laparotomy under Ketalar/xylazine anesthesia. The ureters were exposed and the right ureter was ligated at two sites with 4-0 surgical suture. The peritoneum and skin were closed with 1-0 surgical suture.

The effect of inhibiting C6ST expression by C6ST siRNA administration was checked by PCR method using renal fibrosis model mice prepared by unilateral ureteral obstruction (UUO), as a typical example of renal fibrosis model mice. The renal fibrosis model was prepared by conducting UUO to C57BL/6JcL mice (female, eight weeks old; CLEA Japan Inc.). A mixture of C6ST-1 and C6ST-2 siRNAs (1 μg/head; GeneWorld) or PBS was combined with 0.1% atelocollagen (Koken Co.), which is a vehicle for siRNA, and 200 μl of the resulting mixture was injected into the peritoneal cavity of each mouse. Groups of mice treated as described above were named C6ST siRNA group and control group. On day 8 of the experiment, the mice were dissected to excise the UUO-treated kidney. Thus, samples for immunostaining and gene expression analysis were obtained from the mice. Quantitative PCR was carried out by the same method as described in Example 1.

C6ST-1 siRNA, C6ST-2 primers (Forward, Reverse) (GeneWorld) used herein are shown below.

[Primer Sequences]

*C6ST1 (Chondroitin 6-sulfotransferase-1)

```
Forward:
                                        (SEQ ID NO: 78)
5'-tgtgtggacacacctcccta-3'

Reverse:
                                        (SEQ ID NO: 79)
5'-cttcaaaggtccccttcctc-3'
```

*C6ST2 (Chondroitin 6-sulfotransferase-2)

```
Forward:
                                        (SEQ ID NO: 80)
5'-cagcttgagccatttcaaca-3'

Reverse:
                                        (SEQ ID NO: 81)
5'-gggtgaggcctttaggaaac-3'
```

[C6ST-1 cocktail sequences](Gene Bank accession number NM_016803)
(GeneWorld)

(SEQ ID NO: 82)
5'-gcgccccctctccccatggagaaag-3'

(SEQ ID NO: 83)
5'-gctttgcctcaggatttccgggacc-3'

(SEQ ID NO: 84)
5'-ggttcagccttggtctaccgtgatgtc-3'

(SEQ ID NO: 85)
5'-gcagttgttgctatgcgacctgtat-3'

[C6ST-2 cocktail sequences](Gene Bank accession number NM_021715)
(GeneWorld)

(SEQ ID NO: 86)
5'-tggggagagtgaggattcggtgaa-3'

(SEQ ID NO: 87)
5'-cggacgtgggactcgtcgaggacaaag-3'

(SEQ ID NO: 88)
5'-cgaaagtacctgcccgcccgtttcgc-3'

The result showed that the expression of C6ST-2 (G #10) was enhanced in the kidney (FIG. 41; C6ST-2 is abbreviated as G #10). The expression level was decreased in the C6ST siRNA-treated group. The C6ST-2 gene knockdown was confirmed in the atelocollagen-mediated C6ST siRNA administration (FIG. 41). The C6ST siRNA administration also significantly suppressed the enhanced expression of fibrogenesis markers: TGFβ, αSMA, type I collagen, and CTGF.

[Example 42] Assessment of C6ST siRNA for Fibroblast Infiltration in Renal Fibrosis Model Mice Induced by Unilateral Ureteral Obstruction (UUO)

The isolated tissues were embedded in OCT compound (Sakura Finetechnical Co.), an embedding medium for cryosectioning. Cryoblocks were prepared using liquid nitrogen, and sliced into 6-μm thick sections using Cryostat (Microedge Instruments Co.). The resulting sections were immunostained by the same method as described in Example 28 using an anti-ER-TR7 antibody. The samples were observed under a light microscope (Leica Microsystems). The antibody binding was detected by visualizing it as signals and quantified.

The result showed that the accumulation of fibroblasts in the renal interstitium was significantly suppressed in the UUO-treated kidney in the C6ST siRNA-treated group as compared to the control group (FIG. 42).

The agents of the present invention are thus useful, for example, as agents for suppressing fibroblast accumulation in kidney interstitium.

[Example 43] Assessment of C6ST siRNA in Macrophage Infiltration in Renal Fibrosis Model Mice Induced by Unilateral Ureteral Obstruction (UUO)

Immunostaining and quantitation was carried out by the same method as described in Example 42 using an anti-F4/80 antibody. The result showed that the accumulation of macrophages in the renal interstitium was significantly suppressed in the UUO-treated kidney in the C6ST siRNA-treated group as compared to the control group (FIG. 43).

The agents of the present invention are thus useful, for example, as agents for suppressing macrophage accumulation in kidney interstitium.

[Example 44] Assessment of C6ST siRNA in Collagen Accumulation in a Renal Fibrosis Mouse Model Included by Unilateral Ureteral Obstruction (UUO)

Immunostaining was carried out by the same method as described in Example 42 using an anti-type IV collagen antibody, and quantitation was achieved by the same method as described in Example 34. The result showed that the fibrous thickening of glomerular basement membrane in the UUO-treated kidney was significantly suppressed in the C6ST siRNA-treated group as compared to the control group (FIG. 44). This suggests that the infiltration and fibrogenesis of inflammatory cells can be suppressed by inhibiting the expression of C6ST-2 gene.

The agents of the present invention are thus useful, for example, as agents for suppressing the infiltration of inflammatory cells.

[Example 45] Assessment of C6ST siRNA for Fibroblast Activation in a Renal Fibrosis Mouse Model Induced by Unilateral Ureteral Obstruction (UUO)

Immunostaining was carried out by the same method as described in Example 30 using an αSMA antibody. The result showed that αSMA-positive cells were clearly decreased in the interstitium, juxtaglomerular areas in particular, of the UUO-treated kidneys in the C6ST siRNA-treated group as compared to the control group (FIG. 45). This result suggests that the activation of fibroblasts accumulating in the renal interstitium is suppressed by inhibiting the expression of C6ST-1 and C6ST-2 genes.

The agents of the present invention are thus useful, for example, as agents for suppressing the activation of fibroblasts in the renal interstitium.

[Example 46] Assessment of C6ST siRNA in ACE Expression in a Renal Fibrosis Mouse Model Induced by Unilateral Ureteral Obstruction (UUO)

Immunostaining was carried out by the same method using a rabbit anti-human ACE antibody (Santa Cruz). The result showed that ACE-positive cells were clearly decreased in the interstitium, juxtaglomerular areas in particular, of the UUO-treated kidneys in the C6ST siRNA-treated group as compared to the control group (FIG. 46). This result demonstrates that inhibition of C6ST-2 gene expression results in the suppression of ACE expression with the suppression of the activation of fibroblasts accumulated in the renal interstitium. Suppression of ACE produces a hypotensive effect. Thus, the result described above strongly suggests that C6ST siRNA has antihypertensive activity or arteriosclerosis-suppressing effect.

The agents of the present invention are thus useful, for example, as arteriosclerosis-suppressing agents.

[Ocular Tissue]

Like other organs, fibrotic changes in ocular tissues occur as a result of invasion due to various causes. This leads to impairment and/or loss of vision. Such major diseases include diabetic retinopathy, retinal vein occlusion, retinopathy of prematurity, age-related macular degeneration, and retinitis pigmentosa. The diseases also include fibrogenesis associated with corneal inflammation, glaucoma, or cataract (reviews: Fiedlander M. J Clin Invest 117: 576-586, 2007; Harada T et al. Genes and Dev. 21: 367-378, 2007). From the histopathological viewpoint, damage/decrease of photoreceptor cells caused by fibrogenesis is the major cause of visual loss. Thus, suppressing fibrogenesis in ocular tissues has been expected as a novel therapeutic strategy to prevent visual loss in all ocular diseases.

Next Examples focus on retinal fibrogenesis and the resulting loss of photoreceptor cells in a diabetic retinopathy model.

[Example 47] Assessment of GalNAc4S-6ST (G #1) siRNA in Collagen Accumulation in a Mouse Diabetic Retinopathy Model Gestational Day 14 C57BL6J/JcL mice (CLEA Japan Inc.) were reared and allowed to deliver. 10 mg/ml Streptozocin (SIGMA) was subcutaneously administered at 20 μl/head to Day 2 postnatal female C57BL6J/JcL mice. The mice were reared with sterile water and CE-2 Diet (CLEA Japan Inc.) until they were four weeks old, and then with sterile water and a High Fat Diet (CLEA Japan Inc.) for subsequent two weeks. 1 μg of GalNac4S-6ST (G #1) siRNA (Hokkaido System Science Co.) was combined with 200 μl of 1% atelocollagen (Koken Co.), which is a vehicle, and the resulting mixture was administered into the peritoneal cavity of each mouse in the eighth and ninth week by the same method as described in Example 11. In the 18th week, eye balls were excised from mice of the two groups and immunohistochemically examined to assess the effect of GalNac4S-6ST (G #1) siRNA.

Cryoblocks and sections were prepared from the excised eye balls. The sections were fixed with acetone (Sigma Aldrich Japan) for ten minutes, and then washed with phosphate buffer. A rabbit anti-type IV collagen antiserum (1:2000 dilution; LSL) was added as the primary antibody, and the sections were incubated at room temperature for one hour. Then, a peroxidase-labeled anti-rabbit IgG antibody (1:25 dilution; Cappel) was added as the secondary antibody, and the samples were incubated at room temperature for 30 minutes. After incubation, an enzyme-mediated chromogenic reaction was conducted by adding DAB substrate (Nichirei Biosciences). The samples were observed under a light microscope (Leica Microsystems).

Obtained histology of the retina is shown in FIG. 47. In the control group, the deposition of type IV collagen was increased over the region from ganglion cell layer (GCL) to inner nuclear layer (INL), which is essential for vision. By contrast, the increase of collagen in GCL in particular, was significantly suppressed in the GalNac4S-6ST (G #1) siRNA-administered group.

The agents of the present invention are thus useful, for example, as agents for suppressing collagen increase in the ganglion cell layer.

[Example 48] Assessment of GalNac4S-6ST (G #1) siRNA in the Accumulation of Sodium Chondroitin Sulfate Proteoglycan in a Mouse Diabetic Retinopathy Model The retina was immunohistochemically assessed using the same method as described in Example 47. An anti-chondroitin sulfate proteoglycan (CSPG) antibody (clone CS56, mouse monoclonal antibody, 1:100; Seikagaku Co.) was added as the primary antibody, and the sections were incubated at room temperature for one hour. Then, the secondary antibody reaction was carried out using Histofine Mouse Stain kit (Nichirei; used for mouse monoclonal antibody).

As shown in FIG. 48, a significant enhancement of CS56-positive signals were observed in GCL, and the segment from outer nuclear layer (ONL) to pigmented cell layer of retina in the control group. In contrast, the CS56 signal intensity was markedly reduced in the GalNac4S-6ST (G #1) siRNA-administered group. Thus, gangliocytes and retinal pigment epithelial cells were morphologically well preserved in GCL.

The result described above demonstrates that in vivo administration of GalNac4S-6ST (G #1) siRNA significantly suppresses the induced CSPG deposition in retinal tissues in this model mouse. Together with collagen, CSPG is considered to be essential for the formation of fibrogenic lesions. Furthermore, CSPG has been reported to inhibit the process of axon extension of gangliocyte (Brittis P A et al., Science 255: 733, 1992). Previously published reports only describe results of in vitro experiments and developmental process. Thus, the role in in vivo pathological lesions still remains unknown. However, the result described herein for the first time suggests the role of CSPG in lesional tissues.

[Example 49] Assessment of GalNac4S-6ST (G #1) siRNA in the Accumulation of Glial Cells in a Mouse Diabetic Retinopathy Model Optic nerve regeneration has been reported to serve as a biological defense mechanism after retinal damage. Meanwhile, it is reported that the optic nerve progenitor cells responsible for such regeneration after injury are glial cells (Fischer A J et al., Nature neuroscience 4: 247, 2001; Ooto S et al., PNAS 101: 13645, 2004). In this Example, immunostaining was carried out using a goat anti-GFAP antibody (Santa Cruz) as a glial cell marker by the same method as described in Example 47.

The result is shown in FIG. 49. The number of GFAP-positive glial cells was not altered in both normal and control groups. In contrast, the cell count was markedly increased in the area from INL to GCL in the GalNac4S-6ST (G #1) siRNA-administered group. Optic nerve regeneration has been reported to occur from INL toward GCL. Thus, the result described above suggests the process of active optic nerve regeneration induced by GalNac4S-6ST (G #1) siRNA.

The agents of the present invention are thus useful, for example, as agents for regenerating the optic nerve.

[Example 50] Assessment of GalNac4S-6ST (G #1) siRNA in Gangliocytes in a Mouse Diabetic Retinopathy Model Gangliocytes were quantified using samples prepared in Example 47. The result revealed that GCL gangliocytes were reduced in the diabetic retinopathy model but the loss was significantly recovered by GalNac4S-6ST (G #1) siRNA administration (FIG. 50).

[Example 51] Assessment of GalNac4S-6ST (G #1) siRNA in Gene Expression in a Mouse Diabetic Retinopathy Model RNA was extracted from ocular tissues and quantitative PCR was carried out by the same method as described in Example 1. The ability to regenerate the optic nerve was assessed by analyzing changes in the expression of glutamate synthetase (GS), which is a Muller cell marker. The sequences of PCR primers are shown below.

[Quantitative PCR Primer Sequences]

*mouse GS (Takara Bio Inc.)

```
Forward:
                                      (SEQ ID NO: 89)
5'-CTGTGAGCCCAAGTGTGTGGA-3'

Reverse:
                                      (SEQ ID NO: 90)
5'-GTCTCGAAACATGGCAACAGGA-3'
```

The result is shown in FIG. 51. Administration of GalNac4S-6ST (G #1) siRNA could significantly inhibit the enhanced expression of GalNAc4S-6ST in ocular tissues. The expression inhibition resulted in a significant increase in the expression of GS in ocular tissues in the GalNac4S-6ST (G #1) siRNA-administered group. The result described above shows that GalNac4S-6ST (G #1) siRNA administration results in Muller cell regeneration, i.e., optic nerve restoration.

This Example revealed that fibrotic changes of retinal tissues could be suppressed by inhibiting the expression of GalNAc4S-6ST gene, which led to the prevention of photoreceptor cell loss through the regeneration of gangliocytes. This histological feature is commonly observed in a wide variety of ocular diseases with fibrosis including glaucoma and diabetic retinopathy.

The agents of the present invention are thus useful, for example, as agents for regenerating Muller cells or gangliocytes.

[Liver Tissue]

Fibrotic changes in liver tissues are the progressive or terminal stage of various liver diseases. Liver fibrogenesis results from various liver diseases, including viral hepatitis (type A, B, C, D, E, and G viral hepatitis), alcohol liver disease, nonalcoholic fatty liver diseases (NAFLD and NASH), metabolic liver disease, drug-induced liver disease, idiopathic portal hypertension, Budd-Chiari's syndrome, autoimmune hepatitis, primary biliary cirrhosis, primary sclerosing cholangitis, biliary disorders (including biliary atresia and biliary dilation), biliary atresia caused by pancreatic diseases such as tumor, graft-versus-host reaction, and chronic rejection (Bataller R et al., J Clin Invest 115: 209, 2005; Iredale J P. J Clin Invest 117: 539, 2007). Fibrotic changes of liver at the tissue level were assessed in the next Examples.

[Example 52] Assessment of GalNAcST siRNA in Gene Expression in a Mouse Fatty Liver Disease Model Gestational day 14 C57BL/6JcL mice (CLEA Japan Inc.) were reared and allowed to deliver. Streptozocin (STZ; SIGMA) was administered to Day 2 postnatal C57BL/6JcL mice. STZ (10 mg/ml) was subcutaneously administered at 20 μl/head three times for two days. Thus, a total of 60 μl was administered to the mice. Together with their mothers, the mice were fed with a normal diet until they were four weeks old. After weanling at the age of four weeks, the mice were fed with a High Fat Diet (CLEA Japan Inc.) for two weeks. In the second week, 200 μl of GalNAcST siRNA described in Example 11 was administered into peritoneal cavities once a week (one shot/week) twice in total (for two weeks). On day 14 of the experiment, the mice were dissected and their livers were isolated to prepare samples for gene expression analysis and immunostaining.

Quantitative PCR was carried out by the same method as described in Example 1 using liver tissues. The result is shown in FIG. 52. The expression of GalNAc4S-6ST is enhanced in liver tissues in this model. GalNAcST siRNA administration resulted in significant suppression of the expression.

[Example 53] Assessment of Anti-Fibrogenic Effect of GalNAcST siRNA in a Mouse Fatty Liver Disease Model The expression of fibrogenesis markers in liver tissues was assessed by the same method as described in Example 52. The expression of type I collagen and αSMA was significantly enhanced in this model (FIG. 53), suggesting enhanced fibrotic changes in liver tissues. Meanwhile, the enhanced expression of the fibrogenesis markers was significantly suppressed by administering GalNAcST siRNA.

[Example 54] Assessment of GalNAcST siRNA in Fibroblast Infiltration in a Mouse Fatty Liver Disease Model Next, liver tissues were immunostained by the same method as described in Example 3. A rat anti-mouse fibroblast antibody (clone ER-TR7, 1:500 dilution; BMA) was added as the primary antibody, and the sections were incubated at room temperature for one hour. Then, a peroxidase-labeled anti-rat IgG antibody (1:200 dilution; Biosource International, Inc.) was added as the secondary antibody, and the sections were incubated at room temperature for 30 minutes. After incubation, DAB substrate (Nichirei Biosciences) was added, and the samples were observed under a light microscope (Leica Microsystems). The antibody binding was detected by visualizing it as signals.

Examples of obtained images of immunostained liver tissues are shown in FIG. 53. The accumulation of fibroblasts was clearly observed and a bridge formation was confirmed in the histological picture in the control group. In contrast, there was almost no accumulation of fibroblasts in the GalNAcST siRNA-administered group.

[Example 55] Assessment of GalNAcST siRNA in Fibrogenic Score in a Mouse Fatty Liver Disease Model Each of the samples immunohistochemically stained in Example 54 was assessed for the degree of live fibrogenesis using fibrogenesis scores based on previous reports (Dai K, et al., World J Gactroenterol. 31: 4822-4826, 2005; Hillebrandt S, et al., Nature Genetics 37: 835-843, 2005). The fibrogenesis scores were defined according to the following criteria: 0, normal; 1, few collagen fibrils extend from the central vein; 2, extension of collagen fibrils is apparent but collagen fibrils have not yet encompassed the whole liver; 3, extension of collagen fibrils is apparent and collagen fibrils have encompassed the whole liver; 4, diffuse extension of collagen fibrils is observed in the whole liver and pseudo lobules are formed.

The result is shown as a graph in FIG. 55. Each bar indicates mean±standard deviation of the fibrogenesis score in each group. The fibrogenesis was statistically significantly reduced in the GalNAcST siRNA-administered group as compared to the control group ($p<0.01$; t-test). This finding suggests that GalNAcST siRNA administration also clinically produces a superior liver fibrogenesis-suppressing effect.

[Example 56] Assessment of GalNAcST siRNA in Macrophage Infiltration in a Mouse Fatty Liver Disease Model Next, liver tissues were immunostained by the same method as described in Example 54. A rat anti-mouse F4/80 antibody (clone A3-1, 2 μg/ml; CALTAG LABORATORIES) was added as the primary antibody, and the sections were incubated at room temperature for one hour. Then, a peroxidase-labeled anti-rat IgG antibody (1:200 dilution; Biosource International, Inc.) was added as the secondary antibody, and the sections were incubated at room temperature for 30 minutes. After incubation, DAB substrate (Nichirei Biosciences) was added, and the samples were observed under a light microscope (Leica Microsystems). The antibody binding was detected by visualizing it as signals.

Examples of obtained images of immunostained liver tissues are shown in FIG. 56. The accumulation of macrophages was clearly observed in the control group. Formation of inflammatory accumulation lesions were seen in the histological pictures. In contrast, there was no excessive accumulation of macrophages in the GalNAcST siRNA-administered group.

[Example 57] Assessment of GalNAcST siRNA in the Hepatic Lipid Metabolism in a Mouse Fatty Liver Disease Model The expression of lipid metabolism-related genes in the liver was assessed by the same method as described in Example 52. The enhanced expression of carbohydrate response element-binding protein (ChREBP) and acetyl-CoA carxylase-2 (ACC2) was observed. Meanwhile, the enhanced expression was significantly suppressed in the GalNAcST siRNA-administered group (FIG. 57). This result shows that the glycolipid metabolism can be improved via suppression of fibrotic changes in liver tissues by inhibiting the expression of GAlNAc4ST-1, GalNAc4ST-2, and GalNAc4S-6ST genes.

The agents of the present invention are thus useful, for example, as agents for improving glycolipid metabolism.

[Example 58] Assessment of C4ST-1 siRNA, C4ST-2 siRNA, and C4ST-3 siRNA for Fibroblast Accumulation in a Mouse Fatty Liver Disease Model A fatty liver disease model was prepared by the same method as described in Example 52. C4ST-1 siRNA, C4ST-2 siRNA, and C4ST-3 siRNA described in Example 21 were administered according to the same administration protocol. Liver tissues were collected from the mice.

Next, liver tissues were immunostained by the same method as described in Example 3. A rat anti-mouse fibroblast antibody (clone ER-TR7, 1:500 dilution; BMA) was added as the primary antibody, and the sections were incubated at room temperature for one hour. Then, a peroxidase-labeled anti-rat IgG antibody (1:200 dilution; Biosource International, Inc.) was added as the secondary antibody, and the sections were incubated at room temperature for 30 minutes. After incubation, DAB substrate (Nichirei Biosciences) was added, and the samples were observed under a light microscope (Leica Microsystems). The antibody binding was detected by visualizing it as signals.

Examples of obtained images of immunostained liver tissues are shown in FIG. 58. The accumulation of fibroblasts was clearly observed in the control group. A bridge formation was seen in the histological pictures. In contrast, fibroblast accumulation was not observed in any of the C4ST-1 siRNA-, C4ST-2 siRNA-, and C4ST-3 siRNA-administered group.

[Example 59] Assessment of C4ST-1 siRNA, C4ST-2 siRNA, and C4ST-3 siRNA in the Fibrogenic Score in a Mouse Fatty Liver Disease Model Each sample was assessed for the degree of liver fibrogenesis using the fibrogenesis scores based on the immunohistochemical staining carried out in Example 58. The result is shown in FIG. 59. Each bar indicates mean±standard deviation of the fibrogenesis score in each group. The fibrogenesis was statistically significantly reduced in all of the C4ST-1 siRNA-, C4ST-2 siRNA-, C4ST-3 siRNA-administered groups as compared to the control group ($p<0.001$; t-test). This finding suggests that the administration of siRNAs against C4ST-1, C4ST-2, or C4ST-3 also clinically produces a superior liver fibrogenesis-suppressing effect.

[Example 60] Assessment of C4ST-1 siRNA, C4ST-2 siRNA, and C4ST-3 siRNA in Hepatocyte Disorders in a Mouse Fatty Liver Disease Model When mice were sacrificed, blood was collected from them according to the protocol as described in Example 58. The blood samples were custom-assayed for the serum alanine transferase (ALT) levels through SRL Inc. The result is shown in FIG. 60. The serum ALT level is the most widely used clinical indicator for hepatocyte destruction. The serum ALT level was elevated in the control group. Meanwhile, the mean value was decreased to 50% or less in each of the C4ST-1 siRNA-, C4ST-2 siRNA-, and C4ST-3 siRNA-administered groups as compared to the control group (FIG. 60). This result demonstrates that hepatocyte damages can be reduced via suppression of fibrotic changes by inhibiting the expression of C4ST-1, C4ST-2, or C4ST-3 gene in liver tissues.

The agents of the present invention are thus useful, for example, as agents for reducing hepatocyte damage.

[Example 61] Assessment of the Anti-Fibrogenic Effect of C6ST siRNA in a Mouse Hepatic Fibrosis Model In this Example, experiments were carried out using a mouse cirrhosis model induced by carbon tetrachloride, which is the most widely used cirrhosis model. First, the mouse model was prepared as described below. Carbon tetrachloride (25 μl/100 g body weight; Sigma-Aldrich) was injected into peritoneal cavities of C57BL6/J mice (female, five or six weeks old; CLEA Japan Inc.) twice a week for four weeks (eight times) to induce hepatic fibrosis. Then, carbon tetrachloride was additionally administered twice a week for two weeks (a total of 12 times) to induce cirrhosis. Mice with induced cirrhosis were sacrificed, and their livers were collected (cirrhotic livers). Meanwhile, in the control experiment, livers were collected from C57BL6/J mice (female, CLEA Japan Inc.) of the same age without carbon tetrachloride administration (normal livers).

The same C6ST siRNA as described in Example 41 and a control were administered into peritoneal cavities four times at the same time of additional carbon tetrachloride administration (a total four times from the ninth to twelfth administration). After the additional administration, mice in the both groups were sacrificed. Liver tissue sections were prepared from the mice and immunohistochemically assessed. A rat anti-mouse fibroblast antibody (clone ER-TR7, 1:500 dilution; BMA) was added as the primary antibody, and the sections were incubated at room temperature for one hour. Then, a peroxidase-labeled anti-rat IgG antibody (1:200 dilution; Biosource International, Inc.) was added as the secondary antibody, and the sections were incubated at room temperature for 30 minutes. After incubation, DAB substrate (Nichirei Biosciences) was added, and the samples were observed under a light microscope (Leica Microsystems). The antibody binding was detected by visualizing it as signals.

Examples of obtained images of immunostained liver tissues are shown in FIG. 61. The accumulation of fibroblasts was clearly observed in the control group. A bridge formation was shown in the histological pictures. In contrast, there was no accumulation of fibroblasts in any of the C6ST siRNA-administered groups.

[Example 62] Assessment of C6ST siRNA in the Fibrogenesis Score in a Mouse Hepatic Fibrosis Model The degree of liver fibrogenesis in each sample was assessed using the fibrogenesis scores based on the immunohistochemical staining carried out in Example 61. The result is shown in FIG. 62. Each bar indicates mean±standard deviation of the fibrogenesis score in each group. The fibrogenesis was statistically significantly reduced in the C6ST siRNA-administered group as compared to the control group ($p<0.05$; t-test). This finding suggests that the administration of C4ST-1 siRNA, C4ST-2 siRNA, or C4ST-3 siRNA also produces a clinically beneficial effect of suppressing liver fibrogenesis.

[Example 63] Assessment of the Anti-Fibrogenic Effect of C6ST siRNA in a Mouse Hepatic Fibrosis Model RNA was extracted from liver tissues and quantitative PCR was carried out by the same method as described in Example 1. The result is shown in FIG. 63. The expression of αSMA, type I collagen, CTGF, and TGFβ as fibrogenesis markers was enhanced in the control group. Meanwhile, the expression was significantly suppressed in the C6ST siRNA-administered group. This result suggests that fibrotic changes in liver tissues can be suppressed by inhibiting the expression of C6ST-1 and C6ST-2 genes.

[Cranial Nerve Tissue]

In these Examples, an MPTP-induced Parkinson's disease model was used as a fundamental mouse model for Parkinson's disease. This model is a classical but highly reproducible and simple model, and thus has been widely used as a Parkinson's disease model. The histological features are: infiltration of inflammatory cells into brain parenchymal tissue and reduction in the number of dopamine-producing neurons. Classically, neurofibrillary tangles were thought to be a cause of the reduction in the number of neurons in such pathological conditions.

Thus, such diseases include pathological conditions with neuronal disorders, specifically, not only representative neurodegenerative diseases such as Parkinson's disease, progressive supranuclear palsy, corticobasal degeneration, Alzheimer's disease, polyglutamine disease, amyotrophic lateral sclerosis (ALS), spinal progressive muscular atrophy, spinobulbar muscular atrophy, Huntington's disease, and multiple sclerosis, but also other diseases such as multiple system atrophy (striatonigral degeneration, olivopontocerebellar atrophy, and Shy-Drager syndrome), adrenoleukodystrophy, Guillain-Barre syndrome, myasthenia gravis, Fisher syndrome, chronic inflammatory demyelinating polyneuropathy, Lewis-Sumner syndrome, Crow-Fukase syndrome, normal pressure hydrocephalus, syringomyelia, prion disease (Creutzfeldt-Jakob disease, Gerstmann-Straussler-Scheinker disease, and fatal familial insomnia), subacute sclerosing panencephalitis (SSPE), progressive multifocal leukoencephalopathy (PML), and spinocerebellar degeneration. Such diseases also include posttraumatic cerebral sequelae, sequelae of cerebrovascular disease (cerebral infarction and hemorrhage), sequelae of viral encephalitis, sequelae of bacterial meningitis, sequelae of spinal cord injury, and neurofibrillary tangle in the spinal nerve, peripheral nerve, auditory nerve, and optical nerve, etc. In particular, the above-listed sequelae have long been speculated as a basis for psychiatric disorders such as depression, and thus neurofibrillary tangle is important as a cause of psychiatric symptoms.

[Example 64] Assessment of the Anti-Fibrogenic Effect of GalNAc4S-6ST siRNA Treatment in a C57BL/6JcL Mouse Parkinson's Disease Model Induced by MPTP In this Example, a mouse Parkinson's disease model was prepared by selectively degenerating dopamine neurons using 1-methyl-4-phenyl-1,2,3,6 tetrahydropyridine (MPTP) (Amende et al., (2005) Journal of NeuroEngineering and Rehabilitation 2(20): 1-13). The mice were administered with GalNAc4S-6ST siRNA, and the gene expression and histological features after treatment was assessed.

Gestational day 14 C57BL/6JcL mice (CLEA Japan Inc.) were reared and allowed to deliver. 1 μg of the same GalNAc4S-6ST siRNA (GeneWorld) as described in Example 1 was combined with 1% atelocollagen (Koken Co.), which is a vehicle for siRNA, and the mixture was administered at 200 μl/head to the peritoneal cavities of C57BL/6JcL mice (female, eight weeks old; CLEA Japan Inc.). Two, three, and four days after administration, MPTP (Sigma Aldrich Japan), which selectively destroys dopamine neurons, was administered to the mice at 30 mg/kg (three times in total). The mice were reared, and on day 8 of the experiment 100 μl of 5 mg/ml BrdU (ZyMED Laboratory Inc.) was administered into the tail vein. After one hour, the mice were dissected and their brains were isolated to prepare samples for immunostaining and gene expression analysis.

The gene expression was assessed quantitatively by the same method as described in Example 1. The result is shown in FIG. 64. The expressions of GalNAc4S-6ST, and TGFβ, type I collagen, and αSMA, which are fibrogenesis markers, are enhanced in brain tissues in the Parkinson's disease model. Meanwhile, the expression was significantly suppressed by GalNAc4S-6ST siRNA administration. This demonstrates that fibrotic changes in brain tissues can be suppressed by inhibiting the expression of GalNAc4S-6ST.

The agents of the present invention are thus useful, for example, as agents for suppressing fibrotic changes in brain tissues.

[Example 65] Assessment of GalNAc4S-6ST siRNA Treatment for Fibroblast Accumulation in a C57BL/6JcL Mouse Parkinson's Disease Model Induced by MPTP Brain tissue samples were treated by the same method as described in Example 3 to compare histological features after in vivo administration of GalNAc4S-6ST against fibrogenesis of neurons in the brain. The resulting sections were fixed with 4% PFA-phosphate buffer (Nacalai Tesque) for ten minutes, and then washed with deionized water. An anti-fibroblast antibody (ER-TR7, 1:100 dilution; BMA) was added as the primary antibody, and the sections were incubated at 4° C. overnight. Then, an Alexa488-labeled goat anti-rat IgG antibody (1:200 dilution; Invitrogen) was added as the secondary antibody, and the sections were incubated at room temperature for 30 minutes.

Images of tissues obtained by the method described above are shown in FIG. 65. The strong positive signals in the untreated group suggest intracranial infiltration of fibroblasts around the granular cortex in the splenium of posterior corpus callosum as compared to the control group. The positive signals of fibroblasts were drastically decreased in the GalNAc4S-6ST siRNA-treated group. The result described above demonstrates that the feature represented by ER-TR7-positive signals in brain tissues induced in the mouse Parkinson's disease model was significantly suppressed by in vivo administration of GalNAc4S-6ST siRNA.

[Example 66] Assessment of the Neuroprotective Effect of GalNAc4S-6ST siRNA Treatment in a C57BL/6JcL Mouse Parkinson's Disease Model Induced by MPTP Next, to assess whether the above-described fibrogenesis was associated with the decrease of neurons, the expression of nerve regeneration-related genes in brain tissues was quantified by the same method as described in Example 64. The administration of GalNAc4S-6ST siRNA resulted in enhanced expression of GDNF, which is a factor that regulates the survival and differentiation of dopamine neurons as well as enhances the regeneration of the neurons, and Nurr1, which is a factor for forming dopamine neurons (FIG. 66). This result suggests that the regeneration of dopamine neurons in brain tissues can be stimulated by inhibiting the expression of GalNAc4S-6ST.

The agents of the present invention are thus useful, for example, as agents for stimulating the regeneration of dopamine neurons in brain tissues.

[Example 67] Assessment of the Neuroprotective Effect of GalNAc4S-6ST siRNA Treatment in a C57BL/6JcL Mouse Parkinson's Disease Model Induced by MPTP To finally verify the results described above in the Examples, histological features of the prepared tissue sample sections were weighed by staining dopamine neurons of the sections with an antibody against tyrosine hydroxylase, which is a marker for dopamine neuron. Tyrosine hydroxylase (TH) is an enzyme that converts the dopamine precursor into dopamine. The sections prepared by the same method as described in Example 64 were fixed with 4% PFA-phosphate buffer (Nacalai Tesque) for ten minutes, and then washed with deionized water. A rabbit anti-tyrosine hydroxylase polyclonal antibody (1:50 dilution; Calbiochem) was added as the primary antibody, and the sections were incubated at room temperature for one hour. An Alexa488-labeled donkey anti-rabbit antibody (1:200 dilution; Invitrogen) was added as the secondary antibody, and the sections were incubated at room temperature for 30 minutes.

Histological images for the control, untreated, and GalNAc4S-6ST siRNA-treated groups are shown in FIG. 67 (the original images are in color). Normal expression of tyrosine hydroxylase was confirmed in the superior colliculus of midbrain in the control group. Meanwhile, the signal for the expression was negative in the untreated group. This finding suggests that MPTP selectively destroyed dopamine neurons. On the other hand, a stronger signal was confirmed in the GalNAc4S-6ST siRNA-treated group as compared to the untreated group. In sum, it was concluded that functional recovery of dopamine neurons can be achieved via suppression of fibrotic changes by in vivo administration of GalNAc4S-6ST siRNA.

The agents of the present invention are thus useful, for example, as agents for recovering the function of dopamine neuron.

[Example 68] Assessment of Neuroprotective Effect of GalNAcST siRNA Treatment in a C57BL/6JcL Mouse Parkinson's Disease Model Induced by MPTP By the same procedure as described in Example 64, gestational day 14 of C57BL/6JcL mice (CLEA Japan Inc.) were reared and allowed to deliver. 1 μg of GalNAcST (a mixture of GalNAc4ST-1, GalNAc4ST-2, and GALNAC4S-6ST cocktail sequences) siRNAs (GeneWorld) was combined with 1% atelocollagen (Koken Co.), which is a vehicle for siRNA, and the resulting mixture was administered at 200 μl/head to the peritoneal cavities of C57BL/6JcL mice (female, eight weeks old; CLEA Japan Inc.). Two, three, and four days after administration, MPTP (Sigma Aldrich Japan), which selectively destroys dopamine neurons, was administered to the mice at 30 mg/kg (three times in total). The mice were reared, and on day 8 of the experiment 100 μl of 5 mg/ml BrdU (ZyMED Laboratory Inc.) was administered into the tail vein. After one hour, the mice were dissected and their brains were isolated to prepare samples for immunostaining and gene expression analysis.

The resulting sections were immunostained with an anti-TH antibody by the same method as described in Example 67. The result is shown in FIG. 68. The result demonstrated that the reduction of TH-positive dopamine neurons was suppressed in the GalNAcST siRNA-treated group. Specifically, like Example 67, it was concluded that function recovery of dopamine neurons can be achieved via suppression of neurofibrillary tangle by inhibiting the expression of GalNAc4ST-1, GalNAc4ST-2, and GalNAc4S-6ST.

The agents of the present invention are thus useful, for example, as agents for suppressing neurofibrillary tangle.

[Example 69] Assessment of the Effect of C4-Sulfatase in a Mouse Type 2 Diabetic Retinopathy Model Induced by Streptozotocin: Reduction of Sulfated CSPG Gestational day 14 C57BL/6JcL mice (CLEA Japan Inc.) were reared and allowed to deliver. 10 mg/ml Streptozocin (SIGMA) was subcutaneously administered at 20 μl/head to postnatal Day 2 female C57BL/6JcL mice. The mice were reared with sterile water and CE-2 Diet (CLEA Japan Inc.) until they were four weeks old, and then with sterile water and a High Fat Diet (CLEA Japan Inc.) for subsequent two weeks. In the second week, chondro-4-desulfating enzyme (C4-sulfatase) (20 units/ml; Seikagaku Co.) was administered at 4 units/head or medium (phosphate buffer) was administered into the peritoneal cavities twice a week four times (two weeks). On day 14, eye balls were isolated from mice of both groups and immunohistochemically assayed to assess the effect of C4-sulfatase.

Cryoblocks and sections were prepared from the isolated eye balls. The sections were fixed with acetone (Sigma Aldrich Japan) for ten minutes, and then washed with phosphate buffer. Then, an anti-chondroitin sulfate proteoglycan (CSPG) antibody (clone CS56, mouse monoclonal antibody, 10 μg/ml; Seikagaku Co.) was added as the primary antibody, and the sections were incubated at room temperature for one hour. Next, the secondary antibody reaction was carried out using a Histofine Mouse Stain kit (Nichirei Biosciences; used for mouse monoclonal antibody), and color development was performed by adding DAB substrate (Nichirei Biosciences). The samples were observed under a light microscope (Leica Microsystems).

The obtained histological pictures are shown in FIG. 69 (the original images are in color). In the untreated group, CS56-positive signals are newly found in the vitreous side of the retina. In contrast, the intensity of CS56 is reduced in the enzyme-treated group. CS56 is an antibody that recognizes a sulfate group, and the reduction is suggested to reflect a decrease of sulfate groups at position 4. The result described above demonstrates that the induced deposition of CSPG in retinal tissues is suppressed via modification by in vivo administration of C4-sulfatase.

C4-sulfatase is an enzyme that desulfates GalNAc at position 4. Thus, it was demonstrated that tissue fibrogenesis at the biological level could be suppressed by inhibiting the sulfation of GalNAc at position 4. Specifically, desulfating enzymes for the sulfate group of GalNAc at position 4 are useful as tissue fibrogenesis inhibitors.

[Example 70] Assessment of the Effect of C4-Sulfatase in a Mouse Type 2 Diabetic Retinopathy Model Induced by Streptozotocin: Suppression of Vascular Endothelial Cell Proliferation The sections prepared by the same method as described in Example 69 were fixed with acetone (Sigma Aldrich Japan) for ten minutes, and then washed with phosphate buffer. A rat anti-vascular endothelial cell antibody (CD31; 1:200 dilution; Pharmingen) was added as the primary antibody, and the sections were incubated at room temperature for one hour. Then, a donkey peroxidase-labeled anti-rat IgG antibody (1:200 dilution; Biosource International, Inc.) was added as the secondary antibody, and the sections were incubated at room temperature for 30 minutes. After incubation, DAB substrate (Nichirei Biosciences) was added to the samples. The samples were observed under a light microscope (Leica Microsystems). The obtained histological pictures are shown in FIG. 70 (the original images are in color). The images show that the number of CD31-positive cells was increased in the vitreous side of the retina and some of them were protruded into the vitreum in the untreated group. This indicates that the model reflects the stage of preproliferative retinopathy in diabetic retinopathy and shows the effectiveness of this model. Meanwhile, the number of CD31-positive cells was significantly reduced in the corresponding region in the enzyme-treated group. In sum, it is suggested that the number of vascular endothelial cells is increased in the vitreous side of the retina in type 2 diabetes model, and that such proliferation of blood vessels can be suppressed by administering C4-sulfatase.

Specifically, desulfating enzymes for the sulfate group at position 4 of GalNAc are useful as an agent for suppressing proliferation of blood vessels.

[Example 71] Assessment of the Effect of C4-Sulfatase in a Mouse Type 2 Diabetic Retinopathy Model Induced by Streptozotocin: Suppression of Collagen-Proliferative Alteration The sections prepared by the same method as described in Example 69 were fixed with acetone (Sigma Aldrich Japan) for ten minutes, and then washed with phosphate buffer. A rabbit anti-type IV collagen antibody (1:250 dilution; Sigma) was added as the primary antibody, and the sections were incubated at room temperature for one hour. A peroxidase-labeled anti-rabbit IgG antibody (1:200 dilution; Jackson ImmunoResearch) was added as the secondary antibody, and the sections were incubated at room temperature for 30 minutes. After incubation, DAB substrate (Nichirei) was added to the samples. The samples were observed under a light microscope (Leica Microsystems).

The obtained histological pictures are shown in FIG. 71 (the original images are in color). In the untreated group, type IV collagen-positive signals were increased in the vitreous side of the retina and arranged parallel to the internal limiting membrane of the retina. This suggests morphological aberration of vein and collagen proliferation, i.e., fibrotic changes. In contrast, type IV collagen proliferation was markedly suppressed in the corresponding region in the enzyme-treated group. This demonstrated that retinal collagen proliferation is observed in the type 2 diabetes model but the collagen proliferation can be suppressed by administering C4-sulfatase.

Specifically, desulfating enzymes for the sulfate group at position 4 of GalNAc are useful as agents for treating type 2 diabetic retinopathy.

[Example 72] Localization of Fibroblasts in the Liver of Type 2 Diabetes Model Mouse The anti-fibrogenic effect (using tissue infiltration of fibroblasts as an indicator) of C4-sulfatase on the liver was assessed in Examples 72 using the livers collected from the above-described type 2 diabetes model mice (Examples 69-71). Cryoblock preparation, immunostaining, and such were all achieved by the methods described above. As shown in FIG. 72, infiltration of many fibroblasts was observed in the untreated group. Meanwhile, the degree of fibroblast infiltration was reduced in the C4-sulfatase-treated group as compared to the untreated group. This suggests that C4-sulfatase has the pharmacological effect of suppressing fibroblast infiltration and this effect contributes to the anti-fibrogenic effect.

Specifically, desulfating enzymes for the sulfate group at position 4 of GalNAc are useful as agents for suppressing fibroblast infiltration.

[Example 73] Localization of Macrophages in the Liver of Type 2 Diabetes Model Mouse The anti-inflammatory effect (using tissue infiltration of macrophages as an indicator) of C4-sulfatase on the liver was assessed using the livers collected from the above-described type 2 diabetes model mice (Examples 69-71). Cryoblock preparation, immunostaining, and such were all achieved by the methods described above. As shown in FIG. 73, infiltration of many macrophages accompanying spot formation was observed in the untreated group. Meanwhile, the degree of macrophage infiltration was reduced in the C4-sulfatase-treated group as compared to the untreated group. This result suggests that C4-sulfatase has the pharmacological effect of suppressing macrophage infiltration and this effect contributes to the anti-inflammatory effect.

Specifically, desulfating enzymes for the sulfate group at position 4 of GalNAc are useful as agents for suppressing macrophage infiltration or as anti-inflammatory agents.

[Example 74] Serum Biochemical Test Findings on Type 2 Diabetes Model Mice

An additional analysis was carried out in Example 74 to supplement the results of Examples 72 and 73. This Example assayed aspartate aminotransferase (AST) and alanine aminotransferase (ALT) as indicators for liver function, and triacylglycerol (TG) as an indicator for lipid metabolism, using sera collected from the above-described type 2 diabetes model mice (Example 69-71). The result is shown in FIG. 74. Biochemical tests were outsourced. AST, ALT, and TG values all tended to be increased in the untreated group (unt) as compared to the control group (nor). Meanwhile, the increases in the AST, ALT, and TG values tended to be suppressed in the C4-sulfatase-treated group (C4sul) as compared to the untreated group (unt). The result described above supports the results of Examples 72 and 73, suggesting that the liver function is preserved due to the anti-fibrogenic and anti-inflammatory effects of C4-sulfatase.

Specifically, desulfating enzymes for the sulfate group at position 4 of GalNAc are useful as agents for treating liver function disorders.

[Example 75] Comparison of CSPG Expression in Brain Tissues in a C57BL/6JcL Mouse Model for Parkinson's Disease Induced by MPDP The experiments in this Example was performed by preparing a model using MPDP, which is a metabolite of 1-methyl-4-phenyl-1,2,3,6 tetrahydropyridine (MPTP).

On Day 0 and 2, 100 μl of 4 U/ml C4-sulfatase (Seikagaku Co.) was administered into the peritoneal cavity of each of C57BL/6JcL mice (female, eight weeks old; CLEA Japan Inc.). Alternatively, 200 μl of a mixture of GalNAc4S-6ST siRNA (1 μg; Hokkaido System Science Co.) and 1% atelocollagen was pre-administered on Day 0. On Day 2 to 4, MPDP (Sigma Aldrich Japan) was administered at 30 mg/kg every day.

The nucleotide sequence of mouse GalNac4S-6ST siRNA agent used in this Example is shown below, but the sequences are not limited to these examples.

[mouse GalNac4-6ST siRNAs](Gene Bank accession number NM_029935)

(Hokkaido System Science, Co., Ltd.)

```
                                        (SEQ ID NO: 91)
5'- gcagcccagcaagaugaauaagauc-ag -3'

                                        (SEQ ID NO: 92)
3'-ua-cgucgggucguucuacuuauucuag -5'
```

On day 8, 100 pd of BrdU 5 μg/mL (ZyMED Laboratory.Inc) was administered into mouse tail vein. One hour after administration, mice were dissected and their brains were isolated to prepare samples for immunostaining and gene expression analysis. 1 ml of RNA-Bee (TEL-TEST) was added to 50 mg each of excised organs (brains). The organs were crushed using an electrical homogenizer (DIGITAL HOMOGENIZER; AS ONE), then, 200 μl of chloroform (Sigma-Aldrich Japan) was added to the resulting suspension. The mixture was gently mixed and then cooled on ice for about five minutes, and centrifuged in a centrifuge (Centrifuge 5417R; Eppendorf) at 12,000 rpm and 4° C. for 15 minutes. After centrifugation, 500 μl of the supernatant was transferred to a fresh eppendorf tube, and an equal volume of isopropanol (500 μl; Sigma-Aldrich Japan) was added thereto. The solution was mixed, and then 1 μl of glycogen (Invitrogen) was added thereto. The mixture was cooled on ice for 15 minutes, and then centrifuged at 12,000 rpm and 4° C. for 15 minutes. Next, RNA precipitate obtained after washing three times with 1,000 μl of 75% ethanol (Sigma-Aldrich Japan) was air-dried for 30 minutes to one hour, and then dissolved in Otsuka distilled water (Otsuka Pharmaceutical Co., Ltd). The solution was 100 times diluted with Otsuka distilled water. The RNA concentrations of extracted samples in UV plates (Corning Costar) were determined using a plate reader (POWER Wave XS; BIO-TEK).

Next, an RT reaction (cDNA synthesis) was conducted by the following procedure. The concentrations of the obtained RNA samples were adjusted to 500 ng/20 μl. The samples were heated at 68° C. for three minutes in a BLOCK INCUBATOR (ASTEC), and cooled on ice for ten minutes. After cooling on ice, 80 μl of RT PreMix solution (composition: 18.64 μl of 25 mM $MgCl_2$ (Invitrogen), 20 μl of 5× Buffer (Invitrogen), 6.6 μl of 0.1 M DTT (Invitrogen), 10 μl of 10 mM dNTP mix (Invitrogen), 2 μl of RNase Inhibitor (Invitrogen), 1.2 μl of MMLV Reverse Transcriptase (Invitrogen), 2 μl of Random primer (Invitrogen), and 19.56 μl of sterile distilled water (Otsuka distilled water; Otsuka Pharmaceutical Co., Ltd.)), which had been prepared in advance, was added to the samples. The mixtures were heated in a BLOCK INCUBATOR (ASTEC) at 42° C. for one hour and at 99° C. for five minutes, and then cooled on ice. 100 μl of desired cDNAs were prepared and PCR reaction was carried out using the prepared cDNAs in the following composition.

2 μl of PCR Buffer [composition: 166 mM $(NH_4)_2SO_4$ (Sigma Aldrich Japan), 670 mM Tris pH8.8 (Invitrogen), 67 mM $MgCl_2$·6H2O (Sigma Aldrich Japan), 100 mM 2-mercaptoethanol (WAKO)], 0.8 μl of 25 mM dNTP mix (Invitrogen), 0.6 μl of DMSO (Sigma Aldrich Japan), 0.2 μl of Primer Forward (GeneWorld), 0.2 μl of Primer Reverse (GeneWorld), 15.7 μl of Otsuka distilled water (Otsuka Pharmaceuticals, Inc.), 0.1 μl of Taq polymerase (Perkin Elmer), and 1 μl of cDNA obtained as described above were combined, and reacted using Authorized Thermal Cycler (eppendorf) at 30 cycles of 94° C. for 45 seconds, 55° C. for 45 seconds, 72° C. for 60 seconds. After the reaction, the obtained PCR products were combined with 2 μl of Loading Dye (Invitrogen). 1.5% agarose gel was prepared using UltraPure Agarose (Invitrogen), and the samples were electrophoresed in a Mupid-2 plus (ADVANCE) at 100 V for 20 minutes. After electrophoresis, the gel was shaken for 20 minutes in a stain solution prepared by 10,000 times diluting Ethidium Bromide (Invitrogen) with 1×LoTE (composition: 3 mM Tris-HCl (pH 7.5) (Invitrogen), 0.2 mM EDTA (pH 7.5) (Sigma Aldrich Japan)). The gel was photographed with EXILIM (CASIO) positioned on I-Scope WD (ADVANCE)

and confirmed the gene expression. Cryoblock preparation, immunostaining, and such were all achieved by the methods described above.

The expression of CSPG in the MPDP-induced Parkinson's disease model was assessed by immunostaining using antibody against CS-56 (an anti-CSPG antibody, 1:100 dilution; Seikagaku Co.). The result is shown in FIG. 75. Strong CSPG-positive signals were observed in the untreated group, as shown in FIG. 75. Meanwhile, the positive signals were reduced in the C4-sulfatase-treated group and gene therapy group.

[Example 76] Localization of Dopaminergic Neurons in Brain Tissues in a C57BL/6JcL Mouse Model for Parkinson's Disease Induced by MPDP To assess the pharmacological effects of C4-sulfatase and GalNAc4S-6ST siRNA on dopaminergic neurons, localization of dopaminergic neurons in the MPDP-induced Parkinson's disease model was analyzed by fluorescent immunostaining using an anti-tyrosine hydroxylase (TH) antibody (1:20 dilution) and an Alexa-488-labeled anti-rabbit IgG antibody (1:200 dilution; Invitrogen) for the secondary antibody. As shown in FIG. 76, the positive signals for dopaminergic neurons localized in brain tissues were weaker in the untreated group as compared to the other groups. Meanwhile, there was no great difference of the positive signal intensity in the C4-sulfatase-treated group and gene therapy group compared to the control group. The result suggests that the protective effect or regeneration/repair-promoting effect on dopaminergic neuron is produced by the administration of C4-sulfatase or the siRNA.

Specifically, inhibitors that act on GalNAc at position 4 or 6 (desulfating enzymes for the sulfate group at position 4 of GalNAc, and GalNAc4S-6ST siRNA) are useful as agents for protecting dopaminergic neurons or as agents for promoting the regeneration/repair of dopaminergic neurons.

[Example 77] Analysis of Inflammation-Related Gene Expression in Brain Tissues in a C57BL/6JcL Mouse Parkinson's Disease Model Induced by MPDP To compare the anti-inflammatory effects of C4-sulfatase and GalNAc siRNA, total RNAs were extracted by the method described above from the same samples used to prepare tissue sections described in Examples 75 and 76, and the expression of TNF-α was analyzed by quantitative PCR. For quantitative PCR, SYBR Premix Kit (TAKARA BIO INC.) and Real-time PCR thermal cycler DICE (TAKARA BIO INC.) were used. Conditions of PCR reaction was: 95° C. for 10 seconds, 40 cycles of 95° C. for 5 seconds and 60° C. for 30 seconds, finally, melting curve analysis was conducted. Nucleotide sequences of primers used in the quantitative PCR were described below.

mouse β actin (TAKARA BIO INC.)

```
Forward:
                                  (SEQ ID NO: 93)
5'-CATCCGTAAAGACCTCTATGCCAAC-3'

Reverse:
                                  (SEQ ID NO: 94)
5'-ATGGAGCCACCGATCCACA-3'
```

Tumor Necrosis Factor (TNF-α) (TAKARA BIO INC.)

```
Forward:
                                  (SEQ ID NO: 95)
5'-CAGGAGGGAGAACAGAAACTCCA-3

Reverse:
                                  (SEQ ID NO: 96)
5'-CCTGGTTGGCTGCTTGCTT-3'
```

As shown in FIG. 77, the expression of TNF-α was suppressed in the C4-sulfatase-treated group as compared to the untreated group. Meanwhile, the gene therapy group only showed a tendency of suppressing the expression. The result described above demonstrates that C4-sulfatase has the activity of suppressing inflammation.

Specifically, desulfating enzymes for the sulfate group at position 4 of GalNAc are useful as anti-inflammatory agents.

[Example 78] Analysis of Inflammation-Related Genes for their Expression in Brain Tissues in a C57BL/6JcL Mouse Parkinson's Disease Model Induced by MPDP To complement the results described in Example 77, Examination was conducted using Nurr1, which is a gene involved in the generation of dopaminergic neurons, as a marker in this Example. The effects of C4-sulfatase and GalNAc4S-6ST were evaluated by the above-described quantitative PCR. The result is described below. The nucleotide sequences of primers used are as follows:

Nuclear Receptor Subfamily 4 Group A Member 2 (Nurr1): (TAKARA BIO INC.)

```
Forward:
                                  (SEQ ID NO: 97)
5'-CTGCCCTGGCTATGGTCACA-3'

Reverse:
                                  (SEQ ID NO: 98)
5'-AGACAGGTAGTTGGGTCGGTTCA-3'
```

As shown in FIG. 78, the expression level of Nurr1 was significantly elevated in the C4-sulfatase-treated group and gene therapy group as compared to the untreated group ($P<0.001$). This result supports the result described in Example 76 and shows the dopaminergic neuron-protecting effect or dopaminergic neuron regeneration/repair-promoting effect by administration of C4-sulfatase or the siRNA.

Specifically, inhibitors that act on GalNAc at position 4 or 6 (desulfating enzymes for the sulfate group at position 4 of GalNAc, and GalNAc4S-6ST siRNA) are useful as agents for protecting dopaminergic neurons or as agents for promoting the regeneration/repair of dopaminergic neurons.

INDUSTRIAL APPLICABILITY

The present invention provides agents for suppressing fibrogenesis at the physiological tissue level through inhibiting the functions of sugar chain-related genes. The agents are useful for treating or preventing tissue fibrogenic disorders.

Chronic tissue fibrogenesis (fibrogenic tissue alterations) can develop in any organ in the body, and is a general term for a group of diseases that cause organ dysfunctions, leading to death (review: Wynn T A, J. Clin. Invest. 117: 524-529, 2007).

Fibrogenic disorders are thought to be a terminal stage of chronic inflammation and can develop in any organ of the body. "Fibrogenic disorders" is a general term for a group of diseases that cause organ dysfunctions, leading to death. Fibrogenesis and the resulting dysfunctions are suspected to be the root of diseases with a high mortality rate, such as cardiovascular and cerebrovascular diseases. There is a view that 45% of deaths are caused by fibrogenesis in Western countries. Under this view, causes of individual death from disease are summarized into three groups: cancer, infections, and fibrogenesis. In addition to the conventional definitions of fibrogenic disorders such as cirrhosis, pulmonary fibrosis, and nephrosclerosis, a wide variety of diseases (mainly chronic diseases and excluding cancer and infections), can be defined as "fibrogenic disorders". Particularly, recent changes in lifestyle habits (commonly called "Westernization") have led to a rapid increase of new life-threatening diseases (disease concepts) such as non-alcoholic steatohepatitis (NASH) and chronic kidney disease (CKD). The finding that the diseases are caused by tissue fibrogenesis suggests the urgency of establishing therapeutic agents for "fibrogenic disorders". To date, however, only transplantation and artificial organs are available and there is no fundamental therapeutic method. This is a very urgent problem to be solved.

The present invention provides techniques for suppressing fibrogenic disorders (fibrogenic tissue lesions and resulting dysfunctions) based on a completely new method that targets the recently-identified sugar chain-related genes, functions of which were unknown.

Fibrogenic disorders that lead to clinically intractable dysfunctions are not only a deciding factor of death, but are also disorders that severely impair the daily quality of life (QOL). Thus, it is very important to establish tissue fibrogenesis-suppressing agents. However, no such agents are commercially available to date. Dedicated experimental studies are being conducted to assess TGF-β inhibitors, angiotensin inhibitors, inflammatory cytokine inhibitors, TLR inhibitors, MMP inhibitors, and the like. Still, however, their efficacy has not yet been established (review: Wynn T A, J. Clin. Invest. 117: 524-529, 2007).

The present inventors administered inhibitors that target sugar chain-related genes to subjects, which were model animals for fibrogenic disorders of various organs, in order to relieve fibrogenic lesions and to restore organ function.

The fibrogenic disorders were definitively confirmed based on histopathological features (including immunostaining for fibroblasts or collagen, and Masson staining). The therapeutic effect (fibrogenesis inhibitory effect) was determined based on clinical symptoms and the expression level of collagen in each organ, in addition to the histopathological features.

The therapeutic effect was proven by using as a technical method direct gene knockdown with nucleic acid pharmaceuticals (siRNA) against sugar chain-related genes.

The invention claimed is:

1. A method of treating a fibrogenic disorder, the method comprising:

identifying a subject having a fibrogenic disorder of a tissue selected from the group consisting of cardiac tissue, gastrointestinal tissue, lung tissue, pancreatic tissue, kidney tissue, ocular tissue, cranial nerve tissue, and skin tissue; and administering to the subject a therapeutically effective amount of an siRNA that suppresses expression of a gene encoding a sulfotransferase that transfers a sulfate to position 4 or 6 of N-acetylgalactosamine;

wherein the siRNA suppresses expression of a nucleotide sequence selected from the group consisting of a GalNAc4S-6ST gene, a GalNAc4ST-1 gene, a GalNAc4ST-2 gene, a C4ST-1 gene, a C4ST-2 gene, a C4ST-3 gene, a C6ST-1 gene, a C6ST-2 gene, and a D4ST gene.

2. The method of claim 1, wherein the subject has a fibrogenic disorder of gastrointestinal tissues.

3. The method of claim 2, wherein the siRNA suppresses expression of the GalNAc4S-6ST gene.

4. The method of claim 1, wherein the gene encoding a sulfotransferase is a human gene.

5. A tissue fibrogenesis suppressing-agent, comprising:

an inhibitor of sulfation at position 4 or 6 of N-acetylgalactosamine, wherein the inhibitor is an siRNA that suppresses expression of the GalNAc4S-6ST gene, wherein the siRNA comprises the nucleotide sequences of SEQ ID NO: 25 and SEQ ID NO: 26.

6. The tissue fibrogenesis suppressing-agent of claim 5, comprising:

the inhibitor; and a pharmaceutically acceptable carrier.

7. A siRNA comprising the nucleotide sequences of SEQ ID NO: 25 and SEQ ID NO: 26.

8. A composition, comprising:

the siRNA of claim 7; and a pharmaceutically acceptable carrier.

9. A composition, comprising:

the siRNA of claim 7; and a pharmaceutically acceptable carrier, wherein the composition has a therapeutic effect on a tissue fibrogenic disorder.

10. A composition, comprising:

the siRNA of claim 7; and a pharmaceutically acceptable carrier, wherein the composition has a therapeutic effect on an inflammatory bowel disease.

11. A composition, comprising:

the siRNA of claim 7; and a pharmaceutically acceptable carrier, wherein the composition has a therapeutic effect on Crohn's disease.

12. A composition, comprising:

the siRNA of claim 7; and a pharmaceutically acceptable carrier, wherein the composition has a therapeutic effect on ulcerative colitis.

13. A method of treating a fibrogenic disorder, the method comprising:

identifying a subject having a fibrogenic disorder of a tissue selected from the group consisting of cardiac tissue, gastrointestinal tissue, lung tissue, pancreatic tissue, kidney tissue, ocular tissue, cranial nerve tissue, and skin tissue; and administering to the subject a therapeutically effective amount of an siRNA that suppresses expression of a gene encoding a sulfotransferase that transfers a sulfate to position 4 or 6 of N-acetylgalactosamine;

wherein the siRNA suppresses expression a GalNAc4S-6ST gene, and wherein the siRNA comprises the nucleotide sequences of SEQ ID NO: 25 and SEQ ID NO: 26.

* * * * *

SEQUENCE LISTING

```
<160> NUMBER OF SEQ ID NOS: 98

<210> SEQ ID NO 1
<211> LENGTH: 9120
<212> TYPE: DNA
<213> ORGANISM: Mus musculus

<400> SEQUENCE: 1

tgtatatctg agtatctgtg tatgtgcata tatgtgtgtc tatgtgtatg tgtgggtttg     60

tgcatgtgtg tctgtgtgta catgtctgtg tgtctctgtg tgtgtctgtg tatgtgtgtt    120

tacatgtgtg tgtgtgtttc tgtgtggacg catgtgtatg tgtctccgtg tgcctgcatg    180

tgtgtttgtg tatgtgtgta ggcatgagta catcatggtg tacatgtaga aattgagaga    240

gactcttggg tgtggttctc atctcccacc atatctgaag taaatgtctt attcacacca    300

ctgtgcacat cagaaagcta gccttgacct ccaaggaact ctgtctctgt ctcctgtctt    360

attgtaggta cctggggttt ataagcctat gctgctgcat atggcttcac ttgggttctg    420

gggatttgaa cttaggtcct cacagtttta gggcaagcat tttattcact gaacaatctc    480

ccatgatccc tagagtttat tgtaggcaac ttaaccttta gtcgtcattg agatttagca    540

ttgatttcag ttccagttgt attctgatgt tgagcgctac agcagaggta cccagggact    600

gctgattttc tgtggccatg aatcctctag tgattaataa atttcatcat aatgttctgt    660

ttatttctaa atgtccagac aactctaatt tcaaattaat ctcatcctaa acagcacagg    720

ataaaagtta cagattgtcc tatcttcatt catgtgatgc ctcaaatcag atgtttaatc    780

ctttagtcag ttatttgtga aacggaacct aattacacac actcgcatgc gcgtgcgcgc    840

acacacacac acacacacac acacacacac acacacacac acttgtagat ttgcccacac    900

agctgcttaa gcaatttgga gcaaatgtag aaatattatg aaatttcaca taaaaatggg    960

ttttcctctg tcttcttgag aaatgtgtga gtttcaatat gacagtaatc ttctggtgtt   1020

ggactataac cacttgaacc cctgaggtac taagtgtgta cctactacgt gcctggattc   1080
```

-continued

```
catcatttcc ctacttatat aagcttctcc atcctgtaga tcagcactgt gtaatggagt   1140
aacacaagtc attgaatcat gcaatcattt aatcaattta attggcactt ctgataagag   1200
aagtgggcac atatttagtt gtgtttgcag cctgtgctat gtcatttttc tctatatata   1260
ctttaagatt tttttctttt ttccatttac gggggggggg ttattccatt taatttacat   1320
gcttaatgac atataatttg catatcaggt gttcctttct ttagagttaa cttcttttag   1380
gaccattgtt tataatggat gtatatcatc cctaaattaa atcagccatt gtctacttaa   1440
cacaccagtt tctctgatgt ccctctggct cttcctcctc tgaggttcta gttataggaa   1500
agtctggcat tttgatgttt ttccatggct tcgtgggctc tgatcatcca cttacagtgt   1560
actttcatct cttgtctaca aactgcatat catctattga tctgcgttca aggctactac   1620
attttcatgc aattccactt tgctgttaaa ccttttctat gatccgtttt tatacttata   1680
aacaatccaa gtgttgtact ctttgggtat aaatgttctg tatttcacag gtcttaactt   1740
cttttcagac tatacaaaga aagattttct atttttttta tttgttgtat gcattttatg   1800
catttagcac tgggatttcc ataacaggca gttaagatca ttgaatacat actttgtgtg   1860
gtaaatataa tacggcttat ttgattctcc cccttaaaat gctcccatct tctcagtcat   1920
gtcaggttgc tatggagtcc accctgagca ccatgagtgt gatgctgtac agacactcct   1980
gatatgcctt ctgttatttg aactccacct gcaagttttc attcaagcat agctcctaat   2040
cccattcagt gtgcactttt cttaattgat ttgctggtag agagctatat gtaagcatgg   2100
cttagcatca aattgaactt tctcctctcc ctagcttctt tccagtatat tcttcctcac   2160
cttcatcaga ttttgaggtc ttgagatcta aaccttcatg ttacaatttg cagagatacc   2220
aggatctcta tcagacttga tgtgtctcca tgtaattcta gtatcagcct ttcataagat   2280
aattgcaaaa tatagaaccc cccctctctc cttttgacta ttacagcttt gtttctctcc   2340
caagttaata cagatgtatg caaatcaact aagaaaagca aacactgaat gggataagga   2400
gctatactca aaagaaagct tgcagttgga gttcaaataa cacaagtgga accaagagta   2460
tctgcacagc atcagactca ctgtgctcag gatggaatcc atagcaacct cccataactg   2520
agaggatgtg agcccctttt aaagggaaaa tcaaataagc agtattatat taaccacatg   2580
atgtgtatat tcaatgtaga ttgggctgca ccgaagttat gattttagta atgagtattt   2640
ctccttgggt tttcttctgg accaccctgg ttttcctttt aaaaatagta aaatagcagc   2700
aatgactgct tctcttaaaa tctgaacaac acagagcact tcagcatcct ttcaacctat   2760
ctaaatccat tgtagacctg cactgacttg ctgtgagcta ttgtgtcaca actattattg   2820
tagctaaaca ccttgaattt tcaaagctgc tctggactgt gtcttctttt agaattaaac   2880
ttgctaaaga tattggactc tgagatgctt attcaccact ttctataaaa gagtaaggat   2940
gacaatgctt tgagtagaag aagattgcat acgagggtac cagcatgtca ttatgtcccc   3000
agcagtcagt aaagtaagga tccagtgatg gtagagttat tatgtccatt atggaactaa   3060
tgtaaatgtt tatcaatgac tagaatggct gtaatcacca atccttagac aagtgtgagt   3120
aacatcatgc tcttttctta taataataga tagtcacaca caccatggtc ttaaacatta   3180
cattttgatt tttctctttg tgtctgtctt ttcgtacctc tactccactt acctgagcct   3240
tcagctaggg ctcctccaag acggcagtca cagtactagt gaggataatt ctcatatgga   3300
gacctgaagc agaataacct tcttccaagg aaaccaaaat cctagtcaac atcttctcca   3360
ctctttggtt atttattttt atttctattt ctattttgcc atttaagaat ttttaaactc   3420
```

-continued

```
ttttctgttt tcttatatat attctttttt ttacaacttt tgatattctt tatcaaatga   3480
tttatcccat tgcctttcct cctgcagcta tctgtgagtt ttagcatgga tatttagaat   3540
acaattggaa attatgaagg tcgaataaaa gttctctaag agccaggacc tcactagcct   3600
agttagttgc ttagtttcta atataaggca tggtttatct cctactgtat ggcccttaaa   3660
tccactagac atctgttggc ttccaacagc atacaattgc tgctattgta tgtttaggta   3720
tatattttta tgaaacacta tattctgatt ggtgttcatt cttcctatga aggggaagat   3780
tttattgcct gctcaaattc aagtcagtcc tttttgagta gacaaaggtt gtccaatctt   3840
gctaaaccct tttctttttt gcttggggaa tttctttagg gaaaattctc aaccatgaac   3900
caagcctaga gattgataat agctgaaggc agagtagcca gtcttagtaa gggatgagag   3960
aaagactgac caaagactga ataggaaatg gttgatagca ttcattggga ctagacaata   4020
aagttagcta ccccaacatg ggcaaatgga gaaaatgggg agagtcatat ggatatgtag   4080
ggaggagaag aaaggaaggg gtgagtttga agtatggaag agcctttaaa gcatttgtaa   4140
gatttgtaag aaaaagcttt tgagagacag agtattacct gccttcaaat cccttcaatt   4200
actgtcccta caagacatac ctgtgctcag ctgctcttgg accacaaggg ggcctaagag   4260
catgtttgtg tccctgtctt tatacaggct tctcatctgt atttctcaaa cgtaaataca   4320
aatgggggag ataacaaatg atatttctaa gtggtacaca ggtatgagaa ctgcacacaa   4380
tctatttata tgtataatgg ccagagctct cagcagggaa cagaggaagc ctaggtaact   4440
cctgctccag agcatgtctg tatggagacc tcagttcagc aactatgaaa tctgtgttca   4500
aagggtcatc actgggaaca gtttctggaa tagcagacat attcattctc tctctctctc   4560
tctctctctc tctctctctc tctctctctc tctctctctc tctctgtctg tctctgtctc   4620
tctctgtctg tctgtctgtc tctcccttct gtcaggggta tgcatacatg ggctgggaat   4680
tctatcttcc ctgcctgctg tctttggtgt ctccctaatg tggtgccatg tttacttaac   4740
ctgtctgaaa tggaggataa cctctggtct gataactgtc aagttactga aatgtcaggg   4800
aattgtgaat gaacccctct gaatgctggg cagatgtttt gagcacgtgg gtatccatag   4860
attttttttt cagcaggatt tccttcttta atatattgtg ggaacgaaac attgaagttt   4920
ccaacactaa gaaaagcaat gctctgggtt tgcaaagaag tctccaaagc tgtgggagag   4980
gcaatggctt tgcctcacaa aggtgatcct gatttggatt gggtgttcct cagtctccct   5040
catcctttgt ttgtggacca aacctctgat caaataatca gtatacagac aagtactgac   5100
tgactcctgt cactgtttcc catgtaaatt ctcaaccatg tgtgtcagaa ttgtttgagt   5160
catcaaagtt ccgtgatgct caggatggtg aataccagaa actgaagtct gaaatccaat   5220
ttggcctttc tcgggcactg taaactgagt gcaaatgtgc ccagttccct cgtggcccat   5280
ttatagcaca ataacacagt gcttgcttac aaaatctagt cccgattaaa gtatttattt   5340
aaagttgctt tagacaaata tatttctaaa tggaaggatg aaacagaaag aatattccaa   5400
ctgtacagtc tatattttgt ttctaaaaat ttttattaga attctgactt ttagaaaaca   5460
aatagatatt caaaaactac ttctttaatt aaataataac atcattatag acattctcca   5520
gccatttaga agtagcatga ttacaaagca ttcatgttcc ctttgttttt tgaaacagaa   5580
gtatttatat gacaaataaa aagcaaaaat ctcatatatg tgatagctat agatgcattg   5640
ataggaatta aatttaatca aaaagaactt ttaatggcaa taatgtggct actaacttca   5700
ttgtttgtaa taatgctgca aatgtttaat gaaaactgtt actaacaata caggagaaga   5760
ttacagatat gattaggtcg tgttgataga aatggaaaga gaaaggtcac tcactacctc   5820
```

agccacagaa cttgaggaat gtgtgagggt ttttgaggaa aaaagagaac aatgtaacat 5880
cacagcaaca tcttaatctg aaagtagacg acaaaggttt cagagtaggg gatcagaaat 5940
ttaagtatgc agagaagcaa ggcatatacg gcttagacaa tgtatgaaga acagcagcag 6000
acagcaagtg aaagaaatca cagtccacat ggaaatcaca cagaccacag tgtgcacaca 6060
gagacagaaa tcagcaaggg acacacggct tccagttatg aaagttagac agcaaaattt 6120
aagttgtccc acctaaaaca tgatgtatcg tctctcaaat ggggaagggg aaggagcagc 6180
aaacatctgg atatgtctaa aacctcacag agaacatctg ggatctttgc atttctccct 6240
ctgactttct caatatgtta gctacttcta gatagtttca ataatggtct ctaattgact 6300
atggagagac aggtctcatg tatgtgaaca tccttaacca ggagatggaa tgtgtttcct 6360
tgtcactcat tttctaagga agtgaattcc ttctgcattg cccaggattg gatgttacgt 6420
gaaactaaaa atcattgatt aaaaagaaat gtcattacca cagttgggtt gaatcaatca 6480
agacttatcc tagttacagg catcacctcc ccttaagcac aaatactgag aacagctaag 6540
ctcactttga aatctgggat gaggaggctt taggtcaagc atctgacaat gtgtgtgtgt 6600
atgtgtgtgt gtgtgtgtgt gtgtagtatg attatatgta tatatgtaga tgtgtgtata 6660
tatttatatg tatatatgta tatgtgagta tgtatatatg tatatgtgtg tatgtgtatg 6720
agtgtgtgta tgtatgacta tgagtgtgta tgtattgtgc aagtgtgtgt atatatgtgt 6780
gtatatgttt atgtatatgt gtattgtatg ggtgtgaatg tattatatat gtgtgtaggt 6840
acatatgtgt atatgtttat gcgtgtatat gtgtatgcat tatatgtatg tgtgtatgtg 6900
tgtatgtttt catgtgtatg tagcatatgt atatgcatgt gtgtgtctgt gtgtgtaagc 6960
atgtatttac taagaaaaaa tcagtttctc tagctaatga gtcattgaag tgaagaaacc 7020
ttacgctatc acattactat gtttccagca taaattgcaa tatcagtaag acattcccca 7080
tcataactta atggacactt agattaggtc atgcagcagt aaattatgaa agcgtctatg 7140
ctgagctgag gtgggaaatc gtctttcctg cctccttcct cctgttcttt ctcctaaagg 7200
ccctcatcct ctttctcccc ttcctttctt ttaaaatatt ctatcattga tccaagctaa 7260
ctaacccttc ccttgctcac atgtgacctg cccagaggaa tctatttata gtcaacaata 7320
acaggccaag gacatgcgaa caaatgactt tacttagccc cacttggtga atctattggg 7380
tgaataggta aggggttatt tataggagct tgactgactg gcacagctgt atctctgaaa 7440
agtcccccaa agcatcatgg gtgggaacta aggaaagccg gaaatgctgg agctggaatc 7500
ccaacctgca gtggctacat gatgaatgtg tctcctttcc tactaaatat ttaagactct 7560
gggcaggctg gttagtcttg taaaagtctt gtgggtttct ggagtcctgg gaggctcact 7620
gtccctgcag aagcttgtta ttattgtata tgaaagaaag tgctcaacac tgagtcacaa 7680
aagaagcccc cgagaatcgg tggcagaggt ggaaatagaa gaatccgatg cagttcccga 7740
ggcaagagtt gatcctctcc atggtgacaa gaaaacaaga gccacagaag cctgaaggct 7800
aagactatga cctgtgaggt tctcctctcc taggacttga atgcacttaa ctctgagggc 7860
tagcagggca gagattcagg agcgttctca gaggttgtcc cttctccttg tatgattcta 7920
ggagaagctc agtgcatagg cagaagttgc aaactctaac acattaaccc acatcctgaa 7980
ttgttttata tcaattgttt tataactaca tgttttaact tttgttttgg tttttgaatt 8040
ttgtttgttt gtttgttttc tatttttcat atgtgtgcat gtgagccaga agacaggcta 8100
agggactctg ttctctcttt ccagcatgtg ggtttcaggg atcaaagtta ggtcccaagg 8160
cttcactggg caacgggacc cttagcctct gagtcatctt cttaatcttt ttctttgaaa 8220
ctttttcatt acattgtgtc agtgcacaca cacacacaca cacacatgca tatacatcca 8280
catgcatata catccacatg ccatatgtca tggcacatgt gtggaaagaa atgggtgcct 8340
tgaggaaatc agttttcttc ttccatcacg tggatcttat gacttcaggt aacccatctc 8400
tgctccccaa gcatggctac aagcatttac ctgccaagtc atctccctgg ctcccacatt 8460
aatttataat aatacaccct ttcagcctag agagatgact cagtggttaa gaactctggc 8520
tgtgcttcag aaggttctga gttcaattcc cagcagctat aaggtggctc acaactatct 8580
ctaatgttgt tttctgtcct cttctggcat gcacttgtat gtgcagatag agtacttata 8640
tgcataaata aatataaata cattaataat cttttaaaaa gaaggaaaga ttaaaagaac 8700
aatacaccct ttcttttaag taagaaaaca tgcttagtat atagaataaa tgctggtgtt 8760
gaaaggtgaa attcagaaga aattataggt tggaaatatt tgaactcttt tgtgtcaaac 8820
caaatggtaa agatgatgtg ataataaggt aaggttttct tcctacacat atacttgttt 8880
aataaccagt ataagactat gagtgaacat aactaaaaat acatgaaaaa aaactatttt 8940
aaaaaaacat cactttcaga tgactctggt gaaactcact gataaccagc aatctctttg 9000
atagaccaga gtgtccagtc tgaagttaat tcttttgctt tattctcaaa caatgttgca 9060
gaagtatgaa ccatagtatc aagatacact gtccacatat gcacctggcc tgacttgtgt 9120

<210> SEQ ID NO 2
<211> LENGTH: 2105
<212> TYPE: DNA
<213> ORGANISM: Mus musculus
<220> FEATURE:
<221> NAME/KEY: CDS
<222> LOCATION: (418)..(1671)

<400> SEQUENCE: 2
gagccttccc ggcgcgtgag ccggatccgg tggcaccgcg gggaagagac aggaccgggc 60
ggtggcggca gagacagggg gacgcacccg gtgcagaaga tccaatagga gcacgccgcc 120
gcaacctctc ccgcgcgctc cggtcgccga ctctacgccg atcgcccact ccccgcacct 180
tggactacac cgggaaaaag acgcagcctg gcccgaactg gggcggagat ccttcttgct 240
tcccaagagc tcgggaggga agattctccc gccgccgaga accccgccgg actggaggaa 300
cccgtggcct ggagagcgct ggctgtgcca gaccccagcc tgatggatgt ctggtgtgga 360
taatgaggga agaacgtgcc ttttacaccc aagaggtgac cccggagcgt gccccgg 417 atg acc cca caa ctc gga acg atg cgg cta gcc tgc atg ttc tcg tcc 465
Met Thr Pro Gln Leu Gly Thr Met Arg Leu Ala Cys Met Phe Ser Ser
1 5 10 15 atc ctg ctg ttt gga gct gcg ggc ctg ctc ctc ttc atc agc ctc cag 513
Ile Leu Leu Phe Gly Ala Ala Gly Leu Leu Leu Phe Ile Ser Leu Gln
20 25 30 gac cct ata gag ctc agc ccc cag caa gtt cca ggt ata aag ttc agc 561
Asp Pro Ile Glu Leu Ser Pro Gln Gln Val Pro Gly Ile Lys Phe Ser
35 40 45 atc agg ccc cag caa ccc cag cat gat agc cac ttg agg ata tcc aca 609
Ile Arg Pro Gln Gln Pro Gln His Asp Ser His Leu Arg Ile Ser Thr
50 55 60 gaa aag ggc aca cga gat tca ccc agc ggg tcg cca aga ggc ctc cag 657
Glu Lys Gly Thr Arg Asp Ser Pro Ser Gly Ser Pro Arg Gly Leu Gln
65 70 75 80 ctg caa gcg cct gac caa cct cga cct cac ccg aag gca gcg gga tct 705
Leu Gln Ala Pro Asp Gln Pro Arg Pro His Pro Lys Ala Ala Gly Ser -continued

```
                85                  90                  95

cct ttg cgc ctc cgg cag cgc agg cgg aga ctg ctc atc aaa aag atg      753
Pro Leu Arg Leu Arg Gln Arg Arg Arg Arg Leu Leu Ile Lys Lys Met
            100                 105                 110

cca gcc gca ggg act aac caa ggc aac aac tcg tcc gaa acc ttt atc      801
Pro Ala Ala Gly Thr Asn Gln Gly Asn Asn Ser Ser Glu Thr Phe Ile
        115                 120                 125

cag ccg aga ccc cgc acc atg gac agt cgt tgg gtc agc ctg cac cag      849
Gln Pro Arg Pro Arg Thr Met Asp Ser Arg Trp Val Ser Leu His Gln
    130                 135                 140

acc caa cag gag cgc aag cgt gtg atg cga gaa gcc tgc gct aaa tac      897
Thr Gln Gln Glu Arg Lys Arg Val Met Arg Glu Ala Cys Ala Lys Tyr
145                 150                 155                 160

agg gcc agc agc agc cgc aga gct gtc act ccc cgc cac gtc tcc cgc      945
Arg Ala Ser Ser Ser Arg Arg Ala Val Thr Pro Arg His Val Ser Arg
                165                 170                 175

atc ttc gtg gag gac cgc cac cgt gta ctg tac tgt gaa gta ccc aag      993
Ile Phe Val Glu Asp Arg His Arg Val Leu Tyr Cys Glu Val Pro Lys
            180                 185                 190

gca ggc tgc tcc aac tgg aag agg gtg ctc atg gtg ctg gca ggg tta     1041
Ala Gly Cys Ser Asn Trp Lys Arg Val Leu Met Val Leu Ala Gly Leu
        195                 200                 205

gcc tca tcc acg gca gat atc caa cac aac acc gtc cac tat ggc agc     1089
Ala Ser Ser Thr Ala Asp Ile Gln His Asn Thr Val His Tyr Gly Ser
    210                 215                 220

gcc ctt aag cgc ctg gat act ttt gac cgg cag ggc ata gtg cac cgc     1137
Ala Leu Lys Arg Leu Asp Thr Phe Asp Arg Gln Gly Ile Val His Arg
225                 230                 235                 240

ctc agt acc tac acc aag atg ctc ttt gtc cgg gaa ccc ttt gag cgg     1185
Leu Ser Thr Tyr Thr Lys Met Leu Phe Val Arg Glu Pro Phe Glu Arg
                245                 250                 255

ctg gtc tct gct ttc cga gac aag ttt gag cat cct aac agc tac tat     1233
Leu Val Ser Ala Phe Arg Asp Lys Phe Glu His Pro Asn Ser Tyr Tyr
            260                 265                 270

cat cct gtc ttt ggc aag gct atc ctg gcc cgg tac cgc gcc aac gcc     1281
His Pro Val Phe Gly Lys Ala Ile Leu Ala Arg Tyr Arg Ala Asn Ala
        275                 280                 285

tcg cgg gag gca ctg cgg act ggc tcc ggt gtg cag ttc ccc gag ttc     1329
Ser Arg Glu Ala Leu Arg Thr Gly Ser Gly Val Gln Phe Pro Glu Phe
    290                 295                 300

gtc cag tac ctg ttg gat gtc cac cgg ccc gtg ggc atg gac atc cac     1377
Val Gln Tyr Leu Leu Asp Val His Arg Pro Val Gly Met Asp Ile His
305                 310                 315                 320

tgg gac cat gtt agc cgg ctg tgc agc ccc tgc ctc atc gac tat gac     1425
Trp Asp His Val Ser Arg Leu Cys Ser Pro Cys Leu Ile Asp Tyr Asp
                325                 330                 335

ttt gtg ggc aag ttc gag agc atg gaa gac gat gcc aac ttc ttc ctg     1473
Phe Val Gly Lys Phe Glu Ser Met Glu Asp Asp Ala Asn Phe Phe Leu
            340                 345                 350

cgt ctc atc cat gcg ccc ggg aac ctg act ttc ccg agg ttc aag gac     1521
Arg Leu Ile His Ala Pro Gly Asn Leu Thr Phe Pro Arg Phe Lys Asp
        355                 360                 365

agg cac tcc gag gag gcg cgg acc aca tcg aga atc acc cat cag tac     1569
Arg His Ser Glu Glu Ala Arg Thr Thr Ser Arg Ile Thr His Gln Tyr
    370                 375                 380

ttc gct cag ctc tcc tcg ctg cag cga cag cga acc tac gac ttc tac     1617
Phe Ala Gln Leu Ser Ser Leu Gln Arg Gln Arg Thr Tyr Asp Phe Tyr
385                 390                 395                 400

tac atg gat tac ctg atg ttc aac tac tcc aaa cct ttc tcg gac ctg     1665
```

-continued

```
Tyr Met Asp Tyr Leu Met Phe Asn Tyr Ser Lys Pro Phe Ser Asp Leu
                405                 410                 415

tac tga gggcggggcc tgctggtcag gggcggggtc tgccggtcat gcccactcac      1721
Tyr

ctgcgcatag gcggcctccg gggactgagc tctgaggatg tgaggccttg tggctgtggc   1781

cctagggtgg gccacagagg cccagacaat ggaccttgac ccttgtccca cacccatttc   1841

ctcattgggt tggctgagtt tgagacggag cacgactcgg atggatgctt taagaactca   1901

gctgagctat gctgagctat gctgtccagg gaagcctgag acccagaaga gggccccagc   1961

gtcgagggat gtcctacatc cccttatcct ttgccttgta ccaaaccacg tggtttgctg   2021

cttttctatg acccagggtc atctgaataa agcacatggt tttcagagca aaaaaaaaaa   2081

aaaaaaaaaa aaaaaaaaaa aaaa                                           2105


<210> SEQ ID NO 3
<211> LENGTH: 417
<212> TYPE: PRT
<213> ORGANISM: Mus musculus

<400> SEQUENCE: 3

Met Thr Pro Gln Leu Gly Thr Met Arg Leu Ala Cys Met Phe Ser Ser
1               5                   10                  15

Ile Leu Leu Phe Gly Ala Ala Gly Leu Leu Leu Phe Ile Ser Leu Gln
            20                  25                  30

Asp Pro Ile Glu Leu Ser Pro Gln Gln Val Pro Gly Ile Lys Phe Ser
        35                  40                  45

Ile Arg Pro Gln Gln Pro Gln His Asp Ser His Leu Arg Ile Ser Thr
    50                  55                  60

Glu Lys Gly Thr Arg Asp Ser Pro Ser Gly Ser Pro Arg Gly Leu Gln
65                  70                  75                  80

Leu Gln Ala Pro Asp Gln Pro Arg Pro His Pro Lys Ala Ala Gly Ser
                85                  90                  95

Pro Leu Arg Leu Arg Gln Arg Arg Arg Arg Leu Leu Ile Lys Lys Met
            100                 105                 110

Pro Ala Ala Gly Thr Asn Gln Gly Asn Asn Ser Ser Glu Thr Phe Ile
        115                 120                 125

Gln Pro Arg Pro Arg Thr Met Asp Ser Arg Trp Val Ser Leu His Gln
    130                 135                 140

Thr Gln Gln Glu Arg Lys Arg Val Met Arg Glu Ala Cys Ala Lys Tyr
145                 150                 155                 160

Arg Ala Ser Ser Ser Arg Arg Ala Val Thr Pro Arg His Val Ser Arg
                165                 170                 175

Ile Phe Val Glu Asp Arg His Arg Val Leu Tyr Cys Glu Val Pro Lys
            180                 185                 190

Ala Gly Cys Ser Asn Trp Lys Arg Val Leu Met Val Leu Ala Gly Leu
        195                 200                 205

Ala Ser Ser Thr Ala Asp Ile Gln His Asn Thr Val His Tyr Gly Ser
    210                 215                 220

Ala Leu Lys Arg Leu Asp Thr Phe Asp Arg Gln Gly Ile Val His Arg
225                 230                 235                 240

Leu Ser Thr Tyr Thr Lys Met Leu Phe Val Arg Glu Pro Phe Glu Arg
                245                 250                 255

Leu Val Ser Ala Phe Arg Asp Lys Phe Glu His Pro Asn Ser Tyr Tyr
            260                 265                 270
```

-continued

His Pro Val Phe Gly Lys Ala Ile Leu Ala Arg Tyr Arg Ala Asn Ala
275 280 285

Ser Arg Glu Ala Leu Arg Thr Gly Ser Gly Val Gln Phe Pro Glu Phe
290 295 300

Val Gln Tyr Leu Leu Asp Val His Arg Pro Val Gly Met Asp Ile His
305 310 315 320

Trp Asp His Val Ser Arg Leu Cys Ser Pro Cys Leu Ile Asp Tyr Asp
325 330 335

Phe Val Gly Lys Phe Glu Ser Met Glu Asp Asp Ala Asn Phe Phe Leu
340 345 350

Arg Leu Ile His Ala Pro Gly Asn Leu Thr Phe Pro Arg Phe Lys Asp
355 360 365

Arg His Ser Glu Glu Ala Arg Thr Thr Ser Arg Ile Thr His Gln Tyr
370 375 380

Phe Ala Gln Leu Ser Ser Leu Gln Arg Gln Arg Thr Tyr Asp Phe Tyr
385 390 395 400

Tyr Met Asp Tyr Leu Met Phe Asn Tyr Ser Lys Pro Phe Ser Asp Leu
405 410 415

Tyr

<210> SEQ ID NO 4
<211> LENGTH: 1369
<212> TYPE: DNA
<213> ORGANISM: Mus musculus
<220> FEATURE:
<221> NAME/KEY: CDS
<222> LOCATION: (40)..(1281)

<400> SEQUENCE: 4
attcagacat gaagagagac acagtggtct gaagtggtc atg aaa gcc aaa caa 54
Met Lys Ala Lys Gln
1 5 gtc ttc ttt tct gtc ctg ctg ttt ggg aca gca ggg ctt ctg ctc ttc 102
Val Phe Phe Ser Val Leu Leu Phe Gly Thr Ala Gly Leu Leu Leu Phe
10 15 20 atg tac ttg caa gca tgg att gaa gaa cat cat aca ggg aaa ata gag 150
Met Tyr Leu Gln Ala Trp Ile Glu Glu His His Thr Gly Lys Ile Glu
25 30 35 aag aaa agg gat cag aaa gga gta tcg gtg act acg gga aaa atc cag 198
Lys Lys Arg Asp Gln Lys Gly Val Ser Val Thr Thr Gly Lys Ile Gln
40 45 50 aaa cag atc acg aat cag aac tct gag gtt cac atg cct gaa gat ctg 246
Lys Gln Ile Thr Asn Gln Asn Ser Glu Val His Met Pro Glu Asp Leu
55 60 65 aag aag aaa ggg gga gat ctg ctc aac cta ggg agt cca aca agg gtt 294
Lys Lys Lys Gly Gly Asp Leu Leu Asn Leu Gly Ser Pro Thr Arg Val
70 75 80 85 tta agg aag atc agc cat tca caa agg gag aac gga gct tac aga tca 342
Leu Arg Lys Ile Ser His Ser Gln Arg Glu Asn Gly Ala Tyr Arg Ser
90 95 100 act gaa gca cat caa gga gct aaa att gaa gtt ttt cag aaa ccc atc 390
Thr Glu Ala His Gln Gly Ala Lys Ile Glu Val Phe Gln Lys Pro Ile
105 110 115 cag atg gac tgg cca ctg gtc act cag ccc tta aac aaa agt ttg gtc 438
Gln Met Asp Trp Pro Leu Val Thr Gln Pro Leu Asn Lys Ser Leu Val
120 125 130 caa ggc aac aaa tgg aag aaa gca gat gca acc caa gag aag cgt cgg 486
Gln Gly Asn Lys Trp Lys Lys Ala Asp Ala Thr Gln Glu Lys Arg Arg
135 140 145

-continued

```
tca ttc ctt cat gag ttt tgc aag aaa tat ggt aga gta aat gat ccc      534
Ser Phe Leu His Glu Phe Cys Lys Lys Tyr Gly Arg Val Asn Asp Pro
150                 155                 160                 165

aag ttc aac ctt ttt cat ata gta tct agg ata tat gta gaa gac aaa      582
Lys Phe Asn Leu Phe His Ile Val Ser Arg Ile Tyr Val Glu Asp Lys
                170                 175                 180

cac aaa atc ctg tac tgt gaa gta cca aaa gct ggc tgc tct aat tgg      630
His Lys Ile Leu Tyr Cys Glu Val Pro Lys Ala Gly Cys Ser Asn Trp
            185                 190                 195

aaa aga att ctg atg gtc cta aat gga ttg gct tcc tct gca tac aat      678
Lys Arg Ile Leu Met Val Leu Asn Gly Leu Ala Ser Ser Ala Tyr Asn
        200                 205                 210

atc tcc cat gat act gtg cac tat ggg aag cat ctg aaa aca ctg gat      726
Ile Ser His Asp Thr Val His Tyr Gly Lys His Leu Lys Thr Leu Asp
    215                 220                 225

agt ttt gac tta aaa gga gta cac atg cgt ttg aat aca tat acc aaa      774
Ser Phe Asp Leu Lys Gly Val His Met Arg Leu Asn Thr Tyr Thr Lys
230                 235                 240                 245

gct gtg ttt gtt aga gat ccc atg gaa aga tta gtc tcc gca ttt agg      822
Ala Val Phe Val Arg Asp Pro Met Glu Arg Leu Val Ser Ala Phe Arg
                250                 255                 260

gat aaa ttt gag cat ccc aat agt tac tac cat ccg gtg ttt gga aag      870
Asp Lys Phe Glu His Pro Asn Ser Tyr Tyr His Pro Val Phe Gly Lys
            265                 270                 275

gca att atc aag aaa tat cga cca aat gcc tct gca gaa gca tta aat      918
Ala Ile Ile Lys Lys Tyr Arg Pro Asn Ala Ser Ala Glu Ala Leu Asn
        280                 285                 290

aat gga tct gga gtc aaa ttc aaa gaa ttc gcc tac tat ttg ctg gat      966
Asn Gly Ser Gly Val Lys Phe Lys Glu Phe Ala Tyr Tyr Leu Leu Asp
    295                 300                 305

gct cac cgt cca gta gga atg gat att cac tgg gaa aga gtc agc aaa     1014
Ala His Arg Pro Val Gly Met Asp Ile His Trp Glu Arg Val Ser Lys
310                 315                 320                 325

ctg tgt tat ccg tgt ttg atc aac tat gac ttt gta ggg aag ttt gag     1062
Leu Cys Tyr Pro Cys Leu Ile Asn Tyr Asp Phe Val Gly Lys Phe Glu
                330                 335                 340

acc tta gga gag gat gcc aat tac ttt cta cag ttg att ggt gct cca     1110
Thr Leu Gly Glu Asp Ala Asn Tyr Phe Leu Gln Leu Ile Gly Ala Pro
            345                 350                 355

aaa gag ttg aca ttt cca aac ttt aag gat agg cac tcc tct gat gaa     1158
Lys Glu Leu Thr Phe Pro Asn Phe Lys Asp Arg His Ser Ser Asp Glu
        360                 365                 370

aga acc aat gcc cac gtg gta agg cag tat tta aag gac ctg agc aca     1206
Arg Thr Asn Ala His Val Val Arg Gln Tyr Leu Lys Asp Leu Ser Thr
    375                 380                 385

gcc gaa aga cag ctc atc tat gac ttc tat cac ttg gac tat ttg atg     1254
Ala Glu Arg Gln Leu Ile Tyr Asp Phe Tyr His Leu Asp Tyr Leu Met
390                 395                 400                 405

ttt aat tac aca act cca cat ttg taa tttgcattca tttttctaaa           1301
Phe Asn Tyr Thr Thr Pro His Leu
                410

gccctacata gatttaatga tgatggcctc aaataagcta ctgtaattgt cctacaattc   1361

tctgtatg                                                            1369
```

<210> SEQ ID NO 5
<211> LENGTH: 413
<212> TYPE: PRT
<213> ORGANISM: Mus musculus

<400> SEQUENCE: 5

```
Met Lys Ala Lys Gln Val Phe Phe Ser Val Leu Leu Phe Gly Thr Ala
1               5                   10                  15

Gly Leu Leu Leu Phe Met Tyr Leu Gln Ala Trp Ile Glu Glu His His
            20                  25                  30

Thr Gly Lys Ile Glu Lys Lys Arg Asp Gln Lys Gly Val Ser Val Thr
        35                  40                  45

Thr Gly Lys Ile Gln Lys Gln Ile Thr Asn Gln Asn Ser Glu Val His
    50                  55                  60

Met Pro Glu Asp Leu Lys Lys Lys Gly Gly Asp Leu Leu Asn Leu Gly
65                  70                  75                  80

Ser Pro Thr Arg Val Leu Arg Lys Ile Ser His Ser Gln Arg Glu Asn
                85                  90                  95

Gly Ala Tyr Arg Ser Thr Glu Ala His Gln Gly Ala Lys Ile Glu Val
            100                 105                 110

Phe Gln Lys Pro Ile Gln Met Asp Trp Pro Leu Val Thr Gln Pro Leu
        115                 120                 125

Asn Lys Ser Leu Val Gln Gly Asn Lys Trp Lys Lys Ala Asp Ala Thr
    130                 135                 140

Gln Glu Lys Arg Arg Ser Phe Leu His Glu Phe Cys Lys Lys Tyr Gly
145                 150                 155                 160

Arg Val Asn Asp Pro Lys Phe Asn Leu Phe His Ile Val Ser Arg Ile
                165                 170                 175

Tyr Val Glu Asp Lys His Lys Ile Leu Tyr Cys Glu Val Pro Lys Ala
            180                 185                 190

Gly Cys Ser Asn Trp Lys Arg Ile Leu Met Val Leu Asn Gly Leu Ala
        195                 200                 205

Ser Ser Ala Tyr Asn Ile Ser His Asp Thr Val His Tyr Gly Lys His
    210                 215                 220

Leu Lys Thr Leu Asp Ser Phe Asp Leu Lys Gly Val His Met Arg Leu
225                 230                 235                 240

Asn Thr Tyr Thr Lys Ala Val Phe Val Arg Asp Pro Met Glu Arg Leu
                245                 250                 255

Val Ser Ala Phe Arg Asp Lys Phe Glu His Pro Asn Ser Tyr Tyr His
            260                 265                 270

Pro Val Phe Gly Lys Ala Ile Ile Lys Lys Tyr Arg Pro Asn Ala Ser
        275                 280                 285

Ala Glu Ala Leu Asn Asn Gly Ser Gly Val Lys Phe Lys Glu Phe Ala
    290                 295                 300

Tyr Tyr Leu Leu Asp Ala His Arg Pro Val Gly Met Asp Ile His Trp
305                 310                 315                 320

Glu Arg Val Ser Lys Leu Cys Tyr Pro Cys Leu Ile Asn Tyr Asp Phe
                325                 330                 335

Val Gly Lys Phe Glu Thr Leu Gly Glu Asp Ala Asn Tyr Phe Leu Gln
            340                 345                 350

Leu Ile Gly Ala Pro Lys Glu Leu Thr Phe Pro Asn Phe Lys Asp Arg
        355                 360                 365

His Ser Ser Asp Glu Arg Thr Asn Ala His Val Val Arg Gln Tyr Leu
    370                 375                 380

Lys Asp Leu Ser Thr Ala Glu Arg Gln Leu Ile Tyr Asp Phe Tyr His
385                 390                 395                 400

Leu Asp Tyr Leu Met Phe Asn Tyr Thr Thr Pro His Leu
                405                 410
```

<210> SEQ ID NO 6
<211> LENGTH: 5532
<212> TYPE: DNA
<213> ORGANISM: Mus musculus
<220> FEATURE:
<221> NAME/KEY: CDS
<222> LOCATION: (369)..(1427)

<400> SEQUENCE: 6

```
ccagtgcacg gcggcggcgg caccttcctt ctcgcatccc ggtcgcccgg cccgtgagga      60

ggcagcggcg gccgcaggcg ccagcagagg aggcggcgga gcatcgagca gaggcgaggc     120

ggaccggcag gagcgcgcgg ccggagccac gcatcctcac acttgcacac caactcctgc     180

gcctttcacc ctctagacca gagtcggggc ctcggagagc ctcggtgaag ctagcgggag     240

ccagctccgg agcccagcca gctctgttct gagcctcccc ggtgctggta cccccgcggc     300

ggggtccccg cttctgcgct cgggacgcgc ctcccggaca gccgggtccc cgcggccagg     360

acaaagcc atg aag ccg gcg ctg ctg gaa gtg atg agg atg aac aga att      410
         Met Lys Pro Ala Leu Leu Glu Val Met Arg Met Asn Arg Ile
         1               5                   10

tgc cgg atg gtg ctg gcc act tgc ttc gga tcc ttt atc ttg gtc atc       458
Cys Arg Met Val Leu Ala Thr Cys Phe Gly Ser Phe Ile Leu Val Ile
15                  20                  25                  30

ttc tat ttc caa agt atg ttg cac cca gtc atg cgg agg aac ccc ttc       506
Phe Tyr Phe Gln Ser Met Leu His Pro Val Met Arg Arg Asn Pro Phe
                35                  40                  45

ggt gtg gac atc tgc tgc cgg aag gga tcg aga agt ccc ctg cag gag       554
Gly Val Asp Ile Cys Cys Arg Lys Gly Ser Arg Ser Pro Leu Gln Glu
            50                  55                  60

ctc tac aat ccc atc cag ctg gag cta tcc aac act gcc atc ctg cac       602
Leu Tyr Asn Pro Ile Gln Leu Glu Leu Ser Asn Thr Ala Ile Leu His
        65                  70                  75

cag atg aga cgg gac cag gtg aca gac acc tgc cgg gcc aac agt gcc       650
Gln Met Arg Arg Asp Gln Val Thr Asp Thr Cys Arg Ala Asn Ser Ala
    80                  85                  90

atg agc cgc aag cgc agg gtg ctg acc ccc aac gac ctg aag cac ctg       698
Met Ser Arg Lys Arg Arg Val Leu Thr Pro Asn Asp Leu Lys His Leu
95                  100                 105                 110

gtg gtg gat gag gac cac gaa ctc atc tac tgc tat gtg ccc aag gta       746
Val Val Asp Glu Asp His Glu Leu Ile Tyr Cys Tyr Val Pro Lys Val
                115                 120                 125

gcg tgc acc aac tgg aag agg ctc atg atg gtc ctg agt ggc cgg ggc       794
Ala Cys Thr Asn Trp Lys Arg Leu Met Met Val Leu Ser Gly Arg Gly
            130                 135                 140

aag tac agc gat ccc atg gag atc cca gcc aac gaa gcc cac gtg tcg       842
Lys Tyr Ser Asp Pro Met Glu Ile Pro Ala Asn Glu Ala His Val Ser
        145                 150                 155

gcc aac ctg aag acc ctt aac cag tac agc atc cca gag atc aac cac       890
Ala Asn Leu Lys Thr Leu Asn Gln Tyr Ser Ile Pro Glu Ile Asn His
    160                 165                 170

cgc ttg aaa agc tac atg aag ttc ctg ttc gtg cgg gaa ccc ttc gag       938
Arg Leu Lys Ser Tyr Met Lys Phe Leu Phe Val Arg Glu Pro Phe Glu
175                 180                 185                 190

agg ctg gtg tct gcc tac cgc aac aag ttc acg cag aag tac aac acc       986
Arg Leu Val Ser Ala Tyr Arg Asn Lys Phe Thr Gln Lys Tyr Asn Thr
                195                 200                 205

tcc ttc cac aag cgc tac ggc acc aag atc atc cga cgc cag cgg aag      1034
Ser Phe His Lys Arg Tyr Gly Thr Lys Ile Ile Arg Arg Gln Arg Lys
            210                 215                 220
```

```
aac gcc acg cag gag gcc ctg cgc aag ggg gac gat gtc aag ttc gag     1082
Asn Ala Thr Gln Glu Ala Leu Arg Lys Gly Asp Asp Val Lys Phe Glu
        225                 230                 235

gag ttc gtg gcc tac ctc atc gac ccc cac acc cag cgg gag gag ccc     1130
Glu Phe Val Ala Tyr Leu Ile Asp Pro His Thr Gln Arg Glu Glu Pro
    240                 245                 250

ttc aac gag cac tgg cag acg gtc tac tct ctc tgc cac ccg tgc cac     1178
Phe Asn Glu His Trp Gln Thr Val Tyr Ser Leu Cys His Pro Cys His
255                 260                 265                 270

atc cac tac gac ctc gtg ggc aag tat gag aca ctg gag gag gac tcc     1226
Ile His Tyr Asp Leu Val Gly Lys Tyr Glu Thr Leu Glu Glu Asp Ser
                275                 280                 285

aat tac gta ctg cag ctg gcc gga gtg agc ggc tac ctg aag ttc ccc     1274
Asn Tyr Val Leu Gln Leu Ala Gly Val Ser Gly Tyr Leu Lys Phe Pro
            290                 295                 300

acc tat gca aag tcc acc cga act acc gac gag atg acc acg gag ttc     1322
Thr Tyr Ala Lys Ser Thr Arg Thr Thr Asp Glu Met Thr Thr Glu Phe
        305                 310                 315

ttc cag aac atc agc gcc gag cac cag aca cag ctg tac gaa gtc tac     1370
Phe Gln Asn Ile Ser Ala Glu His Gln Thr Gln Leu Tyr Glu Val Tyr
    320                 325                 330

aaa ctg gac ttt tta atg ttc aac tac tca gtg cca aac tac ctg aag     1418
Lys Leu Asp Phe Leu Met Phe Asn Tyr Ser Val Pro Asn Tyr Leu Lys
335                 340                 345                 350

ttg gat tag agggctgcgg aggggagggg gaggggtggt tgggggagag             1467
Leu Asp

ggagagaatc ctgcttttta atttaagatt tttatttgtc aaaagaattc tatggagact   1527

gggttatttt gtaagttaat atgtcttcgg gggagatgct gcgagcggca tggttaagaa   1587

ttatttaaaa attctccacg gggaaggaca gctgtctttg caggggagcg gggtggaata   1647

tccctgtttt tagaagtgga tactgcaaca ctgtctccaa ggtgtccttg tgttctggtg   1707

aagtccacaa actgcattcc ataaagtcta atgaatctta tttatagtta tttaaacgtg   1767

gtctgtggca gcagcctgct cctgtctgtg cagaggagag tacagtctgt gcttcgctgg   1827

ctatggctca ttgggggagg ggagggggtt atctccccca ctgaccgtgt gtagaatccc   1887

atggtgacag ctgcgggatg tgtgcctgtg gccattcaag aaaccctgct agaaagaagt   1947

caattgtcct tgcactaaga aacagggatg agactggttc aaaccgattg ctagcaaccc   2007

caaagtccct tgtagtaaag aaatgcaaat ttttttaacc caagaagaga gcagatgata   2067

gcgatttctc tttaccgaaa ttagcaggct ataagaatag gctttctgtg gaaatcttta   2127

agtggcactt tccagtgcta gcgaaggcag aataatggtt gttttctagt caataagtat   2187

tgagcatcta ctattctcca ggcttgactg cagatagcac attgagtgaa accaggagcc   2247

ttggccttca gcaagcttta tgtgaacaca gggcatccag ctcaacagtg aaccaacacc   2307

cccatccctt tggtcctcac acagacttta gactattctc aagtggtcca gagggtccag   2367

gaccctagca aatttgcgta tttctacagt tcaaatttga aagccacaca tttggatcag   2427

gccacttaac tagctaagta gttcattgcc caacacaaga aatgacagaa accctttga    2487

tcatgtatat ctagtgcagt gtcttcatag tagaagccta taagccacaa tattctccaa   2547

gcgcaaggat ggaggactgc tgtgattgat tagtgatgtc tgccttgact aaggaaaggg   2607

aggaacattt ctcaagggcc tcctactgtg atctccagtc cacatcttgt cctgcctgcc   2667

acttaaaaca gtgcactgca tacatttgga gactggcgga gttcaagtgt gaaggtcaaa   2727

ggtggagtgt tggtacccac aggcacatgc ccaccctcca tgtcctgcat tggcagagca   2787
```

```
tccaggacct ccctctcctc cagaaggttg gaaatttgct ctttcctgtt ccttgctgat   2847
caatgcccaa acctattcct catttctagt tgtttctgat actttgcggt tgacatttga   2907
gccacattcc catgacagcc agtgtccggg tacgtagcag atgctgtaca tagttctgat   2967
gataagggag ctggtaggct gtaaattttg ctttttgtgt tttgtgggg ttttgtttgt   3027
tttgatgcag tatagagtga agggggtaag aatattctga aaaacataaa attgagtaat   3087
ttattcacag aaactattaa aatggtattg ttaggctcac aaggaggctg gggcagcgg   3147
taactgctac actgtctcgc agaggaaatt attttattta atgtgagaga aatgtgagcc   3207
agagtggctg cctgaggcta tttataaaac gcaggtacct tccccaattt ctctcccctc   3267
gcctttaata aatagattta tgtcatgtgt gtgaccaaga acagtgacag atcttggctg   3327
tccctggaat agagaggcag tcatggtgct caggccctgg gcgtggtgta gctgatgcat   3387
gtcccaccga gcccaggctc tccaaggcat cagtttgtgg tcacatatcc ttagaaaaca   3447
aaattaagtc aggttcctgt ctgcaggagt tttcagagcc ttgaatacat agtctgcctt   3507
gtgaaactgg gagaatgtag catttctggg ctgcatgacc taggtatcct gtatggcaga   3567
ccatgtctta gctggttttt cacacagtag ccttcagtga gggtgatcta gcctgtctga   3627
ggtctgcaaa gattgacagc tgcttcctag atccttccac aaatcagcag aaacagtgtc   3687
catctgggaa ctttatgaga gtgttgcttt acctagttgg ggtgtcttca tctggatact   3747
gccccagaga gtgatcccgt ccctccaagc acagcggagg gaagcctagg gtgttatgga   3807
gtggggcagg tggcttaagg acaccttaaa ggccacttgg tggggataat ggcctcgtgg   3867
ggatactcct cacttccacc cacagtttgg aactgttcac tgtgtgcttc aggagtttta   3927
aatggagatt cgtgttgatt tccatggtcc gcatctgttt gtcttccgtc tgtggtccag   3987
tgctgtgtgc agatggtact tactcccttt ctctctctta cagggagaaa gactgtcctt   4047
ctggggagag tgtatcaata cgcttccaga atgagggagt ctttctcctg tcttgtgttc   4107
acacttccta gtgacaattt tcaaaatatg tatcggcttg actgtttatt gtagagtgta   4167
gaaaggtttc tgtgttcctg gctaaagaca tccattggtg aaatgtgctt ggaaatccaa   4227
gtgttttcta ctgaggaaaa aaaaatgttg gaaaagcttt ctcctgcatg cctcttgtgc   4287
ttagctagaa aggggagctg ccagcgtccc agctctgagc cactgttcaa aggtgcagct   4347
gtgttttagg actaggtaca ggcagagtga taaggacatg cctgcttagt gtactcattt   4407
atcgagaaag tttagactat gagccacagg ggtccctgcc tgcagtccct atagcctccc   4467
cctgccccag tgcctttctc agctggtctg ggaatcaggg cagcccattg agggggctc   4527
agacaaccct ttcttcctgg ttctgggagt aaggctttct ctgcagccac aaggagaaca   4587
tgggaaccag aaacttctct ttggtcagcc cttctgagca cacaggttta gcccatgctc   4647
caagaatgct cctgagcatt gtataagccc ctaggactct tagctcatgt gataatgatt   4707
gcattactat cctgctttaa ctgacaaaac cacagagaat tttgcttgct ttcctactct   4767
cttcctctgc ccaggcctcc tccatacgta tacatacaca catgggcatg tatacacaca   4827
catgcacaat agacatgcac acacacatgc acacatgggt atacatatac acacatgcac   4887
aatagacatg catatataca tatacatgca cacattgata ggcatacaca catgcacagt   4947
agacatgcac acatgggtat acatagacac acatgcacag acatgcatac acacacatgc   5007
acacataaat gtgcacacac acatacacaa attgcccaag cctgtgcact cctggtaccc   5067
atgtcccatc ctggcccacc tctttgtcag caggactgac tccatcactc cctcaggttt   5127
```

-continued

```
tgcccaccag caccccccag ctttccccca gcagagctaa acagcccctc tgaatagaca   5187

acaggacctt ctagaaacag ctgaaccctt ggacagcagc aggcagattt tgatctgctc   5247

tcatcaggta caaaaggtgg tatccgtatt ctcttctgag catgctcagt aagcatatgg   5307

acatagaatt taacatctct gtggagtgtg tgttttttac atatttgtat gcagtcgagg   5367

agggcctgtt gtagaattct ctccctgtat cttactatac tgttaaagaa gctgaattct   5427

atgttgccaa cagatgcgtg aaatgttcct ccaggaaaag ccattcaagc ctgattattt   5487

ttctaagtaa cttcaattaa attgaagaag aaaaaaaaaa aaaaa                   5532


<210> SEQ ID NO 7
<211> LENGTH: 352
<212> TYPE: PRT
<213> ORGANISM: Mus musculus

<400> SEQUENCE: 7

Met Lys Pro Ala Leu Leu Glu Val Met Arg Met Asn Arg Ile Cys Arg
1               5                   10                  15

Met Val Leu Ala Thr Cys Phe Gly Ser Phe Ile Leu Val Ile Phe Tyr
            20                  25                  30

Phe Gln Ser Met Leu His Pro Val Met Arg Arg Asn Pro Phe Gly Val
        35                  40                  45

Asp Ile Cys Cys Arg Lys Gly Ser Arg Ser Pro Leu Gln Glu Leu Tyr
    50                  55                  60

Asn Pro Ile Gln Leu Glu Leu Ser Asn Thr Ala Ile Leu His Gln Met
65                  70                  75                  80

Arg Arg Asp Gln Val Thr Asp Thr Cys Arg Ala Asn Ser Ala Met Ser
                85                  90                  95

Arg Lys Arg Arg Val Leu Thr Pro Asn Asp Leu Lys His Leu Val Val
            100                 105                 110

Asp Glu Asp His Glu Leu Ile Tyr Cys Tyr Val Pro Lys Val Ala Cys
        115                 120                 125

Thr Asn Trp Lys Arg Leu Met Met Val Leu Ser Gly Arg Gly Lys Tyr
    130                 135                 140

Ser Asp Pro Met Glu Ile Pro Ala Asn Glu Ala His Val Ser Ala Asn
145                 150                 155                 160

Leu Lys Thr Leu Asn Gln Tyr Ser Ile Pro Glu Ile Asn His Arg Leu
                165                 170                 175

Lys Ser Tyr Met Lys Phe Leu Phe Val Arg Glu Pro Phe Glu Arg Leu
            180                 185                 190

Val Ser Ala Tyr Arg Asn Lys Phe Thr Gln Lys Tyr Asn Thr Ser Phe
        195                 200                 205

His Lys Arg Tyr Gly Thr Lys Ile Ile Arg Arg Gln Arg Lys Asn Ala
    210                 215                 220

Thr Gln Glu Ala Leu Arg Lys Gly Asp Asp Val Lys Phe Glu Glu Phe
225                 230                 235                 240

Val Ala Tyr Leu Ile Asp Pro His Thr Gln Arg Glu Glu Pro Phe Asn
                245                 250                 255

Glu His Trp Gln Thr Val Tyr Ser Leu Cys His Pro Cys His Ile His
            260                 265                 270

Tyr Asp Leu Val Gly Lys Tyr Glu Thr Leu Glu Glu Asp Ser Asn Tyr
        275                 280                 285

Val Leu Gln Leu Ala Gly Val Ser Gly Tyr Leu Lys Phe Pro Thr Tyr
    290                 295                 300
```

```
Ala Lys Ser Thr Arg Thr Thr Asp Glu Met Thr Thr Glu Phe Phe Gln
305                 310                 315                 320

Asn Ile Ser Ala Glu His Gln Thr Gln Leu Tyr Glu Val Tyr Lys Leu
                325                 330                 335

Asp Phe Leu Met Phe Asn Tyr Ser Val Pro Asn Tyr Leu Lys Leu Asp
            340                 345                 350


<210> SEQ ID NO 8
<211> LENGTH: 1785
<212> TYPE: DNA
<213> ORGANISM: Mus musculus
<220> FEATURE:
<221> NAME/KEY: CDS
<222> LOCATION: (149)..(1408)

<400> SEQUENCE: 8

ggcgatttcg gctgcagaat cagcatcacc agcaacagca gcagcggcgg tgactgtggc      60

gggcgctagg tccgtctcct agggaccatg tcccagctgt gcacaaggct gaagtgaagg     120

gccaggagtg ggcccagccc agggcagc atg acc aag ccg cgg ctc ttc cgg        172
                               Met Thr Lys Pro Arg Leu Phe Arg
                               1               5

ctg tgg ctg gta cta ggg tcg gct ctc atg atc ctt ttg atc att gta       220
Leu Trp Leu Val Leu Gly Ser Ala Leu Met Ile Leu Leu Ile Ile Val
    10                  15                  20

tat tgg gac aac gtg gga acc gcc cac ttc tat ctg cac acg tct ctc       268
Tyr Trp Asp Asn Val Gly Thr Ala His Phe Tyr Leu His Thr Ser Leu
25                  30                  35                  40

tcc agg cca cac atc cta gaa ccc ctt ccc acc cag gga ttg gtg gag       316
Ser Arg Pro His Ile Leu Glu Pro Leu Pro Thr Gln Gly Leu Val Glu
                45                  50                  55

gag aac gtg ttc aca tct gac gtg gat gag ttt ttg gat act ctc ctt       364
Glu Asn Val Phe Thr Ser Asp Val Asp Glu Phe Leu Asp Thr Leu Leu
            60                  65                  70

agt tct gac gcg aag cac aac gac ctt tcc agg aga aaa act gag cag       412
Ser Ser Asp Ala Lys His Asn Asp Leu Ser Arg Arg Lys Thr Glu Gln
        75                  80                  85

ccc ccg gcg ccc gcc ccc agc aag cca gtc ttg agc cac atg gag gag       460
Pro Pro Ala Pro Ala Pro Ser Lys Pro Val Leu Ser His Met Glu Glu
    90                  95                  100

aac gtg aga ggc tac gac tgg tcc act cat gat gcc cat cag aac cct       508
Asn Val Arg Gly Tyr Asp Trp Ser Thr His Asp Ala His Gln Asn Pro
105                 110                 115                 120

gac cgg gac agg cag cag gcc gag agg agg agc ctg ctg aga gac ttc       556
Asp Arg Asp Arg Gln Gln Ala Glu Arg Arg Ser Leu Leu Arg Asp Phe
                125                 130                 135

tgt gcc aac gcc agc ctg gca ttc ccc acc aag gac cgc tct ttt gac       604
Cys Ala Asn Ala Ser Leu Ala Phe Pro Thr Lys Asp Arg Ser Phe Asp
            140                 145                 150

gac atc ccc aac tac gaa ctg aac cac ctg atc gtg gac gac cgc cac       652
Asp Ile Pro Asn Tyr Glu Leu Asn His Leu Ile Val Asp Asp Arg His
        155                 160                 165

ggg gtc atc tac tgc tac gtg ccc aag gtg gcc tgc acc aac tgg aag       700
Gly Val Ile Tyr Cys Tyr Val Pro Lys Val Ala Cys Thr Asn Trp Lys
    170                 175                 180

cga gtg atg atc gtg ctg agc gag agc ctg ctg gac cgg ggc agc ccc       748
Arg Val Met Ile Val Leu Ser Glu Ser Leu Leu Asp Arg Gly Ser Pro
185                 190                 195                 200

tac cga gac ccc ctg gac atc ccc cgg gaa cac gtg cac aac acc agc       796
Tyr Arg Asp Pro Leu Asp Ile Pro Arg Glu His Val His Asn Thr Ser
                205                 210                 215
```

-continued

```
acg cac ctc acc ttc aac aag ttc tgg cgc cgc tac gga aag ttc tcc      844
Thr His Leu Thr Phe Asn Lys Phe Trp Arg Arg Tyr Gly Lys Phe Ser
        220                 225                 230

cgt cac ctc atg aag gtg aag ctg aag aag tac acc aag ttc ctg ttc      892
Arg His Leu Met Lys Val Lys Leu Lys Lys Tyr Thr Lys Phe Leu Phe
        235                 240                 245

gtg cgc gac ccc ttt gtg cgc ctc atc tca gcc ttc cgc agc aag ttc      940
Val Arg Asp Pro Phe Val Arg Leu Ile Ser Ala Phe Arg Ser Lys Phe
        250                 255                 260

gag ctg gag aac gaa gag ttt tac cgc aag ttc gcg gtg ccc atg ctc      988
Glu Leu Glu Asn Glu Glu Phe Tyr Arg Lys Phe Ala Val Pro Met Leu
265                 270                 275                 280

cga ctg tac gcc aac cac acc agc ctg ccc gcc tcg gtg agt gag gct     1036
Arg Leu Tyr Ala Asn His Thr Ser Leu Pro Ala Ser Val Ser Glu Ala
                285                 290                 295

ttc agc gcc ggg ctc aag gtc tcc ttc gcc aac ttc atc cag tac ctc     1084
Phe Ser Ala Gly Leu Lys Val Ser Phe Ala Asn Phe Ile Gln Tyr Leu
                300                 305                 310

cta gac cca cac acg gag aag ctg gcg cct ttc aac gag cac tgg cga     1132
Leu Asp Pro His Thr Glu Lys Leu Ala Pro Phe Asn Glu His Trp Arg
                315                 320                 325

cag gtg tac cgc ctc tgc cac ccg tgc cag ata gac tat gac ttc gtg     1180
Gln Val Tyr Arg Leu Cys His Pro Cys Gln Ile Asp Tyr Asp Phe Val
        330                 335                 340

ggg aag ctg gag acg ctc gat gag gac gct gcc cag ctc ctg agg ttc     1228
Gly Lys Leu Glu Thr Leu Asp Glu Asp Ala Ala Gln Leu Leu Arg Phe
345                 350                 355                 360

ctc aag gta gac tcc cag ctc cac ttc ccc ccc agt tat cgg aac agg     1276
Leu Lys Val Asp Ser Gln Leu His Phe Pro Pro Ser Tyr Arg Asn Arg
                365                 370                 375

acg gcc agc agc tgg gag gaa gac tgg ttt gcc aac atc ccc ctg gca     1324
Thr Ala Ser Ser Trp Glu Glu Asp Trp Phe Ala Asn Ile Pro Leu Ala
                380                 385                 390

tgg agg caa cag ctc tat aaa ctc tac gag gcc gac ttt gtt ctc ttt     1372
Trp Arg Gln Gln Leu Tyr Lys Leu Tyr Glu Ala Asp Phe Val Leu Phe
        395                 400                 405

ggc tac ccc aag cca gaa aac ctg ctc agg gac tga gcccccagaa          1418
Gly Tyr Pro Lys Pro Glu Asn Leu Leu Arg Asp
        410                 415

gccctcacgc tgcccccaac aaattgaatg gctgtcccat gaggccgtcc tttgaggatg   1478

ggaccctgtg gcctcctggg ttctctcctg gcttcctttg cttcctggtg tgacaggcag   1538

aggattccac gcccccccct cgcatctgga gaccgtggta cagccaagac cgaagcacct   1598

cactctccag agttttgcgc tccccacccc cgcccttttg caatctggat ttgtttactc   1658

cacagcctgt attcatggaa cactgtgtta aatactgttt tctaagatta atatatttca   1718

gatatattta atacgaaagt gggaggaagc tggagtaaag tgtggcgccc gcaaaaaaaa   1778

aaaaaaa                                                             1785
```

<210> SEQ ID NO 9
<211> LENGTH: 419
<212> TYPE: PRT
<213> ORGANISM: Mus musculus

<400> SEQUENCE: 9

```
Met Thr Lys Pro Arg Leu Phe Arg Leu Trp Leu Val Leu Gly Ser Ala
1               5                   10                  15

Leu Met Ile Leu Leu Ile Ile Val Tyr Trp Asp Asn Val Gly Thr Ala
```

```
            20                  25                  30

His Phe Tyr Leu His Thr Ser Leu Ser Arg Pro His Ile Leu Glu Pro
        35                  40                  45

Leu Pro Thr Gln Gly Leu Val Glu Glu Asn Val Phe Thr Ser Asp Val
    50                  55                  60

Asp Glu Phe Leu Asp Thr Leu Leu Ser Ser Asp Ala Lys His Asn Asp
65                  70                  75                  80

Leu Ser Arg Arg Lys Thr Glu Gln Pro Pro Ala Pro Ala Pro Ser Lys
                85                  90                  95

Pro Val Leu Ser His Met Glu Glu Asn Val Arg Gly Tyr Asp Trp Ser
            100                 105                 110

Thr His Asp Ala His Gln Asn Pro Asp Arg Asp Arg Gln Gln Ala Glu
        115                 120                 125

Arg Arg Ser Leu Leu Arg Asp Phe Cys Ala Asn Ala Ser Leu Ala Phe
    130                 135                 140

Pro Thr Lys Asp Arg Ser Phe Asp Asp Ile Pro Asn Tyr Glu Leu Asn
145                 150                 155                 160

His Leu Ile Val Asp Asp Arg His Gly Val Ile Tyr Cys Tyr Val Pro
                165                 170                 175

Lys Val Ala Cys Thr Asn Trp Lys Arg Val Met Ile Val Leu Ser Glu
            180                 185                 190

Ser Leu Leu Asp Arg Gly Ser Pro Tyr Arg Asp Pro Leu Asp Ile Pro
        195                 200                 205

Arg Glu His Val His Asn Thr Ser Thr His Leu Thr Phe Asn Lys Phe
    210                 215                 220

Trp Arg Arg Tyr Gly Lys Phe Ser Arg His Leu Met Lys Val Lys Leu
225                 230                 235                 240

Lys Lys Tyr Thr Lys Phe Leu Phe Val Arg Asp Pro Phe Val Arg Leu
                245                 250                 255

Ile Ser Ala Phe Arg Ser Lys Phe Glu Leu Glu Asn Glu Glu Phe Tyr
            260                 265                 270

Arg Lys Phe Ala Val Pro Met Leu Arg Leu Tyr Ala Asn His Thr Ser
        275                 280                 285

Leu Pro Ala Ser Val Ser Glu Ala Phe Ser Ala Gly Leu Lys Val Ser
    290                 295                 300

Phe Ala Asn Phe Ile Gln Tyr Leu Leu Asp Pro His Thr Glu Lys Leu
305                 310                 315                 320

Ala Pro Phe Asn Glu His Trp Arg Gln Val Tyr Arg Leu Cys His Pro
                325                 330                 335

Cys Gln Ile Asp Tyr Asp Phe Val Gly Lys Leu Glu Thr Leu Asp Glu
            340                 345                 350

Asp Ala Ala Gln Leu Leu Arg Phe Leu Lys Val Asp Ser Gln Leu His
        355                 360                 365

Phe Pro Pro Ser Tyr Arg Asn Arg Thr Ala Ser Ser Trp Glu Glu Asp
    370                 375                 380

Trp Phe Ala Asn Ile Pro Leu Ala Trp Arg Gln Gln Leu Tyr Lys Leu
385                 390                 395                 400

Tyr Glu Ala Asp Phe Val Leu Phe Gly Tyr Pro Lys Pro Glu Asn Leu
                405                 410                 415

Leu Arg Asp
```

<210> SEQ ID NO 10
<211> LENGTH: 1728

```
<212> TYPE: DNA
<213> ORGANISM: Mus musculus
<220> FEATURE:
<221> NAME/KEY: CDS
<222> LOCATION: (1)..(1116)

<400> SEQUENCE: 10

atg act gtc gcc tgc cac gcg tgc cag gca cag cat ggg aag acg ctc       48
Met Thr Val Ala Cys His Ala Cys Gln Ala Gln His Gly Lys Thr Leu
1               5                   10                  15

ctg ttg cag gcg gcc ctt gcc ggt ggt ggc aag tct ggg tgc tgc act       96
Leu Leu Gln Ala Ala Leu Ala Gly Gly Gly Lys Ser Gly Cys Cys Thr
            20                  25                  30

cct gct cct gtg cgc cct gcg tcc cgg gta acc aca gga aag gat gcc      144
Pro Ala Pro Val Arg Pro Ala Ser Arg Val Thr Thr Gly Lys Asp Ala
        35                  40                  45

cag gac act gaa tgg cag ggc tcc cca aaa gcc ctt ttg ggg gtt ccg      192
Gln Asp Thr Glu Trp Gln Gly Ser Pro Lys Ala Leu Leu Gly Val Pro
    50                  55                  60

aca ttt gaa aat aaa gct ctg ggc tcc agc tgg ttc ggt gga gtg agg      240
Thr Phe Glu Asn Lys Ala Leu Gly Ser Ser Trp Phe Gly Gly Val Arg
65                  70                  75                  80

aag agt ccc cta cag ctg ttg cgt gac ctg gac cag ggt cca cgc tcc      288
Lys Ser Pro Leu Gln Leu Leu Arg Asp Leu Asp Gln Gly Pro Arg Ser
                85                  90                  95

gcg atg gcc gag gtg cac cag cag cgg cgt gag ctg ctg cgc cgg gcc      336
Ala Met Ala Glu Val His Gln Gln Arg Arg Glu Leu Leu Arg Arg Ala
            100                 105                 110

tgc agc cgc cac acg cga cgc caa cgc ctg ctg cag ccg gag gac ctg      384
Cys Ser Arg His Thr Arg Arg Gln Arg Leu Leu Gln Pro Glu Asp Leu
        115                 120                 125

cgt cac gtg ctg gtg gac gac gcg cac cgg ctg ctg tac tgc tac gtg      432
Arg His Val Leu Val Asp Asp Ala His Arg Leu Leu Tyr Cys Tyr Val
    130                 135                 140

cct aag gtg gcc tgc acc aac tgg aag cgt gtg atg ctg gcg ttg cgc      480
Pro Lys Val Ala Cys Thr Asn Trp Lys Arg Val Met Leu Ala Leu Arg
145                 150                 155                 160

ggc cgt ggg gat cca agc gca atc cct gcg cac gag gcg cat gcg cct      528
Gly Arg Gly Asp Pro Ser Ala Ile Pro Ala His Glu Ala His Ala Pro
                165                 170                 175

ggc ctg ctg ccc tcg ctg gcc gac ttt gcg ccg gct gag gtc aac tgg      576
Gly Leu Leu Pro Ser Leu Ala Asp Phe Ala Pro Ala Glu Val Asn Trp
            180                 185                 190

cgg ctg cgc gac tac ctg acc ttt ctc ttc gtg cgg gag ccc ttc gag      624
Arg Leu Arg Asp Tyr Leu Thr Phe Leu Phe Val Arg Glu Pro Phe Glu
        195                 200                 205

cgc ctg gcg tca gcc tac cgc aac aag ctg gcg cgg cca cac agc gcg      672
Arg Leu Ala Ser Ala Tyr Arg Asn Lys Leu Ala Arg Pro His Ser Ala
    210                 215                 220

gcc ttc cag cgg cgc tat ggc aca cgc atc gtg cgt cgc cta cga cca      720
Ala Phe Gln Arg Arg Tyr Gly Thr Arg Ile Val Arg Arg Leu Arg Pro
225                 230                 235                 240

cac gcg cag ccc gat gcg ctg gcc cgc ggc cac gac gtg cgc ttc gcc      768
His Ala Gln Pro Asp Ala Leu Ala Arg Gly His Asp Val Arg Phe Ala
                245                 250                 255

gag ttc ctg gcc tac ctg ctc gac ccg cgc acg cgc cgt cat gag ccc      816
Glu Phe Leu Ala Tyr Leu Leu Asp Pro Arg Thr Arg Arg His Glu Pro
            260                 265                 270

ttc aac gaa cac tgg gag cgc gca cac gcg ctg tgc cat ccg tgc cta      864
Phe Asn Glu His Trp Glu Arg Ala His Ala Leu Cys His Pro Cys Leu
        275                 280                 285
```

```
gtg cgc tat gat gta gtg ggc aag ttt gag acg ata gca gat gat gct      912
Val Arg Tyr Asp Val Val Gly Lys Phe Glu Thr Ile Ala Asp Asp Ala
    290                 295                 300

gcc ttc gtg ctg gac ctg gtg ggt gag cct ggg cta cgt ttc cct gct      960
Ala Phe Val Leu Asp Leu Val Gly Glu Pro Gly Leu Arg Phe Pro Ala
305                 310                 315                 320

cca ccg ctg agg cca gag aag gac ctt acg cgt gag cag gcc cgg cgc     1008
Pro Pro Leu Arg Pro Glu Lys Asp Leu Thr Arg Glu Gln Ala Arg Arg
                325                 330                 335

ctt ttc cag gac atc agc ccc ttc tac cag cgt cgc ctc ttt aac ctc     1056
Leu Phe Gln Asp Ile Ser Pro Phe Tyr Gln Arg Arg Leu Phe Asn Leu
            340                 345                 350

tat aag atg gac ttt ctg ctc ttc aat tac tct gcc cct tcc tac ctg     1104
Tyr Lys Met Asp Phe Leu Leu Phe Asn Tyr Ser Ala Pro Ser Tyr Leu
        355                 360                 365

cga ctg caa taa gggtgttggg tgcaatagag ccagtggctg ctgtgaccag         1156
Arg Leu Gln
    370

gaggccacca ggaggtctgg aacgaacctg gttgtgtgga ttggagacct tatccagtgg   1216

gcctgaccaa gagtctggcc actggtcaca ctcattccga ctgggtaggg tacaggttgc   1276

tttaggtgac cataaccttg tcaggccgtt tctgctgtta gtttgatgtg tgtctcttcc   1336

tcccactctg cagatgtcag gcttcttcct aggactccag gtttgtagtt ctttggtttg   1396

gtttgagagg ccatttctca gtcttgtctg tgtagaacct gtccgtggca tggtgctaca   1456

agacagaatg tcatggcttg gttcagtgtg gcctaaggtc ttgtcagcat ttactgctta   1516

ggagttaaca tgagctgcct gccaccccag cagtcacagg atggtgagca ctaccactcc   1576

acatctacct ggctgatcta cctttgatct cagccttgca agaggctgga tcttcccctg   1636

tgtcagcaaa ggccaagatg caatactgtg gcagcttttc cagctcactt ttattttttt   1696

tgttgttttt ttaaataaat atgttttgtt ac                                 1728


<210> SEQ ID NO 11
<211> LENGTH: 371
<212> TYPE: PRT
<213> ORGANISM: Mus musculus

<400> SEQUENCE: 11

Met Thr Val Ala Cys His Ala Cys Gln Ala Gln His Gly Lys Thr Leu
1               5                   10                  15

Leu Leu Gln Ala Ala Leu Ala Gly Gly Gly Lys Ser Gly Cys Cys Thr
            20                  25                  30

Pro Ala Pro Val Arg Pro Ala Ser Arg Val Thr Thr Gly Lys Asp Ala
        35                  40                  45

Gln Asp Thr Glu Trp Gln Gly Ser Pro Lys Ala Leu Leu Gly Val Pro
    50                  55                  60

Thr Phe Glu Asn Lys Ala Leu Gly Ser Ser Trp Phe Gly Gly Val Arg
65                  70                  75                  80

Lys Ser Pro Leu Gln Leu Leu Arg Asp Leu Asp Gln Gly Pro Arg Ser
                85                  90                  95

Ala Met Ala Glu Val His Gln Gln Arg Arg Glu Leu Leu Arg Arg Ala
            100                 105                 110

Cys Ser Arg His Thr Arg Arg Gln Arg Leu Leu Gln Pro Glu Asp Leu
        115                 120                 125

Arg His Val Leu Val Asp Asp Ala His Arg Leu Leu Tyr Cys Tyr Val
    130                 135                 140
```

```
Pro Lys Val Ala Cys Thr Asn Trp Lys Arg Val Met Leu Ala Leu Arg
145                 150                 155                 160

Gly Arg Gly Asp Pro Ser Ala Ile Pro Ala His Glu Ala His Ala Pro
                165                 170                 175

Gly Leu Leu Pro Ser Leu Ala Asp Phe Ala Pro Ala Glu Val Asn Trp
            180                 185                 190

Arg Leu Arg Asp Tyr Leu Thr Phe Leu Phe Val Arg Glu Pro Phe Glu
        195                 200                 205

Arg Leu Ala Ser Ala Tyr Arg Asn Lys Leu Ala Arg Pro His Ser Ala
    210                 215                 220

Ala Phe Gln Arg Arg Tyr Gly Thr Arg Ile Val Arg Arg Leu Arg Pro
225                 230                 235                 240

His Ala Gln Pro Asp Ala Leu Ala Arg Gly His Asp Val Arg Phe Ala
                245                 250                 255

Glu Phe Leu Ala Tyr Leu Leu Asp Pro Arg Thr Arg Arg His Glu Pro
            260                 265                 270

Phe Asn Glu His Trp Glu Arg Ala His Ala Leu Cys His Pro Cys Leu
        275                 280                 285

Val Arg Tyr Asp Val Val Gly Lys Phe Glu Thr Ile Ala Asp Asp Ala
    290                 295                 300

Ala Phe Val Leu Asp Leu Val Gly Glu Pro Gly Leu Arg Phe Pro Ala
305                 310                 315                 320

Pro Pro Leu Arg Pro Glu Lys Asp Leu Thr Arg Glu Gln Ala Arg Arg
                325                 330                 335

Leu Phe Gln Asp Ile Ser Pro Phe Tyr Gln Arg Arg Leu Phe Asn Leu
            340                 345                 350

Tyr Lys Met Asp Phe Leu Leu Phe Asn Tyr Ser Ala Pro Ser Tyr Leu
        355                 360                 365

Arg Leu Gln
    370


<210> SEQ ID NO 12
<211> LENGTH: 2073
<212> TYPE: DNA
<213> ORGANISM: Mus musculus
<220> FEATURE:
<221> NAME/KEY: CDS
<222> LOCATION: (129)..(1259)

<400> SEQUENCE: 12

ccggccctgg tccctgcctg caccccggga gctggccacc cactatccct cccctcccga      60

gacctccagc ccctgctgca gtcacctccc ctgcagcctc gaggtcggcg aggtctggcc     120

gcagcacc atg ttt ccc cgc cct ctg acc cca ctg gct gcc ccg aaa agc      170
         Met Phe Pro Arg Pro Leu Thr Pro Leu Ala Ala Pro Lys Ser
         1               5                   10

gcg gag acc ctg ggc cgc acg cca agg cgg gcc cca ttg ggc cgg gcc       218
Ala Glu Thr Leu Gly Arg Thr Pro Arg Arg Ala Pro Leu Gly Arg Ala
15                  20                  25                  30

cgg gct ggg ctc ggg ggg ccg ccc ctg ctg ctg ccg tcc atg ctg atg       266
Arg Ala Gly Leu Gly Gly Pro Pro Leu Leu Leu Pro Ser Met Leu Met
                35                  40                  45

ttc gct gta atc gtg gcc tcc agc gga ctg ctg ctc atg atc gag cga       314
Phe Ala Val Ile Val Ala Ser Ser Gly Leu Leu Leu Met Ile Glu Arg
            50                  55                  60

ggc atc cta tcg gag atg aaa ccc ctt ccc ctg cac cct ccc agc cac       362
Gly Ile Leu Ser Glu Met Lys Pro Leu Pro Leu His Pro Pro Ser His
```

```
        65                  70                  75

aaa ggc gcg gcc tgg agc ggg aca gat cct aag cct aga ggc cta tcc      410
Lys Gly Ala Ala Trp Ser Gly Thr Asp Pro Lys Pro Arg Gly Leu Ser
    80                  85                  90

ttg gat gct ggg gac tcg gac ttg caa gtg agg gag gac atc cga aac      458
Leu Asp Ala Gly Asp Ser Asp Leu Gln Val Arg Glu Asp Ile Arg Asn
95                  100                 105                 110

cgg acc ttg agg gcc gtg tgc gga caa cca ggc atg ccc cgg gac ccc      506
Arg Thr Leu Arg Ala Val Cys Gly Gln Pro Gly Met Pro Arg Asp Pro
                115                 120                 125

tgg gac ttg ccg gtg gga cag cgg cgc acc ctg ctg cgc cac att ctc      554
Trp Asp Leu Pro Val Gly Gln Arg Arg Thr Leu Leu Arg His Ile Leu
            130                 135                 140

gta agt gac cgc tac cgc ttc ctc tac tgc tat gtc ccc aaa gtg gcc      602
Val Ser Asp Arg Tyr Arg Phe Leu Tyr Cys Tyr Val Pro Lys Val Ala
        145                 150                 155

tgc tct aac tgg aaa cgt gtg ctg aag gtg ctg gct ggc gtc ctg aac      650
Cys Ser Asn Trp Lys Arg Val Leu Lys Val Leu Ala Gly Val Leu Asn
    160                 165                 170

aac gtg gat gtc cgc ctc aag atg gac cac ccc agt gac ttg gtg ttt      698
Asn Val Asp Val Arg Leu Lys Met Asp His Pro Ser Asp Leu Val Phe
175                 180                 185                 190

ctg gca gac ctg cgg cct gag gag att cgc tac cgt ctg cag cac tac      746
Leu Ala Asp Leu Arg Pro Glu Glu Ile Arg Tyr Arg Leu Gln His Tyr
                195                 200                 205

ttc aag ttc ctg ttt gtg cga gac ccc ttg gaa cgc ctc ctg tct gct      794
Phe Lys Phe Leu Phe Val Arg Asp Pro Leu Glu Arg Leu Leu Ser Ala
            210                 215                 220

tac cgt aac aag ttt gga gag atc cga gag tac cag cag cga tat ggg      842
Tyr Arg Asn Lys Phe Gly Glu Ile Arg Glu Tyr Gln Gln Arg Tyr Gly
        225                 230                 235

gcc gaa att gtc agg cgc tac agg gct gga gct ggt ccc agc cct gca      890
Ala Glu Ile Val Arg Arg Tyr Arg Ala Gly Ala Gly Pro Ser Pro Ala
    240                 245                 250

ggg gac gat gtc acc ttc cca gag ttc ctg aga tac ctg gtg gat gag      938
Gly Asp Asp Val Thr Phe Pro Glu Phe Leu Arg Tyr Leu Val Asp Glu
255                 260                 265                 270

gat cct gaa cat atg aat gag cat tgg atg cct gtg tac cac ctg tgc      986
Asp Pro Glu His Met Asn Glu His Trp Met Pro Val Tyr His Leu Cys
                275                 280                 285

caa cca tgt gct gtg cac tac gac ttc gtg ggt tcc tat gag agg ctg     1034
Gln Pro Cys Ala Val His Tyr Asp Phe Val Gly Ser Tyr Glu Arg Leu
            290                 295                 300

gag gct gat gcc aac cag gtg ctg gag tgg gtg cgg gcc cca ccc cat     1082
Glu Ala Asp Ala Asn Gln Val Leu Glu Trp Val Arg Ala Pro Pro His
        305                 310                 315

gtc cgg ttc cca gct cgc cag gcc tgg tac cgg cca gcc agc cca gaa     1130
Val Arg Phe Pro Ala Arg Gln Ala Trp Tyr Arg Pro Ala Ser Pro Glu
    320                 325                 330

agt ctg cat tac cac ttg tgc aat gtt cca cgg gcc ctg ctt caa gat     1178
Ser Leu His Tyr His Leu Cys Asn Val Pro Arg Ala Leu Leu Gln Asp
335                 340                 345                 350

gtg cta cct aag tat atc ctg gac ttc tcc ctc ttt gct tac cca ctg     1226
Val Leu Pro Lys Tyr Ile Leu Asp Phe Ser Leu Phe Ala Tyr Pro Leu
                355                 360                 365

ccc aat gtc acc aag gaa gcc tgt cac caa tga cagtaggcca gcaccttttg   1279
Pro Asn Val Thr Lys Glu Ala Cys His Gln
            370                 375

gagtttgggt ttaatgatat cagctttggg atgtctttca gagaaactcc tggctctggg   1339
```

```
tggcttcctg gtttctctag gtgtctccat atctcagtgg taaggactgt ccttggaggt   1399

ccttgtccac agtggctcag aggacagagc tagaaaggag gcctgctgct ttcactggtg   1459

aactgcctct cttaggggcc tgtggtatcc gtgtctgcag ggcaccagtg gttattaaag   1519

ccatatgttt gatcgaaaga ctgacttcag ccccctggct gctgggtcta tgcagtccac   1579

ctggtctgtt gtaatttaac ctgtggccaa atcccaaata tgacactagc caagcacatg   1639

atcatgccta ggaccaatgg ctgtgacccc ctattcaccc atcccatgga cctcaggact   1699

ggagtgagct gtggtgcctt agaaatgaaa tgtgtgcaat tctactccag acttttacat   1759

ttcctcctct tgctaggtct gaatcatttt tctaaggaaa gagaaacgga agtggggccc   1819

ttacctcgaa gctctaaagc ccagcccctc aagcatccaa agacgcctgt gcctgacctc   1879

ttcctagggc tcctggagca tcttcaataa gcctcccttc cctacaaacc tttggagact   1939

atgtgagact gtatggccca tatatctggc tgtcacttgt ctaatgcatt tatttaaaat   1999

gtgtatattt taataggatc cttgtaaggg ctgactttta ataaagcttt ttcatataca   2059

aaaaaaaaaa aaaa                                                     2073
```

<210> SEQ ID NO 13
<211> LENGTH: 376
<212> TYPE: PRT
<213> ORGANISM: Mus musculus

<400> SEQUENCE: 13

```
Met Phe Pro Arg Pro Leu Thr Pro Leu Ala Ala Pro Lys Ser Ala Glu
1               5                   10                  15

Thr Leu Gly Arg Thr Pro Arg Arg Ala Pro Leu Gly Arg Ala Arg Ala
            20                  25                  30

Gly Leu Gly Gly Pro Pro Leu Leu Leu Pro Ser Met Leu Met Phe Ala
        35                  40                  45

Val Ile Val Ala Ser Ser Gly Leu Leu Leu Met Ile Glu Arg Gly Ile
    50                  55                  60

Leu Ser Glu Met Lys Pro Leu Pro Leu His Pro Pro Ser His Lys Gly
65                  70                  75                  80

Ala Ala Trp Ser Gly Thr Asp Pro Lys Pro Arg Gly Leu Ser Leu Asp
                85                  90                  95

Ala Gly Asp Ser Asp Leu Gln Val Arg Glu Asp Ile Arg Asn Arg Thr
            100                 105                 110

Leu Arg Ala Val Cys Gly Gln Pro Gly Met Pro Arg Asp Pro Trp Asp
        115                 120                 125

Leu Pro Val Gly Gln Arg Arg Thr Leu Leu Arg His Ile Leu Val Ser
    130                 135                 140

Asp Arg Tyr Arg Phe Leu Tyr Cys Tyr Val Pro Lys Val Ala Cys Ser
145                 150                 155                 160

Asn Trp Lys Arg Val Leu Lys Val Leu Ala Gly Val Leu Asn Asn Val
                165                 170                 175

Asp Val Arg Leu Lys Met Asp His Pro Ser Asp Leu Val Phe Leu Ala
            180                 185                 190

Asp Leu Arg Pro Glu Glu Ile Arg Tyr Arg Leu Gln His Tyr Phe Lys
        195                 200                 205

Phe Leu Phe Val Arg Asp Pro Leu Glu Arg Leu Leu Ser Ala Tyr Arg
    210                 215                 220

Asn Lys Phe Gly Glu Ile Arg Glu Tyr Gln Gln Arg Tyr Gly Ala Glu
225                 230                 235                 240
```

-continued

```
Ile Val Arg Arg Tyr Arg Ala Gly Ala Gly Pro Ser Pro Ala Gly Asp
              245              250              255

Asp Val Thr Phe Pro Glu Phe Leu Arg Tyr Leu Val Asp Glu Asp Pro
              260              265              270

Glu His Met Asn Glu His Trp Met Pro Val Tyr His Leu Cys Gln Pro
              275              280              285

Cys Ala Val His Tyr Asp Phe Val Gly Ser Tyr Glu Arg Leu Glu Ala
              290              295              300

Asp Ala Asn Gln Val Leu Glu Trp Val Arg Ala Pro Pro His Val Arg
305              310              315              320

Phe Pro Ala Arg Gln Ala Trp Tyr Arg Pro Ala Ser Pro Glu Ser Leu
              325              330              335

His Tyr His Leu Cys Asn Val Pro Arg Ala Leu Leu Gln Asp Val Leu
              340              345              350

Pro Lys Tyr Ile Leu Asp Phe Ser Leu Phe Ala Tyr Pro Leu Pro Asn
              355              360              365

Val Thr Lys Glu Ala Cys His Gln
              370              375
```

```
<210> SEQ ID NO 14
<211> LENGTH: 6000
<212> TYPE: DNA
<213> ORGANISM: Mus musculus
<220> FEATURE:
<221> NAME/KEY: CDS
<222> LOCATION: (496)..(1914)

<400> SEQUENCE: 14
```

```
cttagccact gaaccatctc tccagcctct gttttggggt gtttgtttga gacagaatca      60

aaaggctggt ctaaagtaca tattgtagct aaagatggct tccaactcct gccttgcctc     120

cagagtgtta gggtgtgacc tttaaatgac ctattaaaga aaccccaaca ggtgtagagt     180

acacctgtga tcccagctct taggaggttg gacagatgga taaagaggtc caggtgtccc     240

ggactacata gagagaccct atctcaaaag agaggcgaag acttaggttt tgagagtggg     300

cctgaggtct ctcttcaaaa gttttataga aagatgtctc tgttccctgt ctatgaacac     360

ggatggcctg agcacctgtc tcttcacagg atcagagtgt cccccacctg aagagggctg     420

attgggtccc aagctatgct cctgagctga gtgcctgcag ccagtctgag gaactccatg     480
```

```
gcgccccctc tcccc atg gag aaa gga ctc gct ttg cct cag gat ttc cgg      531
             Met Glu Lys Gly Leu Ala Leu Pro Gln Asp Phe Arg
             1               5                   10

gac ctt gta cac agc cta aag att cga ggc aga tac gtc ttg ttc ctg      579
Asp Leu Val His Ser Leu Lys Ile Arg Gly Arg Tyr Val Leu Phe Leu
        15              20              25

gca ttt gtg gtc ata gtt ttt atc ttc att gaa aag gaa aat aaa atc      627
Ala Phe Val Val Ile Val Phe Ile Phe Ile Glu Lys Glu Asn Lys Ile
    30              35              40

ata tcc agg gtc tcc gac aag ctg aag cag atc cct cat ttt gtg gca      675
Ile Ser Arg Val Ser Asp Lys Leu Lys Gln Ile Pro His Phe Val Ala
45              50              55              60

gat gcc aac agc act gac cca gcc ctg ctc tta tcg gag aat gca tct      723
Asp Ala Asn Ser Thr Asp Pro Ala Leu Leu Leu Ser Glu Asn Ala Ser
            65              70              75

ctc ttg tcc ctg agc gag ttg gat tcc acc ttt tcc cat ctg cgg agc      771
Leu Leu Ser Leu Ser Glu Leu Asp Ser Thr Phe Ser His Leu Arg Ser
        80              85              90
```

-continued

```
cgc ctg cac aac ctg agc ctg cag ctg ggc gtg gag cca gca atg gag      819
Arg Leu His Asn Leu Ser Leu Gln Leu Gly Val Glu Pro Ala Met Glu
        95                  100                 105

agc cag gag gct ggg gca gag aag cca tcc cag cag gct gga gca ggg      867
Ser Gln Glu Ala Gly Ala Glu Lys Pro Ser Gln Gln Ala Gly Ala Gly
    110                 115                 120

acc cgg cgc cac gtg ctt ctc atg gcc acc acc cgc acg ggt tcc tcg      915
Thr Arg Arg His Val Leu Leu Met Ala Thr Thr Arg Thr Gly Ser Ser
125                 130                 135                 140

ttc gtg ggc gag ttc ttc aac cag cag ggc aat atc ttc tac ctc ttc      963
Phe Val Gly Glu Phe Phe Asn Gln Gln Gly Asn Ile Phe Tyr Leu Phe
                145                 150                 155

gag cca ctg tgg cac atc gag cgc acc gtg ttc ttc cag cag cga ggc     1011
Glu Pro Leu Trp His Ile Glu Arg Thr Val Phe Phe Gln Gln Arg Gly
            160                 165                 170

gcc agc gcg gct ggt tca gcc ttg gtc tac cgt gat gtc ctc aag cag     1059
Ala Ser Ala Ala Gly Ser Ala Leu Val Tyr Arg Asp Val Leu Lys Gln
        175                 180                 185

ttg ttg cta tgc gac ctg tat gtg ctg gag ccc ttc atc agc cct ccg     1107
Leu Leu Leu Cys Asp Leu Tyr Val Leu Glu Pro Phe Ile Ser Pro Pro
    190                 195                 200

ccc gag gac cac ttg act cag ttc ctg ttc cgc cgg gga tcc agc cgt     1155
Pro Glu Asp His Leu Thr Gln Phe Leu Phe Arg Arg Gly Ser Ser Arg
205                 210                 215                 220

tca ctc tgc gag gat ccg gtg tgc aca ccc ttc gtc aag aag gtc ttt     1203
Ser Leu Cys Glu Asp Pro Val Cys Thr Pro Phe Val Lys Lys Val Phe
                225                 230                 235

gag aag tac cac tgc agg aac cgt cgc tgc ggg cca ctc aac gtg acc     1251
Glu Lys Tyr His Cys Arg Asn Arg Arg Cys Gly Pro Leu Asn Val Thr
            240                 245                 250

ttg gcg ggc gag gcc tgc cgc cgc aag gac cac gtg gcc ctc aag gct     1299
Leu Ala Gly Glu Ala Cys Arg Arg Lys Asp His Val Ala Leu Lys Ala
        255                 260                 265

gtg cgc atc cgt cag ctg gag ttc ctg cag ccg cta gtt gag gac ccg     1347
Val Arg Ile Arg Gln Leu Glu Phe Leu Gln Pro Leu Val Glu Asp Pro
    270                 275                 280

agg ttg gat cta cga gtc att cag ctg gtg cgc gac ccc cgg gcc gtg     1395
Arg Leu Asp Leu Arg Val Ile Gln Leu Val Arg Asp Pro Arg Ala Val
285                 290                 295                 300

ctg gct tca cgc ata gtg gcc ttt gcg ggc aag tat gag aac tgg aag     1443
Leu Ala Ser Arg Ile Val Ala Phe Ala Gly Lys Tyr Glu Asn Trp Lys
                305                 310                 315

aag tgg ctg tcc gag ggg cag gac cag ctg agc gag gat gag gtg cag     1491
Lys Trp Leu Ser Glu Gly Gln Asp Gln Leu Ser Glu Asp Glu Val Gln
            320                 325                 330

cga ttg cgg ggc aac tgt gag agc atc cgc ctg tct gca gag ctg ggc     1539
Arg Leu Arg Gly Asn Cys Glu Ser Ile Arg Leu Ser Ala Glu Leu Gly
        335                 340                 345

ttg cgg cag cca gcc tgg ctg cgc ggt cgt tac atg ctg gtg cgc tat     1587
Leu Arg Gln Pro Ala Trp Leu Arg Gly Arg Tyr Met Leu Val Arg Tyr
    350                 355                 360

gag gat gtg gca cgc agg cca ctg cag aag gcc cga gag atg tac agc     1635
Glu Asp Val Ala Arg Arg Pro Leu Gln Lys Ala Arg Glu Met Tyr Ser
365                 370                 375                 380

ttt gcg ggc atc ccc ttg acc ccg cag gtg gag gac tgg atc cag aag     1683
Phe Ala Gly Ile Pro Leu Thr Pro Gln Val Glu Asp Trp Ile Gln Lys
                385                 390                 395

aac acg cag gcg aca cgc gac agc agc gat gtc tac tcc act cag aaa     1731
Asn Thr Gln Ala Thr Arg Asp Ser Ser Asp Val Tyr Ser Thr Gln Lys
            400                 405                 410
```

```
aac tct tct gag cag ttt gag aag tgg cgc ttc agc atg cct ttc aag     1779
Asn Ser Ser Glu Gln Phe Glu Lys Trp Arg Phe Ser Met Pro Phe Lys
        415                 420                 425

ctg gca cag gtg gta cag gct gcc tgt ggc ccg acc atg cac ctc ttt     1827
Leu Ala Gln Val Val Gln Ala Ala Cys Gly Pro Thr Met His Leu Phe
    430                 435                 440

ggc tac aag ttg gcc agg gat gcc gcc tca ctc acc aac cgc tcc atc     1875
Gly Tyr Lys Leu Ala Arg Asp Ala Ala Ser Leu Thr Asn Arg Ser Ile
445                 450                 455                 460

agc ctg ctg gag gag cgg ggc acc ttc tgg gtc acg tag tgggggatgt      1924
Ser Leu Leu Glu Glu Arg Gly Thr Phe Trp Val Thr
                465                 470

ctgggaccct tggaactcct tcttgtgaaa ggctggccct gcttccctca cacccagcct   1984

ggcagtgaga catagccctg gcagaaagtc aaaatgggga gcgatgatgg gaacatagcc   2044

cctggctgta gcggtagggc cccctgccag ctagactccc cagagcagct acagctaggg   2104

ccttgggctc ctctgaggac accctgtctc cttagtggta ctggtcataa ggtgtcctca   2164

ccctatgacc tgcagtgtcc cgagcaggtc aaggtaggtt cctgtgtgtg gacacacctc   2224

cctagctctt tctcacacag tctacacgaa gcctgtaaag gcctgtaggt tgtgtgggct   2284

ggagtccaag tatttaacaa ccagaagggg tgtagaccct ctgcagcctc tcagacctcc   2344

tactgtatta agtgttaacc tcttccgctc tgagtcagag aagctgggat ctggctgagt   2404

cctgggaagg aggaggacag cctagggtga ggaaggggac ctttgaagct cctcagggaa   2464

cagtggctgt gtaccagctc atagaaaatg gtttgatcag ctgttctagt cactcatgag   2524

tatcaatcag cctgtgtaga gcaagacaca caaagtgcat tgaaaacaga caaggccagg   2584

ggtgtggctc agcggtaaag cccttgcctc tctcatgccc agggccctag gtgtgattct   2644

tagcactata aatataaggg aaaataagcc atacatacgt gtgcagtaca gagagagaca   2704

gaaaagcgta ataaacattc cccctctca taagcacacg ctctgcctct gtctctgtct   2764

ctgtctctct ctgtctctgt ctctctctgt ctctctctct cactctctct ctctctctct   2824

ctctctcaca cacacacaca cacacacaca cacaaacaca cacacacaca ctggtacaga   2884

aaagcttccc ttctccactc tttatgctca ccatgttttt aggatttttg tttgtttgtt   2944

ttgttttggg tttctatata tctaaacaag gagccttaaa ttacatcttt ttgggattac   3004

gtggcgaggg ggagcagcag ggagcatttg cttctggtaa aaggatagac cagaaaggac   3064

ttccccttgg atgatcggag tcatgcagag cccccagggt cccacatgtt ctgtgtgaac   3124

ttcatgtgga atgactcaca gaagtgacta ccttaggcgc tcgctctgta gctcaatgtg   3184

cgtagagttt gtctattgta taggaagccc tgggttctgt gccctgcccc acaccatata   3244

ggtatgatgg cgtgtaccca tatcccagca ttcaggaaat caaaggttgg cggtcaaaag   3304

ttcaaggtgc agctatgtat cttttgagat gtccgagtct ataagctccc tctactgaga   3364

gctgctagta ttccttctca agaacaggtt atttgaaaat ctcttcttgt aagccccaac   3424

atttggggga ggggaggatg ggggaactct tgactgagca gctaggtttc cccaagcaga   3484

agttcttctc tcccagtgca agctgaggtt tagtgccccg gctagcctcg gaactggctc   3544

agtgggggtt ggcacgctga cttcctggac aattgctgca tctgacactg tgagcgccca   3604

ggacaccgga tgtgtagcat ggatgtgggc ctagcacagg tgtggaagag gacagtcagg   3664

acactcactg ttggtgtttg ttatccacct gttcagccgc cgggtcccac acataggtca   3724

tctttcgtca ctcaagccgg cctctgtttt tgattttaac aatccaagag caagtgtgta   3784
```

-continued

```
ggggacaaag agacaccagc tcttcatact tgatggagac cgggacagga tgctgcaggc   3844
aggctcggga gtgcattatc gtttcttctg agctcttcat ccaggccata ttccctttc    3904
tgcatcgcat ctggggtggg aggggctgag ctgggagttt ccgtccttct tccctgtggg   3964
ggtgggagat ggggctcaag gtctccatct ctcggctccc tgaggacaga acccccacag   4024
tggacctttg ggccttctca ggacattgac aatgttgtgt gcactgcaag ttgactttat   4084
ttattttgta ggaaaaagag atggtattct ttagcaggat ctgaaactgt accctagtca   4144
agaagtacaa ttaataacat tattattaat aacaattggg atgattcaaa ggtcacacac   4204
acaccagacc acccaagaac catgtaggag atgaggcgga gccaggtcat ggaagcccag   4264
aatgctacag agattctgtg ggtctattat tgatcagaaa atacaacatg ggggggcctt   4324
ttctatggca taactcaggt gtctgcaaag acagagcagc tcaggtgggt ggataggcag   4384
gcagatggag ccttgaatca catcccctga ggctcagcca gccagtgcga atcctcaagg   4444
ttcggaaagg gacagtgtag cggcaaacta ctgggcatct tctctgatgc ttagaggctc   4504
ttaccaagga gcttgatgga gaaagtggcc atgttggtgg catgggacaa ctgctcaccc   4564
aacttcaaag atcaaagggc acccaggtgg cctatgacag tgacactctt tcctaccatt   4624
aggggtgtct gcccccactg aaagccatga aatttctggc cctaaggggg taggaaggac   4684
ttaggagtag cagatggttt gatcccatcc cccccacaca cacacacaca tccctcagct   4744
gtcttccaca ttagagccac ttcagttgtc catggacttg tccctttgag acatcctgga   4804
ttttgaagga tagaaacatc cccaagatgg tctcgtgtta atcccacaac agaggcagaa   4864
gggtcatact gagagagaga gagagagaga gagagagaga gagaggagtg ggggccagac   4924
cctcaagaag ccaagtgggt ctggtcaacc tgtgcacatg agaaggaggg aacatcacta   4984
aaatcagggc ctgggctggt gtgttgttgg tgagatcccg tggagtggct ggctagatat   5044
ggatgagttt tctgagcatg ctcacacacc cccaacttca cattcttaga aatagcacaa   5104
ccataatgcc ttacctcaaa aggatgaggc aaagcttgca attaattccc agtgtctgaa   5164
gacctccggg atcctttgag ctgtgtgtcc ttgtcagtac atggggacag gctccttagg   5224
tattcctgac atagaggtaa ggtgctgccc ttgctgcctt gcataagctg tgacaagctt   5284
cttactgggc acatagaacg gctctgtcat ctgcttccac taaatttggg cttggacttt   5344
gcctcctgcc aaatctccat ctctgctgga tagtctagtc cctagggtct aaccaccacc   5404
ctccacttcc tggtgggtcc tacaagcgct gtctttgtgc cagtacccgg atggtgtcct   5464
gcctcatggc taaatggtac aggacatctt cccagactga gtggtcatgg catgtgcatg   5524
tatgttcatg agtacatgca tggtgtgtgg gggtggatgg gtgcattctg ttctgcttct   5584
ggtgcagcta cacagccaca acctctttct gtcattgacc ttcttggtct tcttgtagcc   5644
acagataatc ttccaatgcc cgattctgct gttctcatct gagagctgac aacccagcgc   5704
tcagagtaga gttcatgacc taggaaaccc ttctcctggt agcttactga acttatttaa   5764
ttaaaaacga acatataggg gttggagaga tggttcattg gttaagagca ccggctgctt   5824
ttgcaaagga cctgagttca aatcccagca accatatggt ggcttacaac catctgtaat   5884
gagttctggt gccctcttct ggcatgcagg tgtacatgca gatagagcac tcctatgcat   5944
aaaataaata aatcttttaa ataaataaat aaatgaacat gaaaaaaaaa aaaaaa       6000
```

<210> SEQ ID NO 15
<211> LENGTH: 472
<212> TYPE: PRT
<213> ORGANISM: Mus musculus

<400> SEQUENCE: 15

Met Glu Lys Gly Leu Ala Leu Pro Gln Asp Phe Arg Asp Leu Val His
1               5                   10                  15

Ser Leu Lys Ile Arg Gly Arg Tyr Val Leu Phe Leu Ala Phe Val Val
            20                  25                  30

Ile Val Phe Ile Phe Ile Glu Lys Glu Asn Lys Ile Ile Ser Arg Val
        35                  40                  45

Ser Asp Lys Leu Lys Gln Ile Pro His Phe Val Ala Asp Ala Asn Ser
    50                  55                  60

Thr Asp Pro Ala Leu Leu Leu Ser Glu Asn Ala Ser Leu Leu Ser Leu
65                  70                  75                  80

Ser Glu Leu Asp Ser Thr Phe Ser His Leu Arg Ser Arg Leu His Asn
                85                  90                  95

Leu Ser Leu Gln Leu Gly Val Glu Pro Ala Met Glu Ser Gln Glu Ala
            100                 105                 110

Gly Ala Glu Lys Pro Ser Gln Gln Ala Gly Ala Gly Thr Arg Arg His
        115                 120                 125

Val Leu Leu Met Ala Thr Thr Arg Thr Gly Ser Ser Phe Val Gly Glu
    130                 135                 140

Phe Phe Asn Gln Gln Gly Asn Ile Phe Tyr Leu Phe Glu Pro Leu Trp
145                 150                 155                 160

His Ile Glu Arg Thr Val Phe Phe Gln Gln Arg Gly Ala Ser Ala Ala
                165                 170                 175

Gly Ser Ala Leu Val Tyr Arg Asp Val Leu Lys Gln Leu Leu Leu Cys
            180                 185                 190

Asp Leu Tyr Val Leu Glu Pro Phe Ile Ser Pro Pro Pro Glu Asp His
        195                 200                 205

Leu Thr Gln Phe Leu Phe Arg Arg Gly Ser Ser Arg Ser Leu Cys Glu
    210                 215                 220

Asp Pro Val Cys Thr Pro Phe Val Lys Lys Val Phe Glu Lys Tyr His
225                 230                 235                 240

Cys Arg Asn Arg Arg Cys Gly Pro Leu Asn Val Thr Leu Ala Gly Glu
                245                 250                 255

Ala Cys Arg Arg Lys Asp His Val Ala Leu Lys Ala Val Arg Ile Arg
            260                 265                 270

Gln Leu Glu Phe Leu Gln Pro Leu Val Glu Asp Pro Arg Leu Asp Leu
        275                 280                 285

Arg Val Ile Gln Leu Val Arg Asp Pro Arg Ala Val Leu Ala Ser Arg
    290                 295                 300

Ile Val Ala Phe Ala Gly Lys Tyr Glu Asn Trp Lys Lys Trp Leu Ser
305                 310                 315                 320

Glu Gly Gln Asp Gln Leu Ser Glu Asp Glu Val Gln Arg Leu Arg Gly
                325                 330                 335

Asn Cys Glu Ser Ile Arg Leu Ser Ala Glu Leu Gly Leu Arg Gln Pro
            340                 345                 350

Ala Trp Leu Arg Gly Arg Tyr Met Leu Val Arg Tyr Glu Asp Val Ala
        355                 360                 365

Arg Arg Pro Leu Gln Lys Ala Arg Glu Met Tyr Ser Phe Ala Gly Ile
    370                 375                 380

Pro Leu Thr Pro Gln Val Glu Asp Trp Ile Gln Lys Asn Thr Gln Ala
385                 390                 395                 400

Thr Arg Asp Ser Ser Asp Val Tyr Ser Thr Gln Lys Asn Ser Ser Glu

```
                405                 410                 415

Gln Phe Glu Lys Trp Arg Phe Ser Met Pro Phe Lys Leu Ala Gln Val
            420                 425                 430

Val Gln Ala Ala Cys Gly Pro Thr Met His Leu Phe Gly Tyr Lys Leu
        435                 440                 445

Ala Arg Asp Ala Ala Ser Leu Thr Asn Arg Ser Ile Ser Leu Leu Glu
    450                 455                 460

Glu Arg Gly Thr Phe Trp Val Thr
465                 470


<210> SEQ ID NO 16
<211> LENGTH: 2080
<212> TYPE: DNA
<213> ORGANISM: Mus musculus
<220> FEATURE:
<221> NAME/KEY: CDS
<222> LOCATION: (147)..(1601)

<400> SEQUENCE: 16

caccgcccgg ctgctccact ccgctccacc caacattgag ggagacccga agaggccgga      60

gccgaggact ttgggctggg ttttctggac agaaccagca ggcgcctact ctgctctggg     120

tggggagagt gaggattcgg tgaact atg aag ggc cgg cgg cgg cgg cgc cga     173
                             Met Lys Gly Arg Arg Arg Arg Arg Arg
                             1               5

aag tat tgc aag ttc acg ctg ctc ttg gcg ctg tac acg ctt ttg cta      221
Lys Tyr Cys Lys Phe Thr Leu Leu Leu Ala Leu Tyr Thr Leu Leu Leu
10                  15                  20                  25

ctt ctt gtc ccc tct gta ctg gac agc cac agc gag cag gac aag ggc      269
Leu Leu Val Pro Ser Val Leu Asp Ser His Ser Glu Gln Asp Lys Gly
                30                  35                  40

agg aac tgc ccc ggc ctg cag cgc agc ttg ggt gtg tgg agc ctg gag      317
Arg Asn Cys Pro Gly Leu Gln Arg Ser Leu Gly Val Trp Ser Leu Glu
            45                  50                  55

gcg gcg gcg gcc ggg gaa cgt gag cag ggc gct gag gtg cgg tcc ctg      365
Ala Ala Ala Ala Gly Glu Arg Glu Gln Gly Ala Glu Val Arg Ser Leu
        60                  65                  70

gcc gaa gga aac ccg gat cga tcc ccc ggg tcc ccc ggc aac ctc agc      413
Ala Glu Gly Asn Pro Asp Arg Ser Pro Gly Ser Pro Gly Asn Leu Ser
    75                  80                  85

gcc gtc ggt gag gcg gtg acc cag gaa aag caa cac atc tat gtg cat      461
Ala Val Gly Glu Ala Val Thr Gln Glu Lys Gln His Ile Tyr Val His
90                  95                  100                 105

gcc acc tgg cgc acc ggc tcg tcc ttc ttg ggc gaa ctc ttc aac cag      509
Ala Thr Trp Arg Thr Gly Ser Ser Phe Leu Gly Glu Leu Phe Asn Gln
                110                 115                 120

cac ccg gac gtt ttc tac ttg tac gac ccc atg tgg cat ctg tgg cag      557
His Pro Asp Val Phe Tyr Leu Tyr Asp Pro Met Trp His Leu Trp Gln
            125                 130                 135

gca ctg tat ccg ggc gac gcg gag agc ctg cag ggc gca cta aga gac      605
Ala Leu Tyr Pro Gly Asp Ala Glu Ser Leu Gln Gly Ala Leu Arg Asp
        140                 145                 150

atg ctg cgc tcc ctc ttc cgc tgt gat ttc tct gtg ctg cgc ctg tac      653
Met Leu Arg Ser Leu Phe Arg Cys Asp Phe Ser Val Leu Arg Leu Tyr
    155                 160                 165

gcg cag cct ggg gac cct ggg gag cga gca ccg gac tcg gcc aac ctc      701
Ala Gln Pro Gly Asp Pro Gly Glu Arg Ala Pro Asp Ser Ala Asn Leu
170                 175                 180                 185

acc acg gcc atg ctt ttc cgc tgg cgg acc aac aag gtc atc tgc tcg      749
Thr Thr Ala Met Leu Phe Arg Trp Arg Thr Asn Lys Val Ile Cys Ser
```

-continued

```
                190                 195                 200

ccg cct ctg tgc ccc gcc gcg ccc cgg gca cgc gcg gac gtg gga ctc      797
Pro Pro Leu Cys Pro Ala Ala Pro Arg Ala Arg Ala Asp Val Gly Leu
            205                 210                 215

gtc gag gac aaa gcc tgc gaa agt acc tgc ccg ccc gtt tcg ctc cgc      845
Val Glu Asp Lys Ala Cys Glu Ser Thr Cys Pro Pro Val Ser Leu Arg
        220                 225                 230

gcc ctg gag gcc gag tgc cgc aag tac ccg gtg gtg gtc atc aaa gac      893
Ala Leu Glu Ala Glu Cys Arg Lys Tyr Pro Val Val Val Ile Lys Asp
    235                 240                 245

gtg cgg cta ctg gac ctg gga gtg ctg gtc cct ctg ctg cgt gac cca      941
Val Arg Leu Leu Asp Leu Gly Val Leu Val Pro Leu Leu Arg Asp Pro
250                 255                 260                 265

ggc ctc aac cta aag gtg gtg caa ctc ttc cga gac cct cgg gcc gtg      989
Gly Leu Asn Leu Lys Val Val Gln Leu Phe Arg Asp Pro Arg Ala Val
                270                 275                 280

cac aac tcg cgc ctc aag tcg agg cag gga ctg ctg cgc gaa agc atc     1037
His Asn Ser Arg Leu Lys Ser Arg Gln Gly Leu Leu Arg Glu Ser Ile
            285                 290                 295

cag gtg ctg cgc acg cgc cag agg ggc gac cac ttc cac cgg gtg ctg     1085
Gln Val Leu Arg Thr Arg Gln Arg Gly Asp His Phe His Arg Val Leu
        300                 305                 310

ctg gcg cat gga gtg gat gcc cgt ccg gga ggc cag gcc cgg gct ctg     1133
Leu Ala His Gly Val Asp Ala Arg Pro Gly Gly Gln Ala Arg Ala Leu
    315                 320                 325

ccc tcg gcg cca cgc gct gat ttc ttc tta acc agc gcg ctt gag gtg     1181
Pro Ser Ala Pro Arg Ala Asp Phe Phe Leu Thr Ser Ala Leu Glu Val
330                 335                 340                 345

atc tgt gaa gcg tgg ctt cgc gac ctg cta ttc acc cgc ggc gcg ccc     1229
Ile Cys Glu Ala Trp Leu Arg Asp Leu Leu Phe Thr Arg Gly Ala Pro
                350                 355                 360

gcc tgg ctg agg cgt cgc tac ctg cgg ctg cgt tat gag gac ctg gtg     1277
Ala Trp Leu Arg Arg Arg Tyr Leu Arg Leu Arg Tyr Glu Asp Leu Val
            365                 370                 375

tgg cag ccc caa gcc cag ctg cgc cgc ctg ctg cgc ttc tct ggg ttg     1325
Trp Gln Pro Gln Ala Gln Leu Arg Arg Leu Leu Arg Phe Ser Gly Leu
        380                 385                 390

cgg aca ctc gcc gcg ctt gat gcc ttc gca ttc aat atg acg cgg ggc     1373
Arg Thr Leu Ala Ala Leu Asp Ala Phe Ala Phe Asn Met Thr Arg Gly
    395                 400                 405

tcg gcc tac ggc gcc gat cgt ccc ttc cac ttg tct gcg cgg gac gcc     1421
Ser Ala Tyr Gly Ala Asp Arg Pro Phe His Leu Ser Ala Arg Asp Ala
410                 415                 420                 425

cga gag gct gtg cac gcc tgg cgc gaa cgt ctg agc caa gag cag gtg     1469
Arg Glu Ala Val His Ala Trp Arg Glu Arg Leu Ser Gln Glu Gln Val
                430                 435                 440

cgc caa gtg gaa acc gcc tgc gcc cct gcc atg cgt ctg ctt gcc tac     1517
Arg Gln Val Glu Thr Ala Cys Ala Pro Ala Met Arg Leu Leu Ala Tyr
            445                 450                 455

cct cga agt ggg gac gaa cgc gac agg aag acc gtc agg gaa ggg gag     1565
Pro Arg Ser Gly Asp Glu Arg Asp Arg Lys Thr Val Arg Glu Gly Glu
        460                 465                 470

aca cca ctg gag acc aag gcc aat tgg gct gtg taa taccctgatc          1611
Thr Pro Leu Glu Thr Lys Ala Asn Trp Ala Val
    475                 480

cctgaaccct gccccggggc gtattcaggt cagtggccat aaaaaggtga actcagcatg   1671

ctgcccccgc actggagagg ctgcacggtg gaggcgatct atcacactgt gagacactgg   1731

gactgatttg gtatcaactg ctgtgccatt ctcctggtca ggagcatcac aagctgttaa   1791
```

```
gtaatgacag acaccttggc tgagatgaag tttccagaaa ggaagtaaca gtgcaatgtg   1851

gatatttgtg accacaacat aggaaaagct gtacttccca ggctgaactt ggctcagctt   1911

gagccatttc aacaaggcat cctcacaata atgaagagat gtgatctggt ttcctttcac   1971

atcagccaag atgtctggac aaaaccatca atgtgaataa gggccaagtg cagttgtgtc   2031

tctcttgatt aaattacttc atattaaata aaaaaaaaaa aaaaaaaaa               2080


<210> SEQ ID NO 17
<211> LENGTH: 484
<212> TYPE: PRT
<213> ORGANISM: Mus musculus

<400> SEQUENCE: 17

Met Lys Gly Arg Arg Arg Arg Arg Arg Lys Tyr Cys Lys Phe Thr Leu
1               5                   10                  15

Leu Leu Ala Leu Tyr Thr Leu Leu Leu Leu Leu Val Pro Ser Val Leu
            20                  25                  30

Asp Ser His Ser Glu Gln Asp Lys Gly Arg Asn Cys Pro Gly Leu Gln
        35                  40                  45

Arg Ser Leu Gly Val Trp Ser Leu Glu Ala Ala Ala Ala Gly Glu Arg
    50                  55                  60

Glu Gln Gly Ala Glu Val Arg Ser Leu Ala Glu Gly Asn Pro Asp Arg
65                  70                  75                  80

Ser Pro Gly Ser Pro Gly Asn Leu Ser Ala Val Gly Glu Ala Val Thr
                85                  90                  95

Gln Glu Lys Gln His Ile Tyr Val His Ala Thr Trp Arg Thr Gly Ser
            100                 105                 110

Ser Phe Leu Gly Glu Leu Phe Asn Gln His Pro Asp Val Phe Tyr Leu
        115                 120                 125

Tyr Asp Pro Met Trp His Leu Trp Gln Ala Leu Tyr Pro Gly Asp Ala
    130                 135                 140

Glu Ser Leu Gln Gly Ala Leu Arg Asp Met Leu Arg Ser Leu Phe Arg
145                 150                 155                 160

Cys Asp Phe Ser Val Leu Arg Leu Tyr Ala Gln Pro Gly Asp Pro Gly
                165                 170                 175

Glu Arg Ala Pro Asp Ser Ala Asn Leu Thr Thr Ala Met Leu Phe Arg
            180                 185                 190

Trp Arg Thr Asn Lys Val Ile Cys Ser Pro Pro Leu Cys Pro Ala Ala
        195                 200                 205

Pro Arg Ala Arg Ala Asp Val Gly Leu Val Glu Asp Lys Ala Cys Glu
    210                 215                 220

Ser Thr Cys Pro Pro Val Ser Leu Arg Ala Leu Glu Ala Glu Cys Arg
225                 230                 235                 240

Lys Tyr Pro Val Val Val Ile Lys Asp Val Arg Leu Leu Asp Leu Gly
                245                 250                 255

Val Leu Val Pro Leu Leu Arg Asp Pro Gly Leu Asn Leu Lys Val Val
            260                 265                 270

Gln Leu Phe Arg Asp Pro Arg Ala Val His Asn Ser Arg Leu Lys Ser
        275                 280                 285

Arg Gln Gly Leu Leu Arg Glu Ser Ile Gln Val Leu Arg Thr Arg Gln
    290                 295                 300

Arg Gly Asp His Phe His Arg Val Leu Leu Ala His Gly Val Asp Ala
305                 310                 315                 320
```

```
Arg Pro Gly Gly Gln Ala Arg Ala Leu Pro Ser Ala Pro Arg Ala Asp
                325                 330                 335

Phe Phe Leu Thr Ser Ala Leu Glu Val Ile Cys Glu Ala Trp Leu Arg
            340                 345                 350

Asp Leu Leu Phe Thr Arg Gly Ala Pro Ala Trp Leu Arg Arg Arg Tyr
            355                 360                 365

Leu Arg Leu Arg Tyr Glu Asp Leu Val Trp Gln Pro Gln Ala Gln Leu
        370                 375                 380

Arg Arg Leu Leu Arg Phe Ser Gly Leu Arg Thr Leu Ala Ala Leu Asp
385                 390                 395                 400

Ala Phe Ala Phe Asn Met Thr Arg Gly Ser Ala Tyr Gly Ala Asp Arg
                405                 410                 415

Pro Phe His Leu Ser Ala Arg Asp Ala Arg Glu Ala Val His Ala Trp
            420                 425                 430

Arg Glu Arg Leu Ser Gln Glu Gln Val Arg Gln Val Glu Thr Ala Cys
            435                 440                 445

Ala Pro Ala Met Arg Leu Leu Ala Tyr Pro Arg Ser Gly Asp Glu Arg
        450                 455                 460

Asp Arg Lys Thr Val Arg Glu Gly Glu Thr Pro Leu Glu Thr Lys Ala
465                 470                 475                 480

Asn Trp Ala Val

<210> SEQ ID NO 18
<211> LENGTH: 4713
<212> TYPE: DNA
<213> ORGANISM: Homo sapiens
<220> FEATURE:
<221> NAME/KEY: CDS
<222> LOCATION: (514)..(2199)

<400> SEQUENCE: 18

ggaaatctgg cattttttaa agtttgcgcc ccacaaagag gaaatattcc aaaggtactc     60

aggatgtaaa aggggagatc ttcacagatg cctccgtgga tggcatggca atccatccat    120

caatgagaag accatgattt cttttaattt tctgtgtgtt tccacattcc ccagtgagaa    180

ttcttccacc tttttttgtg ccatgggaaa aacctgaagg gcaggcagag ctgctcccga    240

acttgtgacc ttctctgagg ttgcagcggc tcttgtagaa catgactctg ggacatcact    300

tccttttgtt ttctttcgga gctgaaccaa agaatgtgca ccctctttct ctagtgctgt    360

ggtgtctgct tattttgta tttgtgcttt ccatccatct tctgtgatca caaggcattc    420

ttaaggtttt ctagcacgac ttgcggacat ccagactcgt ggggggccca cccatggctc    480

ggtaagccag cagcccaggg cactggcact acc atg agg cac tgc att aat tgc    534
                                     Met Arg His Cys Ile Asn Cys
                                       1               5

tgc ata cag ctg tta ccc gac ggc gca cac aag cag cag gtc aac tgc    582
Cys Ile Gln Leu Leu Pro Asp Gly Ala His Lys Gln Gln Val Asn Cys
          10               15               20

caa ggg ggc ccc cat cac ggt cac cag gcg tgc ccc acg tgc aaa gga    630
Gln Gly Gly Pro His His Gly His Gln Ala Cys Pro Thr Cys Lys Gly
      25               30               35

gaa aac aaa att ctg ttt cgt gtg gac agt aag cag atg aac ttg ctt    678
Glu Asn Lys Ile Leu Phe Arg Val Asp Ser Lys Gln Met Asn Leu Leu
40               45               50               55

gct gtt ctc gaa gtg agg act gaa ggg aac gaa aac tgg ggt ggg ttt    726
Ala Val Leu Glu Val Arg Thr Glu Gly Asn Glu Asn Trp Gly Gly Phe
              60               65               70
```

-continued

```
ttg cgc ttc aaa aag ggg aag cga tgt agc ctc gtt ttt gga ctg ata      774
Leu Arg Phe Lys Lys Gly Lys Arg Cys Ser Leu Val Phe Gly Leu Ile
            75                  80                  85

ata atg acc ttg gta atg gct tct tac atc ctt tct ggg gcc cac caa      822
Ile Met Thr Leu Val Met Ala Ser Tyr Ile Leu Ser Gly Ala His Gln
        90                  95                  100

gag ctt ctg atc tca tca cct ttc cat tac gga ggc ttc ccc agc aac      870
Glu Leu Leu Ile Ser Ser Pro Phe His Tyr Gly Gly Phe Pro Ser Asn
    105                 110                 115

ccc agc ttg atg gac agc gaa aac cca agt gac aca aag gag cat cac      918
Pro Ser Leu Met Asp Ser Glu Asn Pro Ser Asp Thr Lys Glu His His
120                 125                 130                 135

cac caa tcc tct gta aat aat att tca tac atg aag gac tat cca agc      966
His Gln Ser Ser Val Asn Asn Ile Ser Tyr Met Lys Asp Tyr Pro Ser
                140                 145                 150

att aaa tta att atc aac agc atc aca act agg att gag ttc acg acc     1014
Ile Lys Leu Ile Ile Asn Ser Ile Thr Thr Arg Ile Glu Phe Thr Thr
            155                 160                 165

aga cag ctc cca gac tta gaa gac ctt aag aag cag gag ttg cat atg     1062
Arg Gln Leu Pro Asp Leu Glu Asp Leu Lys Lys Gln Glu Leu His Met
        170                 175                 180

ttt tca gtc atc ccc aac aaa ttc ctt cca aac agt aag agc ccc tgt     1110
Phe Ser Val Ile Pro Asn Lys Phe Leu Pro Asn Ser Lys Ser Pro Cys
    185                 190                 195

tgg tac gag gag ttc tcg ggg cag aac acc acc gac ccc tac ctc acc     1158
Trp Tyr Glu Glu Phe Ser Gly Gln Asn Thr Thr Asp Pro Tyr Leu Thr
200                 205                 210                 215

aac tcc tac gtg ctc tac tcc aag cgc ttc cgc tcc acc ttc gac gcc     1206
Asn Ser Tyr Val Leu Tyr Ser Lys Arg Phe Arg Ser Thr Phe Asp Ala
                220                 225                 230

ctg cgc aag gcc ttc tgg ggc cac ctg gcg cac gcg cac ggg aag cac     1254
Leu Arg Lys Ala Phe Trp Gly His Leu Ala His Ala His Gly Lys His
            235                 240                 245

ttc cgc ctg cgc tgc ctg ccg cac ttc tac atc ata ggg cag ccc aag     1302
Phe Arg Leu Arg Cys Leu Pro His Phe Tyr Ile Ile Gly Gln Pro Lys
        250                 255                 260

tgc ggg acc aca gac ctc tat gac cgc ctg cgg ctg cac cct gag gtc     1350
Cys Gly Thr Thr Asp Leu Tyr Asp Arg Leu Arg Leu His Pro Glu Val
    265                 270                 275

aag ttc tcc gcc atc aag gag cca cac tgg tgg acc cgg aag cgc ttt     1398
Lys Phe Ser Ala Ile Lys Glu Pro His Trp Trp Thr Arg Lys Arg Phe
280                 285                 290                 295

gga atc gtc cgc cta aga gat ggg ctg cga gac cgc tat ccc gtg gaa     1446
Gly Ile Val Arg Leu Arg Asp Gly Leu Arg Asp Arg Tyr Pro Val Glu
                300                 305                 310

gat tat ctg gac ctc ttt gac ctg gcc gca cac cag atc cat caa gga     1494
Asp Tyr Leu Asp Leu Phe Asp Leu Ala Ala His Gln Ile His Gln Gly
            315                 320                 325

ctg cag gcc agc tct gca aag gag cag agc aag atg aat aca atc att     1542
Leu Gln Ala Ser Ser Ala Lys Glu Gln Ser Lys Met Asn Thr Ile Ile
        330                 335                 340

atc ggg gag gcc agt gcc tcc acg atg tgg gat aat aat gcc tgg acg     1590
Ile Gly Glu Ala Ser Ala Ser Thr Met Trp Asp Asn Asn Ala Trp Thr
    345                 350                 355

ttc ttc tac gac aac agc acg gat ggc gag cca ccg ttt ctg acg cag     1638
Phe Phe Tyr Asp Asn Ser Thr Asp Gly Glu Pro Pro Phe Leu Thr Gln
360                 365                 370                 375

gac ttc atc cac gcc ttt cag cca aat gcc aga ctg att gtc atg ctc     1686
Asp Phe Ile His Ala Phe Gln Pro Asn Ala Arg Leu Ile Val Met Leu
                380                 385                 390
```

-continued

```
agg gac cct gtg gag agg ttg tac tca gac tat ctc tac ttt gca agt     1734
Arg Asp Pro Val Glu Arg Leu Tyr Ser Asp Tyr Leu Tyr Phe Ala Ser
            395                 400                 405

tcg aat aaa tcc gcg gac gac ttc cat gag aaa gtg aca gaa gca ctg     1782
Ser Asn Lys Ser Ala Asp Asp Phe His Glu Lys Val Thr Glu Ala Leu
        410                 415                 420

cag ctg ttt gaa aat tgc atg ctt gat tat tca ctg cgc gcc tgc gtc     1830
Gln Leu Phe Glu Asn Cys Met Leu Asp Tyr Ser Leu Arg Ala Cys Val
    425                 430                 435

tac aac aac acc ctc aac aac gcc atg cct gtg agg ctc cag gtt ggg     1878
Tyr Asn Asn Thr Leu Asn Asn Ala Met Pro Val Arg Leu Gln Val Gly
440                 445                 450                 455

ctc tat gct gtg tac ctt ctg gac tgg ctc agc gtt ttt gac aag caa     1926
Leu Tyr Ala Val Tyr Leu Leu Asp Trp Leu Ser Val Phe Asp Lys Gln
                460                 465                 470

cag ttt ctc att ctt cgc ctg gaa gat cat gca tcc aac gtc aag tac     1974
Gln Phe Leu Ile Leu Arg Leu Glu Asp His Ala Ser Asn Val Lys Tyr
            475                 480                 485

acc atg cac aag gtc ttc cag ttt ctg aac cta ggg ccc tta agt gag     2022
Thr Met His Lys Val Phe Gln Phe Leu Asn Leu Gly Pro Leu Ser Glu
        490                 495                 500

aag cag gag gct ttg atg acc aag agc ccc gca tcc aat gca cgg cgt     2070
Lys Gln Glu Ala Leu Met Thr Lys Ser Pro Ala Ser Asn Ala Arg Arg
    505                 510                 515

ccc gag gac cgg aac ctg ggg ccc atg tgg ccc atc aca cag aag att     2118
Pro Glu Asp Arg Asn Leu Gly Pro Met Trp Pro Ile Thr Gln Lys Ile
520                 525                 530                 535

ctg cgg gat ttc tac agg ccc ttc aac gct agg ctg gcg cag gtc ctc     2166
Leu Arg Asp Phe Tyr Arg Pro Phe Asn Ala Arg Leu Ala Gln Val Leu
                540                 545                 550

gcg gat gag gcg ttt gcg tgg aag acg acg tga gagctgaatt gttgctgcac   2219
Ala Asp Glu Ala Phe Ala Trp Lys Thr Thr
            555                 560

gtgctgggcc cgccaatgcc gtcatcatca ggattttaca aatctctttg cggggaactg   2279

tttcactcat ggtatggaaa accccaggac tctgccactc taggcacaca tgaattataa   2339

ccattttgga atttccttcg tgatgttcga gagctcagca atggacccct cacagagctc   2399

ctctatccga ggccattgga gaccccagtt tctcaagaat tcagctctgc tctgagcgtc   2459

ctggagcttg gggatgcagc cagctggcct gcactgggtg tggagagaac acctagggaa   2519

ggcagcctgg ccctgcccgc ctccgccttc tggagagcct ctgggttctg agtcagcaag   2579

ccagaggtca tgccacaggc ctggctggaa cttacacttc acgttccctt tttttccccc   2639

tagagatggg gtctcgccgt gttgcacaga ctgtctgtat tcaatggcta tcttcacagg   2699

tgtgatcata ccacattcac ttctgaaaca ctcttgttgc gatcgctaac ctcactggga   2759

cagagaaccg cagtctttcg agaatggagg ctcttcattt tttttttctc ctttactcca   2819

aactcagccc tccagtttct tcagatgtaa accctgttaa cgtcactgtt tccaaaagga   2879

aaaaaataag tcagtttttg gcagcacctt catctttctg acctcctcct attctgtcct   2939

tgtggactta tgtttaacat agaaaatgaa tgcgtttaaa acaaaaccac tttctgcatt   2999

taaccagtcc tggctctctc tctgctgcct cttcatacgt tttctcaaga acttcagttt   3059

ataattggaa gagaaatttt tgctgttaat gccagaatga gcaacctcaa ggaattgaac   3119

acttcttgga aaatctaggt aattcaagcc ctcatcaggt ttacaagatc atcagagaaa   3179

cagaggattt taatttttag ttctggccgg ctacaggctc catttctctg ccttcccatt   3239
```

```
ggaaatagtt tatttccaca ttctccactg cgtgtggtca aagttcctca cccagcaagg   3299

gactatagat actcgtgtcc caattccaaa acacaatgca caagctgaac ttgggctgaa   3359

cgtggcgtgt tgagatttgg aatgaggttt ctaagagccg tgttcttcat ggaattttcc   3419

aggccacttg gcagcttggt ttaccgatgg atgggctaga gatcttgtcg tttcttggaa   3479

gtcacaggga agattgaaga gaacgcttga gcatccttgg caacagccca ggtgggacct   3539

ggatgaagct ttgcactcaa gtattgtcaa gggaagcttc ctgtgaacca aagttctcag   3599

gccaaggtct cgcccaccaa agccagaaag tgcaagcacc cgtctaccca gctctaactt   3659

gtatgtgtga gacagaccag gcttcggggg taggaggatc tgcagttgtt cagccgtctt   3719

tctgctggtg ttgtctttct gccatcagag aagggacaca cagcccgttc gaaggtgtgc   3779

agagggctct gagcgccagg atggccaggg ctgtttttgc tactgaagga gcgtgtgtcc   3839

tgaactccca cttgcaggga cagtccccac cttctctata gccggcactg ggagcagccg   3899

ccagcaggga aatctggcct gagcacaagg atgctttagg gagagatcac ttcagtgtgt   3959

gtgtatattt atttgcagta cagtgcgcgc gtgtgtgtgt gtgtacgcgc acgtgtgggt   4019

gagtgcgtct tctgagtggg ttctgttcag ttgctaatga ggctcctccg ctctggacac   4079

aaccctttta tagattaatt tctctgccaa ttaacttgtc attttcagta catattttac   4139

tattccacac caaccataat tacaacaagg gatttttctt atgcactcct atgcatgtga   4199

ataacatgtg gtgtaattct gcttcttaca gaagtattac tgaaggtatt atttccaata   4259

ttatttggtt tattatgcgg atcttttta tatatgcagt cccatccctt ctgtgccact    4319

caatgccatc cagacatggt tttccctcc aggggccttt ctctccagag ggcacttcgg    4379

ctgcctctgc ttcctctcat tcgaggcccg gctcttgctg acagaatagg ttccgttctg   4439

ggcggtggtt ctcgagcctg ccattcaaaa ccaaagcaaa ttggagcatt tctcacaaca   4499

tggtattgaa gttccttttt gttctcaaaa gttgtgaccg tgttaaattg tactccctta   4559

gtcctgtaag gtatgttaag tgaatcgcag ttacgctgta cttttattaa tatttaacat   4619

aattaaagat ggacccataa gagtgacgcc tgtggagcgc gtgctcttcc tctgcagcca   4679

aaaaaaaaaa aaaaaaaaaa aaaaaaaaaa aaaa                               4713
```

<210> SEQ ID NO 19
<211> LENGTH: 561
<212> TYPE: PRT
<213> ORGANISM: Homo sapiens

<400> SEQUENCE: 19

```
Met Arg His Cys Ile Asn Cys Cys Ile Gln Leu Leu Pro Asp Gly Ala
1               5                   10                  15

His Lys Gln Gln Val Asn Cys Gln Gly Gly Pro His His Gly His Gln
            20                  25                  30

Ala Cys Pro Thr Cys Lys Gly Glu Asn Lys Ile Leu Phe Arg Val Asp
        35                  40                  45

Ser Lys Gln Met Asn Leu Leu Ala Val Leu Glu Val Arg Thr Glu Gly
    50                  55                  60

Asn Glu Asn Trp Gly Gly Phe Leu Arg Phe Lys Lys Gly Lys Arg Cys
65                  70                  75                  80

Ser Leu Val Phe Gly Leu Ile Ile Met Thr Leu Val Met Ala Ser Tyr
                85                  90                  95

Ile Leu Ser Gly Ala His Gln Glu Leu Leu Ile Ser Ser Pro Phe His
            100                 105                 110
```

-continued

```
Tyr Gly Gly Phe Pro Ser Asn Pro Ser Leu Met Asp Ser Glu Asn Pro
        115                 120                 125

Ser Asp Thr Lys Glu His His His Gln Ser Ser Val Asn Asn Ile Ser
    130                 135                 140

Tyr Met Lys Asp Tyr Pro Ser Ile Lys Leu Ile Ile Asn Ser Ile Thr
145                 150                 155                 160

Thr Arg Ile Glu Phe Thr Thr Arg Gln Leu Pro Asp Leu Glu Asp Leu
                165                 170                 175

Lys Lys Gln Glu Leu His Met Phe Ser Val Ile Pro Asn Lys Phe Leu
            180                 185                 190

Pro Asn Ser Lys Ser Pro Cys Trp Tyr Glu Glu Phe Ser Gly Gln Asn
        195                 200                 205

Thr Thr Asp Pro Tyr Leu Thr Asn Ser Tyr Val Leu Tyr Ser Lys Arg
    210                 215                 220

Phe Arg Ser Thr Phe Asp Ala Leu Arg Lys Ala Phe Trp Gly His Leu
225                 230                 235                 240

Ala His Ala His Gly Lys His Phe Arg Leu Arg Cys Leu Pro His Phe
                245                 250                 255

Tyr Ile Ile Gly Gln Pro Lys Cys Gly Thr Thr Asp Leu Tyr Asp Arg
            260                 265                 270

Leu Arg Leu His Pro Glu Val Lys Phe Ser Ala Ile Lys Glu Pro His
        275                 280                 285

Trp Trp Thr Arg Lys Arg Phe Gly Ile Val Arg Leu Arg Asp Gly Leu
    290                 295                 300

Arg Asp Arg Tyr Pro Val Glu Asp Tyr Leu Asp Leu Phe Asp Leu Ala
305                 310                 315                 320

Ala His Gln Ile His Gln Gly Leu Gln Ala Ser Ser Ala Lys Glu Gln
                325                 330                 335

Ser Lys Met Asn Thr Ile Ile Ile Gly Glu Ala Ser Ala Ser Thr Met
            340                 345                 350

Trp Asp Asn Asn Ala Trp Thr Phe Phe Tyr Asp Asn Ser Thr Asp Gly
        355                 360                 365

Glu Pro Pro Phe Leu Thr Gln Asp Phe Ile His Ala Phe Gln Pro Asn
    370                 375                 380

Ala Arg Leu Ile Val Met Leu Arg Asp Pro Val Glu Arg Leu Tyr Ser
385                 390                 395                 400

Asp Tyr Leu Tyr Phe Ala Ser Ser Asn Lys Ser Ala Asp Asp Phe His
                405                 410                 415

Glu Lys Val Thr Glu Ala Leu Gln Leu Phe Glu Asn Cys Met Leu Asp
            420                 425                 430

Tyr Ser Leu Arg Ala Cys Val Tyr Asn Asn Thr Leu Asn Asn Ala Met
        435                 440                 445

Pro Val Arg Leu Gln Val Gly Leu Tyr Ala Val Tyr Leu Leu Asp Trp
    450                 455                 460

Leu Ser Val Phe Asp Lys Gln Gln Phe Leu Ile Leu Arg Leu Glu Asp
465                 470                 475                 480

His Ala Ser Asn Val Lys Tyr Thr Met His Lys Val Phe Gln Phe Leu
                485                 490                 495

Asn Leu Gly Pro Leu Ser Glu Lys Gln Glu Ala Leu Met Thr Lys Ser
            500                 505                 510

Pro Ala Ser Asn Ala Arg Arg Pro Glu Asp Arg Asn Leu Gly Pro Met
        515                 520                 525

Trp Pro Ile Thr Gln Lys Ile Leu Arg Asp Phe Tyr Arg Pro Phe Asn
```

530 535 540

Ala Arg Leu Ala Gln Val Leu Ala Asp Glu Ala Phe Ala Trp Lys Thr
545 550 555 560

Thr

<210> SEQ ID NO 20
<211> LENGTH: 536
<212> TYPE: DNA
<213> ORGANISM: Mus musculus

<400> SEQUENCE: 20
acaaagccat gaagccggcg ctgctggaag tgatgaggat gaacagaatt tgccggatgg 60
tgctggccac ttgcttcgga tcctttatct tggtcatctt ctatttccaa agtatgttgc 120
acccagtcat gcggaggaac cccttcggtg tggacatctg ctgccggaag ggatcgagaa 180
gtcccctgca ggagctctac aatcccatcc agctggagct atccaacact gccatcctgc 240
accagatgag acgggaccag gtgacagaca cctgccgggc caacagtgcc atgagccgca 300
agcgcagggt gctgaccccc aacgacctga agcacctggt ggtggatgag gaccacgaac 360
tcatctactg ctatgtgccc aaggtagcgt gcaccaactg gaagaggctc atgatggtcc 420
tgagtggccg ggcaagtac agcgatccca tggagatccc agccaacgaa gcccacgtgt 480
cggccaacct gaagaccctt aaccagtaca gcatcccaga gatcaaccac cgcttg 536

<210> SEQ ID NO 21
<211> LENGTH: 660
<212> TYPE: DNA
<213> ORGANISM: Mus musculus

<400> SEQUENCE: 21
gccaggagtg ggcccagccc agggcagcat gaccaagccg cggctcttcc ggctgtggct 60
ggtactaggg tcggctctca tgatcctttt gatcattgta tattgggaca acgtgggaac 120
cgcccacttc tatctgcaca cgtctctctc caggccacac atcctagaac cccttcccac 180
ccagggattg gtggaggaga acgtgttcac atctgacgtg gatgagtttt tggatactct 240
ccttagttct gacgcgaagc acaacgacct ttccaggaga aaaactgagc agcccccggc 300
gcccgccccc agcaagccag tcttgagcca catggaggag aacgtgagag gctacgactg 360
gtccactcat gatgcccatc agaaccctga ccgggacagg cagcaggccg agaggaggag 420
cctgctgaga gacttctgtg ccaacgccag cctggcattc ccaccaagg accgctcttt 480 tgacgacatc cccaactacg aactgaacca cctgatcgtg gacgaccgcc acggggtcat 540
ctactgctac gtgcccaagg tggcctgcac caactggaag cgagtgatga tcgtgctgag 600
cgagagcctg ctggaccggg gcagccccta ccgagacccc ctggacatcc cccgggaaca 660

<210> SEQ ID NO 22
<211> LENGTH: 600
<212> TYPE: DNA
<213> ORGANISM: Mus musculus

<400> SEQUENCE: 22
atgactgtcg cctgccacgc gtgccaggca cagcatggga agacgctcct gttgcaggcg 60
gcccttgccg gtggtggcaa gtctgggtgc tgcactcctg ctcctgtgcg ccctgcgtcc 120
cgggtaacca caggaaagga tgcccaggac actgaatggc agggctcccc aaaagccctt 180
ttgggggttc cgacatttga aaataaagct ctgggctcca gctggttcgg tggagtgagg 240

-continued

```
aagagtcccc tacagctgtt gcgtgacctg gaccagatgt ttggcagctg tgagctatgg    300

gtagtcagtg gggagcggca gaaagtgggt ccacgctccg cgatggccga ggtgcaccag    360

cagcggcgtg agctgctgcg ccgggcctgc agccgccaca cgcgacgcca acgcctgctg    420

cagccggagg acctgcgtca cgtgctggtg gacgacgcgc accggctgct gtactgctac    480

gtgcctaagg tggcctgcac caactggaag cgtgtgatgc tggcgttgcg cggccgtggg    540

gatccaagcg caatccctgc gcacgaggcg catgcgcctg gcctgctgcc ctcgctggcc    600
```

<210> SEQ ID NO 23
<211> LENGTH: 600
<212> TYPE: DNA
<213> ORGANISM: Mus musculus

<400> SEQUENCE: 23

```
gcgcccccctc tccccatgga gaaaggactc gctttgcctc aggatttccg ggaccttgta     60

cacagcctaa agattcgagg cagatacgtc ttgttcctgg catttgtggt catagttttt    120

atcttcattg aaaaggaaaa taaaatcata tccagggtct ccgacaagct gaagcagatc    180

cctcattttg tggcagatgc caacagcact gacccagccc tgctcttatc ggagaatgca    240

tctctcttgt ccctgagcga gttggattcc accttttccc atctgcggag ccgcctgcac    300

aacctgagcc tgcagctggg cgtggagcca gcaatggaga gccaggaggc tggggcagag    360

aagccatccc agcaggctgg agcagggacc cggcgccacg tgcttctcat ggccaccacc    420

cgcacgggtt cctcgttcgt gggcgagttc ttcaaccagc agggcaatat cttctacctc    480

ttcgagccac tgtggcacat cgagcgcacc gtgttcttcc agcagcgagg cgccagcgcg    540

gctggttcag ccttggtcta ccgtgatgtc ctcaagcagt tgttgctatg cgacctgtat    600
```

<210> SEQ ID NO 24
<211> LENGTH: 720
<212> TYPE: DNA
<213> ORGANISM: Mus musculus

<400> SEQUENCE: 24

```
tggggagagt gaggattcgg tgaactatga agggccggcg gcggcggcgc cgagagtatt     60

gcaagttcac gctgctcttg gcgctgtaca cgcttttgct acttcttgtc ccctctgtac    120

tggacagcca cagcgagcag gacaagggca ggaactgccc cggcctgcag cgcagcttgg    180

gtgtgtggag cctggaggcg gcggcggccg gggaacgtga gcagggcgct gaggtgcggt    240

ccctggccga aggaaacccg gatcgatccc ccgggtcccc cggcaacctc agcgccgtcg    300

gtgaggcggt gacccaggaa aagcaacaca tctatgtgca tgccacctgg cgcaccggct    360

cgtccttctt gggcgaactc ttcaaccagc acccggacgt tttctacttg tacgagccca    420

tgtggcatct gtggcaggca ctgtatccgg gcgacgcgga gagcctgcag ggcgcactaa    480

gagacatgct gcgctccctc ttccgctgtg atttctctgt gctgcgcctg tacgcgcagc    540

ctggggaccc tggggagcga gcaccggact cggccaacct caccacggcc atgcttttcc    600

gctggcggac caacaaggtc atctgctcgc cgcctctgtg ccccgccgcg ccccgggcac    660

gcgcggacgt gggactcgtc gaggacaaag cctgcgaaag tacctgcccg cccgtttcgc    720
```

<210> SEQ ID NO 25
<211> LENGTH: 27
<212> TYPE: RNA
<213> ORGANISM: Artificial
<220> FEATURE:
<223> OTHER INFORMATION: an artificially synthesized sequence

<400> SEQUENCE: 25
ggagcagagc aagaugaaua caaucag 27

<210> SEQ ID NO 26
<211> LENGTH: 27
<212> TYPE: RNA
<213> ORGANISM: Artificial
<220> FEATURE:
<223> OTHER INFORMATION: an artificially synthesized sequence

<400> SEQUENCE: 26
gauuguauuc aucuugcucu gcuccau 27

<210> SEQ ID NO 27
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 27
gtgagttctg ctgcggtcca 20

<210> SEQ ID NO 28
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 28
agtccatgct gatgcccaga g 21

<210> SEQ ID NO 29
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 29
acccgatggc aacaatgga 19

<210> SEQ ID NO 30
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 30
accagcaggg ccttgttcac 20

<210> SEQ ID NO 31
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 31
catccgtaaa gacctctatg ccaac 25

<210> SEQ ID NO 32

<211> LENGTH: 19
<212> TYPE: DNA
<213> ORGANISM: Artificial
<220> FEATURE:
<223> OTHER INFORMATION: an artificially synthesized primer sequence

<400> SEQUENCE: 32
atggagccac cgatccaca 19

<210> SEQ ID NO 33
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 33
ttctggccaa cggtctagac aac 23

<210> SEQ ID NO 34
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 34
ccagtggtct tggtgtgctg a 21

<210> SEQ ID NO 35
<211> LENGTH: 25
<212> TYPE: DNA
<213> ORGANISM: Artificial
<220> FEATURE:
<223> OTHER INFORMATION: an artificially synthesized sequence

<400> SEQUENCE: 35
acccccaact cggaacgatg cggct 25

<210> SEQ ID NO 36
<211> LENGTH: 24
<212> TYPE: DNA
<213> ORGANISM: Artificial
<220> FEATURE:
<223> OTHER INFORMATION: an artificially synthesized sequence

<400> SEQUENCE: 36
tgcatgttct cgtccatcct gctg 24

<210> SEQ ID NO 37
<211> LENGTH: 26
<212> TYPE: DNA
<213> ORGANISM: Artificial
<220> FEATURE:
<223> OTHER INFORMATION: an artificially synthesized sequence

<400> SEQUENCE: 37
cgccaccgtg tactgtactg tgaagt 26

<210> SEQ ID NO 38
<211> LENGTH: 25
<212> TYPE: DNA
<213> ORGANISM: Artificial
<220> FEATURE:
<223> OTHER INFORMATION: an artificially synthesized sequence

<400> SEQUENCE: 38
aggctgctcc aactggaaga gggtg 25

<210> SEQ ID NO 39
<211> LENGTH: 24
<212> TYPE: DNA
<213> ORGANISM: Artificial
<220> FEATURE:
<223> OTHER INFORMATION: an artificially synthesized sequence

<400> SEQUENCE: 39
atatagtatc taggatatat gtag 24

<210> SEQ ID NO 40
<211> LENGTH: 25
<212> TYPE: DNA
<213> ORGANISM: Artificial
<220> FEATURE:
<223> OTHER INFORMATION: an artificially synthesized sequence

<400> SEQUENCE: 40
gaagtaccaa aagctggctg ctcta 25

<210> SEQ ID NO 41
<211> LENGTH: 26
<212> TYPE: DNA
<213> ORGANISM: Artificial
<220> FEATURE:
<223> OTHER INFORMATION: an artificially synthesized sequence

<400> SEQUENCE: 41
ttctatcact tggactattt gatgtt 26

<210> SEQ ID NO 42
<211> LENGTH: 25
<212> TYPE: DNA
<213> ORGANISM: Artificial
<220> FEATURE:
<223> OTHER INFORMATION: an artificially synthesized sequence

<400> SEQUENCE: 42
tacacaactc cacatttgta atttg 25

<210> SEQ ID NO 43
<211> LENGTH: 24
<212> TYPE: DNA
<213> ORGANISM: Artificial
<220> FEATURE:
<223> OTHER INFORMATION: an artificially synthesized sequence

<400> SEQUENCE: 43
ccagaagcca agctcattgt tatg 24

<210> SEQ ID NO 44
<211> LENGTH: 25
<212> TYPE: DNA
<213> ORGANISM: Artificial
<220> FEATURE:
<223> OTHER INFORMATION: an artificially synthesized sequence

<400> SEQUENCE: 44
ctgtggagag gttgtactca gacta 25

<210> SEQ ID NO 45
<211> LENGTH: 26
<212> TYPE: DNA

<213> ORGANISM: Artificial
<220> FEATURE:
<223> OTHER INFORMATION: an artificially synthesized sequence

<400> SEQUENCE: 45
atttgcctgg aagacaacgt gagagc 26

<210> SEQ ID NO 46
<211> LENGTH: 27
<212> TYPE: DNA
<213> ORGANISM: Artificial
<220> FEATURE:
<223> OTHER INFORMATION: an artificially synthesized sequence

<400> SEQUENCE: 46
gtcccttctg cagaagctgg gcccact 27

<210> SEQ ID NO 47
<211> LENGTH: 25
<212> TYPE: DNA
<213> ORGANISM: Artificial
<220> FEATURE:
<223> OTHER INFORMATION: an artificially synthesized sequence

<400> SEQUENCE: 47 gcgcccccctc tccccatgga gaaag 25

<210> SEQ ID NO 48
<211> LENGTH: 25
<212> TYPE: DNA
<213> ORGANISM: Artificial
<220> FEATURE:
<223> OTHER INFORMATION: an artificially synthesized sequence

<400> SEQUENCE: 48
gctttgcctc aggatttccg ggacc 25

<210> SEQ ID NO 49
<211> LENGTH: 27
<212> TYPE: DNA
<213> ORGANISM: Artificial
<220> FEATURE:
<223> OTHER INFORMATION: an artificially synthesized sequence

<400> SEQUENCE: 49
ggttcagcct tggtctaccg tgatgtc 27

<210> SEQ ID NO 50
<211> LENGTH: 25
<212> TYPE: DNA
<213> ORGANISM: Artificial
<220> FEATURE:
<223> OTHER INFORMATION: an artificially synthesized sequence

<400> SEQUENCE: 50
gcagttgttg ctatgcgacc tgtat 25

<210> SEQ ID NO 51
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 51
tgttcctggc atttgtggtc ata 23

<210> SEQ ID NO 52
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 52
ccaactcgct cagggacaag a 21

<210> SEQ ID NO 53
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 53
gtgtggagca acatgtggaa ctcta 25

<210> SEQ ID NO 54
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 54
ttggttcagc cactgccgta 20

<210> SEQ ID NO 55
<211> LENGTH: 50
<212> TYPE: DNA
<213> ORGANISM: Artificial
<220> FEATURE:
<223> OTHER INFORMATION: an artificially synthesized sequence

<400> SEQUENCE: 55
acaaagccat gaagccggcg ctgctggaag tgatgaggat gaacagaatt 50

<210> SEQ ID NO 56
<211> LENGTH: 26
<212> TYPE: DNA
<213> ORGANISM: Artificial
<220> FEATURE:
<223> OTHER INFORMATION: an artificially synthesized sequence

<400> SEQUENCE: 56
caacctgaag acccttaacc agtaca 26

<210> SEQ ID NO 57
<211> LENGTH: 26
<212> TYPE: DNA
<213> ORGANISM: Artificial
<220> FEATURE:
<223> OTHER INFORMATION: an artificially synthesized sequence

<400> SEQUENCE: 57
gcatcccaga gatcaaccac cgcttg 26

<210> SEQ ID NO 58
<211> LENGTH: 25
<212> TYPE: DNA
<213> ORGANISM: Artificial
<220> FEATURE:

<223> OTHER INFORMATION: an artificially synthesized sequence

<400> SEQUENCE: 58
gccaggagtg ggcccagccc agggc 25

<210> SEQ ID NO 59
<211> LENGTH: 27
<212> TYPE: DNA
<213> ORGANISM: Artificial
<220> FEATURE:
<223> OTHER INFORMATION: an artificially synthesized sequence

<400> SEQUENCE: 59
atgaccaagc cgcggctctt ccggctg 27

<210> SEQ ID NO 60
<211> LENGTH: 28
<212> TYPE: DNA
<213> ORGANISM: Artificial
<220> FEATURE:
<223> OTHER INFORMATION: an artificially synthesized sequence

<400> SEQUENCE: 60
agagcctgct ggaccggggc agccccta 28

<210> SEQ ID NO 61
<211> LENGTH: 28
<212> TYPE: DNA
<213> ORGANISM: Artificial
<220> FEATURE:
<223> OTHER INFORMATION: an artificially synthesized sequence

<400> SEQUENCE: 61
gagaccccct ggacatcccc cgggaaca 28

<210> SEQ ID NO 62
<211> LENGTH: 26
<212> TYPE: DNA
<213> ORGANISM: Artificial
<220> FEATURE:
<223> OTHER INFORMATION: an artificially synthesized sequence

<400> SEQUENCE: 62
atgactgtcg cctgccacgc gtgcca 26

<210> SEQ ID NO 63
<211> LENGTH: 26
<212> TYPE: DNA
<213> ORGANISM: Artificial
<220> FEATURE:
<223> OTHER INFORMATION: an artificially synthesized sequence

<400> SEQUENCE: 63
cagcatggga agacgctcct gttgca 26

<210> SEQ ID NO 64
<211> LENGTH: 28
<212> TYPE: DNA
<213> ORGANISM: Artificial
<220> FEATURE:
<223> OTHER INFORMATION: an artificially synthesized sequence

<400> SEQUENCE: 64
tccaagcgca atccctgcgc acgaggcg 28

<210> SEQ ID NO 65
<211> LENGTH: 25
<212> TYPE: DNA
<213> ORGANISM: Artificial
<220> FEATURE:
<223> OTHER INFORMATION: an artificially synthesized sequence

<400> SEQUENCE: 65
gcctggcctg ctgccctcgc tggcc 25

<210> SEQ ID NO 66
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 66
ctgccaagta tgacatca 18

<210> SEQ ID NO 67
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 67
tactccttgg aggccatgta g 21

<210> SEQ ID NO 68
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 68
gtggatgagg accacgaact 20

<210> SEQ ID NO 69
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 69
cttttcaagc ggtggttgat 20

<210> SEQ ID NO 70
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 70
acctcctaga cccacacacg 20

<210> SEQ ID NO 71
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 71
ggatgttggc aaaccagtct 20

<210> SEQ ID NO 72
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 72
atgagccctt caacgaacac 20

<210> SEQ ID NO 73
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 73
tggtagaagg ggctgatgtc 20

<210> SEQ ID NO 74
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 74
ttccaggctt tgggcatca 19

<210> SEQ ID NO 75
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 75
atgttcagca tgttcagcag tgtg 24

<210> SEQ ID NO 76
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 76
catccgtaaa gacctctatg ccaac 25

<210> SEQ ID NO 77
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 77
atggagccac cgatccaca 19

<210> SEQ ID NO 78
<211> LENGTH: 20

<212> TYPE: DNA
<213> ORGANISM: Artificial
<220> FEATURE:
<223> OTHER INFORMATION: an artificially synthesized primer sequence

<400> SEQUENCE: 78
tgtgtggaca cacctcccta 20

<210> SEQ ID NO 79
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 79
cttcaaaggt ccccttcctc 20

<210> SEQ ID NO 80
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 80
cagcttgagc catttcaaca 20

<210> SEQ ID NO 81
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 81
gggtgaggcc tttaggaaac 20

<210> SEQ ID NO 82
<211> LENGTH: 25
<212> TYPE: DNA
<213> ORGANISM: Artificial
<220> FEATURE:
<223> OTHER INFORMATION: an artificially synthesized sequence

<400> SEQUENCE: 82
gcgccccctc tccccatgga gaaag 25

<210> SEQ ID NO 83
<211> LENGTH: 25
<212> TYPE: DNA
<213> ORGANISM: Artificial
<220> FEATURE:
<223> OTHER INFORMATION: an artificially synthesized sequence

<400> SEQUENCE: 83
gctttgcctc aggatttccg ggacc 25

<210> SEQ ID NO 84
<211> LENGTH: 27
<212> TYPE: DNA
<213> ORGANISM: Artificial
<220> FEATURE:
<223> OTHER INFORMATION: an artificially synthesized sequence

<400> SEQUENCE: 84
ggttcagcct tggtctaccg tgatgtc 27

<210> SEQ ID NO 85
<211> LENGTH: 25
<212> TYPE: DNA
<213> ORGANISM: Artificial
<220> FEATURE:
<223> OTHER INFORMATION: an artificially synthesized sequence

<400> SEQUENCE: 85
gcagttgttg ctatgcgacc tgtat 25

<210> SEQ ID NO 86
<211> LENGTH: 24
<212> TYPE: DNA
<213> ORGANISM: Artificial
<220> FEATURE:
<223> OTHER INFORMATION: an artificially synthesized sequence

<400> SEQUENCE: 86
tggggagagt gaggattcgg tgaa 24

<210> SEQ ID NO 87
<211> LENGTH: 27
<212> TYPE: DNA
<213> ORGANISM: Artificial
<220> FEATURE:
<223> OTHER INFORMATION: an artificially synthesized sequence

<400> SEQUENCE: 87
cggacgtggg actcgtcgag gacaaag 27

<210> SEQ ID NO 88
<211> LENGTH: 26
<212> TYPE: DNA
<213> ORGANISM: Artificial
<220> FEATURE:
<223> OTHER INFORMATION: an artificially synthesized sequence

<400> SEQUENCE: 88
cgaaagtacc tgcccgcccg tttcgc 26

<210> SEQ ID NO 89
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 89
ctgtgagccc aagtgtgtgg a 21

<210> SEQ ID NO 90
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 90
gtctcgaaac atggcaacag ga 22

<210> SEQ ID NO 91
<211> LENGTH: 27
<212> TYPE: RNA
<213> ORGANISM: Artificial

<220> FEATURE:
<223> OTHER INFORMATION: An artificially synthesized siRNA sequence

<400> SEQUENCE: 91
gcagcccagc aagaugaaua agaucag 27

<210> SEQ ID NO 92
<211> LENGTH: 27
<212> TYPE: RNA
<213> ORGANISM: Artificial
<220> FEATURE:
<223> OTHER INFORMATION: An artificially synthesized siRNA sequence

<400> SEQUENCE: 92
gaucuuauuc aucuugcugg gcugcau 27

<210> SEQ ID NO 93
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 93
catccgtaaa gacctctatg ccaac 25

<210> SEQ ID NO 94
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 94
atggagccac cgatccaca 19

<210> SEQ ID NO 95
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 95
caggagggag aacagaaact cca 23

<210> SEQ ID NO 96
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 96
cctggttggc tgcttgctt 19

<210> SEQ ID NO 97
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 97
ctgccctggc tatggtcaca 20

-continued

```
<210> SEQ ID NO 98
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 98

agacaggtag ttgggtcggt tca                                              23
```